US012486513B2

(12) United States Patent
Zeidler et al.

(10) Patent No.: US 12,486,513 B2
(45) Date of Patent: Dec. 2, 2025

(54) MODULATION OF CARBON FLUX THROUGH THE MEG AND C3 PATHWAYS FOR THE IMPROVED PRODUCTION OF MONOETHYLENE GLYCOL AND C3 COMPOUNDS

(71) Applicant: Braskem S.A., Sao Paulo (BR)

(72) Inventors: Ane Fernanda Beraldi Zeidler, Campinas (BR); Beatriz Leite Magalhaes, Campinas (BR); Lucas Pedersen Parizzi, Campinas (BR); Veronica Maria Rodege Gogola Kolling, Campinas (BR)

(73) Assignee: Braskem S.A., Sao Paulo (BR)

(*) Notice: Subject to any disclaimer, the term of this patent is extended or adjusted under 35 U.S.C. 154(b) by 1322 days.

(21) Appl. No.: 16/728,509

(22) Filed: Dec. 27, 2019

(65) Prior Publication Data

US 2020/0208160 A1 Jul. 2, 2020

Related U.S. Application Data

(60) Provisional application No. 62/786,294, filed on Dec. 28, 2018, provisional application No. 62/786,298, filed on Dec. 28, 2018, provisional application No. 62/786,282, filed on Dec. 28, 2018, provisional application No. 62/786,283, filed on Dec. 28, 2018, provisional application No. 62/786,304, filed on Dec. 28, 2018.

(51) Int. Cl.

| | |
|---|---|
| *C12N 15/00* | (2006.01) |
| *C12N 15/52* | (2006.01) |
| *C12P 7/28* | (2006.01) |

(52) U.S. Cl.

CPC ................ *C12N 15/52* (2013.01); *C12P 7/28* (2013.01); *C12Y 401/01047* (2013.01); *C12Y 402/03003* (2013.01)

(58) Field of Classification Search

CPC ........ C12N 9/1029; C12N 9/88; C12N 15/52; C12N 9/0006; C12Y 102/03003; C12Y 101/01175; C12Y 602/01016; C12P 5/026; C12P 7/04; C12P 7/28

USPC ..... 435/252.2, 166, 160, 157, 189, 195, 233

See application file for complete search history.

(56) References Cited

U.S. PATENT DOCUMENTS

| | | | |
|---|---|---|---|
| 7,531,337 | B2 | 5/2009 | Escalante-Semerena et al. |
| 7,935,511 | B2 | 5/2011 | San et al. |
| 8,460,726 | B2 | 6/2013 | Harel et al. |
| 8,524,472 | B2 | 9/2013 | Muramatsu et al. |
| 8,637,286 | B2 | 1/2014 | Burgard et al. |
| 2005/0170482 | A1 | 8/2005 | San et al. |
| 2006/0073577 | A1 | 4/2006 | Ka-Yiu et al. |
| 2007/0249018 | A1 | 10/2007 | Vemuri et al. |
| 2009/0253164 | A1 | 10/2009 | Unrean et al. |
| 2015/0329877 | A1 | 11/2015 | Bockrath |
| 2016/0265005 | A1 | 9/2016 | Zelle et al. |
| 2016/0326553 | A1 | 11/2016 | Burgard et al. |
| 2017/0260551 | A1 | 9/2017 | Koch et al. |
| 2018/0023101 | A1 | 1/2018 | Koch et al. |
| 2018/0087074 | A1 | 3/2018 | Reed et al. |
| 2018/0179558 | A1 | 6/2018 | Koch et al. |
| 2018/0312887 | A1 | 11/2018 | Lynch et al. |

FOREIGN PATENT DOCUMENTS

| | | | |
|---|---|---|---|
| EP | 1546304 | B1 | 5/2013 |
| KR | 10-1351879 | B1 | 1/2014 |
| WO | WO 2005/087940 | A1 | 9/2005 |
| WO | 2006034156 | A2 | 3/2006 |
| WO | 2010076324 | A1 | 7/2010 |
| WO | WO 2011/012697 | A2 | 2/2011 |
| WO | WO 2013/007786 | A1 | 1/2013 |
| WO | WO 2013/126721 | A1 | 8/2013 |
| WO | WO 2013/163230 | A2 | 10/2013 |
| WO | WO 2014/076232 | A2 | 5/2014 |
| WO | WO 2014/102180 | A1 | 7/2014 |
| WO | WO 2015/042588 | A1 | 3/2015 |
| WO | 2017165397 | A1 | 9/2017 |
| WO | WO 2017/156166 | A1 | 9/2017 |
| WO | WO2018013701 | A1 | 1/2018 |
| WO | WO2018071563 | A1 | 4/2018 |
| WO | WO 2018/148703 | A1 | 8/2018 |

OTHER PUBLICATIONS

Devos et al., (Proteins: Structure, Function and Genetics, 2000, vol. 41: 98-107.*

Whisstock et al., (Quarterly Reviews of Biophysics 2003, vol. 36 (3): 307-340.*

Witkowski et al., (Biochemistry 38:11643-11650, 1999.*

Kisselev L., (Structure, 2002, vol. 10: 8-9.*

Alkim, Ceren, et al. "Optimization of ethylene glycol production from (D)-xylose via a synthetic pathway implemented in *Escherichia coli*." Microbial Cell Factories (2015); 14.1: 127.

Berzin et al., "Selective production of acetone during continuoussynthesis gas fermentation by engineered biocatalyst *Clostridium*sp. MAceT113," Letters in Applied Microbiology, (2012) 55, 149-154.

Boonstra et al., "The udhA Gene of *Escherichia coli* Encodes a Soluble Pyridine Nucleotide Transhydrogenase," Journal of Bacteriology, Feb. 1999, 181(3): 1030-1034.

(Continued)

*Primary Examiner* — Teckhand Saidha
*Assistant Examiner* — Mohammad Y Meah
(74) *Attorney, Agent, or Firm* — Morgan, Lewis & Bockius LLP

(57) ABSTRACT

The present disclosure provides methods of modulating the flux of carbon through the monoethylene glycol (MEG) biosynthesis pathway and one or more C3 compound biosynthesis pathways by expressing enzymes that are essential for improving C3 compounds and modulating other genetic aspects of MEG and C3 compound biosynthesis. The disclosure is further drawn to modified microbes comprising the disrupted sequences and overexpressed sequences, and compositions thereof.

15 Claims, 30 Drawing Sheets

Specification includes a Sequence Listing.

(56) References Cited

OTHER PUBLICATIONS

Cabulong et al., "Enhanced yield of ethylene glycol production from D-xylose bypathway optimization in *Escherichia coli*," Enzyme and Microbial Technology 97 (2017) 11-20.
Canonaco et al., "Metabolic flux response to phosphoglucose isomerase knock-out in *Escherichia coli* and impact of overexpression of the soluble transhydrogenase UdhA," FEMS Microbiology Letters, (2001) 204: 247-252.
Castaño-Cerezo et al., "An insight into the role of phosphotransacetylase (pta) and the acetate/acetyl-CoA node in *Escherichia coli*," Microbial Cell Factories, Oct. 2009, 8:54, 19 pages.
Causey et al., "Engineering *Escherichia coli* for efficient conversion of glucose to pyruvate," PNAS, Feb. 24, 2004, 101(8), 2235-2240.
Charusanti et al., "Genetic Basis of Growth Adaptation of *Escherichia coli* after Deletion of pgi, a Major Metabolic Gene," PLoS Genetics, (2010) 6(11):e1001186, 13 pages.
Chen, Zhen, et al. "Metabolic engineering of Corynebacterium glutamicum for the de novo production of ethylene glycol from glucose." Metabolic Engineering (2016); 33: 12-18.
Dittrich et al., "Redistribution of Metabolic Fluxes in the Central Aerobic Metabolic Pathway of *E. coli* Mutant Strains with Deletion of the ackA-pta and poxB Pathways for the Synthesis of Isoamyl Acetate," Biotechnology Progress, 2005, 21(2), 627-631.
Ehrenberger et al., "Structure-Guided Engineering of Xylitol Dehydrogenase Cosubstrate Specificity," Structure, Mar. 2006, 14: 567-575.
Hao and Berry, "A thermostable variant of fructose bisphosphate aldolase constructed by directed evolution also shows increased stability in organic solvents," Protein Engineering, Design & Selection, 2004, vol. 17, No. 9, pp. 689-697.
Jarboe, LR, "YqhD: a broad-substrate range aldehyde reductase with various applications in production of biorenewable fuels and chemicals," Applied Microbiology and Biotechnology 2010, 89:249-257.
Klasson et al., "Bioconversion of synthesis gas into liquid or gaseous fuels," Enzyme and Microbial Technology, Aug. 1992, vol. 14, pp. 602-608.
Klasson et al., "Bioreactor design for synthesis gas fermentations," Fuel, (1991), 70:605-614.
Klasson et al., "Bioreactors for synthesis gas fermentations," Resources, Conservation and Recycling, 1991, 5:145-165.
Li et al., "Enhanced activity of yqhD oxidoreductase in synthesis of 1,3-propanediol by error-prone PCR," Progress in Natural Science, 2008, 18: 1519-1524.
Lin et al., "Acetyl-CoA synthetase overexpression in *Escherichia coli* demonstrates more efficient acetate assimilation and lower acetate accumulation: a potential tool in metabolic engineering," Applied Microbiology and Biotechnology, 2006, 71(6), 870-874.
Liu et al., "Biosynthesis of ethylene glycol in *Escherichia coli*," Applied Microbiology and Biotechnology Apr. 2013; 97(8):3409-3417.
Patel et al., "Engineering of the catalytic site of xylose isomerase to enhance bioconversion of a non-preferential substrate," Protein Engineering, Design & Selection, 2012, vol. 25, No. 7, pp. 331-336.
Peebo et al., "Coordinated activation of PTA-ACS and TCA cycles strongly reduces overflow metabolism of acetate in *Escherichia coli*," Applied Microbiology and Biotechnology, 2014, 98(11), 5131-5143.
Sauer et al., "The Soluble and Membrane-bound Transhydrogenases UdhA and PntAB have Divergent Functions in NADPH Metabolism of *Escherichia coli*," The Journal of Biological Chemistry, (2004) 279(8): 6613-6619.
Sulzenbacher et al., "Crystal Structure of *E. coli* Alcohol Dehydrogenase YqhD: Evidence of a Covalently Modified NADP Coenzyme," J. Mol. Biol. 2004, 342(2):489-502.
Vega et al., "Design of Bioreactors for Coal Synthesis Gas Fermentations," Resources, Conservation and Recycling, (1990), 3:149-160.
Vega et al., "Study of gaseous substrate fermentations: Carbon monoxide conversion to acetate. 1. Batch culture," Biotech. Bioeng., (1989), 34(6):774-784.
Vega et al., "Study of Gaseous Substrate Fermentation: Carbon Monoxide Conversion to Acetate. 2. Continuous Culture," Biotech. Bioeng., (1989), 34(6):785-793.
Yomano et al., "Deletion of methylglyoxal synthase gene (mgsA) increased sugar co-metabolism in ethanol-producing *Escherichia coli*," Biotechnol Lett (2009) 31:1389-1398.

* cited by examiner

SEQUENCE LISTING

<160> NUMBER OF SEQ ID NOS: 120

<210> SEQ ID NO 1
<211> LENGTH: 873
<212> TYPE: DNA
<213> ORGANISM: Pseudomonas cichorii

<400> SEQUENCE: 1
gtgaacaaag ttggcatgtt ctacacctac tggtcgactg agtggatggt cgactttccg 60
gcgactgcga agcgcattgc cgggctcggc ttcgacttaa tggaaatctc gctcggcgag 120
tttcacaatc tttccgacgc gaagaagcgt gagctaaaag ccgtggctga tgatctgggg 180
ctcacggtga tgtgctgtat cggactgaag tctgagtacg actttgcctc gccggacaag 240
agcgttcgtg atgccggcac ggaatatgtg aagcgcttgc tcgacgactg tcacctcctc 300
ggcgcgccgg tctttgctgg ccttacgttc tgcgcgtggc cccaatctcc gccgctggac 360
atgaaggata agcgccctta cgtcgaccgt gcaatcgaaa gcgttcgtcg tgttatcaag 420
gtagctgaag actacggcat tatttatgca ctggaagtgg tgaaccgatt cgagcagtgg 480
ctttgcaatg acgccaagga agcaattgcg tttgccgacg cggttgacag tccggcgtgc 540
aaggtccagc tcgacacatt ccacatgaat atcgaagaga cttccttccg cgatgcaatc 600
cttgcctgca agggcaagat gggccatttc catttgggcg aagcgaaccg tctgccgccg 660
ggcgagggtc gcctgccgtg ggatgaaata ttcggggcgc tgaaggaaat cggatatgac 720
ggcaccatcg ttatggaacc gttcatgcgc aagggcggct cggtcagccg cgcggtgggc 780
gtatggcggg atatgtcgaa cggtgcgacg gacgaagaga tggacgagcg cgctcgccgc 840
tcgttgcagt ttgttcgtga caagctggcc tga 873

<210> SEQ ID NO 2
<211> LENGTH: 873
<212> TYPE: DNA
<213> ORGANISM: Pseudomonas cichorii

<400> SEQUENCE: 2

```
atgaacaaag tgggtatgtt ctatacgtac tggtccacgg aatggatggt tgactttccg     60

gcaaccgcga aacgtattgc gggcctgggc ttcgacctga tggaaatttc tctgggcgaa    120

tttcacaacc tgtccgatgc gaaaaagcgt gaactgaaag ccgttgccga cgatctgggt    180

ctgactgtga tgtgctgtat cggcctgaaa tctgaatacg atttcgcgag cccggataaa    240

agcgttcgcg acgccggtac tgaatatgtc aaacgtctgc tggatgactg tcacctgctg    300

ggcgcaccag tgttcgcggg tctgaccttc tgtgcgtggc cgcagtcccc accgctggac    360

atgaaggata aacgtccgta cgtggaccgt gccatcgaaa gcgtgcgccg cgtaatcaaa    420

gtcgctgaag attatggcat tatttacgct ctggaagttg ttaaccgttt cgaacagtgg    480

ctgtgcaacg acgcgaaaga ggccattgcc ttcgctgacg cggtggattc tccggcttgc    540

aaagttcagc tggacacttt ccatatgaac atcgaggaaa cctccttccg tgacgcgatc    600

ctggcttgca agggtaaaat gggccatttc catctgggcg aagcaaaccg cctgccgccg    660

ggcgaaggtc gtctgccgtg ggacgaaatt tttggcgctc tgaaggaaat cggctacgat    720

ggcacgattg ttatggagcc gttcatgcgc aaaggtggct ccgtttcccg tgcagttggt    780

gtttggcgtg atatgtctaa cggtgccacc gatgaagaaa tggacgaacg tgcacgtcgc    840

tccctgcaat tcgttcgcga taaactggcg taa                                 873
```

<210> SEQ ID NO 3
<211> LENGTH: 290
<212> TYPE: PRT
<213> ORGANISM: Pseudomonas cichorii

<400> SEQUENCE: 3

```
Met Asn Lys Val Gly Met Phe Tyr Thr Tyr Trp Ser Thr Glu Trp Met
1               5                   10                  15

Val Asp Phe Pro Ala Thr Ala Lys Arg Ile Ala Gly Leu Gly Phe Asp
            20                  25                  30

Leu Met Glu Ile Ser Leu Gly Glu Phe His Asn Leu Ser Asp Ala Lys
        35                  40                  45

Lys Arg Glu Leu Lys Ala Val Ala Asp Asp Leu Gly Leu Thr Val Met
    50                  55                  60

Cys Cys Ile Gly Leu Lys Ser Glu Tyr Asp Phe Ala Ser Pro Asp Lys
65                  70                  75                  80

Ser Val Arg Asp Ala Gly Thr Glu Tyr Val Lys Arg Leu Leu Asp Asp
                85                  90                  95

Cys His Leu Leu Gly Ala Pro Val Phe Ala Gly Leu Thr Phe Cys Ala
            100                 105                 110

Trp Pro Gln Ser Pro Pro Leu Asp Met Lys Asp Lys Arg Pro Tyr Val
        115                 120                 125

Asp Arg Ala Ile Glu Ser Val Arg Arg Val Ile Lys Val Ala Glu Asp
    130                 135                 140

Tyr Gly Ile Ile Tyr Ala Leu Glu Val Val Asn Arg Phe Glu Gln Trp
145                 150                 155                 160

Leu Cys Asn Asp Ala Lys Glu Ala Ile Ala Phe Ala Asp Ala Val Asp
                165                 170                 175
```

-continued

```
Ser Pro Ala Cys Lys Val Gln Leu Asp Thr Phe His Met Asn Ile Glu
            180                 185                 190

Glu Thr Ser Phe Arg Asp Ala Ile Leu Ala Cys Lys Gly Lys Met Gly
        195                 200                 205

His Phe His Leu Gly Glu Ala Asn Arg Leu Pro Pro Gly Glu Gly Arg
    210                 215                 220

Leu Pro Trp Asp Glu Ile Phe Gly Ala Leu Lys Glu Ile Gly Tyr Asp
225                 230                 235                 240

Gly Thr Ile Val Met Glu Pro Phe Met Arg Lys Gly Gly Ser Val Ser
                245                 250                 255

Arg Ala Val Gly Val Trp Arg Asp Met Ser Asn Gly Ala Thr Asp Glu
            260                 265                 270

Glu Met Asp Glu Arg Ala Arg Arg Ser Leu Gln Phe Val Arg Asp Lys
        275                 280                 285

Leu Ala
    290


<210> SEQ ID NO 4
<211> LENGTH: 888
<212> TYPE: DNA
<213> ORGANISM: Rhodobacter sphaeroides

<400> SEQUENCE: 4

gtgaaaaatc ctgtcggcat catctcgatg cagttcatcc ggcccttcac ctcggagtcg      60

ctgcatttcc tgaagaagtc ccgggccctg ggcttcgatt tcatcgagct tctcgtgccc     120

gagcccgaag acgggctcga cgcggccgag gtgcggcgca tctgcgaggg cgaggggctg     180

ggcctcgttc tggccgcgcg cgtgaacctc cagcgctcga tcgcgagcga ggaggccgcg     240

gcgcgggccg gcgggcgcga ctatctgaaa tactgcatcg aggccgccga ggcgctcggc     300

gcgaccatcg tcggcggccc gctctatggc gagccgctgg tcttcgccgg ccgcccgccc     360

ttcccctgga cggccgagca gatcgccacc cgcgccgccc gcaccgtcga ggggctggcc     420

gaagtggccc cgctcgccgc gagcgcgggc aaggtcttcg ggctcgagcc gctgaaccgc     480

ttcgagaccg acatcgtgaa cacgaccgca caggccatcg aggtggtgga tgcggtgggc     540

tcgcccggtc tcggcgtcat gctcgacacg ttccacatga acatggagga acgctcgatc     600

cccgatgcga tccgcgccac aggcgcgcgc ctcgtccatt ttcaggccaa cgagaaccac     660

cgcggcttcc ccggcaccgg caccatggac tggacggcca tcgcgcgggc gctggggcag     720

gcgggctacg cgggtccggt ctcgctcgag cctttccggc gcgacgacga gcgcgtggcg     780

ctgcccatcg cccactggcg cgccccgcac gaggacgagg acgagaagct gcgcgcgggg     840

ctgggtctca tccgctccgc gatcaccctg gcggaggtga cccactga                  888


<210> SEQ ID NO 5
<211> LENGTH: 295
<212> TYPE: PRT
<213> ORGANISM: Rhodobacter sphaeroides

<400> SEQUENCE: 5

Met Lys Asn Pro Val Gly Ile Ile Ser Met Gln Phe Ile Arg Pro Phe
1               5                   10                  15

Thr Ser Glu Ser Leu His Phe Leu Lys Lys Ser Arg Ala Leu Gly Phe
            20                  25                  30

Asp Phe Ile Glu Leu Leu Val Pro Glu Pro Glu Asp Gly Leu Asp Ala
        35                  40                  45
```

Ala Glu Val Arg Arg Ile Cys Glu Gly Glu Gly Leu Gly Leu Val Leu
50 55 60

Ala Ala Arg Val Asn Leu Gln Arg Ser Ile Ala Ser Glu Glu Ala Ala
65 70 75 80

Ala Arg Ala Gly Gly Arg Asp Tyr Leu Lys Tyr Cys Ile Glu Ala Ala
85 90 95

Glu Ala Leu Gly Ala Thr Ile Val Gly Gly Pro Leu Tyr Gly Glu Pro
100 105 110

Leu Val Phe Ala Gly Arg Pro Pro Phe Pro Trp Thr Ala Glu Gln Ile
115 120 125

Ala Thr Arg Ala Ala Arg Thr Val Glu Gly Leu Ala Glu Val Ala Pro
130 135 140

Leu Ala Ala Ser Ala Gly Lys Val Phe Gly Leu Glu Pro Leu Asn Arg
145 150 155 160

Phe Glu Thr Asp Ile Val Asn Thr Thr Ala Gln Ala Ile Glu Val Val
165 170 175

Asp Ala Val Gly Ser Pro Gly Leu Gly Val Met Leu Asp Thr Phe His
180 185 190

Met Asn Met Glu Glu Arg Ser Ile Pro Asp Ala Ile Arg Ala Thr Gly
195 200 205

Ala Arg Leu Val His Phe Gln Ala Asn Glu Asn His Arg Gly Phe Pro
210 215 220

Gly Thr Gly Thr Met Asp Trp Thr Ala Ile Ala Arg Ala Leu Gly Gln
225 230 235 240

Ala Gly Tyr Ala Gly Pro Val Ser Leu Glu Pro Phe Arg Arg Asp Asp
245 250 255

Glu Arg Val Ala Leu Pro Ile Ala His Trp Arg Ala Pro His Glu Asp
260 265 270

Glu Asp Glu Lys Leu Arg Ala Gly Leu Gly Leu Ile Arg Ser Ala Ile
275 280 285

Thr Leu Ala Glu Val Thr His
290 295

<210> SEQ ID NO 6
<211> LENGTH: 1422
<212> TYPE: DNA
<213> ORGANISM: Escherichia coli

<400> SEQUENCE: 6
atgatgaaac aagaagttat cctggtactc gactgtggcg cgaccaatgt cagggccatc 60
gcggttaatc ggcagggcaa aattgttgcc cgcgcctcaa cgcctaatgc cagcgatatc 120
gcgatggaaa acaacacctg gcaccagtgg tctttagacg ccattttgca acgctttgct 180
gattgctgtc ggcaaatcaa tagtgaactg actgaatgcc acatccgcgg tatcgccgtc 240
accacctttg gtgtggatgg cgctctggta gataagcaag gcaatctgct ctatccgatt 300
attagctgga aatgtccgcg aacagcagcg gttatggaca atattgaacg gttaatctcc 360
gcacagcggt tgcaggctat ttctggcgtc ggagccttta gtttcaatac gttatataag 420
ttggtgtggt tgaaagaaaa tcatccacaa ctgctggaac gcgcgcacgc ctggctcttt 480
atttcgtcgc tgattaacca ccgtttaacc ggcgaattca ctactgatat cacgatggcc 540
ggaaccagcc agatgctgga tatccagcaa cgcgatttca gtccgcaaat tttacaagcc 600
accggtattc cacgccgact cttccctcgt ctggtggaag cgggtgaaca gattggtacg 660
ctacagaaca gcgccgcagc aatgctcggc ttacccgttg gcataccggt gatttccgca 720
ggtcacgata cccagttcgc ccttttggc gctggtgctg aacaaaatga acccgtgctc 780
tcttccggta catgggaaat tttaatggtt cgcagcgccc aggttgatac ttcgctgtta 840
agtcagtacg ccggttccac ctgcgaactg gatagccagg cagggttgta taacccaggt 900
atgcaatggc tggcatccgg cgtgctggaa tgggtgagaa aactgttctg gacggctgaa 960
acaccctggc aaatgttgat tgaagaagct cgtctgatcg cgcctggcgc ggatggcgta 1020
aaaatgcagt gtgatttatt gtcgtgtcag aacgctggct ggcaaggagt gacgcttaat 1080
accacgcggg ggcatttcta tcgcgcggcg ctggaagggt taactgcgca attacagcgc 1140
aatctacaga tgctggaaaa aatcgggcac tttaaggcct ctgaattatt gttagtcggt 1200
ggaggaagtc gcaacacatt gtggaatcag attaaagcca atatgcttga tattccggta 1260
aaagttctcg acgacgccga aacgaccgtc gcaggagctg cgctgttcgg ttggtatggc 1320
gtaggggaat ttaacagccc ggaagaagcc cgcgcacaga ttcattatca gtaccgttat 1380
ttctacccgc aaactgaacc tgaatttata gaggaagtgt ga 1422

<210> SEQ ID NO 7
<211> LENGTH: 1422
<212> TYPE: DNA
<213> ORGANISM: Escherichia coli

<400> SEQUENCE: 7
atgatgaaac aagaagttat cctggtactc gactgtggcg cgaccaatgt cagggccatc 60
gcggttaatc ggcagggcaa aattgttgcc cgcgcctcaa cgcctaatgc cagcgatatc 120
gcgatggaaa acaacacctg gcaccagtgg tctttagacg ccattttgca acgctttgct 180
gattgctgtc ggcaaatcaa tagtgaactg actgaatgcc acatccgcgg tatcgccgtc 240
accacctttg gtgtggatgg cgctctggta gataagcaag gcaatctgct ctatccgatt 300
attagctgga aatgtccgcg aacagcagcg gttatggaca atattgaacg gttaatctcc 360
gcacagcggt tgcaggctat ttctggcgtc ggagccttta gtttcaatac gttatataag 420
ttggtgtggt tgaaagaaaa tcatccacaa ctgctggaac gcgcgcacgc ctggctcttt 480
atttcgtcgc tgattaacca ccgtttaacc ggcgaattca ctactgatat cacgatggcc 540
ggaaccagcc agatgctgga tatccagcaa cgcgatttca gtccgcaaat tttacaagcc 600
accggtattc cacgccgact cttccctcgt ctggtggaag cgggtgaaca gattggtacg 660
ctacagaaca gcgccgcagc aatgctcggc ttacccgttg gcataccggt gatttccgca 720
ggtcacgata cccagttcgc ccttttggc gctggtgctg aacaaaatga acccgtgctc 780
tcttccggta catgggaaat tttaatggtt cgcagcgccc aggttgatac ttcgctgtta 840
agtcagtacg ccggttccac ctgcgaactg gatagccagg cagggttgta taacccaggt 900
atgcaatggc tggcatccgg cgtgctggaa tgggtgagaa aactgttctg gacggctgaa 960
acaccctggc aaatgttgat tgaagaagct cgtctgatcg cgcctggcgc ggatggcgta 1020
aaaatgcagt gtgatttatt gtcgtgtcag aacgctggct ggcaaggagt gacgcttaat 1080
accacgcggg ggcatttcta tcgcgcggcg ctggaagggt taactgcgca attacagcgc 1140
aatctacaga tgctggaaaa aatcgggcac tttaaggcct ctgaattatt gttagtcggt 1200
ggaggaagtc gcaacacatt gtggaatcag attaaagcca atatgcttga tattccggta 1260
aaagttctcg acgacgccga aacgaccgtc gcaggagctg cgctgttcgg ttggtatggc 1320
gtaggggaat ttaacagccc ggaagaagcc cgcgcacaga ttcattatca gtaccgttat 1380

-continued ttctacccgc aaactgaacc tgaatttata gaggaagtgt ga 1422

<210> SEQ ID NO 8
<211> LENGTH: 473
<212> TYPE: PRT
<213> ORGANISM: Escherichia coli

<400> SEQUENCE: 8

Met Met Lys Gln Glu Val Ile Leu Val Leu Asp Cys Gly Ala Thr Asn
1 5 10 15

Val Arg Ala Ile Ala Val Asn Arg Gln Gly Lys Ile Val Ala Arg Ala
20 25 30

Ser Thr Pro Asn Ala Ser Asp Ile Ala Met Glu Asn Asn Thr Trp His
35 40 45

Gln Trp Ser Leu Asp Ala Ile Leu Gln Arg Phe Ala Asp Cys Cys Arg
50 55 60

Gln Ile Asn Ser Glu Leu Thr Glu Cys His Ile Arg Gly Ile Ala Val
65 70 75 80

Thr Thr Phe Gly Val Asp Gly Ala Leu Val Asp Lys Gln Gly Asn Leu
85 90 95

Leu Tyr Pro Ile Ile Ser Trp Lys Cys Pro Arg Thr Ala Ala Val Met
100 105 110

Asp Asn Ile Glu Arg Leu Ile Ser Ala Gln Arg Leu Gln Ala Ile Ser
115 120 125

Gly Val Gly Ala Phe Ser Phe Asn Thr Leu Tyr Lys Leu Val Trp Leu
130 135 140

Lys Glu Asn His Pro Gln Leu Leu Glu Arg Ala His Ala Trp Leu Phe
145 150 155 160

Ile Ser Ser Leu Ile Asn His Arg Leu Thr Gly Glu Phe Thr Thr Asp
165 170 175

Ile Thr Met Ala Gly Thr Ser Gln Met Leu Asp Ile Gln Gln Arg Asp
180 185 190

Phe Ser Pro Gln Ile Leu Gln Ala Thr Gly Ile Pro Arg Arg Leu Phe
195 200 205

Pro Arg Leu Val Glu Ala Gly Glu Gln Ile Gly Thr Leu Gln Asn Ser
210 215 220

Ala Ala Ala Met Leu Gly Leu Pro Val Gly Ile Pro Val Ile Ser Ala
225 230 235 240

Gly His Asp Thr Gln Phe Ala Leu Phe Gly Ala Gly Ala Glu Gln Asn
245 250 255

Glu Pro Val Leu Ser Ser Gly Thr Trp Glu Ile Leu Met Val Arg Ser
260 265 270

Ala Gln Val Asp Thr Ser Leu Leu Ser Gln Tyr Ala Gly Ser Thr Cys
275 280 285

Glu Leu Asp Ser Gln Ala Gly Leu Tyr Asn Pro Gly Met Gln Trp Leu
290 295 300

Ala Ser Gly Val Leu Glu Trp Val Arg Lys Leu Phe Trp Thr Ala Glu
305 310 315 320

Thr Pro Trp Gln Met Leu Ile Glu Glu Ala Arg Leu Ile Ala Pro Gly
325 330 335

Ala Asp Gly Val Lys Met Gln Cys Asp Leu Leu Ser Cys Gln Asn Ala
340 345 350

Gly Trp Gln Gly Val Thr Leu Asn Thr Thr Arg Gly His Phe Tyr Arg
355 360 365

-continued

```
Ala Ala Leu Glu Gly Leu Thr Ala Gln Leu Gln Arg Asn Leu Gln Met
    370                 375                 380

Leu Glu Lys Ile Gly His Phe Lys Ala Ser Glu Leu Leu Leu Val Gly
385                 390                 395                 400

Gly Gly Ser Arg Asn Thr Leu Trp Asn Gln Ile Lys Ala Asn Met Leu
                405                 410                 415

Asp Ile Pro Val Lys Val Leu Asp Asp Ala Glu Thr Thr Val Ala Gly
            420                 425                 430

Ala Ala Leu Phe Gly Trp Tyr Gly Val Gly Glu Phe Asn Ser Pro Glu
        435                 440                 445

Glu Ala Arg Ala Gln Ile His Tyr Gln Tyr Arg Tyr Phe Tyr Pro Gln
    450                 455                 460

Thr Glu Pro Glu Phe Ile Glu Glu Val
465                 470


<210> SEQ ID NO 9
<211> LENGTH: 648
<212> TYPE: DNA
<213> ORGANISM: Escherichia coli

<400> SEQUENCE: 9

atggaacgaa ataaacttgc tcgtcagatt attgacactt gcctggaaat gacccgcctg     60

ggactgaacc aggggacagc ggggaacgtc agtgtacgtt atcaggatgg gatgctgatt    120

acgcctacag gcattccata tgaaaaactg acggagtcgc atattgtctt tattgatggc    180

aacggtaaac atgaggaagg aaagctcccc tcaagcgaat ggcgtttcca tatggcagcc    240

tatcaaagca gaccggatgc caacgcggtt gttcacaatc atgccgttca ttgcacggca    300

gtttccattc ttaaccgatc gatccccgct attcactaca tgattgcggc ggctggcggt    360

aattctattc cttgcgcgcc ttatgcgacc tttggaacac gcgaactttc tgaacatgtt    420

gcgctggctc tcaaaaatcg taaggcaact ttgttacaac atcatgggct tatcgcttgt    480

gaggtgaatc tggaaaaagc gttatggctg gcgcatgaag ttgaagtgct ggcgcaactt    540

tacctgacga ccctggcgat tacggacccg gtgccagtgc tgagcgatga agagattgcc    600

gtagtgctgg agaaattcaa aacctatggg ttacgaattg aagagtaa                 648


<210> SEQ ID NO 10
<211> LENGTH: 648
<212> TYPE: DNA
<213> ORGANISM: Escherichia coli

<400> SEQUENCE: 10

atggaacgaa ataaacttgc tcgtcagatt attgacactt gcctggaaat gacccgcctg     60

ggactgaacc aggggacagc ggggaacgtc agtgtacgtt atcaggatgg gatgctgatt    120

acgcctacag gcattccata tgaaaaactg acggagtcgc atattgtctt tattgatggc    180

aacggtaaac atgaggaagg aaagctcccc tcaagcgaat ggcgtttcca tatggcagcc    240

tatcaaagca gaccggatgc caacgcggtt gttcacaatc atgccgttca ttgcacggca    300

gtttccattc ttaaccgatc gatccccgct attcactaca tgattgcggc ggctggcggt    360

aattctattc cttgcgcgcc ttatgcgacc tttggaacac gcgaactttc tgaacatgtt    420

gcgctggctc tcaaaaatcg taaggcaact ttgttacaac atcatgggct tatcgcttgt    480

gaggtgaatc tggaaaaagc gttatggctg gcgcatgaag ttgaagtgct ggcgcaactt    540

tacctgacga ccctggcgat tacggacccg gtgccagtgc tgagcgatga agagattgcc    600
```

-continued

```
gtagtgctgg agaaattcaa aacctatggg ttacgaattg aagagtaa                648


<210> SEQ ID NO 11
<211> LENGTH: 215
<212> TYPE: PRT
<213> ORGANISM: Escherichia coli

<400> SEQUENCE: 11

Met Glu Arg Asn Lys Leu Ala Arg Gln Ile Ile Asp Thr Cys Leu Glu
1               5                   10                  15

Met Thr Arg Leu Gly Leu Asn Gln Gly Thr Ala Gly Asn Val Ser Val
            20                  25                  30

Arg Tyr Gln Asp Gly Met Leu Ile Thr Pro Thr Gly Ile Pro Tyr Glu
        35                  40                  45

Lys Leu Thr Glu Ser His Ile Val Phe Ile Asp Gly Asn Gly Lys His
    50                  55                  60

Glu Glu Gly Lys Leu Pro Ser Ser Glu Trp Arg Phe His Met Ala Ala
65                  70                  75                  80

Tyr Gln Ser Arg Pro Asp Ala Asn Ala Val Val His Asn His Ala Val
                85                  90                  95

His Cys Thr Ala Val Ser Ile Leu Asn Arg Ser Ile Pro Ala Ile His
            100                 105                 110

Tyr Met Ile Ala Ala Ala Gly Gly Asn Ser Ile Pro Cys Ala Pro Tyr
        115                 120                 125

Ala Thr Phe Gly Thr Arg Glu Leu Ser Glu His Val Ala Leu Ala Leu
    130                 135                 140

Lys Asn Arg Lys Ala Thr Leu Leu Gln His His Gly Leu Ile Ala Cys
145                 150                 155                 160

Glu Val Asn Leu Glu Lys Ala Leu Trp Leu Ala His Glu Val Glu Val
                165                 170                 175

Leu Ala Gln Leu Tyr Leu Thr Thr Leu Ala Ile Thr Asp Pro Val Pro
            180                 185                 190

Val Leu Ser Asp Glu Glu Ile Ala Val Val Leu Glu Lys Phe Lys Thr
        195                 200                 205

Tyr Gly Leu Arg Ile Glu Glu
    210                 215


<210> SEQ ID NO 12
<211> LENGTH: 1104
<212> TYPE: DNA
<213> ORGANISM: Escherichia coli

<400> SEQUENCE: 12

atggaccgca ttattcaatc accgggtaaa tacatccagg gcgctgatgt gattaatcgt      60

ctgggcgaat acctgaagcc gctggcagaa cgctggttag tggtgggtga caaatttgtt     120

ttaggttttg ctcaatccac tgtcgagaaa agctttaaag atgctggact ggtagtagaa     180

attgcgccgt ttggcggtga atgttcgcaa aatgagatcg accgtctgcg tggcatcgcg     240

gagactgcgc agtgtggcgc aattctcggt atcggtggcg gaaaaaccct cgatactgcc     300

aaagcactgg cacatttcat gggtgttccg gtagcgatcg caccgactat cgcctctacc     360

gatgcaccgt gcagcgcatt gtctgttatc tacaccgatg agggtgagtt tgaccgctat     420

ctgctgttgc caaataaccc gaatatggtc attgtcgaca ccaaaatcgt cgctggcgca     480

cctgcacgtc tgttagcggc gggtatcggc gatgcgctgg caacctggtt tgaagcgcgt     540

gcctgctctc gtagcggcgc gaccaccatg gcgggcggca agtgcaccca ggctgcgctg     600
```

```
gcactggctg aactgtgcta caacaccctg ctggaagaag gcgaaaaagc gatgcttgct    660

gccgaacagc atgtagtgac tccggcgctg gagcgcgtga ttgaagcgaa cacctatttg    720

agcggtgttg gttttgaaag tggtggtctg gctgcggcgc acgcagtgca taacggcctg    780

accgctatcc cggacgcgca tcactattat cacggtgaaa aagtggcatt cggtacgctg    840

acgcagctgg ttctggaaaa tgcgccggtg gaggaaatcg aaaccgtagc tgcccttagc    900

catgcggtag gtttgccaat aactctcgct caactggata ttaaagaaga tgtcccggcg    960

aaaatgcgaa ttgtggcaga agcggcatgt gcagaaggtg aaaccattca caacatgcct   1020

ggcggcgcga cgccagatca ggtttacgcc gctctgctgg tagccgacca gtacggtcag   1080

cgtttcctgc aagagtggga ataa                                          1104
```

<210> SEQ ID NO 13
<211> LENGTH: 367
<212> TYPE: PRT
<213> ORGANISM: Escherichia coli

<400> SEQUENCE: 13

```
Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
```

```
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365


<210> SEQ ID NO 14
<211> LENGTH: 1029
<212> TYPE: DNA
<213> ORGANISM: Saccharomyces cerevisiae

<400> SEQUENCE: 14

atgtcagttt tcgtttcagg tgctaacggg ttcattgccc aacacattgt cgatctcctg      60

ttgaaggaag actataaggt catcggttct gccagaagtc aagaaaaggc cgagaattta     120

acggaggcct ttggtaacaa cccaaaattc tccatggaag ttgtcccaga catatctaag     180

ctggacgcat ttgaccatgt tttccaaaag cacggcaagg atatcaagat agttctacat     240

acggcctctc cattctgctt tgatatcact gacagtgaac gcgatttatt aattcctgct     300

gtgaacggtg ttaagggaat tctccactca attaaaaaat acgccgctga ttctgtagaa     360

cgtgtagttc tcacctcttc ttatgcagct gtgttcgata tggcaaaaga aaacgataag     420

tctttaacat ttaacgaaga atcctggaac ccagctacct gggagagttg ccaaagtgac     480

ccagttaacg cctactgtgg ttctaagaag tttgctgaaa aagcagcttg ggaatttcta     540

gaggagaata gagactctgt aaaattcgaa ttaactgccg ttaacccagt ttacgttttt     600

ggtccgcaaa tgtttgacaa agatgtgaaa aaacacttga acacatcttg cgaactcgtc     660

aacagcttga tgcatttatc accagaggac aagataccgg aactatttgg tggatacatt     720

gatgttcgtg atgttgcaaa ggctcattta gttgccttcc aaaagaggga aacaattggt     780

caaagactaa tcgtatcgga ggccagattt actatgcagg atgttctcga tatccttaac     840

gaagacttcc ctgttctaaa aggcaatatt ccagtgggga aaccaggttc tggtgctacc     900

cataacaccc ttggtgctac tcttgataat aaaaagagta agaaattgtt aggtttcaag     960

ttcaggaact tgaaagagac cattgacgac actgcctccc aaattttaaa atttgagggc    1020

agaatataa                                                            1029


<210> SEQ ID NO 15
<211> LENGTH: 342
<212> TYPE: PRT
<213> ORGANISM: Saccharomyces cerevisiae

<400> SEQUENCE: 15

Met Ser Val Phe Val Ser Gly Ala Asn Gly Phe Ile Ala Gln His Ile
1               5                   10                  15

Val Asp Leu Leu Leu Lys Glu Asp Tyr Lys Val Ile Gly Ser Ala Arg
            20                  25                  30

Ser Gln Glu Lys Ala Glu Asn Leu Thr Glu Ala Phe Gly Asn Asn Pro
        35                  40                  45

Lys Phe Ser Met Glu Val Val Pro Asp Ile Ser Lys Leu Asp Ala Phe
```

-continued

```
    50                  55                  60

Asp His Val Phe Gln Lys His Gly Lys Asp Ile Lys Ile Val Leu His
65                  70                  75                  80

Thr Ala Ser Pro Phe Cys Phe Asp Ile Thr Asp Ser Glu Arg Asp Leu
                85                  90                  95

Leu Ile Pro Ala Val Asn Gly Val Lys Gly Ile Leu His Ser Ile Lys
            100                 105                 110

Lys Tyr Ala Ala Asp Ser Val Glu Arg Val Val Leu Thr Ser Ser Tyr
        115                 120                 125

Ala Ala Val Phe Asp Met Ala Lys Glu Asn Asp Lys Ser Leu Thr Phe
    130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
            180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340


<210> SEQ ID NO 16
<211> LENGTH: 984
<212> TYPE: DNA
<213> ORGANISM: Saccharomyces cerevisiae

<400> SEQUENCE: 16

atgtcttcac tggttactct taataacggt ctgaaaatgc ccctagtcgg cttagggtgc      60

tggaaaattg acaaaaaagt ctgtgcgaat caaatttatg aagctatcaa attaggctac     120

cgtttattcg atggtgcttg cgactacggc aacgaaaagg aagttggtga aggtatcagg     180

aaagccatct ccgaaggtct tgtttctaga aaggatatat ttgttgtttc aaagttatgg     240

aacaattttc accatcctga tcatgtaaaa ttagctttaa agaagacctt aagcgatatg     300

ggacttgatt atttagacct gtattatatt cacttcccaa tcgccttcaa atatgttcca     360

tttgaagaga aataccctcc aggattctat acgggcgcag atgacgagaa gaaaggtcac     420

atcaccgaag cacatgtacc aatcatagat acgtaccggg ctctggaaga atgtgttgat     480
```

```
gaaggcttga ttaagtctat tggtgtttcc aactttcagg gaagcttgat tcaagattta    540

ttacgtggtt gtagaatcaa gcccgtggct ttgcaaattg aacaccatcc ttatttgact    600

caagaacacc tagttgagtt ttgtaaatta cacgatatcc aagtagttgc ttactcctcc    660

ttcggtcctc aatcattcat tgagatggac ttacagttgg caaaaaccac gccaactctg    720

ttcgagaatg atgtaatcaa gaaggtctca caaaaccatc caggcagtac cacttcccaa    780

gtattgctta gatgggcaac tcagagaggc attgccgtca ttccaaaatc ttccaagaag    840

gaaaggttac ttggcaacct agaaatcgaa aaaaagttca ctttaacgga gcaagaattg    900

aaggatattt ctgcactaaa tgccaacatc agatttaatg atccatggac ctggttggat    960

ggtaaattcc ccacttttgc ctga                                           984


<210> SEQ ID NO 17
<211> LENGTH: 327
<212> TYPE: PRT
<213> ORGANISM: Saccharomyces cerevisiae

<400> SEQUENCE: 17

Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
    210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
```

-continued

```
        275                 280                 285

Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325
```

<210> SEQ ID NO 18
<211> LENGTH: 1164
<212> TYPE: DNA
<213> ORGANISM: Escherichia coli

<400> SEQUENCE: 18

```
atgaacaact ttaatctgca caccccaacc cgcattctgt ttggtaaagg cgcaatcgct     60

ggtttacgcg aacaaattcc tcacgatgct cgcgtattga ttacctacgg cggcggcagc    120

gtgaaaaaaa ccggcgttct cgatcaagtt ctggatgccc tgaaaggcat ggacgtgctg    180

gaatttggcg gtattgagcc aaacccggct tatgaaacgc tgatgaacgc cgtgaaactg    240

gttcgcgaac agaaagtgac tttcctgctg gcggttggcg gcggttctgt actggacggc    300

accaaattta tcgccgcagc ggctaactat ccggaaaata tcgatccgtg gcacattctg    360

caaacgggcg gtaaagagat taaaagcgcc atcccgatgg gctgtgtgct gacgctgcca    420

gcaaccggtt cagaatccaa cgcagaagcg gtgatctccc gtaaaaccac aggcgacaag    480

caggcgttcc attctgccca tgttcagccg gtatttgccg tgctcgatcc ggtttatacc    540

tacaccctgc cgccgcgtca ggtggctaac ggcgtagtgg acgcctttgt acacaccgtg    600

gaacagtatg ttaccaaacc ggttgatgcc aaaattcagg accgtttcgc agaaggcatt    660

ttgctgacgc taatcgaaga tggtccgaaa gccctgaaag agccagaaaa ctacgatgtg    720

cgcgccaacg tcatgtgggc ggcgactcag gcgctgaacg gtttgattgg cgctggcgta    780

ccgcaggact gggcaacgca tatgctgggc cacgaactga ctgcgatgca cggtctggat    840

cacgcgcaaa cactggctat cgtcctgcct gcactgtgga atgaaaaacg cgataccaag    900

cgcgctaagc tgctgcaata tgctgaacgc gtctggaaca tcactgaagg ttccgatgat    960

gagcgtattg acgccgcgat tgccgcaacc cgcaatttct ttgagcaatt aggcgtgccg   1020

acccacctct ccgactacgg tctggacggc agctccatcc cggctttgct gaaaaaactg   1080

gaagagcacg gcatgaccca actgggcgaa aatcatgaca ttacgttgga tgtcagccgc   1140

cgtatatacg aagccgcccg ctaa                                          1164
```

<210> SEQ ID NO 19
<211> LENGTH: 1167
<212> TYPE: DNA
<213> ORGANISM: Escherichia coli

<400> SEQUENCE: 19

```
atgaacaatt ttaatttgca tactccaact agaatattat ttggaaaagg tgcaattgca     60

ggtttaaggg aacaaatacc acatgatgca agggtattaa tcacatacgg tggtggttct    120

gtcaagaaaa ctggtgtatt ggatcaagta ttggatgctt taaagggtat ggatgtcttg    180

gaatttggag gaatcgaacc aaaccctgct tacgagactt taatgaatgc tgtcaaattg    240

gtcagagaac aaaaggtaac attcttattg gctgttggag gtggatcagt attagatggt    300

acaaagttca ttgctgctgc agcaaattat ccagaaaaca ttgatccatg gcatatattg    360
```

-continued

```
caaactggtg gtaaggaaat aaagtcagct atcccaatgg gatgtgtttt gacattgcct    420

gcaacaggat cagaatcaaa cgctgaagca gtcatctcaa gaaagactac aggtgacaaa    480

caggcattcc attctgccca tgtccaacct gtatttgctg ttttagaccc tgtatacact    540

tacacattac caccaaggca agtcgcaaat ggagttgtcg atgcctttgt tcacactgta    600

gaacagtacg tcaccaaacc agtcgatgca aagatccagg acaggtttgc agaaggtatt    660

ttattgacat taatcgaaga tggaccaaaa gcattgaaag agccagagaa ctatgacgtt    720

agggcaaatg ttatgtgggc tgctacccag gcattgaacg gtttaattgg tgcaggagtt    780

ccacaagatt gggctacaca catgttgggt cacgagttga ccgccatgca cggtttggac    840

catgcacaga ctttagccat tgttttgcct gccttatgga acgagaaaag agatactaag    900

agggctaagt tattacaata cgctgaaagg gtttggaata tcaccgaggg atctgatgat    960

gaaaggattg atgccgctat tgcagccact agaaacttct ttgaacaatt aggtgttcca   1020

actcacttgt ctgactatgg tttagatgga tcatctattc cagctttgtt gaagaaattg   1080

gaagagcacg gtatgaccca gttgggtgag aatcatgata taaccttaga tgtatctagg   1140

agaatctacg aggctgctag ataatga                                       1167
```

<210> SEQ ID NO 20
<211> LENGTH: 387
<212> TYPE: PRT
<213> ORGANISM: Escherichia coli

<400> SEQUENCE: 20

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Glu Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
```

-continued

```
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385


<210> SEQ ID NO 21
<211> LENGTH: 1164
<212> TYPE: DNA
<213> ORGANISM: Escherichia coli

<400> SEQUENCE: 21

atgaacaact ttaatctgca caccccaacc cgcattctgt ttggtaaagg cgcaatcgct      60

ggtttacgcg aacaaattcc tcacgatgct cgcgtattga ttacctacgg cggcggcagc     120

gtgaaaaaaa ccggcgttct cgatcaagtt ctggatgccc tgaaaggcat ggacgtgctg     180

gaatttggcg gtattgagcc aaacccggct tatgaaacgc tgatgaacgc cgtgaaactg     240

gttcgcgaac agaaagtgac tttcctgctg gcggttggcg gcggttctgt actggacggc     300

accaaattta tcgccgcagc ggctaactat ccggaaaata tcgatccgtg gcacattctg     360

caaacgggcg gtaaagagat taaaagcgcc atcccgatgg gctgtgtgct gacgctgcca     420

gcaaccggtt cagaatccaa cgcaggcgcg gtgatctccc gtaaaaccac aggcgacaag     480

caggcgttcc attctgccca tgttcagccg gtatttgccg tgctcgatcc ggtttatacc     540

tacaccctgc cgccgcgtca ggtggctaac ggcgtagtgg acgcctttgt acacaccgtg     600

gaacagtatg ttaccaaacc ggttgatgcc aaaattcagg accgtttcgc agaaggcatt     660

ttgctgacgc taatcgaaga tggtccgaaa gccctgaaag agccagaaaa ctacgatgtg     720

cgcgccaacg tcatgtgggc ggcgactcag gcgctgaacg gtttgattgg cgctggcgta     780

ccgcaggact gggcaacgca tatgctgggc cacgaactga ctgcgatgca cggtctggat     840

cacgcgcaaa cactggctat cgtcctgcct gcactgtgga atgaaaaacg cgataccaag     900

cgcgctaagc tgctgcaata tgctgaacgc gtctggaaca tcactgaagg ttccgatgat     960

gagcgtattg acgccgcgat tgccgcaacc cgcaatttct ttgagcaatt aggcgtgccg    1020

acccacctct ccgactacgg tctggacggc agctccatcc cggctttgct gaaaaaactg    1080

gaagagcacg gcatgaccca actgggcgaa aatcatgaca ttacgttgga tgtcagccgc    1140

cgtatatacg aagccgcccg ctaa                                           1164
```

<210> SEQ ID NO 22
<211> LENGTH: 1164
<212> TYPE: DNA
<213> ORGANISM: Escherichia coli

<400> SEQUENCE: 22
atgaacaact ttaatctgca caccccaacc cgcattctgt ttggtaaagg cgcaatcgct 60
ggtttacgcg aacaaattcc tcacgatgct cgcgtattga ttacctacgg cggcggcagc 120
gtgaaaaaaa ccggcgttct cgatcaagtt ctggatgccc tgaaaggcat ggacgtgctg 180
gaatttggcg gtattgagcc aaacccggct tatgaaacgc tgatgaacgc cgtgaaactg 240
gttcgcgaac agaaagtgac tttcctgctg gcggttggcg gcggttctgt actggacggc 300
accaaattta tcgccgcagc ggctaactat ccggaaaata tcgatccgtg gcacattctg 360
caaacgggcg gtaaagagat taaaagcgcc atcccgatgg gctgtgtgct gacgctgcca 420
gcaaccggtt cagaatccaa cgcaggcgcg gtgatctccc gtaaaaccac aggcgacaag 480
caggcgttcc attctgccca tgttcagccg gtatttgccg tgctcgatcc ggtttatacc 540
tacaccctgc cgccgcgtca ggtggctaac ggcgtagtgg acgcctttgt acacaccgtg 600
gaacagtatg ttaccaaacc ggttgatgcc aaaattcagg accgtttcgc agaaggcatt 660
ttgctgacgc taatcgaaga tggtccgaaa gccctgaaag agccagaaaa ctacgatgtg 720
cgcgccaacg tcatgtgggc ggcgactcag gcgctgaacg gtttgattgg cgctggcgta 780
ccgcaggact gggcaacgca tatgctgggc cacgaactga ctgcgatgca cggtctggat 840
cacgcgcaaa cactggctat cgtcctgcct gcactgtgga atgaaaaacg cgataccaag 900
cgcgctaagc tgctgcaata tgctgaacgc gtctggaaca tcactgaagg ttccgatgat 960
gagcgtattg acgccgcgat tgccgcaacc cgcaatttct ttgagcaatt aggcgtgccg 1020
acccacctct ccgactacgg tctggacggc agctccatcc cggctttgct gaaaaaactg 1080
gaagagcacg gcatgaccca actgggcgaa aatcatgaca ttacgttgga tgtcagccgc 1140
cgtatatacg aagccgcccg ctaa 1164

<210> SEQ ID NO 23
<211> LENGTH: 387
<212> TYPE: PRT
<213> ORGANISM: Escherichia coli

<400> SEQUENCE: 23

Met Asn Asn Phe Asn Leu His Thr Pro Thr Arg Ile Leu Phe Gly Lys
1 5 10 15

Gly Ala Ile Ala Gly Leu Arg Glu Gln Ile Pro His Asp Ala Arg Val
20 25 30

Leu Ile Thr Tyr Gly Gly Gly Ser Val Lys Lys Thr Gly Val Leu Asp
35 40 45

Gln Val Leu Asp Ala Leu Lys Gly Met Asp Val Leu Glu Phe Gly Gly
50 55 60

Ile Glu Pro Asn Pro Ala Tyr Glu Thr Leu Met Asn Ala Val Lys Leu
65 70 75 80

Val Arg Glu Gln Lys Val Thr Phe Leu Leu Ala Val Gly Gly Gly Ser
85 90 95

Val Leu Asp Gly Thr Lys Phe Ile Ala Ala Ala Ala Asn Tyr Pro Glu
100 105 110

Asn Ile Asp Pro Trp His Ile Leu Gln Thr Gly Gly Lys Glu Ile Lys

-continued

```
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385


<210> SEQ ID NO 24
<211> LENGTH: 981
<212> TYPE: DNA
<213> ORGANISM: Escherichia coli

<400> SEQUENCE: 24

atgaaaaaga tacctttagg cacaacggat attacgcttt cgcgaatggg gttggggaca      60

tgggccattg gcggcggtcc tgcatggaat ggcgatctcg atcggcaaat atgtattgat     120

acgattcttg aagcccatcg ttgtggcatt aatctgattg atactgcgcc aggatataac     180

tttggcaata gtgaagttat cgtcggtcag gcgttaaaaa aactgccccg tgaacaggtt     240

gtagtagaaa ccaaatgcgg cattgtctgg gaacgaaaag gaagtttatt caacaaagtt     300

ggcgatcggc agttgtataa aaacctttcc ccggaatcta tccgcgaaga ggtagcagcg     360

agcttgcaac gtctgggtat tgattacatc gatatctaca tgacgcactg gcagtcggtg     420

ccgccatttt ttacgccgat cgctgaaact gtcgcagtgc ttaatgagtt aaagtctgaa     480

gggaaaattc gcgctatagg cgctgctaac gtcgatgctg accatatccg cgagtatctg     540
```

-continued

```
caatatggtg aactggatat tattcaggcg aaatacagta tcctcgaccg ggcaatggaa    600

aacgaactgc tgccactatg tcgtgataat ggcattgtgg ttcaggttta ttccccgcta    660

gagcagggat tgttgaccgg caccatcact cgtgattacg ttccgggcgg cgctcgggca    720

aataaagtct ggttccagcg tgaaaacatg ctgaaagtga ttgatatgct tgaacagtgg    780

cagccacttt gtgctcgtta tcagtgcaca attcccactc tggcactggc gtggatatta    840

aaacagagtg atttaatctc cattcttagt ggggctactg caccggaaca ggtacgcgaa    900

aatgtcgcgg cactgaatat caacttatcg gatgcagacg caacattgat gagggaaatg    960

gcagaggccc tggagcgtta a                                              981
```

<210> SEQ ID NO 25
<211> LENGTH: 326
<212> TYPE: PRT
<213> ORGANISM: Escherichia coli

<400> SEQUENCE: 25

```
Met Lys Lys Ile Pro Leu Gly Thr Thr Asp Ile Thr Leu Ser Arg Met
1               5                   10                  15

Gly Leu Gly Thr Trp Ala Ile Gly Gly Gly Pro Ala Trp Asn Gly Asp
            20                  25                  30

Leu Asp Arg Gln Ile Cys Ile Asp Thr Ile Leu Glu Ala His Arg Cys
        35                  40                  45

Gly Ile Asn Leu Ile Asp Thr Ala Pro Gly Tyr Asn Phe Gly Asn Ser
    50                  55                  60

Glu Val Ile Val Gly Gln Ala Leu Lys Lys Leu Pro Arg Glu Gln Val
65                  70                  75                  80

Val Val Glu Thr Lys Cys Gly Ile Val Trp Glu Arg Lys Gly Ser Leu
                85                  90                  95

Phe Asn Lys Val Gly Asp Arg Gln Leu Tyr Lys Asn Leu Ser Pro Glu
            100                 105                 110

Ser Ile Arg Glu Glu Val Ala Ala Ser Leu Gln Arg Leu Gly Ile Asp
        115                 120                 125

Tyr Ile Asp Ile Tyr Met Thr His Trp Gln Ser Val Pro Pro Phe Phe
    130                 135                 140

Thr Pro Ile Ala Glu Thr Val Ala Val Leu Asn Glu Leu Lys Ser Glu
145                 150                 155                 160

Gly Lys Ile Arg Ala Ile Gly Ala Ala Asn Val Asp Ala Asp His Ile
                165                 170                 175

Arg Glu Tyr Leu Gln Tyr Gly Glu Leu Asp Ile Ile Gln Ala Lys Tyr
            180                 185                 190

Ser Ile Leu Asp Arg Ala Met Glu Asn Glu Leu Leu Pro Leu Cys Arg
        195                 200                 205

Asp Asn Gly Ile Val Val Gln Val Tyr Ser Pro Leu Glu Gln Gly Leu
    210                 215                 220

Leu Thr Gly Thr Ile Thr Arg Asp Tyr Val Pro Gly Gly Ala Arg Ala
225                 230                 235                 240

Asn Lys Val Trp Phe Gln Arg Glu Asn Met Leu Lys Val Ile Asp Met
                245                 250                 255

Leu Glu Gln Trp Gln Pro Leu Cys Ala Arg Tyr Gln Cys Thr Ile Pro
            260                 265                 270

Thr Leu Ala Leu Ala Trp Ile Leu Lys Gln Ser Asp Leu Ile Ser Ile
        275                 280                 285

Leu Ser Gly Ala Thr Ala Pro Glu Gln Val Arg Glu Asn Val Ala Ala
```

-continued 290 295 300

Leu Asn Ile Asn Leu Ser Asp Ala Asp Ala Thr Leu Met Arg Glu Met
305 310 315 320

Ala Glu Ala Leu Glu Arg
325

<210> SEQ ID NO 26
<211> LENGTH: 1149
<212> TYPE: DNA
<213> ORGANISM: Escherichia coli

<400> SEQUENCE: 26
atggctaaca gaatgattct gaacgaaacg gcatggtttg gtcggggtgc tgttggggct 60
ttaaccgatg aggtgaaacg ccgtggttat cagaaggcgc tgatcgtcac cgataaaacg 120
ctggtgcaat gcggcgtggt ggcgaaagtg accgataaga tggatgctgc agggctggca 180
tgggcgattt acgacggcgt agtgcccaac ccaacaatta ctgtcgtcaa agaagggctc 240
ggtgtattcc agaatagcgg cgcggattac ctgatcgcta ttggtggtgg ttctccacag 300
gatacttgta aagcgattgg cattatcagc aacaacccgg agtttgccga tgtgcgtagc 360
ctggaagggc tttccccgac caataaaccc agtgtaccga ttctggcaat tcctaccaca 420
gcaggtactg cggcagaagt gaccattaac tacgtgatca ctgacgaaga gaaacggcgc 480
aagtttgttt gcgttgatcc gcatgatatc ccgcaggtgg cgtttattga cgctgacatg 540
atggatggta tgcctccagc gctgaaagct gcgacgggtg tcgatgcgct cactcatgct 600
attgaggggt atattacccg tggcgcgtgg gcgctaaccg atgcactgca cattaaagcg 660
attgaaatca ttgctggggc gctgcgagga tcggttgctg gtgataagga tgccggagaa 720
gaaatggcgc tcgggcagta tgttgcgggt atgggcttct cgaatgttgg gttagggttg 780
gtgcatggta tggcgcatcc actgggcgcg ttttataaca ctccacacgg tgttgcgaac 840
gccatcctgt taccgcatgt catgcgttat aacgctgact ttaccggtga gaagtaccgc 900
gatatcgcgc gcgttatggg cgtgaaagtg gaaggtatga gcctggaaga ggcgcgtaat 960
gccgctgttg aagcggtgtt tgctctcaac cgtgatgtcg gtattccgcc acatttgcgt 1020
gatgttggtg tacgcaagga agacattccg gcactggcgc aggcggcact ggatgatgtt 1080
tgtaccggtg gcaacccgcg tgaagcaacg cttgaggata ttgtagagct ttaccatacc 1140
gcctggtaa 1149

<210> SEQ ID NO 27
<211> LENGTH: 1149
<212> TYPE: DNA
<213> ORGANISM: Escherichia coli

<400> SEQUENCE: 27
atggctaaca gaatgattct gaacgaaacg gcatggtttg gtcggggtgc tgttggggct 60
ttaaccgatg aggtgaaacg ccgtggttat cagaaggcgc tgatcgtcac cgataaaacg 120
ctggtgcaat gcggcgtggt ggcgaaagtg accgataaga tggatgctgc agggctggca 180
tgggcgattt acgacggcgt agtgcccaac ccaacaatta ctgtcgtcaa agaagggctc 240
ggtgtattcc agaatagcgg cgcggattac ctgatcgcta ttggtggtgg ttctccacag 300
gatacttgta aagcgattgg cattatcagc aacaacccgg agtttgccga tgtgcgtagc 360
ctggaagggc tttccccgac caataaaccc agtgtaccga ttctggcaat tcctaccaca 420
gcaggtactg cggcagaagt gaccattaac tacgtgatca ctgacgaaga gaaacggcgc 480

```
aagtttgttt gcgttgatcc gcatgatatc ccgcaggtgg cgtttattga cgctgacatg    540

atggatggta tgcctccagc gctgaaagct gcgacgggtg tcgatgcgct cactcatgct    600

attgaggggt atattacccg tggcgcgtgg gcgctaaccg atgcactgca cattaaagcg    660

attgaaatca ttgctggggc gctgcgagga tcggttgctg gtgataagga tgccggagaa    720

gaaatggcgc tcgggcagta tgttgcgggt atgggcttct cgaatgttgg gttagggttg    780

gtgcatggta tggcgcatcc actgggcgcg ttttataaca ctccacacgg tgttgcgaac    840

gccatcctgt taccgcatgt catgcgttat aacgctgact ttaccggtga gaagtaccgc    900

gatatcgcgc gcgttatggg cgtgaaagtg gaaggtatga gcctggaaga ggcgcgtaat    960

gccgctgttg aagcggtgtt tgctctcaac cgtgatgtcg gtattccgcc acatttgcgt   1020

gatgttggtg tacgcaagga agacattccg gcactggcgc aggcggcact ggatgatgtt   1080

tgtaccggtg gcaacccgcg tgaagcaacg cttgaggata ttgtagagct ttaccatacc   1140

gcctggtaa                                                           1149
```

<210> SEQ ID NO 28
<211> LENGTH: 382
<212> TYPE: PRT
<213> ORGANISM: Escherichia coli

<400> SEQUENCE: 28

```
Met Ala Asn Arg Met Ile Leu Asn Glu Thr Ala Trp Phe Gly Arg Gly
1               5                   10                  15

Ala Val Gly Ala Leu Thr Asp Glu Val Lys Arg Arg Gly Tyr Gln Lys
            20                  25                  30

Ala Leu Ile Val Thr Asp Lys Thr Leu Val Gln Cys Gly Val Val Ala
        35                  40                  45

Lys Val Thr Asp Lys Met Asp Ala Ala Gly Leu Ala Trp Ala Ile Tyr
    50                  55                  60

Asp Gly Val Val Pro Asn Pro Thr Ile Thr Val Val Lys Glu Gly Leu
65                  70                  75                  80

Gly Val Phe Gln Asn Ser Gly Ala Asp Tyr Leu Ile Ala Ile Gly Gly
                85                  90                  95

Gly Ser Pro Gln Asp Thr Cys Lys Ala Ile Gly Ile Ile Ser Asn Asn
            100                 105                 110

Pro Glu Phe Ala Asp Val Arg Ser Leu Glu Gly Leu Ser Pro Thr Asn
        115                 120                 125

Lys Pro Ser Val Pro Ile Leu Ala Ile Pro Thr Thr Ala Gly Thr Ala
    130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
        195                 200                 205

Ala Trp Ala Leu Thr Asp Ala Leu His Ile Lys Ala Ile Glu Ile Ile
    210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
```

-continued

```
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
        275                 280                 285

Arg Tyr Asn Ala Asp Phe Thr Gly Glu Lys Tyr Arg Asp Ile Ala Arg
    290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
                325                 330                 335

Pro His Leu Arg Asp Val Gly Val Arg Lys Glu Asp Ile Pro Ala Leu
            340                 345                 350

Ala Gln Ala Ala Leu Asp Asp Val Cys Thr Gly Gly Asn Pro Arg Glu
        355                 360                 365

Ala Thr Leu Glu Asp Ile Val Glu Leu Tyr His Thr Ala Trp
    370                 375                 380


<210> SEQ ID NO 29
<211> LENGTH: 804
<212> TYPE: DNA
<213> ORGANISM: Escherichia coli

<400> SEQUENCE: 29

atggctatcc ctgcatttgg tttaggtact ttccgtctga aagacgacgt tgttatttca      60

tctgtgataa cggcgcttga acttggttat cgcgcaattg ataccgcaca aatctatgat     120

aacgaagccg cagtaggtca ggcgattgca gaaagtggcg tgccacgtca tgaactctac     180

atcaccacta aaatctggat tgaaaatctc agcaaagaca aattgatccc aagtctgaaa     240

gagagcctgc aaaaattgcg taccgattat gttgatctga cgctaatcca ctggccgtca     300

ccaaacgatg aagtctctgt tgaagagttt atgcaggcgc tgctggaagc caaaaaacaa     360

gggctgacgc gtgagatcgg tatttccaac ttcacgatcc cgttgatgga aaaagcgatt     420

gctgctgttg gtgctgaaaa catcgctact aaccagattg aactctctcc ttatctgcaa     480

aaccgtaaag tggttgcctg ggctaaacag cacggcatcc atattacttc ctatatgacg     540

ctggcgtatg gtaaggccct gaaagatgag gttattgctc gtatcgcagc taaacacaat     600

gcgactccgg cacaagtgat tctggcgtgg gctatggggg aaggttactc agtaattcct     660

tcttctacta aacgtaaaaa cctggaaagt aatcttaagg cacaaaattt acagcttgat     720

gccgaagata aaaaagcgat cgccgcactg gattgcaacg accgcctggt tagcccggaa     780

ggtctggctc ctgaatggga ttaa                                            804


<210> SEQ ID NO 30
<211> LENGTH: 267
<212> TYPE: PRT
<213> ORGANISM: Escherichia coli

<400> SEQUENCE: 30

Met Ala Ile Pro Ala Phe Gly Leu Gly Thr Phe Arg Leu Lys Asp Asp
1               5                   10                  15

Val Val Ile Ser Ser Val Ile Thr Ala Leu Glu Leu Gly Tyr Arg Ala
            20                  25                  30

Ile Asp Thr Ala Gln Ile Tyr Asp Asn Glu Ala Ala Val Gly Gln Ala
        35                  40                  45
```

-continued

```
Ile Ala Glu Ser Gly Val Pro Arg His Glu Leu Tyr Ile Thr Thr Lys
    50                  55                  60

Ile Trp Ile Glu Asn Leu Ser Lys Asp Lys Leu Ile Pro Ser Leu Lys
65                  70                  75                  80

Glu Ser Leu Gln Lys Leu Arg Thr Asp Tyr Val Asp Leu Thr Leu Ile
                85                  90                  95

His Trp Pro Ser Pro Asn Asp Glu Val Ser Val Glu Glu Phe Met Gln
            100                 105                 110

Ala Leu Leu Glu Ala Lys Lys Gln Gly Leu Thr Arg Glu Ile Gly Ile
        115                 120                 125

Ser Asn Phe Thr Ile Pro Leu Met Glu Lys Ala Ile Ala Ala Val Gly
    130                 135                 140

Ala Glu Asn Ile Ala Thr Asn Gln Ile Glu Leu Ser Pro Tyr Leu Gln
145                 150                 155                 160

Asn Arg Lys Val Val Ala Trp Ala Lys Gln His Gly Ile His Ile Thr
                165                 170                 175

Ser Tyr Met Thr Leu Ala Tyr Gly Lys Ala Leu Lys Asp Glu Val Ile
            180                 185                 190

Ala Arg Ile Ala Ala Lys His Asn Ala Thr Pro Ala Gln Val Ile Leu
        195                 200                 205

Ala Trp Ala Met Gly Glu Gly Tyr Ser Val Ile Pro Ser Ser Thr Lys
    210                 215                 220

Arg Lys Asn Leu Glu Ser Asn Leu Lys Ala Gln Asn Leu Gln Leu Asp
225                 230                 235                 240

Ala Glu Asp Lys Lys Ala Ile Ala Ala Leu Asp Cys Asn Asp Arg Leu
                245                 250                 255

Val Ser Pro Glu Gly Leu Ala Pro Glu Trp Asp
            260                 265
```

<210> SEQ ID NO 31
<211> LENGTH: 828
<212> TYPE: DNA
<213> ORGANISM: Escherichia coli

<400> SEQUENCE: 31

```
atggctaatc caaccgttat taagctacag gatggcaatg tcatgcccca gctgggactg      60

ggcgtctggc aagcaagtaa tgaggaagta atcaccgcca ttcaaaaagc gttagaagtg     120

ggttatcgct cgattgatac cgccgcggcc tacaagaacg aagaaggtgt cggcaaagcc     180

ctgaaaaatg cctcagtcaa cagagaagaa ctgttcatca ccactaagct gtggaacgac     240

gaccacaagc gcccccgcga agccctgctc gacagcctga aaaaactcca gcttgattat     300

atcgacctct acttaatgca ctggcccgtt cccgctatcg accattatgt cgaagcatgg     360

aaaggcatga tcgaattgca aaaagaggga ttaatcaaaa gcatcggcgt gtgcaacttc     420

cagatccatc acctgcaacg cctgattgat gaaactggcg tgacgcctgt gataaaccag     480

atcgaacttc atccgctgat gcaacaacgc cagctacacg cctggaacgc gacacacaaa     540

atccagaccg aatcctggag cccattagcg caaggaggga aaggcgtttt cgatcagaaa     600

gtcattcgcg atctggcaga taaatacggc aaaaccccgg cgcagattgt tatccgctgg     660

catctggata gcggcctggt ggtgatcccg aaatcggtca caccttcacg tattgccgaa     720

aactttgatg tctgggattt ccgtctcgac aaagacgaac tcggcgaaat tgcaaaactc     780

gatcagggca agcgtctcgg tcccgatcct gaccagttcg gcggctaa                  828
```

-continued

<210> SEQ ID NO 32
<211> LENGTH: 275
<212> TYPE: PRT
<213> ORGANISM: Escherichia coli

<400> SEQUENCE: 32

Met Ala Asn Pro Thr Val Ile Lys Leu Gln Asp Gly Asn Val Met Pro
1               5                   10                  15

Gln Leu Gly Leu Gly Val Trp Gln Ala Ser Asn Glu Glu Val Ile Thr
            20                  25                  30

Ala Ile Gln Lys Ala Leu Glu Val Gly Tyr Arg Ser Ile Asp Thr Ala
        35                  40                  45

Ala Ala Tyr Lys Asn Glu Glu Gly Val Gly Lys Ala Leu Lys Asn Ala
    50                  55                  60

Ser Val Asn Arg Glu Glu Leu Phe Ile Thr Thr Lys Leu Trp Asn Asp
65                  70                  75                  80

Asp His Lys Arg Pro Arg Glu Ala Leu Leu Asp Ser Leu Lys Lys Leu
                85                  90                  95

Gln Leu Asp Tyr Ile Asp Leu Tyr Leu Met His Trp Pro Val Pro Ala
            100                 105                 110

Ile Asp His Tyr Val Glu Ala Trp Lys Gly Met Ile Glu Leu Gln Lys
        115                 120                 125

Glu Gly Leu Ile Lys Ser Ile Gly Val Cys Asn Phe Gln Ile His His
    130                 135                 140

Leu Gln Arg Leu Ile Asp Glu Thr Gly Val Thr Pro Val Ile Asn Gln
145                 150                 155                 160

Ile Glu Leu His Pro Leu Met Gln Gln Arg Gln Leu His Ala Trp Asn
                165                 170                 175

Ala Thr His Lys Ile Gln Thr Glu Ser Trp Ser Pro Leu Ala Gln Gly
            180                 185                 190

Gly Lys Gly Val Phe Asp Gln Lys Val Ile Arg Asp Leu Ala Asp Lys
        195                 200                 205

Tyr Gly Lys Thr Pro Ala Gln Ile Val Ile Arg Trp His Leu Asp Ser
    210                 215                 220

Gly Leu Val Val Ile Pro Lys Ser Val Thr Pro Ser Arg Ile Ala Glu
225                 230                 235                 240

Asn Phe Asp Val Trp Asp Phe Arg Leu Asp Lys Asp Glu Leu Gly Glu
                245                 250                 255

Ile Ala Lys Leu Asp Gln Gly Lys Arg Leu Gly Pro Asp Pro Asp Gln
            260                 265                 270

Phe Gly Gly
        275

<210> SEQ ID NO 33
<211> LENGTH: 1179
<212> TYPE: DNA
<213> ORGANISM: Clostridium acetobutylicum

<400> SEQUENCE: 33
atgaaagaag ttgtaatagc tagtgcagta agaacagcga ttggatctta tggaaagtct 60
cttaaggatg taccagcagt agatttagga gctacagcta taaaggaagc agttaaaaaa 120
gcaggaataa aaccagagga tgttaatgaa gtcattttag gaaatgttct tcaagcaggt 180
ttaggacaga atccagcaag acaggcatct tttaaagcag gattaccagt tgaaattcca 240
gctatgacta ttaataaggt ttgtggttca ggacttagaa cagttagctt agcagcacaa 300

-continued

```
attataaaag caggagatgc tgacgtaata atagcaggtg gtatggaaaa tatgtctaga    360
gctccttact tagcgaataa cgctagatgg ggatatagaa tgggaaacgc taaatttgtt    420
gatgaaatga tcactgacgg attgtgggat gcatttaatg attaccacat gggaataaca    480
gcagaaaaca tagctgagag atggaacatt tcaagagaag aacaagatga gtttgctctt    540
gcatcacaaa aaaaagctga agaagctata aaatcaggtc aatttaaaga tgaaatagtt    600
cctgtagtaa ttaaaggcag aaagggagaa actgtagttg atacagatga gcaccctaga    660
tttggatcaa ctatagaagg acttgcaaaa ttaaaacctg ccttcaaaaa agatggaaca    720
gttacagctg gtaatgcatc aggattaaat gactgtgcag cagtacttgt aatcatgagt    780
gcagaaaaag ctaaagagct tggagtaaaa ccacttgcta agatagtttc ttatggttca    840
gcaggagttg acccagcaat aatgggatat ggacctttct atgcaacaaa agcagctatt    900
gaaaaagcag gttggacagt tgatgaatta gatttaatag aatcaaatga agcttttgca    960
gctcaaagtt tagcagtagc aaaagattta aaatttgata tgaataaagt aaatgtaaat   1020
ggaggagcta ttgcccttgg tcatccaatt ggagcatcag gtgcaagaat actcgttact   1080
cttgtacacg caatgcaaaa aagagatgca aaaaaaggct tagcaacttt atgtataggt   1140
ggcggacaag gaacagcaat attgctagaa aagtgctag                          1179
```

<210> SEQ ID NO 34
<211> LENGTH: 1179
<212> TYPE: DNA
<213> ORGANISM: Clostridium acetobutylicum

<400> SEQUENCE: 34

```
atgaaagaag ttgttattgc gagcgcggtt cgtaccgcga ttggcagcta tggcaagagc     60
ctgaaggatg ttccggcggt ggacctgggt gcgaccgcga tcaaagaggc ggttaagaaa    120
gcgggcatta aaccggagga tgtgaacgaa gttatcctgg gtaacgtgct gcaagcgggt    180
ctgggccaaa acccggcgcg tcaggcgagc ttcaaggcgg gcctgccggt tgaaatcccg    240
gcgatgacca ttaacaaagt ttgcggtagc ggcctgcgta ccgtgagcct ggcggcgcaa    300
atcattaagg cgggtgacgc ggatgttatc attgcgggtg gcatggagaa catgagccgt    360
gcgccgtacc tggcgaacaa cgcgcgttgg ggttatcgta tgggcaacgc gaaattcgtg    420
gacgaaatga ttaccgacgg tctgtgggat gcgtttaacg actaccacat gggcatcacc    480
gcggagaaca ttgcggaacg ttggaacatt agccgtgagg aacaagatga gttcgcgctg    540
gcgagccaga agaaagcgga ggaagcgatc aagagcggcc agtttaaaga cgaaatcgtt    600
ccggtggtta ttaagggtcg taagggtgaa accgtggtgg acaccgatga acacccgcgt    660
ttcggtagca ccattgaggg cctggcgaag ctgaaaccgg cgtttaagaa agatggcacc    720
gtgaccgcgg gtaacgcgag cggcctgaac gactgcgcgg cggtgctggt tatcatgagc    780
gcggagaagg cgaaagaact gggtgtgaag ccgctggcga aaattgttag ctacggtagc    840
gcgggtgtgg acccggcgat catgggttac ggcccgtttt atgcgaccaa ggcggcgatt    900
gagaaagcgg gttggaccgt ggacgaactg gatctgatcg agagcaacga agcgttcgcg    960
gcgcaaagcc tggcggtggc gaaggatctg aaatttgaca tgaacaaggt gaacgtgaac   1020
ggtggtgcga ttgcgctggg tcacccgatt ggtgcgagcg gcgcgcgtat cctggtgacc   1080
ctggttcacg cgatgcagaa acgtgacgcg aagaaaggtc tggcgaccct gtgcattggt   1140
ggtggtcaag gcaccgcgat tctgctggaa aagtgctaa                          1179
```

<210> SEQ ID NO 35
<211> LENGTH: 392
<212> TYPE: PRT
<213> ORGANISM: Clostridium acetobutylicum

<400> SEQUENCE: 35

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380
```

Thr Ala Ile Leu Leu Glu Lys Cys
385 390

<210> SEQ ID NO 36
<211> LENGTH: 1185
<212> TYPE: DNA
<213> ORGANISM: Escherichia coli

<400> SEQUENCE: 36
atgaaaaatt gtgtcatcgt cagtgcggta cgtactgcta tcggtagttt taacggttca 60
ctcgcttcca ccagcgccat cgacctgggg gcgacagtaa ttaaagccgc cattgaacgt 120
gcaaaaatcg attcacaaca cgttgatgaa gtgattatgg gtaacgtgtt acaagccggg 180
ctggggcaaa atccggcgcg tcaggcactg ttaaaaagcg ggctggcaga aacggtgtgc 240
ggattcacgg tcaataaagt atgtggttcg ggtcttaaaa gtgtggcgct tgccgcccag 300
gccattcagg caggtcaggc gcagagcatt gtggcggggg gtatggaaaa tatgagttta 360 gcccccctact tactcgatgc aaaagcacgc tctggttatc gtcttggaga cggacaggtt 420
tatgacgtaa tcctgcgcga tggcctgatg tgcgccaccc atggttatca tatggggatt 480
accgccgaaa acgtggctaa agagtacgga attacccgtg aaatgcagga tgaactggcg 540
ctacattcac agcgtaaagc ggcagccgca attgagtccg gtgcttttac agccgaaatc 600
gtcccggtaa atgttgtcac tcgaaagaaa accttcgtct tcagtcaaga cgaattcccg 660
aaagcgaatt caacggctga agcgttaggt gcattgcgcc cggccttcga taaagcagga 720
acagtcaccg ctgggaacgc gtctggtatt aacgacggtg ctgccgctct ggtgattatg 780
gaagaatctg cggcgctggc agcaggcctt acccccctgg ctcgcattaa aagttatgcc 840
agcggtggcg tgcccccccgc attgatgggt atggggccag tacctgccac gcaaaaagcg 900
ttacaactgg cggggctgca actggcggat attgatctca ttgaggctaa tgaagcattt 960
gctgcacagt tccttgccgt tgggaaaaac ctgggctttg attctgagaa agtgaatgtc 1020
aacggcgggg ccatcgcgct cgggcatcct atcggtgcca gtggtgctcg tattctggtc 1080
acactattac atgccatgca ggcacgcgat aaaacgctgg ggctggcaac actgtgcatt 1140
ggcggcggtc agggaattgc gatggtgatt gaacggttga attaa 1185

<210> SEQ ID NO 37
<211> LENGTH: 394
<212> TYPE: PRT
<213> ORGANISM: Escherichia coli

<400> SEQUENCE: 37

Met Lys Asn Cys Val Ile Val Ser Ala Val Arg Thr Ala Ile Gly Ser
1 5 10 15

Phe Asn Gly Ser Leu Ala Ser Thr Ser Ala Ile Asp Leu Gly Ala Thr
20 25 30

Val Ile Lys Ala Ala Ile Glu Arg Ala Lys Ile Asp Ser Gln His Val
35 40 45

Asp Glu Val Ile Met Gly Asn Val Leu Gln Ala Gly Leu Gly Gln Asn
50 55 60

Pro Ala Arg Gln Ala Leu Leu Lys Ser Gly Leu Ala Glu Thr Val Cys
65 70 75 80

Gly Phe Thr Val Asn Lys Val Cys Gly Ser Gly Leu Lys Ser Val Ala
85 90 95

Leu Ala Ala Gln Ala Ile Gln Ala Gly Gln Ala Gln Ser Ile Val Ala
100 105 110

```
Gly Gly Met Glu Asn Met Ser Leu Ala Pro Tyr Leu Leu Asp Ala Lys
        115                 120                 125

Ala Arg Ser Gly Tyr Arg Leu Gly Asp Gly Gln Val Tyr Asp Val Ile
    130                 135                 140

Leu Arg Asp Gly Leu Met Cys Ala Thr His Gly Tyr His Met Gly Ile
145                 150                 155                 160

Thr Ala Glu Asn Val Ala Lys Glu Tyr Gly Ile Thr Arg Glu Met Gln
                165                 170                 175

Asp Glu Leu Ala Leu His Ser Gln Arg Lys Ala Ala Ala Ala Ile Glu
            180                 185                 190

Ser Gly Ala Phe Thr Ala Glu Ile Val Pro Val Asn Val Val Thr Arg
        195                 200                 205

Lys Lys Thr Phe Val Phe Ser Gln Asp Glu Phe Pro Lys Ala Asn Ser
    210                 215                 220

Thr Ala Glu Ala Leu Gly Ala Leu Arg Pro Ala Phe Asp Lys Ala Gly
225                 230                 235                 240

Thr Val Thr Ala Gly Asn Ala Ser Gly Ile Asn Asp Gly Ala Ala Ala
                245                 250                 255

Leu Val Ile Met Glu Glu Ser Ala Ala Leu Ala Ala Gly Leu Thr Pro
            260                 265                 270

Leu Ala Arg Ile Lys Ser Tyr Ala Ser Gly Gly Val Pro Pro Ala Leu
        275                 280                 285

Met Gly Met Gly Pro Val Pro Ala Thr Gln Lys Ala Leu Gln Leu Ala
    290                 295                 300

Gly Leu Gln Leu Ala Asp Ile Asp Leu Ile Glu Ala Asn Glu Ala Phe
305                 310                 315                 320

Ala Ala Gln Phe Leu Ala Val Gly Lys Asn Leu Gly Phe Asp Ser Glu
                325                 330                 335

Lys Val Asn Val Asn Gly Gly Ala Ile Ala Leu Gly His Pro Ile Gly
            340                 345                 350

Ala Ser Gly Ala Arg Ile Leu Val Thr Leu Leu His Ala Met Gln Ala
        355                 360                 365

Arg Asp Lys Thr Leu Gly Leu Ala Thr Leu Cys Ile Gly Gly Gly Gln
    370                 375                 380

Gly Ile Ala Met Val Ile Glu Arg Leu Asn
385                 390
```

<210> SEQ ID NO 38
<211> LENGTH: 1197
<212> TYPE: DNA
<213> ORGANISM: Saccharomyces cerevisiae

<400> SEQUENCE: 38

```
atgtctcaga acgtttacat tgtatcgact gccagaaccc caattggttc attccagggt      60

tctctatcct ccaagacagc agtggaattg ggtgctgttg ctttaaaagg cgccttggct     120

aaggttccag aattggatgc atccaaggat tttgacgaaa ttatttttgg taacgttctt     180

tctgccaatt tgggccaagc tccggccaga caagttgctt tggctgccgg tttgagtaat     240

catatcgttg caagcacagt taacaaggtc tgtgcatccg ctatgaaggc aatcattttg     300

ggtgctcaat ccatcaaatg tggtaatgct gatgttgtcg tagctggtgg ttgtgaatct     360

atgactaacg caccatacta catgccagca gcccgtgcgg gtgccaaatt tggccaaact     420

gttcttgttg atggtgtcga aagagatggg ttgaacgatg cgtacgatgg tctagccatg     480
```

-continued

```
ggtgtacacg cagaaaagtg tgcccgtgat tgggatatta ctagagaaca acaagacaat    540

tttgccatcg aatcctacca aaaatctcaa aaatctcaaa aggaaggtaa attcgacaat    600

gaaattgtac ctgttaccat taagggattt agaggtaagc ctgatactca agtcacgaag    660

gacgaggaac ctgctagatt acacgttgaa aaattgagat ctgcaaggac tgtttttccaa    720

aaagaaaacg gtactgttac tgccgctaac gcttctccaa tcaacgatgg tgctgcagcc    780

gtcatcttgg tttccgaaaa agttttgaag gaaaagaatt tgaagccttt ggctattatc    840

aaaggttggg gtgaggccgc tcatcaacca gctgatttta catgggctcc atctcttgca    900

gttccaaagg ctttgaaaca tgctggcatc gaagacatca attctgttga ttactttgaa    960

ttcaatgaag ccttttcggt tgtcggtttg gtgaacacta agattttgaa gctagaccca   1020

tctaaggtta atgtatatgg tggtgctgtt gctctaggtc acccattggg ttgttctggt   1080

gctagagtgg ttgttacact gctatccatc ttacagcaag aaggaggtaa gatcggtgtt   1140

gccgccattt gtaatggtgg tggtggtgct tcctctattg tcattgaaaa gatatga      1197
```

<210> SEQ ID NO 39
<211> LENGTH: 1197
<212> TYPE: DNA
<213> ORGANISM: Saccharomyces cerevisiae

<400> SEQUENCE: 39

```
atgtctcaga acgtttacat tgtatcgact gccagaaccc caattggttc attccagggt     60

tctctatcct ccaagacagc agtggaattg ggtgctgttg ctttaaaagg cgccttggct    120

aaggttccag aattggatgc atccaaggat tttgacgaaa ttatttttgg taacgttctt    180

tctgccaatt tgggccaagc tccggccaga caagttgctt tggctgccgg tttgagtaat    240

catatcgttg caagcacagt taacaaggtc tgtgcatccg ctatgaaggc aatcattttg    300

ggtgctcaat ccatcaaatg tggtaatgct gatgttgtcg tagctggtgg ttgtgaatct    360

atgactaacg caccatacta catgccagca gcccgtgcgg gtgccaaatt tggccaaact    420

gttcttgttg atggtgtcga aagagatggg ttgaacgatg cgtacgatgg tctagccatg    480

ggtgtacacg cagaaaagtg tgcccgtgat tgggatatta ctagagaaca acaagacaat    540

tttgccatcg aatcctacca aaaatctcaa aaatctcaaa aggaaggtaa attcgacaat    600

gaaattgtac ctgttaccat taagggattt agaggtaagc ctgatactca agtcacgaag    660

gacgaggaac ctgctagatt acacgttgaa aaattgagat ctgcaaggac tgttttccaa    720

aaagaaaacg gtactgttac tgccgctaac gcttctccaa tcaacgatgg tgctgcagcc    780

gtcatcttgg tttccgaaaa agttttgaag gaaaagaatt tgaagccttt ggctattatc    840

aaaggttggg gtgaggccgc tcatcaacca gctgatttta catgggctcc atctcttgca    900

gttccaaagg ctttgaaaca tgctggcatc gaagacatca attctgttga ttactttgaa    960

ttcaatgaag ccttttcggt tgtcggtttg gtgaacacta agattttgaa gctagaccca   1020

tctaaggtta atgtatatgg tggtgctgtt gctctaggtc acccattggg ttgttctggt   1080

gctagagtgg ttgttacact gctatccatc ttacagcaag aaggaggtaa gatcggtgtt   1140

gccgccattt gtaatggtgg tggtggtgct tcctctattg tcattgaaaa gatatga      1197
```

<210> SEQ ID NO 40
<211> LENGTH: 398
<212> TYPE: PRT
<213> ORGANISM: Saccharomyces cerevisiae

<400> SEQUENCE: 40

-continued

```
Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Val Thr Leu Leu
        355                 360                 365

Ser Ile Leu Gln Gln Glu Gly Gly Lys Ile Gly Val Ala Ala Ile Cys
    370                 375                 380

Asn Gly Gly Gly Gly Ala Ser Ser Ile Val Ile Glu Lys Ile
385                 390                 395
```

<210> SEQ ID NO 41
<211> LENGTH: 651

<212> TYPE: DNA
<213> ORGANISM: Escherichia coli

<400> SEQUENCE: 41

```
atggatgcga aacaacgtat tgcgcgccgt gtggcgcaag agcttcgtga tggtgacatc      60
gttaacttag ggatcggttt acccacaatg gtcgccaatt atttaccgga gggtattcat     120
atcactctgc aatcggaaaa cggcttcctc ggtttaggcc cggtcacgac agcgcatcca     180
gatctggtga acgctggcgg gcaaccgtgc ggtgttttac ccggtgcagc catgtttgat     240
agcgccatgt catttgcgct aatccgtggc ggtcatattg atgcctgcgt gctcggcggt     300
ttgcaagtag acgaagaagc aaacctcgcg aactgggtag tgcctgggaa aatggtgccc     360
ggtatgggtg gcgcgatgga tctggtgacc gggtcgcgca aagtgatcat cgccatggaa     420
cattgcgcca aagatggttc agcaaaaatt ttgcgccgct gcaccatgcc actcactgcg     480
caacatgcgg tgcatatgct ggttactgaa ctggctgtct ttcgttttat tgacggcaaa     540
atgtggctca ccgaaattgc cgacgggtgt gatttagcca ccgtgcgtgc caaaacagaa     600
gctcggtttg aagtcgccgc cgatctgaat acgcaacggg gtgatttatg a              651
```

<210> SEQ ID NO 42
<211> LENGTH: 651
<212> TYPE: DNA
<213> ORGANISM: Escherichia coli

<400> SEQUENCE: 42

```
atggatgcga aacaacgtat tgcgcgccgt gtggcgcaag agcttcgtga tggtgacatc      60
gttaacttag ggatcggttt acccacaatg gtcgccaatt atttaccgga gggtattcat     120
atcactctgc aatcggaaaa cggcttcctc ggtttaggcc cggtcacgac agcgcatcca     180
gatctggtga acgctggcgg gcaaccgtgc ggtgttttac ccggtgcagc catgtttgat     240
agcgccatgt catttgcgct aatccgtggc ggtcatattg atgcctgcgt gctcggcggt     300
ttgcaagtag acgaagaagc aaacctcgcg aactgggtag tgcctgggaa aatggtgccc     360
ggtatgggtg gcgcgatgga tctggtgacc gggtcgcgca aagtgatcat cgccatggaa     420
cattgcgcca aagatggttc agcaaaaatt ttgcgccgct gcaccatgcc actcactgcg     480
caacatgcgg tgcatatgct ggttactgaa ctggctgtct ttcgttttat tgacggcaaa     540
atgtggctca ccgaaattgc cgacgggtgt gatttagcca ccgtgcgtgc caaaacagaa     600
gctcggtttg aagtcgccgc cgatctgaat acgcaacggg gtgatttatg a              651
```

<210> SEQ ID NO 43
<211> LENGTH: 216
<212> TYPE: PRT
<213> ORGANISM: Escherichia coli

<400> SEQUENCE: 43

```
Met Asp Ala Lys Gln Arg Ile Ala Arg Arg Val Ala Gln Glu Leu Arg
1               5                   10                  15

Asp Gly Asp Ile Val Asn Leu Gly Ile Gly Leu Pro Thr Met Val Ala
            20                  25                  30

Asn Tyr Leu Pro Glu Gly Ile His Ile Thr Leu Gln Ser Glu Asn Gly
        35                  40                  45

Phe Leu Gly Leu Gly Pro Val Thr Thr Ala His Pro Asp Leu Val Asn
    50                  55                  60

Ala Gly Gly Gln Pro Cys Gly Val Leu Pro Gly Ala Ala Met Phe Asp
65                  70                  75                  80
```

```
Ser Ala Met Ser Phe Ala Leu Ile Arg Gly Gly His Ile Asp Ala Cys
                85                  90                  95

Val Leu Gly Gly Leu Gln Val Asp Glu Glu Ala Asn Leu Ala Asn Trp
            100                 105                 110

Val Val Pro Gly Lys Met Val Pro Gly Met Gly Gly Ala Met Asp Leu
        115                 120                 125

Val Thr Gly Ser Arg Lys Val Ile Ile Ala Met Glu His Cys Ala Lys
    130                 135                 140

Asp Gly Ser Ala Lys Ile Leu Arg Arg Cys Thr Met Pro Leu Thr Ala
145                 150                 155                 160

Gln His Ala Val His Met Leu Val Thr Glu Leu Ala Val Phe Arg Phe
                165                 170                 175

Ile Asp Gly Lys Met Trp Leu Thr Glu Ile Ala Asp Gly Cys Asp Leu
            180                 185                 190

Ala Thr Val Arg Ala Lys Thr Glu Ala Arg Phe Glu Val Ala Ala Asp
        195                 200                 205

Leu Asn Thr Gln Arg Gly Asp Leu
    210                 215
```

<210> SEQ ID NO 44
<211> LENGTH: 663
<212> TYPE: DNA
<213> ORGANISM: Escherichia coli

<400> SEQUENCE: 44

```
atgaaaacaa aattgatgac attacaagac gccaccggct tctttcgtga cggcatgacc     60

atcatggtgg gcggatttat ggggattggc actccatccc gcctggttga agcattactg    120

gaatctggtg ttcgcgacct gacattgata gccaatgata ccgcgtttgt tgataccggc    180

atcggtccgc tcatcgtcaa tggtcgagtc cgcaaagtga ttgcttcaca tatcggcacc    240

aacccggaaa caggtcggcg catgatatct ggtgagatgg acgtcgttct ggtgccgcaa    300

ggtacgctaa tcgagcaaat tcgctgtggt ggagctggac ttggtggttt tctcacccca    360

acgggtgtcg gcaccgtcgt agaggaaggc aaacagacac tgacactcga cggtaaaacc    420

tggctgctcg aacgcccact gcgcgccgac ctggcgctaa ttcgcgctca tcgttgcgac    480

acacttggca acctgaccta tcaacttagc gcccgcaact ttaaccccct gatagccctt    540

gcggctgata tcacgctggt agagccagat gaactggtcg aaaccggcga gctgcaacct    600

gaccatattg tcacccctgg tgccgttatc gaccacatca tcgtttcaca ggagagcaaa    660

taa                                                                  663
```

<210> SEQ ID NO 45
<211> LENGTH: 663
<212> TYPE: DNA
<213> ORGANISM: Escherichia coli

<400> SEQUENCE: 45

```
atgaaaacaa aattgatgac attacaagac gccaccggct tctttcgtga cggcatgacc     60

atcatggtgg gcggatttat ggggattggc actccatccc gcctggttga agcattactg    120

gaatctggtg ttcgcgacct gacattgata gccaatgata ccgcgtttgt tgataccggc    180

atcggtccgc tcatcgtcaa tggtcgagtc cgcaaagtga ttgcttcaca tatcggcacc    240

aacccggaaa caggtcggcg catgatatct ggtgagatgg acgtcgttct ggtgccgcaa    300

ggtacgctaa tcgagcaaat tcgctgtggt ggagctggac ttggtggttt tctcacccca    360
```

```
acgggtgtcg gcaccgtcgt agaggaaggc aaacagacac tgacactcga cggtaaaacc    420

tggctgctcg aacgcccact gcgcgccgac ctggcgctaa ttcgcgctca tcgttgcgac    480

acacttggca acctgaccta tcaacttagc gcccgcaact ttaacccccct gatagccctt    540

gcggctgata tcacgctggt agagccagat gaactggtcg aaaccggcga gctgcaacct    600

gaccatattg tcacccctgg tgccgttatc gaccacatca tcgtttcaca ggagagcaaa    660

taa                                                                  663
```

<210> SEQ ID NO 46
<211> LENGTH: 220
<212> TYPE: PRT
<213> ORGANISM: Escherichia coli

<400> SEQUENCE: 46

```
Met Lys Thr Lys Leu Met Thr Leu Gln Asp Ala Thr Gly Phe Phe Arg
1               5                   10                  15

Asp Gly Met Thr Ile Met Val Gly Gly Phe Met Gly Ile Gly Thr Pro
            20                  25                  30

Ser Arg Leu Val Glu Ala Leu Leu Glu Ser Gly Val Arg Asp Leu Thr
        35                  40                  45

Leu Ile Ala Asn Asp Thr Ala Phe Val Asp Thr Gly Ile Gly Pro Leu
    50                  55                  60

Ile Val Asn Gly Arg Val Arg Lys Val Ile Ala Ser His Ile Gly Thr
65                  70                  75                  80

Asn Pro Glu Thr Gly Arg Arg Met Ile Ser Gly Glu Met Asp Val Val
                85                  90                  95

Leu Val Pro Gln Gly Thr Leu Ile Glu Gln Ile Arg Cys Gly Gly Ala
            100                 105                 110

Gly Leu Gly Gly Phe Leu Thr Pro Thr Gly Val Gly Thr Val Val Glu
        115                 120                 125

Glu Gly Lys Gln Thr Leu Thr Leu Asp Gly Lys Thr Trp Leu Leu Glu
    130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
            180                 185                 190

Val Glu Thr Gly Glu Leu Gln Pro Asp His Ile Val Thr Pro Gly Ala
        195                 200                 205

Val Ile Asp His Ile Ile Val Ser Gln Glu Ser Lys
    210                 215                 220
```

<210> SEQ ID NO 47
<211> LENGTH: 735
<212> TYPE: DNA
<213> ORGANISM: Clostridium acetobutylicum

<400> SEQUENCE: 47

```
atgttaaagg atgaagtaat taaacaaatt agcacgccat taacttcgcc tgcatttcct     60

agaggaccct ataaatttca taatcgtgag tattttaaca ttgtatatcg tacagatatg    120

gatgcacttc gtaaagttgt gccagagcct ttagaaattg atgagccctt agtcaggttt    180

gaaattatgg caatgcatga tacgagtgga cttggttgtt atacagaaag cggacaggct    240
```

-continued

```
attcccgtaa gctttaatgg agttaaggga gattatcttc atatgatgta tttagataat    300

gagcctgcaa ttgcagtagg aagggaatta agtgcatatc ctaaaaagct cgggtatcca    360

aagctttttg tggattcaga tactttagta ggaactttag actatggaaa acttagagtt    420

gcgacagcta caatggggta caaacataaa gccttagatg ctaatgaagc aaaggatcaa    480

atttgtcgcc ctaattatat gttgaaaata atacccaatt atgatggaag ccctagaata    540

tgtgagctta taaatgcgaa aatcacagat gttaccgtac atgaagcttg gacaggacca    600

actcgactgc agttatttga tcacgctatg gcgccactta atgatttgcc agtaaaagag    660

attgtttcta gctctcacat tcttgcagat ataatattgc ctagagctga agttatatat    720

gattatctta agtaa                                                     735
```

<210> SEQ ID NO 48
<211> LENGTH: 735
<212> TYPE: DNA
<213> ORGANISM: Clostridium acetobutylicum

<400> SEQUENCE: 48

```
atgctgaagg acgaggttat taagcagatt agcaccccgc tgaccagccc ggcgttcccg     60

cgtggtccgt acaagttcca taatcgcgaa tacttcaaca ttgtgtatcg taccgacatg    120

gatgcgctgc gtaaggtggt tccggagccg ctggaaattg acgagccgct ggttcgtttc    180

gaaatcatgg cgatgcacga taccagcggt ctgggctgct acaccgagag cggtcaggcg    240

attccggtga gctttaacgg tgttaaaggc gactacctgc acatgatgta tctggataac    300

gaaccggcga ttgcggtggg tcgtgagctg agcgcgtacc cgaagaaact gggctatccg    360

aagctgttcg tggacagcga taccctggtg ggcaccctgg actacggcaa actgcgtgtt    420

gcgaccgcga ccatgggcta taagcacaaa gcgctggacg cgaacgaagc gaaggatcag    480

atttgccgtc cgaactacat gctgaaaatc attccgaact atgacggtag cccgcgtatc    540

tgcgaactga ttaacgcgaa gatcaccgat gttaccgttc atgaggcgtg gaccggcccg    600

acccgtctgc aactgtttga ccacgcgatg gcgccgctga acgatctgcc ggtgaaagag    660

atcgttagca gcagccacat cctggcggac atcatcctgc cgcgtgcgga agttatctac    720

gattacctga agtaa                                                     735
```

<210> SEQ ID NO 49
<211> LENGTH: 244
<212> TYPE: PRT
<213> ORGANISM: Clostridium acetobutylicum

<400> SEQUENCE: 49

```
Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
            20                  25                  30

Asn Ile Val Tyr Arg Thr Asp Met Asp Ala Leu Arg Lys Val Val Pro
        35                  40                  45

Glu Pro Leu Glu Ile Asp Glu Pro Leu Val Arg Phe Glu Ile Met Ala
    50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
```

-continued

```
            100                 105                 110

Tyr Pro Lys Lys Leu Gly Tyr Pro Lys Leu Phe Val Asp Ser Asp Thr
        115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys


<210> SEQ ID NO 50
<211> LENGTH: 741
<212> TYPE: DNA
<213> ORGANISM: Clostridium beijerinckii

<400> SEQUENCE: 50

atgttagaaa gtgaagtatc taaacaaatt acaactccac ttgctgctcc agcgtttcct      60

agaggaccat ataggtttca caatagagaa tatctaaaca ttatttatcg aactgattta     120

gatgctcttc gaaaaatagt accagagcca cttgaattag atagagcata tgttagattt     180

gaaatgatgg ctatgcctga tacaaccgga ctaggctcat atacagaatg tggtcaagct     240

attccagtaa aatataatgg tgttaagggt gactacttgc atatgatgta tctagataat     300

gaacctgcta ttgctgttgg aagagaaagt agcgcttatc caaaaaagct tggctatcca     360

aagctatttg ttgattcaga tactttagtt gggacactta aatatggtac attaccagta     420

gctactgcaa caatgggata taagcacgag cctctagatc ttaaagaagc ctatgctcaa     480

attgcaagac ccaattttat gctaaaaatc attcaaggtt acgatggtaa gccaagaatt     540

tgtgaactaa tatgtgcaga aaatactgat ataactattc acggtgcttg gactggaagt     600

gcacgtctac aattatttag ccatgcacta gctcctcttg ctgatttacc tgtattagag     660

attgtatcag catctcatat cctcacagat ttaactcttg gaacacctaa ggttgtacat     720

gattatcttt cagtaaaata a                                               741


<210> SEQ ID NO 51
<211> LENGTH: 741
<212> TYPE: DNA
<213> ORGANISM: Clostridium beijerinckii

<400> SEQUENCE: 51

atgctggaga gcgaagttag caaacaaatc accaccccgc tggcggcgcc ggcgttcccg      60

cgtggcccgt accgttttca taaccgtgag tacctgaaca tcatttatcg taccgacctg     120

gatgcgctgc gtaagattgt gccggagccg ctggaactgg accgtgcgta cgttcgtttc     180

gagatgatgg cgatgccgga taccaccggt ctgggcagct acaccgaatg cggtcaggcg     240

atcccggtga agtataacgg tgttaaaggc gactacctgc acatgatgta tctggataac     300
```

-continued

```
gagccggcga ttgcggtggg tcgtgaaagc agcgcgtacc cgaagaaact gggctatccg    360

aagctgtttg tggacagcga taccctggtg ggcaccctga aatatggcac cctgccggtt    420

gcgaccgcga ccatgggcta caagcacgag ccgctggacc tgaaagaagc gtatgcgcag    480

attgcgcgtc cgaacttcat gctgaagatc attcaaggtt atgacggcaa accgcgtatc    540

tgcgagctga tttgcgcgga aaacaccgat atcaccatcc atggtgcgtg gaccggcagc    600

gcgcgtctgc aactgtttag ccatgcgctg gcgccgctgg cggatctgcc ggtgctggaa    660

atcgttagcg cgagccacat tctgaccgat ctgaccctgg gcaccccgaa ggttgtgcat    720

gactatctga gcgtgaagta a                                              741
```

<210> SEQ ID NO 52
<211> LENGTH: 246
<212> TYPE: PRT
<213> ORGANISM: Clostridium beijerinckii

<400> SEQUENCE: 52

```
Met Leu Glu Ser Glu Val Ser Lys Gln Ile Thr Thr Pro Leu Ala Ala
1               5                   10                  15

Pro Ala Phe Pro Arg Gly Pro Tyr Arg Phe His Asn Arg Glu Tyr Leu
            20                  25                  30

Asn Ile Ile Tyr Arg Thr Asp Leu Asp Ala Leu Arg Lys Ile Val Pro
        35                  40                  45

Glu Pro Leu Glu Leu Asp Arg Ala Tyr Val Arg Phe Glu Met Met Ala
    50                  55                  60

Met Pro Asp Thr Thr Gly Leu Gly Ser Tyr Thr Glu Cys Gly Gln Ala
65                  70                  75                  80

Ile Pro Val Lys Tyr Asn Gly Val Lys Gly Asp Tyr Leu His Met Met
                85                  90                  95

Tyr Leu Asp Asn Glu Pro Ala Ile Ala Val Gly Arg Glu Ser Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Lys Tyr Gly Thr Leu Pro Val Ala Thr Ala Thr
    130                 135                 140

Met Gly Tyr Lys His Glu Pro Leu Asp Leu Lys Glu Ala Tyr Ala Gln
145                 150                 155                 160

Ile Ala Arg Pro Asn Phe Met Leu Lys Ile Ile Gln Gly Tyr Asp Gly
                165                 170                 175

Lys Pro Arg Ile Cys Glu Leu Ile Cys Ala Glu Asn Thr Asp Ile Thr
            180                 185                 190

Ile His Gly Ala Trp Thr Gly Ser Ala Arg Leu Gln Leu Phe Ser His
        195                 200                 205

Ala Leu Ala Pro Leu Ala Asp Leu Pro Val Leu Glu Ile Val Ser Ala
    210                 215                 220

Ser His Ile Leu Thr Asp Leu Thr Leu Gly Thr Pro Lys Val Val His
225                 230                 235                 240

Asp Tyr Leu Ser Val Lys
                245
```

<210> SEQ ID NO 53
<211> LENGTH: 897
<212> TYPE: DNA
<213> ORGANISM: Homo sapiens -continued

<400> SEQUENCE: 53
atggaagaga agcagatcct gtgcgtgggg ctagtggtgc tggacgtcat cagcctggtg 60
gacaagtacc ctaaggagga ctcggagata aggtgtttgt cccagagatg gcagcgcgga 120
ggcaacgcgt ccaactcctg caccgttctc tccctgctcg gagcccctg tgccttcatg 180 ggctcaatgg ctcctggcca tgttgctgat tttgtcctgg atgacctccg ccgctattct 240
gtggacctac gctacacagt ctttcagacc acaggctccg tccccatcgc cacggtcatc 300
atcaacgagg ccagtggtag ccgcaccatc ctatactatg acaggagcct gccagatgtg 360
tctgctacag actttgagaa ggttgatctg acccagttca agtggatcca cattgagggc 420
cggaacgcat cggagcaggt gaagatgctg cagcggatag acgcacacaa caccaggcag 480
cctccagagc agaagatccg ggtgtccgtg gaggtggaga agccacgaga ggagctcttc 540
cagctgtttg gctacggaga cgtggtgttt gtcagcaaag atgtggccaa gcacttgggg 600
ttccagtcag cagaggaagc cttgaggggc ttgtatggtc gtgtgaggaa aggggctgtg 660
cttgtctgtg cctgggctga ggagggcgcc gacgccctgg gccctgatgg caaattgctc 720
cactcggatg ctttcccgcc accccgcgtg gtggatacac tgggagctgg agacaccttc 780
aatgcctccg tcatcttcag cctctcccag gggaggagcg tgcaggaagc actgagattc 840
gggtgccagg tggccggcaa gaagtgtggc ctgcagggct ttgatggcat cgtttaa 897

<210> SEQ ID NO 54
<211> LENGTH: 897
<212> TYPE: DNA
<213> ORGANISM: Homo sapiens

<400> SEQUENCE: 54
atggaggaaa agcaaattct gtgcgttggt ctggtggttc tggacgtgat tagcctggtt 60
gataagtacc cgaaagagga tagcgaaatc cgttgcctga gccagcgttg gcaacgtggt 120
ggcaacgcga gcaatagctg caccgttctg agcctgctgg gtgcgccgtg cgcgttcatg 180
ggtagcatgg cgccgggtca tgttgcggac ttcctggtgg cggattttcg tcgtcgtggt 240
gtggacgtta gccaggttgc gtggcaaagc aagggcgata ccccgagctc ctgctgcatc 300
attaacaaca gcaacggtaa ccgtaccatt gtgctgcacg acaccagcct gccggatgtt 360
agcgcgaccg acttcgagaa ggtggatctg acccagttta aatggattca cattgagggc 420
cgtaacgcga gcgaacaggt taaaatgctg caacgtattg atgcgcacaa cacccgtcag 480
ccgccggaac aaaagattcg tgtgagcgtt gaggtggaaa aaccgcgtga ggaactgttc 540
caactgtttg gttacggcga cgtggttttc gttagcaagg atgtggcgaa acacctgggt 600
tttcaaagcg cggaggaagc gctgcgtggt ctgtatggcc gtgtgcgtaa aggcgcggtt 660
ctggtgtgcg cgtgggcgga ggaaggcgcg gatgcgctgg gtccggatgg caaactgctg 720
cacagcgatg cgttcccgcc gccgcgtgtg gttgacaccc tgggtgcggg cgataccttc 780
aacgcgagcg ttatctttag cctgagccag ggccgtagcg tgcaagaggc gctgcgtttc 840
ggctgccaag ttgcgggtaa aaaatgcggt ctgcaaggct ttgacggtat cgtgtaa 897

<210> SEQ ID NO 55
<211> LENGTH: 298
<212> TYPE: PRT
<213> ORGANISM: Homo sapiens

<400> SEQUENCE: 55

Met Glu Glu Lys Gln Ile Leu Cys Val Gly Leu Val Val Leu Asp Val

-continued

```
1               5                   10                  15

Ile Ser Leu Val Asp Lys Tyr Pro Lys Glu Asp Ser Glu Ile Arg Cys
            20                  25                  30

Leu Ser Gln Arg Trp Gln Arg Gly Gly Asn Ala Ser Asn Ser Cys Thr
        35                  40                  45

Val Leu Ser Leu Leu Gly Ala Pro Cys Ala Phe Met Gly Ser Met Ala
    50                  55                  60

Pro Gly His Val Ala Asp Phe Leu Val Ala Asp Phe Arg Arg Arg Gly
65                  70                  75                  80

Val Asp Val Ser Gln Val Ala Trp Gln Ser Lys Gly Asp Thr Pro Ser
                85                  90                  95

Ser Cys Cys Ile Ile Asn Asn Ser Asn Gly Asn Arg Thr Ile Val Leu
            100                 105                 110

His Asp Thr Ser Leu Pro Asp Val Ser Ala Thr Asp Phe Glu Lys Val
        115                 120                 125

Asp Leu Thr Gln Phe Lys Trp Ile His Ile Glu Gly Arg Asn Ala Ser
    130                 135                 140

Glu Gln Val Lys Met Leu Gln Arg Ile Asp Ala His Asn Thr Arg Gln
145                 150                 155                 160

Pro Pro Glu Gln Lys Ile Arg Val Ser Val Glu Val Glu Lys Pro Arg
                165                 170                 175

Glu Glu Leu Phe Gln Leu Phe Gly Tyr Gly Asp Val Val Phe Val Ser
            180                 185                 190

Lys Asp Val Ala Lys His Leu Gly Phe Gln Ser Ala Glu Glu Ala Leu
        195                 200                 205

Arg Gly Leu Tyr Gly Arg Val Arg Lys Gly Ala Val Leu Val Cys Ala
    210                 215                 220

Trp Ala Glu Glu Gly Ala Asp Ala Leu Gly Pro Asp Gly Lys Leu Leu
225                 230                 235                 240

His Ser Asp Ala Phe Pro Pro Pro Arg Val Val Asp Thr Leu Gly Ala
                245                 250                 255

Gly Asp Thr Phe Asn Ala Ser Val Ile Phe Ser Leu Ser Gln Gly Arg
            260                 265                 270

Ser Val Gln Glu Ala Leu Arg Phe Gly Cys Gln Val Ala Gly Lys Lys
        275                 280                 285

Cys Gly Leu Gln Gly Phe Asp Gly Ile Val
    290                 295
```

<210> SEQ ID NO 56
<211> LENGTH: 1095
<212> TYPE: DNA
<213> ORGANISM: Homo sapiens

<400> SEQUENCE: 56

```
atggcccacc gatttccagc cctcacccag gagcagaaga aggagctctc agaaattgcc     60

cagagcattg ttgccaatgg aaaggggatc ctggctgcag atgaatctgt aggtaccatg    120

gggaaccgcc tgcagaggat caaggtggaa aacactgaag agaaccgccg gcagttccga    180

gaaatcctct tctctgtgga cagttccatc aaccagagca tcgggggtgt gatccttttc    240

cacgagaccc tctaccagaa ggacagccag ggaaagctgt tcagaaacat cctcaaggaa    300

aaggggatcg tggtgggaat caagttagac caaggaggtg ctcctcttgc aggaacaaac    360

aaagaaacca ccattcaagg gcttgatggc ctctcagagc gctgtgctca gtacaagaaa    420

gatggtgttg actttgggaa gtggcgtgct gtgctgagga ttgccgacca gtgtccatcc    480
```

-continued

```
agcctcgcta tccaggaaaa cgccaacgcc ctggctcgct acgccagcat ctgtcagcag    540

aatggactgg tacctattgt tgaaccagag gtaattcctg atggagacca tgacctggaa    600

cactgccagt atgttactga gaaggtcctg gctgctgtct acaaggccct gaatgaccat    660

catgtttacc tggagggcac cctgctaaag cccaacatgg tgactgctgg acatgcctgc    720

accaagaagt atactccaga acaagtagct atggccaccg taacagctct ccaccgtact    780

gttcctgcag ctgttcctgg catctgcttt ttgtctggtg gcatgagtga agaggatgcc    840

actctcaacc tcaatgctat caacctttgc cctctaccaa agccctggaa actaagtttc    900

tcttatggac gggccctgca ggccagtgca ctggctgcct ggggtggcaa ggctgcaaac    960

aaggaggcaa cccaggaggc ttttatgaag cgggccatgg ctaactgcca ggcggccaaa   1020

ggacagtatg ttcacacggg ttcttctggg gctgcttcca cccagtcgct cttcacagcc   1080

tgctatacct actag                                                    1095
```

<210> SEQ ID NO 57
<211> LENGTH: 1095
<212> TYPE: DNA
<213> ORGANISM: Homo sapiens

<400> SEQUENCE: 57

```
atggcgcacc gttttccggc gctgacccaa gagcagaaga aggagctgag cgagattgcg     60

cagagcatcg tggcgaatgg taaaggtatt ctggcggcgg atgagagcgt tggtaccatg    120

ggcaaccgtc tgcagcgtat taaggtggag aacaccgagg aaaaccgtcg tcaattccgt    180

gaaatcctgt ttagcgttga tagcagcatc aaccagagca ttggtggcgt gatcctgttc    240

cacgaaaccc tgtaccagaa ggacagccaa ggtaaactgt ttcgtaacat tctgaaggaa    300

aaaggtattg tggttggcat caagctggat caaggtggcg cgccgctggc gggcaccaac    360

aaggaaacca ccatccaggg tctggacggc ctgagcgaac gttgcgcgca atataagaaa    420

gatggtgttg acttcggcaa gtggcgtgcg gtgctgcgta ttgcggacca gtgcccgagc    480

agcctggcga tccaagaaaa cgcgaacgcg ctggcgcgtt acgcgagcat ctgccagcaa    540

aacggtctgg tgccgattgt tgagccggaa gttatcccgg acggcgatca cgacctggag    600

cactgccagt atgtgaccga aaaggttctg gcggcggtgt acaaagcgct gaacgatcac    660

cacgtttatc tggagggtac cctgctgaaa ccgaacatgg tgaccgcggg ccatgcgtgc    720

accaagaaat acaccccgga acaggtggcg atggcgaccg tgaccgcgct gcaccgtacc    780

gttccggcgg cggtgccggg tatttgcttt ctgagcggtg gcatgagcga agaggacgcg    840

accctgaacc tgaacgcgat caacctgtgc ccgctgccga agccgtggaa actgagcttc    900

agctacggcc gtgcgctgca ggcgagcgcg ctggcggcgt ggggtggcaa ggcggcgaac    960

aaagaggcga cccaagaagc gtttatgaag cgtgcgatgg cgaactgcca ggcggcgaaa   1020

ggtcaatatg tgcataccgg cagcagcggt gcggcgagca cccagagcct gtttaccgcg   1080

tgctatacct attaa                                                    1095
```

<210> SEQ ID NO 58
<211> LENGTH: 364
<212> TYPE: PRT
<213> ORGANISM: Homo sapiens

<400> SEQUENCE: 58

```
Met Ala His Arg Phe Pro Ala Leu Thr Gln Glu Gln Lys Lys Glu Leu
1               5                   10                  15
```

-continued

```
Ser Glu Ile Ala Gln Ser Ile Val Ala Asn Gly Lys Gly Ile Leu Ala
            20                  25                  30

Ala Asp Glu Ser Val Gly Thr Met Gly Asn Arg Leu Gln Arg Ile Lys
        35                  40                  45

Val Glu Asn Thr Glu Glu Asn Arg Arg Gln Phe Arg Glu Ile Leu Phe
    50                  55                  60

Ser Val Asp Ser Ser Ile Asn Gln Ser Ile Gly Gly Val Ile Leu Phe
65                  70                  75                  80

His Glu Thr Leu Tyr Gln Lys Asp Ser Gln Gly Lys Leu Phe Arg Asn
                85                  90                  95

Ile Leu Lys Glu Lys Gly Ile Val Val Gly Ile Lys Leu Asp Gln Gly
            100                 105                 110

Gly Ala Pro Leu Ala Gly Thr Asn Lys Glu Thr Thr Ile Gln Gly Leu
        115                 120                 125

Asp Gly Leu Ser Glu Arg Cys Ala Gln Tyr Lys Lys Asp Gly Val Asp
    130                 135                 140

Phe Gly Lys Trp Arg Ala Val Leu Arg Ile Ala Asp Gln Cys Pro Ser
145                 150                 155                 160

Ser Leu Ala Ile Gln Glu Asn Ala Asn Ala Leu Ala Arg Tyr Ala Ser
                165                 170                 175

Ile Cys Gln Gln Asn Gly Leu Val Pro Ile Val Glu Pro Glu Val Ile
            180                 185                 190

Pro Asp Gly Asp His Asp Leu Glu His Cys Gln Tyr Val Thr Glu Lys
        195                 200                 205

Val Leu Ala Ala Val Tyr Lys Ala Leu Asn Asp His His Val Tyr Leu
    210                 215                 220

Glu Gly Thr Leu Leu Lys Pro Asn Met Val Thr Ala Gly His Ala Cys
225                 230                 235                 240

Thr Lys Lys Tyr Thr Pro Glu Gln Val Ala Met Ala Thr Val Thr Ala
                245                 250                 255

Leu His Arg Thr Val Pro Ala Ala Val Pro Gly Ile Cys Phe Leu Ser
            260                 265                 270

Gly Gly Met Ser Glu Glu Asp Ala Thr Leu Asn Leu Asn Ala Ile Asn
        275                 280                 285

Leu Cys Pro Leu Pro Lys Pro Trp Lys Leu Ser Phe Ser Tyr Gly Arg
    290                 295                 300

Ala Leu Gln Ala Ser Ala Leu Ala Ala Trp Gly Gly Lys Ala Ala Asn
305                 310                 315                 320

Lys Glu Ala Thr Gln Glu Ala Phe Met Lys Arg Ala Met Ala Asn Cys
                325                 330                 335

Gln Ala Ala Lys Gly Gln Tyr Val His Thr Gly Ser Ser Gly Ala Ala
            340                 345                 350

Ser Thr Gln Ser Leu Phe Thr Ala Cys Tyr Thr Tyr
        355                 360
```

<210> SEQ ID NO 59
<211> LENGTH: 747
<212> TYPE: DNA
<213> ORGANISM: Caulobacter crescentus

<400> SEQUENCE: 59

```
atgtcctcag ccatctatcc cagcctgaag ggcaagcgcg tcgtcatcac cggcggcggc      60

tcgggcatcg gggccggcct caccgccggc ttcgcccgtc agggcgcgga ggtgatcttc     120
```

-continued

```
ctcgacatcg ccgacgagga ctccagggct cttgaggccg agctggccgg ctcgccgatc    180

ccgccggtct acaagcgctg cgacctgatg aacctcgagg cgatcaaggc ggtcttcgcc    240

gagatcggcg acgtcgacgt gctggtcaac aacgccggca atgacgaccg ccacaagctg    300

gccgacgtga ccggcgccta ttgggacgag cggatcaacg tcaacctgcg ccacatgctg    360

ttctgcaccc aggccgtcgc gccgggcatg aagaagcgtg gcggcggggc ggtgatcaac    420

ttcggttcga tcagctggca cctggggctt gaggacctcg tcctctacga aaccgccaag    480

gccggcatcg aaggcatgac ccgcgcgctg gcccgggagc tgggtcccga cgacatccgc    540

gtcacctgcg tggtgccggg caacgtcaag accaagcgcc aggagaagtg gtacacgccc    600

gaaggcgagg cccagatcgt ggcggcccaa tgcctgaagg gccgcatcgt cccggagaac    660

gtcgccgcgc tggtgctgtt cctggcctcg gatgacgcgt cgctctgcac cggccacgaa    720

tactggatcg acgccggctg gcgttga                                         747
```

<210> SEQ ID NO 60
<211> LENGTH: 747
<212> TYPE: DNA
<213> ORGANISM: Caulobacter crescentus

<400> SEQUENCE: 60

```
atgagcagcg cgatctaccc gagcctgaaa ggtaaacgtg tggtgattac cggcggcggc     60

agcggcattg gtgcgggcct gaccgcgggc ttcgcgcgtc agggtgcgga agtgatcttt    120

ctggacattg cggacgaaga tagccgtgcg ctggaggcgg aactggcggg cagcccgatc    180

ccgccggtgt acaagcgttg cgatctgatg aacctggagg cgatcaaagc ggtttttcgcg   240

gaaattggcg acgtggatgt tctggtgaac aacgcgggta acgacgaccg tcacaagctg    300

gcggatgtga ccggtgcgta ttgggatgag cgtattaacg ttaacctgcg tcacatgctg    360

ttctgcaccc aggcggtggc gccgggtatg aagaaacgtg gtggcggtgc ggttatcaac    420

tttggcagca ttagctggca cctgggtctg gaggacctgg tgctgtacga aaccgcgaaa    480

gcgggcatcg agggtatgac ccgtgcgctg gcgcgtgaac tgggtccgga cgatattcgt    540

gtgacctgcg tggttccggg taacgttaag accaaacgtc aagagaagtg gtataccccg    600

gagggtgaag cgcagattgt tgcggcgcaa tgcctgaaag gtcgtattgt tccggaaaac    660

gtggcggcgc tggttctgtt tctggcgagc gatgatgcga gcctgtgcac cggccatgag    720

tattggattg atgcgggctg gcgttaa                                         747
```

<210> SEQ ID NO 61
<211> LENGTH: 248
<212> TYPE: PRT
<213> ORGANISM: Caulobacter crescentus

<400> SEQUENCE: 61

```
Met Ser Ser Ala Ile Tyr Pro Ser Leu Lys Gly Lys Arg Val Val Ile
1               5                   10                  15

Thr Gly Gly Gly Ser Gly Ile Gly Ala Gly Leu Thr Ala Gly Phe Ala
            20                  25                  30

Arg Gln Gly Ala Glu Val Ile Phe Leu Asp Ile Ala Asp Glu Asp Ser
        35                  40                  45

Arg Ala Leu Glu Ala Glu Leu Ala Gly Ser Pro Ile Pro Pro Val Tyr
    50                  55                  60

Lys Arg Cys Asp Leu Met Asn Leu Glu Ala Ile Lys Ala Val Phe Ala
65                  70                  75                  80
```

```
Glu Ile Gly Asp Val Asp Val Leu Val Asn Asn Ala Gly Asn Asp Asp
                85                  90                  95

Arg His Lys Leu Ala Asp Val Thr Gly Ala Tyr Trp Asp Glu Arg Ile
            100                 105                 110

Asn Val Asn Leu Arg His Met Leu Phe Cys Thr Gln Ala Val Ala Pro
        115                 120                 125

Gly Met Lys Lys Arg Gly Gly Gly Ala Val Ile Asn Phe Gly Ser Ile
    130                 135                 140

Ser Trp His Leu Gly Leu Glu Asp Leu Val Leu Tyr Glu Thr Ala Lys
145                 150                 155                 160

Ala Gly Ile Glu Gly Met Thr Arg Ala Leu Ala Arg Glu Leu Gly Pro
                165                 170                 175

Asp Asp Ile Arg Val Thr Cys Val Val Pro Gly Asn Val Lys Thr Lys
            180                 185                 190

Arg Gln Glu Lys Trp Tyr Thr Pro Glu Gly Glu Ala Gln Ile Val Ala
        195                 200                 205

Ala Gln Cys Leu Lys Gly Arg Ile Val Pro Glu Asn Val Ala Ala Leu
    210                 215                 220

Val Leu Phe Leu Ala Ser Asp Asp Ala Ser Leu Cys Thr Gly His Glu
225                 230                 235                 240

Tyr Trp Ile Asp Ala Gly Trp Arg
                245
```

<210> SEQ ID NO 62
<211> LENGTH: 1173
<212> TYPE: DNA
<213> ORGANISM: Haloferax volcanii

<400> SEQUENCE: 62

```
atgagccccg cccccaccga catcgtcgag gagttcacgc gccgcgactg gcagggagac     60

gacgtgacgg gcaccgtgcg ggtcgccatg atcggcctcg gctggtggac ccgcgacgag    120

gcgattcccg cggtcgaggc gtccgagttc tgcgagacga cggtcgtcgt cagcagttcg    180

aaggagaaag ccgagggcgc gacggcgttg accgagtcga taacccacgg cctcacctac    240

gacgagttcc acgagggggt cgccgccgac gcctacgacg cggtgtacgt cgtcacgccg    300

aacggtctgc atctcccgta cgtcgagacc gccgccgagt tggggaaggc ggtcctctgc    360

gagaaaccgc tggaagcgtc ggtcgagcgg gccgaaaagc tcgtcgccgc ctgcgaccgc    420

gccgacgtgc ccctgatggt cgcctatcgg atgcagaccg agccggccgt ccggcgcgcc    480

cgcgaactcg tcgaggccgg cgtcatcggc gagccggtgt tcgtccacgg ccacatgtcc    540

cagcgcctgc tcgacgaggt cgtccccgac cccgaccagt ggcggctcga ccccgaactc    600

tccggcggcg cgaccgtcat ggacatcggg ctctacccgc tgaacaccgc ccggttcgtc    660

ctcgacgccg accccgtccg cgtcagggcg accgcccgcg tcgacgacga ggcgttcgag    720

gccgtcggcg acgagcacgt cagtttcggc gtcgacttcg acgacggcac gctcgcggtc    780

tgcaccgcca gccagtcggc ttaccagttg agccacctcc gggtgaccgg caccgagggc    840

gaactcgaaa tcgagcccgc gttctacaac cgccaaaagc ggggattccg actgtcgtgg    900

ggggaccagt ccgccgacta cgacttcgag caggtaaacc agatgacgga ggagttcgac    960

tacttcgcgt cccggctcct gtcggattcc gaccccgcgc ccgacggcga ccacgcgctc   1020

gtggacatgc gcgcgatgga cgcgatttac gccgcggcgg agcgcgggac cgatgtcgcc   1080

gtcgacgccg ccgactccga ttccgccgac tccgattccg ccgacgctgc cgccgccaac   1140
```

-continued cacgacgccg accccgattc cgacgggacg tag 1173

<210> SEQ ID NO 63
<211> LENGTH: 390
<212> TYPE: PRT
<213> ORGANISM: Haloferax volcanii

<400> SEQUENCE: 63

Met Ser Pro Ala Pro Thr Asp Ile Val Glu Glu Phe Thr Arg Arg Asp
1 5 10 15

Trp Gln Gly Asp Asp Val Thr Gly Thr Val Arg Val Ala Met Ile Gly
20 25 30

Leu Gly Trp Trp Thr Arg Asp Glu Ala Ile Pro Ala Val Glu Ala Ser
35 40 45

Glu Phe Cys Glu Thr Thr Val Val Val Ser Ser Ser Lys Glu Lys Ala
50 55 60

Glu Gly Ala Thr Ala Leu Thr Glu Ser Ile Thr His Gly Leu Thr Tyr
65 70 75 80

Asp Glu Phe His Glu Gly Val Ala Ala Asp Ala Tyr Asp Ala Val Tyr
85 90 95

Val Val Thr Pro Asn Gly Leu His Leu Pro Tyr Val Glu Thr Ala Ala
100 105 110

Glu Leu Gly Lys Ala Val Leu Cys Glu Lys Pro Leu Glu Ala Ser Val
115 120 125

Glu Arg Ala Glu Lys Leu Val Ala Ala Cys Asp Arg Ala Asp Val Pro
130 135 140

Leu Met Val Ala Tyr Arg Met Gln Thr Glu Pro Ala Val Arg Arg Ala
145 150 155 160

Arg Glu Leu Val Glu Ala Gly Val Ile Gly Glu Pro Val Phe Val His
165 170 175

Gly His Met Ser Gln Arg Leu Leu Asp Glu Val Val Pro Asp Pro Asp
180 185 190

Gln Trp Arg Leu Asp Pro Glu Leu Ser Gly Gly Ala Thr Val Met Asp
195 200 205

Ile Gly Leu Tyr Pro Leu Asn Thr Ala Arg Phe Val Leu Asp Ala Asp
210 215 220

Pro Val Arg Val Arg Ala Thr Ala Arg Val Asp Asp Glu Ala Phe Glu
225 230 235 240

Ala Val Gly Asp Glu His Val Ser Phe Gly Val Asp Phe Asp Asp Gly
245 250 255

Thr Leu Ala Val Cys Thr Ala Ser Gln Ser Ala Tyr Gln Leu Ser His
260 265 270

Leu Arg Val Thr Gly Thr Glu Gly Glu Leu Glu Ile Glu Pro Ala Phe
275 280 285

Tyr Asn Arg Gln Lys Arg Gly Phe Arg Leu Ser Trp Gly Asp Gln Ser
290 295 300

Ala Asp Tyr Asp Phe Glu Gln Val Asn Gln Met Thr Glu Glu Phe Asp
305 310 315 320

Tyr Phe Ala Ser Arg Leu Leu Ser Asp Ser Asp Pro Ala Pro Asp Gly
325 330 335

Asp His Ala Leu Val Asp Met Arg Ala Met Asp Ala Ile Tyr Ala Ala
340 345 350

Ala Glu Arg Gly Thr Asp Val Ala Val Asp Ala Ala Asp Ser Asp Ser
355 360 365

-continued

```
Ala Asp Ser Asp Ser Ala Asp Ala Ala Ala Ala Asn His Asp Ala Asp
    370                 375                 380

Pro Asp Ser Asp Gly Thr
385                 390


<210> SEQ ID NO 64
<211> LENGTH: 1176
<212> TYPE: DNA
<213> ORGANISM: Trichoderma reesei

<400> SEQUENCE: 64

atggcgtctg gaaaccctta caccctgaaa tggggcatca tggccaccgg cggaatcgca      60

gagaccttct gcaaggatct cctgtgcaac cccgcgattc gaggcgccga tgatgtgcgc     120

cacgagattg tggccgtggc ctcttccagc agcagcaaga gagcagagga gttcctccag     180

agaatcgacg gtgcctttga cgccaagacg tacggatcat acccggaact tgtggcagac     240

cccaacgtcg acatcgtcta tgtggcaact ccccacagcc accacttcca gaacaccatg     300

ctggcgctgg aagccggcaa gaacgtcttg tgcgaaaagg ctttcaccgt gacggccgcg     360

caggcccgaa agctggttga gacggccaag gccaagaagc tcttcctgat ggaagctgtg     420

tggacacggt actttccgct gagtatcaag attcgagagc tcattgccgc cggcgagatt     480

ggcactgtct ttcgaacaat cgccgacttg tccatcaacg caaactcaga gcagggtcaa     540

gccctgaaat tcgcagactc acatcgaatg gtcaacccgg acctcgcagg cggtgccacc     600

ttggatctcg gagtctatcc cttgacctgg gtgttccaga ccctgtatca tttgcaaccg     660

gaggaagaca aggaggctcc caccgtggtt gcttccagca acaagtacac cactggcgca     720

gacgagaata ccgccatcat ctgcagcttc cctcgccaca acagcattgg aattgcttcg     780

acgacgatga gggcggacac cgaccccgag aaggacacca ttccggcggt ccgaattcaa     840

ggatccaagg gagaaatcca agtcttcttc ccgacctacc gaccgctcaa gtacaaggtg     900

gtgaagacga acggcgaggc gcagacggtt gactgcccca tccccggaga ccccgcgcgc     960

aagggctcgg gccacggaat gttctgggag gcggacgagt gtgctcgatg ccttcgcgat    1020

ggcaagttgg agagtgccac gttgccatgg aaggagagca ttgtcattat ggaaacgatg    1080

gaggaggcgc tgaggcaggg tggcgtcacg tatccggagc tgattaccac ggatgtctat    1140

gatcccaaga gccctctcaa cacggggaat cagtag                              1176


<210> SEQ ID NO 65
<211> LENGTH: 391
<212> TYPE: PRT
<213> ORGANISM: Trichoderma reesei

<400> SEQUENCE: 65

Met Ala Ser Gly Asn Pro Tyr Thr Leu Lys Trp Gly Ile Met Ala Thr
1               5                   10                  15

Gly Gly Ile Ala Glu Thr Phe Cys Lys Asp Leu Leu Cys Asn Pro Ala
            20                  25                  30

Ile Arg Gly Ala Asp Asp Val Arg His Glu Ile Val Ala Val Ala Ser
        35                  40                  45

Ser Ser Ser Ser Lys Arg Ala Glu Glu Phe Leu Gln Arg Ile Asp Gly
    50                  55                  60

Ala Phe Asp Ala Lys Thr Tyr Gly Ser Tyr Pro Glu Leu Val Ala Asp
65                  70                  75                  80

Pro Asn Val Asp Ile Val Tyr Val Ala Thr Pro His Ser His His Phe
                85                  90                  95
```

-continued

```
Gln Asn Thr Met Leu Ala Leu Glu Ala Gly Lys Asn Val Leu Cys Glu
            100                 105                 110

Lys Ala Phe Thr Val Thr Ala Ala Gln Ala Arg Lys Leu Val Glu Thr
        115                 120                 125

Ala Lys Ala Lys Lys Leu Phe Leu Met Glu Ala Val Trp Thr Arg Tyr
    130                 135                 140

Phe Pro Leu Ser Ile Lys Ile Arg Glu Leu Ile Ala Ala Gly Glu Ile
145                 150                 155                 160

Gly Thr Val Phe Arg Thr Ile Ala Asp Leu Ser Ile Asn Ala Asn Ser
                165                 170                 175

Glu Gln Gly Gln Ala Leu Lys Phe Ala Asp Ser His Arg Met Val Asn
            180                 185                 190

Pro Asp Leu Ala Gly Gly Ala Thr Leu Asp Leu Gly Val Tyr Pro Leu
        195                 200                 205

Thr Trp Val Phe Gln Thr Leu Tyr His Leu Gln Pro Glu Glu Asp Lys
    210                 215                 220

Glu Ala Pro Thr Val Val Ala Ser Ser Asn Lys Tyr Thr Thr Gly Ala
225                 230                 235                 240

Asp Glu Asn Thr Ala Ile Ile Cys Ser Phe Pro Arg His Asn Ser Ile
                245                 250                 255

Gly Ile Ala Ser Thr Thr Met Arg Ala Asp Thr Asp Pro Glu Lys Asp
            260                 265                 270

Thr Ile Pro Ala Val Arg Ile Gln Gly Ser Lys Gly Glu Ile Gln Val
        275                 280                 285

Phe Phe Pro Thr Tyr Arg Pro Leu Lys Tyr Lys Val Val Lys Thr Asn
    290                 295                 300

Gly Glu Ala Gln Thr Val Asp Cys Pro Ile Pro Gly Asp Pro Ala Arg
305                 310                 315                 320

Lys Gly Ser Gly His Gly Met Phe Trp Glu Ala Asp Glu Cys Ala Arg
                325                 330                 335

Cys Leu Arg Asp Gly Lys Leu Glu Ser Ala Thr Leu Pro Trp Lys Glu
            340                 345                 350

Ser Ile Val Ile Met Glu Thr Met Glu Glu Ala Leu Arg Gln Gly Gly
        355                 360                 365

Val Thr Tyr Pro Glu Leu Ile Thr Thr Asp Val Tyr Asp Pro Lys Ser
    370                 375                 380

Pro Leu Asn Thr Gly Asn Gln
385                 390
```

<210> SEQ ID NO 66
<211> LENGTH: 870
<212> TYPE: DNA
<213> ORGANISM: Caulobacter crescentus

<400> SEQUENCE: 66

```
atgaccgctc aagtcacttg cgtatgggat ctgaaggcca cgttgggcga aggcccgatc      60

tggcatggcg acaccctgtg gttcgtcgac atcaagcagc gtaaaatcca caactaccac     120

cccgccaccg gcgagcgctt cagcttcgac gcgccggatc aggtgacctt cctcgcgccg     180

atcgtcggcg cgaccggctt tgtcgtcggt ctgaagaccg ggattcaccg cttccacccg     240

gccacgggct tcagcctgct gctcgaggtc gaggacgcgg cgctgaacaa ccgcccccaac    300

gacgccacgg tcgacgcgca aggccgtctg tggttcggca ccatgcacga cggggaagag     360

aacaatagcg gctcgctcta tcggatggac ctcaccggcg tcgcccggat ggaccgcgac     420
```

atctgcatca ccaacggccc gtgcgtctcg cccgacggca agaccttcta ccacaccgac 480
accctggaaa agacgatcta cgccttcgac ctggccgagg acggcctgct gtcgaacaag 540
cgcgtcttcg tgcagttcgc cctgggcgac gatgtctatc cggacggttc ggtcgtcgat 600
tccgaaggct atctgtggac cgccctgtgg ggcggtttcg gcgcggtccg cttctcgccg 660
caaggcgacg ccgtgacgcg catcgaactg cccgcccccca acgtcaccaa gccctgcttc 720
ggcgggcctg acctgaagac cctctatttc accaccgccc gcaagggcct gagcgacgag 780
accctggccc agtacccgct ggccggcggt gtgttcgccg ttccggtcga tgtggccggc 840
caaccccagc atgaggtccg ccttgtctaa 870

<210> SEQ ID NO 67
<211> LENGTH: 289
<212> TYPE: PRT
<213> ORGANISM: Caulobacter crescentus

<400> SEQUENCE: 67

Met Thr Ala Gln Val Thr Cys Val Trp Asp Leu Lys Ala Thr Leu Gly
1 5 10 15

Glu Gly Pro Ile Trp His Gly Asp Thr Leu Trp Phe Val Asp Ile Lys
20 25 30

Gln Arg Lys Ile His Asn Tyr His Pro Ala Thr Gly Glu Arg Phe Ser
35 40 45

Phe Asp Ala Pro Asp Gln Val Thr Phe Leu Ala Pro Ile Val Gly Ala
50 55 60

Thr Gly Phe Val Val Gly Leu Lys Thr Gly Ile His Arg Phe His Pro
65 70 75 80

Ala Thr Gly Phe Ser Leu Leu Leu Glu Val Glu Asp Ala Ala Leu Asn
85 90 95

Asn Arg Pro Asn Asp Ala Thr Val Asp Ala Gln Gly Arg Leu Trp Phe
100 105 110

Gly Thr Met His Asp Gly Glu Glu Asn Asn Ser Gly Ser Leu Tyr Arg
115 120 125

Met Asp Leu Thr Gly Val Ala Arg Met Asp Arg Asp Ile Cys Ile Thr
130 135 140

Asn Gly Pro Cys Val Ser Pro Asp Gly Lys Thr Phe Tyr His Thr Asp
145 150 155 160

Thr Leu Glu Lys Thr Ile Tyr Ala Phe Asp Leu Ala Glu Asp Gly Leu
165 170 175

Leu Ser Asn Lys Arg Val Phe Val Gln Phe Ala Leu Gly Asp Asp Val
180 185 190

Tyr Pro Asp Gly Ser Val Val Asp Ser Glu Gly Tyr Leu Trp Thr Ala
195 200 205

Leu Trp Gly Gly Phe Gly Ala Val Arg Phe Ser Pro Gln Gly Asp Ala
210 215 220

Val Thr Arg Ile Glu Leu Pro Ala Pro Asn Val Thr Lys Pro Cys Phe
225 230 235 240

Gly Gly Pro Asp Leu Lys Thr Leu Tyr Phe Thr Thr Ala Arg Lys Gly
245 250 255

Leu Ser Asp Glu Thr Leu Ala Gln Tyr Pro Leu Ala Gly Gly Val Phe
260 265 270

Ala Val Pro Val Asp Val Ala Gly Gln Pro Gln His Glu Val Arg Leu
275 280 285

-continued

Val

<210> SEQ ID NO 68
<211> LENGTH: 1776
<212> TYPE: DNA
<213> ORGANISM: Caulobacter crescentus

<400> SEQUENCE: 68
ttgtctaacc gcacgccccg ccggttccgg tcccgcgatt ggttcgataa ccccgaccat 60
atcgacatga ccgcgctcta tctggagcgc ttcatgaact acgggatcac gccggaggag 120
ctgcgcagcg gcaagccgat catcggcatc gcccagaccg gcagcgacat ctcgccctgc 180
aaccgcatcc acctggacct ggtccagcgg gtgcgggacg ggatccgcga cgccgggggc 240
atccccatgg agttcccggt ccatccgatc ttcgagaact gccgtcgccc gacggcggcg 300
ctggaccgga acctctcgta cctgggtctc gtcgagaccc tgcacggcta tccgatcgac 360
gccgtggttc tgaccaccgg ctgcgacaag accaccccgg ccgggatcat ggccgccacc 420
acggtcaata tcccggccat cgtgctgtcg ggcggcccga tgctggacgg ctggcacgag 480
aacgagctcg tgggctcggg caccgtgatc tggcgctcgc gccgcaagct ggcggccggc 540
gagatcaccg aggaagagtt catcgaccgc gccgccagct cggcgccgtc ggcgggccac 600
tgcaacacca tgggcacggc ctcgaccatg aacgccgtgg ccgaggcgct gggcctgtcg 660
ctgaccggct gcgcggccat ccccgccccc taccgcgagc gcggccagat ggcctacaag 720
accggccagc gcatcgtcga tctggcctat gacgacgtca aaccgctcga catcctgacc 780
aagcaagcct tcgagaacgc catcgccctg gtggcggcgg ccggcggctc gaccaacgcc 840
cagccgcaca tcgtggccat ggcccgtcac gccggcgtcg agatcaccgc cgacgactgg 900
cgcgcggcct atgacatccc gctgatcgtc aacatgcagc cggccggcaa gtatctgggc 960
gagcgcttcc accgagccgg cggcgcgccg gcggtgctgt gggagctgtt gcagcaaggc 1020
cgcctgcacg gcgacgtgct gaccgtcacc ggcaagacga tgagcgagaa cctgcaaggc 1080
cgcgaaacca gcgaccgcga ggtgatcttc ccgtaccacg agccgctggc cgagaaggcc 1140
gggttcctgg ttctcaaggg caacctcttc gacttcgcga tcatgaagtc cagcgtgatc 1200
ggcgaggagt tccgcaagcg ctacctgtcg cagcccggcc aggaaggcgt gttcgaagcc 1260
cgcgccatcg tgttcgacgg ctcggacgac tatcacaagc ggatcaacga tccggccctg 1320
gagatcgacg agcgctgcat cctggtgatc cgcggcgcgg gtccgatcgg ctggcccggc 1380
tcggccgagg tcgtcaacat gcagccgccg gatcaccttc tgaagaaggg gatcatgagc 1440
ctgcccaccc tgggcgatgg ccgtcagtcg ggcaccgccg acagcccctc gatcctgaac 1500
gcctcgcccg aaagcgcgat cggcggcggc ctgtcgtggc tgcgcaccgg cgacaccatc 1560
cgcatcgacc tcaacaccgg ccgctgcgac gccctggtcg acgaggcgac gatcgccgcg 1620
cgcaagcagg acggcatccc ggcggttccc gccaccatga cgccctggca ggaaatctac 1680
cgcgcccacg ccagtcagct cgacaccggc ggcgtgctgg agttcgcggt caagtaccag 1740
gacctggcgg ccaagctgcc ccgccacaac cactga 1776

<210> SEQ ID NO 69
<211> LENGTH: 591
<212> TYPE: PRT
<213> ORGANISM: Caulobacter crescentus

<400> SEQUENCE: 69

Met Ser Asn Arg Thr Pro Arg Arg Phe Arg Ser Arg Asp Trp Phe Asp

-continued

```
1               5                   10                  15

Asn Pro Asp His Ile Asp Met Thr Ala Leu Tyr Leu Glu Arg Phe Met
            20                  25                  30

Asn Tyr Gly Ile Thr Pro Glu Glu Leu Arg Ser Gly Lys Pro Ile Ile
        35                  40                  45

Gly Ile Ala Gln Thr Gly Ser Asp Ile Ser Pro Cys Asn Arg Ile His
    50                  55                  60

Leu Asp Leu Val Gln Arg Val Arg Asp Gly Ile Arg Asp Ala Gly Gly
65                  70                  75                  80

Ile Pro Met Glu Phe Pro Val His Pro Ile Phe Glu Asn Cys Arg Arg
                85                  90                  95

Pro Thr Ala Ala Leu Asp Arg Asn Leu Ser Tyr Leu Gly Leu Val Glu
            100                 105                 110

Thr Leu His Gly Tyr Pro Ile Asp Ala Val Val Leu Thr Thr Gly Cys
        115                 120                 125

Asp Lys Thr Thr Pro Ala Gly Ile Met Ala Ala Thr Thr Val Asn Ile
    130                 135                 140

Pro Ala Ile Val Leu Ser Gly Gly Pro Met Leu Asp Gly Trp His Glu
145                 150                 155                 160

Asn Glu Leu Val Gly Ser Gly Thr Val Ile Trp Arg Ser Arg Arg Lys
                165                 170                 175

Leu Ala Ala Gly Glu Ile Thr Glu Glu Glu Phe Ile Asp Arg Ala Ala
            180                 185                 190

Ser Ser Ala Pro Ser Ala Gly His Cys Asn Thr Met Gly Thr Ala Ser
        195                 200                 205

Thr Met Asn Ala Val Ala Glu Ala Leu Gly Leu Ser Leu Thr Gly Cys
    210                 215                 220

Ala Ala Ile Pro Ala Pro Tyr Arg Glu Arg Gly Gln Met Ala Tyr Lys
225                 230                 235                 240

Thr Gly Gln Arg Ile Val Asp Leu Ala Tyr Asp Asp Val Lys Pro Leu
                245                 250                 255

Asp Ile Leu Thr Lys Gln Ala Phe Glu Asn Ala Ile Ala Leu Val Ala
            260                 265                 270

Ala Ala Gly Gly Ser Thr Asn Ala Gln Pro His Ile Val Ala Met Ala
        275                 280                 285

Arg His Ala Gly Val Glu Ile Thr Ala Asp Asp Trp Arg Ala Ala Tyr
    290                 295                 300

Asp Ile Pro Leu Ile Val Asn Met Gln Pro Ala Gly Lys Tyr Leu Gly
305                 310                 315                 320

Glu Arg Phe His Arg Ala Gly Gly Ala Pro Ala Val Leu Trp Glu Leu
                325                 330                 335

Leu Gln Gln Gly Arg Leu His Gly Asp Val Leu Thr Val Thr Gly Lys
            340                 345                 350

Thr Met Ser Glu Asn Leu Gln Gly Arg Glu Thr Ser Asp Arg Glu Val
        355                 360                 365

Ile Phe Pro Tyr His Glu Pro Leu Ala Glu Lys Ala Gly Phe Leu Val
    370                 375                 380

Leu Lys Gly Asn Leu Phe Asp Phe Ala Ile Met Lys Ser Ser Val Ile
385                 390                 395                 400

Gly Glu Glu Phe Arg Lys Arg Tyr Leu Ser Gln Pro Gly Gln Glu Gly
                405                 410                 415

Val Phe Glu Ala Arg Ala Ile Val Phe Asp Gly Ser Asp Asp Tyr His
            420                 425                 430
```

```
Lys Arg Ile Asn Asp Pro Ala Leu Glu Ile Asp Glu Arg Cys Ile Leu
        435                 440                 445

Val Ile Arg Gly Ala Gly Pro Ile Gly Trp Pro Gly Ser Ala Glu Val
    450                 455                 460

Val Asn Met Gln Pro Pro Asp His Leu Leu Lys Lys Gly Ile Met Ser
465                 470                 475                 480

Leu Pro Thr Leu Gly Asp Gly Arg Gln Ser Gly Thr Ala Asp Ser Pro
                485                 490                 495

Ser Ile Leu Asn Ala Ser Pro Glu Ser Ala Ile Gly Gly Gly Leu Ser
            500                 505                 510

Trp Leu Arg Thr Gly Asp Thr Ile Arg Ile Asp Leu Asn Thr Gly Arg
        515                 520                 525

Cys Asp Ala Leu Val Asp Glu Ala Thr Ile Ala Ala Arg Lys Gln Asp
    530                 535                 540

Gly Ile Pro Ala Val Pro Ala Thr Met Thr Pro Trp Gln Glu Ile Tyr
545                 550                 555                 560

Arg Ala His Ala Ser Gln Leu Asp Thr Gly Gly Val Leu Glu Phe Ala
                565                 570                 575

Val Lys Tyr Gln Asp Leu Ala Ala Lys Leu Pro Arg His Asn His
            580                 585                 590
```

<210> SEQ ID NO 70
<211> LENGTH: 1968
<212> TYPE: DNA
<213> ORGANISM: Escherichia coli

<400> SEQUENCE: 70

```
atgtctgttc gcaatatttt tgctgacgag agccacgata tttacaccgt cagaacgcac     60

gccgatggcc cggacggcga actcccatta accgcagaga tgcttatcaa ccgcccgagc    120

ggggatctgt tcggtatgac catgaatgcc ggaatgggtt ggtctccgga cgagctggat    180

cgggacggta ttttactgct cagtacactc ggtggcttac gcggcgcaga cggtaaaccc    240

gtggcgctgg cgttgcacca ggggcattac gaactggaca tccagatgaa agcggcggcc    300

gaggttatta aagccaacca tgccctgccc tatgccgtgt acgtctccga tccttgtgac    360

gggcgtactc agggtacaac ggggatgttt gattcgctac cataccgaaa tgacgcatcg    420

atggtaatgc gccgccttat tcgctctctg cccgacgcga aagcagttat tggtgtggcg    480

agttgcgata aggggcttcc ggccaccatg atggcactcg ccgcgcagca caacatcgca    540

accgtgctgg tccccggcgg cgcgacgctg cccgcaaagg atggagaaga caacggcaag    600

gtgcaaacca ttggcgcacg cttcgccaat ggcgaattat ctctacagga cgcacgccgt    660

gcgggctgta aagcctgtgc ctcttccggc ggcggctgtc aatttttggg cactgccggg    720

acatctcagg tggtggccga aggattggga ctggcaatcc cacattcagc cctggcccct    780

tccggtgagc ctgtgtggcg ggagatcgcc agagcttccg cgcgagctgc gctgaacctg    840

agtcaaaaag gcatcaccac ccgggaaatt ctcaccgata aagcgataga gaatgcgatg    900

acggtccatg ccgcgttcgg tggttcaaca aacctgctgt tacacatccc ggcaattgct    960

caccaggcag gttgccatat cccgaccgtt gatgactgga tccgcatcaa caagcgcgtg   1020

ccccgactgg tgagcgtact gcctaatggc ccggtttatc atccaacggt caatgccttt   1080

atggcaggtg gtgtgccgga agtcatgttg catctgcgca gcctcggatt gttgcatgaa   1140

gacgttatga cggttaccgg cagcacgctg aaagaaaacc tcgactggtg ggagcactcc   1200
```

```
gaacggcgtc agcggttcaa gcaactcctg ctcgatcagg aacaaatcaa cgctgacgaa   1260

gtgatcatgt ctccgcagca agcaaaagcg cgcggattaa cctcaactat caccttcccg   1320

gtgggcaata ttgcgccaga aggttcggtg atcaaatcca ccgccattga cccctcgatg   1380

attgatgagc aaggtatcta ttaccataaa ggtgtggcga aggtttatct gtccgagaaa   1440

agtgcgattt acgatatcaa acatgacaag atcaaggcgg gcgatattct ggtcattatt   1500

ggcgttggac cttcaggtac agggatggaa gaaacctacc aggttaccag tgccctgaag   1560

catctgtcat acggtaagca tgtttcgtta atcaccgatg cacgtttctc gggcgtttct   1620

actggcgcgt gcatcggcca tgtggggcca gaagcgctgg ccggaggccc catcggtaaa   1680

ttacgcaccg ggatttaat tgaaattaaa attgattgtc gcgagcttca cggcgaagtc   1740

aatttcctcg gaacccgtag cgatgaacaa ttaccttcac aggaggaggc aactgcaata   1800

ttaaatgcca gacccagcca tcaggattta cttcccgatc ctgaattgcc agatgatacc   1860

cggctatggg caatgcttca ggccgtgagt ggtgggacat ggaccggttg tatttatgat   1920

gtaaacaaaa ttggcgcggc tttgcgcgat tttatgaata aaaactga                1968
```

```
<210> SEQ ID NO 71
<211> LENGTH: 1968
<212> TYPE: DNA
<213> ORGANISM: Escherichia coli

<400> SEQUENCE: 71
```

```
atgtctgttc gcaatatttt tgctgacgag agccacgata tttacaccgt cagaacgcac     60

gccgatggcc cggacggcga actcccatta accgcagaga tgcttatcaa ccgcccgagc    120

ggggatctgt tcggtatgac catgaatgcc ggaatgggtt ggtctccgga cgagctggat    180

cgggacggta ttttactgct cagtacactc ggtggcttac gcggcgcaga cggtaaaccc    240

gtggcgctgg cgttgcacca ggggcattac gaactggaca tccagatgaa agcggcggcc    300

gaggttatta aagccaacca tgccctgccc tatgccgtgt acgtctccga tccttgtgac    360

gggcgtactc agggtacaac ggggatgttt gattcgctac cataccgaaa tgacgcatcg    420

atggtaatgc gccgccttat tcgctctctg cccgacgcga aagcagttat tggtgtggcg    480

agttgcgata aggggcttcc ggccaccatg atggcactcg ccgcgcagca caacatcgca    540

accgtgctgg tccccggcgg cgcgacgctg cccgcaaagg atggagaaga caacggcaag    600

gtgcaaacca ttggcgcacg cttcgccaat ggcgaattat ctctacagga cgcacgccgt    660

gcgggctgta aagcctgtgc ctcttccggc ggcggctgtc aatttttggg cactgccggg    720

acatctcagg tggtggccga aggattggga ctggcaatcc cacattcagc cctggcccct    780

tccggtgagc ctgtgtggcg ggagatcgcc agagcttccg cgcgagctgc gctgaacctg    840

agtcaaaaag gcatcaccac ccgggaaatt ctcaccgata aagcgataga gaatgcgatg    900

acggtccatg ccgcgttcgg tggttcaaca aacctgctgt tacacatccc ggcaattgct    960

caccaggcag gttgccatat cccgaccgtt gatgactgga tccgcatcaa caagcgcgtg   1020

ccccgactgg tgagcgtact gcctaatggc ccggtttatc atccaacggt caatgccttt   1080

atggcaggtg gtgtgccgga agtcatgttg catctgcgca gcctcggatt gttgcatgaa   1140

gacgttatga cggttaccgg cagcacgctg aaagaaaacc tcgactggtg ggagcactcc   1200

gaacggcgtc agcggttcaa gcaactcctg ctcgatcagg aacaaatcaa cgctgacgaa   1260

gtgatcatgt ctccgcagca agcaaaagcg cgcggattaa cctcaactat caccttcccg   1320

gtgggcaata ttgcgccaga aggttcggtg atcaaatcca ccgccattga cccctcgatg   1380
```

attgatgagc aaggtatcta ttaccataaa ggtgtggcga aggtttatct gtccgagaaa 1440
agtgcgattt acgatatcaa acatgacaag atcaaggcgg gcgatattct ggtcattatt 1500
ggcgttggac cttcaggtac agggatggaa gaaacctacc aggttaccag tgccctgaag 1560
catctgtcat acggtaagca tgtttcgtta atcaccgatg cacgtttctc gggcgtttct 1620
actggcgcgt gcatcggcca tgtggggcca gaagcgctgg ccggaggccc catcggtaaa 1680
ttacgcaccg gggatttaat tgaaattaaa attgattgtc gcgagcttca cggcgaagtc 1740
aatttcctcg gaacccgtag cgatgaacaa ttaccttcac aggaggaggc aactgcaata 1800
ttaaatgcca gacccagcca tcaggattta cttcccgatc ctgaattgcc agatgatacc 1860
cggctatggg caatgcttca ggccgtgagt ggtgggacat ggaccggttg tatttatgat 1920
gtaaacaaaa ttggcgcggc tttgcgcgat tttatgaata aaaactga 1968

<210> SEQ ID NO 72
<211> LENGTH: 655
<212> TYPE: PRT
<213> ORGANISM: Escherichia coli

<400> SEQUENCE: 72

Met Ser Val Arg Asn Ile Phe Ala Asp Glu Ser His Asp Ile Tyr Thr
1               5                   10                  15

Val Arg Thr His Ala Asp Gly Pro Asp Gly Glu Leu Pro Leu Thr Ala
            20                  25                  30

Glu Met Leu Ile Asn Arg Pro Ser Gly Asp Leu Phe Gly Met Thr Met
        35                  40                  45

Asn Ala Gly Met Gly Trp Ser Pro Asp Glu Leu Asp Arg Asp Gly Ile
    50                  55                  60

Leu Leu Leu Ser Thr Leu Gly Gly Leu Arg Gly Ala Asp Gly Lys Pro
65                  70                  75                  80

Val Ala Leu Ala Leu His Gln Gly His Tyr Glu Leu Asp Ile Gln Met
                85                  90                  95

Lys Ala Ala Ala Glu Val Ile Lys Ala Asn His Ala Leu Pro Tyr Ala
            100                 105                 110

Val Tyr Val Ser Asp Pro Cys Asp Gly Arg Thr Gln Gly Thr Thr Gly
        115                 120                 125

Met Phe Asp Ser Leu Pro Tyr Arg Asn Asp Ala Ser Met Val Met Arg
    130                 135                 140

Arg Leu Ile Arg Ser Leu Pro Asp Ala Lys Ala Val Ile Gly Val Ala
145                 150                 155                 160

Ser Cys Asp Lys Gly Leu Pro Ala Thr Met Met Ala Leu Ala Ala Gln
                165                 170                 175

His Asn Ile Ala Thr Val Leu Val Pro Gly Gly Ala Thr Leu Pro Ala
            180                 185                 190

Lys Asp Gly Glu Asp Asn Gly Lys Val Gln Thr Ile Gly Ala Arg Phe
        195                 200                 205

Ala Asn Gly Glu Leu Ser Leu Gln Asp Ala Arg Arg Ala Gly Cys Lys
    210                 215                 220

Ala Cys Ala Ser Ser Gly Gly Gly Cys Gln Phe Leu Gly Thr Ala Gly
225                 230                 235                 240

Thr Ser Gln Val Val Ala Glu Gly Leu Gly Leu Ala Ile Pro His Ser
                245                 250                 255

Ala Leu Ala Pro Ser Gly Glu Pro Val Trp Arg Glu Ile Ala Arg Ala
            260                 265                 270

-continued

```
Ser Ala Arg Ala Ala Leu Asn Leu Ser Gln Lys Gly Ile Thr Thr Arg
        275                 280                 285

Glu Ile Leu Thr Asp Lys Ala Ile Glu Asn Ala Met Thr Val His Ala
    290                 295                 300

Ala Phe Gly Gly Ser Thr Asn Leu Leu Leu His Ile Pro Ala Ile Ala
305                 310                 315                 320

His Gln Ala Gly Cys His Ile Pro Thr Val Asp Asp Trp Ile Arg Ile
                325                 330                 335

Asn Lys Arg Val Pro Arg Leu Val Ser Val Leu Pro Asn Gly Pro Val
            340                 345                 350

Tyr His Pro Thr Val Asn Ala Phe Met Ala Gly Gly Val Pro Glu Val
        355                 360                 365

Met Leu His Leu Arg Ser Leu Gly Leu Leu His Glu Asp Val Met Thr
    370                 375                 380

Val Thr Gly Ser Thr Leu Lys Glu Asn Leu Asp Trp Trp Glu His Ser
385                 390                 395                 400

Glu Arg Arg Gln Arg Phe Lys Gln Leu Leu Leu Asp Gln Glu Gln Ile
                405                 410                 415

Asn Ala Asp Glu Val Ile Met Ser Pro Gln Gln Ala Lys Ala Arg Gly
            420                 425                 430

Leu Thr Ser Thr Ile Thr Phe Pro Val Gly Asn Ile Ala Pro Glu Gly
        435                 440                 445

Ser Val Ile Lys Ser Thr Ala Ile Asp Pro Ser Met Ile Asp Glu Gln
    450                 455                 460

Gly Ile Tyr Tyr His Lys Gly Val Ala Lys Val Tyr Leu Ser Glu Lys
465                 470                 475                 480

Ser Ala Ile Tyr Asp Ile Lys His Asp Lys Ile Lys Ala Gly Asp Ile
                485                 490                 495

Leu Val Ile Ile Gly Val Gly Pro Ser Gly Thr Gly Met Glu Glu Thr
            500                 505                 510

Tyr Gln Val Thr Ser Ala Leu Lys His Leu Ser Tyr Gly Lys His Val
        515                 520                 525

Ser Leu Ile Thr Asp Ala Arg Phe Ser Gly Val Ser Thr Gly Ala Cys
    530                 535                 540

Ile Gly His Val Gly Pro Glu Ala Leu Ala Gly Gly Pro Ile Gly Lys
545                 550                 555                 560

Leu Arg Thr Gly Asp Leu Ile Glu Ile Lys Ile Asp Cys Arg Glu Leu
                565                 570                 575

His Gly Glu Val Asn Phe Leu Gly Thr Arg Ser Asp Glu Gln Leu Pro
            580                 585                 590

Ser Gln Glu Glu Ala Thr Ala Ile Leu Asn Ala Arg Pro Ser His Gln
        595                 600                 605

Asp Leu Leu Pro Asp Pro Glu Leu Pro Asp Asp Thr Arg Leu Trp Ala
    610                 615                 620

Met Leu Gln Ala Val Ser Gly Gly Thr Trp Thr Gly Cys Ile Tyr Asp
625                 630                 635                 640

Val Asn Lys Ile Gly Ala Ala Leu Arg Asp Phe Met Asn Lys Asn
                645                 650                 655
```

<210> SEQ ID NO 73
<211> LENGTH: 1968
<212> TYPE: DNA
<213> ORGANISM: Escherichia coli

<400> SEQUENCE: 73
atgaccattg agaaaatttt caccccgcag gacgacgcgt tttatgcggt gatcacccac 60
gcggcggggc cgcagggcgc tctgccgctg accccgcaga tgctgatgga atctcccagc 120
ggcaacctgt tcggcatgac gcagaacgcc gggatgggct gggacgccaa caagctcacc 180
ggcaaagagg tgctgattat cggcactcag ggcggcatcc gcgccggaga cggacgccca 240
atcgcgctgg gctaccacac cggcattgg gagatcggca tgcagatgca ggcggcggcg 300
aaggagatca cccgcaatgg cgggatcccg ttcgcggcct tcgtcagcga tccgtgcgac 360
gggcgctcgc agggcacgca cggtatgttc gattccctgc cgtaccgcaa cgacgcggcg 420
atcgtgtttc gccgcctgat ccgctccctg ccgacgcggc gggcggtgat cggcgtagcg 480
acctgcgata aagggctgcc cgccaccatg attgcgctgg ccgcgatgca cgacctgccg 540
actattctgg tgccgggcgg ggcgacgctg ccgccgaccg tcggggaaga cgcgggcaag 600
gtgcagacca tcggcgcgcg tttcgccaac cacgaactct ccctgcagga ggccgccgaa 660
ctgggctgtc gcgcctgcgc ctcgccgggc ggcgggtgtc agttcctcgg cacggcgggc 720
acctcgcagg tggtcgcgga ggcgctgggt ctggcgctgc cgcactccgc gctggcgccg 780
tccgggcagg cggtgtggct ggagatcgcc cgccagtcgg cgcgcgcggt cagcgagctg 840
gatagccgcg gcatcaccac gcgggatatc ctctccgata aagccatcga aaacgcgatg 900
gtgatccacg cggcgttcgg cggctccacc aatttactgc tgcacattcc ggccatcgcc 960
cacgcggcgg gctgcacgat cccggacgtt gagcactgga cgcgcatcaa ccgtaaagtg 1020
ccgcgtctgg tgagcgtgct gcccaacggc ccggactatc acccgaccgt gcgcgccttc 1080
ctcgcgggcg gcgtgccgga ggtgatgctc cacctgcgcg acctcggcct gctgcatctg 1140
gacgccatga ccgtgaccgg ccagacggtg ggcgagaacc ttgaatggtg gcaggcgtcc 1200
gagcgccggg cgcgcttccg ccagtgcctg cgcgagcagg acggcgtaga gccggatgac 1260
gtgatcctgc cgccggagaa ggcaaaagcg aaagggctga cctcgacggt ctgcttcccg 1320
acgggcaaca tcgctccgga aggttcggtg atcaaggcca cggcgatcga cccgtcggtg 1380
gtgggcgaag atggcgtata ccaccacacc ggccgggtgc gggtgtttgt ctcggaagcg 1440
caggcgatca aggcgatcaa gcgggaagag attgtgcagg gcgatatcat ggtggtgatc 1500
ggcggcgggc cgtccggcac cggcatggaa gagacctacc agctcacctc cgcgctaaag 1560
catatctcgt ggggcaagac ggtgtcgctc atcaccgatg cgcgcttctc gggcgtgtcg 1620
acgggcgcct gcttcggcca cgtgtcgccg gaggcgctgg cgggcgggcc gattggcaag 1680
ctgcgcgata acgacatcat cgagattgcc gtggatcgtc tgacgttaac tggcagcgtg 1740
aacttcatcg gcaccgcgga caacccgctg acgccggaag agggcgcgcg cgagctggcg 1800
cggcggcaga cgcacccgga cctgcacgcc cacgactttt tgccggacga cacccggctg 1860
tgggcggcac tgcagtcggt gagcggcggc acctggaaag gctgtattta tgacaccgat 1920
aaaattatcg aggtaattaa cgccggtaaa aaagcgctcg gaatttaa 1968

<210> SEQ ID NO 74
<211> LENGTH: 1968
<212> TYPE: DNA
<213> ORGANISM: Escherichia coli

<400> SEQUENCE: 74
atgaccattg agaaaatttt caccccgcag gacgacgcgt tttatgcggt gatcacccac 60
gcggcggggc cgcagggcgc tctgccgctg accccgcaga tgctgatgga atctcccagc 120

-continued

```
ggcaacctgt tcggcatgac gcagaacgcc gggatgggct gggacgccaa caagctcacc    180
ggcaaagagg tgctgattat cggcactcag ggcggcatcc gcgccggaga cggacgccca    240
atcgcgctgg gctaccacac cggcattgg gagatcggca tgcagatgca ggcggcggcg    300
aaggagatca cccgcaatgg cgggatcccg ttcgcggcct tcgtcagcga tccgtgcgac    360
gggcgctcgc agggcacgca cggtatgttc gattccctgc cgtaccgcaa cgacgcggcg    420
atcgtgtttc gccgcctgat ccgctccctg ccgacgcggc gggcggtgat cggcgtagcg    480
acctgcgata aagggctgcc cgccaccatg attgcgctgg ccgcgatgca cgacctgccg    540
actattctgg tgccgggcgg ggcgacgctg ccgccgaccg tcggggaaga cgcgggcaag    600
gtgcagacca tcggcgcgcg tttcgccaac cacgaactct ccctgcagga ggccgccgaa    660
ctgggctgtc gcgcctgcgc ctcgccgggc ggcgggtgtc agttcctcgg cacggcgggc    720
acctcgcagg tggtcgcgga ggcgctgggt ctggcgctgc cgcactccgc gctggcgccg    780
tccgggcagg cggtgtggct ggagatcgcc cgccagtcgg cgcgcgcggt cagcgagctg    840
gatagccgcg gcatcaccac gcgggatatc ctctccgata aagccatcga aaacgcgatg    900
gtgatccacg cggcgttcgg cggctccacc aatttactgc tgcacattcc ggccatcgcc    960
cacgcggcgg gctgcacgat cccggacgtt gagcactgga cgcgcatcaa ccgtaaagtg   1020
ccgcgtctgg tgagcgtgct gcccaacggc ccggactatc acccgaccgt gcgcgccttc   1080
ctcgcgggcg gcgtgccgga ggtgatgctc cacctgcgcg acctcggcct gctgcatctg   1140
gacgccatga ccgtgaccgg ccagacggtg ggcgagaacc ttgaatggtg gcaggcgtcc   1200
gagcgccggg cgcgcttccg ccagtgcctg cgcgagcagg acggcgtaga gccggatgac   1260
gtgatcctgc cgccggagaa ggcaaaagcg aaagggctga cctcgacggt ctgcttcccg   1320
acgggcaaca tcgctccgga aggttcggtg atcaaggcca cggcgatcga cccgtcggtg   1380
gtgggcgaag atggcgtata ccaccacacc ggccgggtgc gggtgtttgt ctcggaagcg   1440
caggcgatca aggcgatcaa gcgggaagag attgtgcagg gcgatatcat ggtggtgatc   1500
ggcggcgggc cgtccggcac cggcatggaa gagacctacc agctcacctc cgcgctaaag   1560
catatctcgt ggggcaagac ggtgtcgctc atcaccgatg cgcgcttctc gggcgtgtcg   1620
acgggcgcct gcttcggcca cgtgtcgccg gaggcgctgg cgggcgggcc gattggcaag   1680
ctgcgcgata acgacatcat cgagattgcc gtggatcgtc tgacgttaac tggcagcgtg   1740
aacttcatcg gcaccgcgga caacccgctg acgccggaag agggcgcgcg cgagctggcg   1800
cggcggcaga cgcacccgga cctgcacgcc cacgactttt tgccggacga cacccggctg   1860
tgggcggcac tgcagtcggt gagcggcggc acctggaaag gctgtattta tgacaccgat   1920
aaaattatcg aggtaattaa cgccggtaaa aaagcgctcg gaatttaa                1968
```

<210> SEQ ID NO 75
<211> LENGTH: 655
<212> TYPE: PRT
<213> ORGANISM: Escherichia coli

<400> SEQUENCE: 75

```
Met Thr Ile Glu Lys Ile Phe Thr Pro Gln Asp Asp Ala Phe Tyr Ala
1               5                   10                  15

Val Ile Thr His Ala Ala Gly Pro Gln Gly Ala Leu Pro Leu Thr Pro
            20                  25                  30

Gln Met Leu Met Glu Ser Pro Ser Gly Asn Leu Phe Gly Met Thr Gln
        35                  40                  45
```

-continued

```
Asn Ala Gly Met Gly Trp Asp Ala Asn Lys Leu Thr Gly Lys Glu Val
    50                  55                  60

Leu Ile Ile Gly Thr Gln Gly Gly Ile Arg Ala Gly Asp Gly Arg Pro
65                  70                  75                  80

Ile Ala Leu Gly Tyr His Thr Gly His Trp Glu Ile Gly Met Gln Met
                85                  90                  95

Gln Ala Ala Ala Lys Glu Ile Thr Arg Asn Gly Gly Ile Pro Phe Ala
            100                 105                 110

Ala Phe Val Ser Asp Pro Cys Asp Gly Arg Ser Gln Gly Thr His Gly
        115                 120                 125

Met Phe Asp Ser Leu Pro Tyr Arg Asn Asp Ala Ala Ile Val Phe Arg
    130                 135                 140

Arg Leu Ile Arg Ser Leu Pro Thr Arg Arg Ala Val Ile Gly Val Ala
145                 150                 155                 160

Thr Cys Asp Lys Gly Leu Pro Ala Thr Met Ile Ala Leu Ala Ala Met
                165                 170                 175

His Asp Leu Pro Thr Ile Leu Val Pro Gly Gly Ala Thr Leu Pro Pro
            180                 185                 190

Thr Val Gly Glu Asp Ala Gly Lys Val Gln Thr Ile Gly Ala Arg Phe
        195                 200                 205

Ala Asn His Glu Leu Ser Leu Gln Glu Ala Ala Glu Leu Gly Cys Arg
    210                 215                 220

Ala Cys Ala Ser Pro Gly Gly Gly Cys Gln Phe Leu Gly Thr Ala Gly
225                 230                 235                 240

Thr Ser Gln Val Val Ala Glu Ala Leu Gly Leu Ala Leu Pro His Ser
                245                 250                 255

Ala Leu Ala Pro Ser Gly Gln Ala Val Trp Leu Glu Ile Ala Arg Gln
            260                 265                 270

Ser Ala Arg Ala Val Ser Glu Leu Asp Ser Arg Gly Ile Thr Thr Arg
        275                 280                 285

Asp Ile Leu Ser Asp Lys Ala Ile Glu Asn Ala Met Val Ile His Ala
    290                 295                 300

Ala Phe Gly Gly Ser Thr Asn Leu Leu Leu His Ile Pro Ala Ile Ala
305                 310                 315                 320

His Ala Ala Gly Cys Thr Ile Pro Asp Val Glu His Trp Thr Arg Ile
                325                 330                 335

Asn Arg Lys Val Pro Arg Leu Val Ser Val Leu Pro Asn Gly Pro Asp
            340                 345                 350

Tyr His Pro Thr Val Arg Ala Phe Leu Ala Gly Gly Val Pro Glu Val
        355                 360                 365

Met Leu His Leu Arg Asp Leu Gly Leu Leu His Leu Asp Ala Met Thr
    370                 375                 380

Val Thr Gly Gln Thr Val Gly Glu Asn Leu Glu Trp Trp Gln Ala Ser
385                 390                 395                 400

Glu Arg Arg Ala Arg Phe Arg Gln Cys Leu Arg Glu Gln Asp Gly Val
                405                 410                 415

Glu Pro Asp Asp Val Ile Leu Pro Pro Glu Lys Ala Lys Ala Lys Gly
            420                 425                 430

Leu Thr Ser Thr Val Cys Phe Pro Thr Gly Asn Ile Ala Pro Glu Gly
        435                 440                 445

Ser Val Ile Lys Ala Thr Ala Ile Asp Pro Ser Val Val Gly Glu Asp
    450                 455                 460
```

-continued

```
Gly Val Tyr His His Thr Gly Arg Val Arg Val Phe Val Ser Glu Ala
465                 470                 475                 480

Gln Ala Ile Lys Ala Ile Lys Arg Glu Glu Ile Val Gln Gly Asp Ile
                485                 490                 495

Met Val Val Ile Gly Gly Gly Pro Ser Gly Thr Gly Met Glu Glu Thr
            500                 505                 510

Tyr Gln Leu Thr Ser Ala Leu Lys His Ile Ser Trp Gly Lys Thr Val
        515                 520                 525

Ser Leu Ile Thr Asp Ala Arg Phe Ser Gly Val Ser Thr Gly Ala Cys
    530                 535                 540

Phe Gly His Val Ser Pro Glu Ala Leu Ala Gly Gly Pro Ile Gly Lys
545                 550                 555                 560

Leu Arg Asp Asn Asp Ile Ile Glu Ile Ala Val Asp Arg Leu Thr Leu
                565                 570                 575

Thr Gly Ser Val Asn Phe Ile Gly Thr Ala Asp Asn Pro Leu Thr Pro
            580                 585                 590

Glu Glu Gly Ala Arg Glu Leu Ala Arg Arg Gln Thr His Pro Asp Leu
        595                 600                 605

His Ala His Asp Phe Leu Pro Asp Asp Thr Arg Leu Trp Ala Ala Leu
    610                 615                 620

Gln Ser Val Ser Gly Gly Thr Trp Lys Gly Cys Ile Tyr Asp Thr Asp
625                 630                 635                 640

Lys Ile Ile Glu Val Ile Asn Ala Gly Lys Lys Ala Leu Gly Ile
                645                 650                 655
```

<210> SEQ ID NO 76
<211> LENGTH: 906
<212> TYPE: DNA
<213> ORGANISM: Escherichia coli

<400> SEQUENCE: 76

```
atgaaaaaat tcagcggcat tattccaccg gtatccagca cgtttcatcg tgacggaacc     60

cttgataaaa aggcaatgcg cgaagttgcc gacttcctga ttaataaagg ggtcgacggg    120

ctgttttatc tgggtaccgg tggtgaattt agccaaatga atacagccca gcgcatggca    180

ctcgccgaag aagctgtaac cattgtcgac gggcgagtgc cggtattgat tggcgtcggt    240

tccccttcca ctgacgaagc ggtcaaactg gcgcagcatg cgcaagccta cggcgctgat    300

ggtatcgtcg ccatcaaccc ctactactgg aaagtcgcac cacgaaatct tgacgactat    360

taccagcaga tcgcccgtag cgtcacccta ccggtgatcc tgtacaactt tccggatctg    420

acgggtcagg acttaacccc ggaaaccgtg acgcgtctgg ctctgcaaaa cgagaatatc    480

gttggcatca aagacaccat cgacagcgtt ggtcacttgc gtacgatgat caacacagtt    540

aagtcggtac gcccgtcgtt ttcggtattc tgcggttacg atgatcattt gctgaatacg    600

atgctgctgg gcggcgacgg tgcgataacc gccagcgcta actttgctcc ggaactctcc    660

gtcggcatct accgcgcctg gcgtgaaggc gatctggcga ccgctgcgac gctgaataaa    720

aaactactac aactgcccgc tatttacgcc ctcgaaacac cgtttgtctc actgatcaaa    780

tacagcatgc agtgtgtcgg gctgcctgta gagacatatt gcttaccacc gattcttgaa    840

gcatctgaag aagcaaaaga taaagtccac gtgctgctta ccgcgcaggg cattttacca    900

gtctga                                                                906
```

<210> SEQ ID NO 77
<211> LENGTH: 906

-continued

<212> TYPE: DNA
<213> ORGANISM: Escherichia coli

<400> SEQUENCE: 77

```
atgaaaaaat tcagcggcat tattccaccg gtatccagca cgtttcatcg tgacggaacc     60

cttgataaaa aggcaatgcg cgaagttgcc gacttcctga ttaataaagg ggtcgacggg    120

ctgttttatc tgggtaccgg tggtgaattt agccaaatga atacagccca gcgcatggca    180

ctcgccgaag aagctgtaac cattgtcgac gggcgagtgc cggtattgat tggcgtcggt    240

tccccttcca ctgacgaagc ggtcaaactg gcgcagcatg cgcaagccta cggcgctgat    300

ggtatcgtcg ccatcaaccc ctactactgg aaagtcgcac cacgaaatct tgacgactat    360

taccagcaga tcgcccgtag cgtcacccta ccggtgatcc tgtacaactt tccggatctg    420

acgggtcagg acttaacccc ggaaaccgtg acgcgtctgg ctctgcaaaa cgagaatatc    480

gttggcatca aagacaccat cgacagcgtt ggtcacttgc gtacgatgat caacacagtt    540

aagtcggtac gcccgtcgtt ttcggtattc tgcggttacg atgatcattt gctgaatacg    600

atgctgctgg gcggcgacgg tgcgataacc gccagcgcta actttgctcc ggaactctcc    660

gtcggcatct accgcgcctg gcgtgaaggc gatctggcga ccgctgcgac gctgaataaa    720

aaactactac aactgcccgc tatttacgcc ctcgaaacac cgtttgtctc actgatcaaa    780

tacagcatgc agtgtgtcgg gctgcctgta gagacatatt gcttaccacc gattcttgaa    840

gcatctgaag aagcaaaaga taaagtccac gtgctgctta ccgcgcaggg catttacca     900

gtctga                                                               906
```

<210> SEQ ID NO 78
<211> LENGTH: 301
<212> TYPE: PRT
<213> ORGANISM: Escherichia coli

<400> SEQUENCE: 78

```
Met Lys Lys Phe Ser Gly Ile Ile Pro Pro Val Ser Ser Thr Phe His
1               5                   10                  15

Arg Asp Gly Thr Leu Asp Lys Lys Ala Met Arg Glu Val Ala Asp Phe
            20                  25                  30

Leu Ile Asn Lys Gly Val Asp Gly Leu Phe Tyr Leu Gly Thr Gly Gly
        35                  40                  45

Glu Phe Ser Gln Met Asn Thr Ala Gln Arg Met Ala Leu Ala Glu Glu
    50                  55                  60

Ala Val Thr Ile Val Asp Gly Arg Val Pro Val Leu Ile Gly Val Gly
65                  70                  75                  80

Ser Pro Ser Thr Asp Glu Ala Val Lys Leu Ala Gln His Ala Gln Ala
                85                  90                  95

Tyr Gly Ala Asp Gly Ile Val Ala Ile Asn Pro Tyr Tyr Trp Lys Val
            100                 105                 110

Ala Pro Arg Asn Leu Asp Asp Tyr Tyr Gln Gln Ile Ala Arg Ser Val
        115                 120                 125

Thr Leu Pro Val Ile Leu Tyr Asn Phe Pro Asp Leu Thr Gly Gln Asp
    130                 135                 140

Leu Thr Pro Glu Thr Val Thr Arg Leu Ala Leu Gln Asn Glu Asn Ile
145                 150                 155                 160

Val Gly Ile Lys Asp Thr Ile Asp Ser Val Gly His Leu Arg Thr Met
                165                 170                 175

Ile Asn Thr Val Lys Ser Val Arg Pro Ser Phe Ser Val Phe Cys Gly
```

-continued

```
            180                 185                 190

Tyr Asp Asp His Leu Leu Asn Thr Met Leu Leu Gly Gly Asp Gly Ala
        195                 200                 205

Ile Thr Ala Ser Ala Asn Phe Ala Pro Glu Leu Ser Val Gly Ile Tyr
    210                 215                 220

Arg Ala Trp Arg Glu Gly Asp Leu Ala Thr Ala Ala Thr Leu Asn Lys
225                 230                 235                 240

Lys Leu Leu Gln Leu Pro Ala Ile Tyr Ala Leu Glu Thr Pro Phe Val
                245                 250                 255

Ser Leu Ile Lys Tyr Ser Met Gln Cys Val Gly Leu Pro Val Glu Thr
            260                 265                 270

Tyr Cys Leu Pro Pro Ile Leu Glu Ala Ser Glu Glu Ala Lys Asp Lys
        275                 280                 285

Val His Val Leu Leu Thr Ala Gln Gly Ile Leu Pro Val
    290                 295                 300
```

<210> SEQ ID NO 79
<211> LENGTH: 909
<212> TYPE: DNA
<213> ORGANISM: Escherichia coli

<400> SEQUENCE: 79

```
atgccgcagt ccgcgttgtt cacgggaatc attccccctg tctccaccat ttttaccgcc      60

gacggccagc tcgataagcc gggcaccgcc gcgctgatcg acgatctgat caaagcaggc     120

gttgacggcc tgttcttcct gggcagcggt ggcgagttct cccagctcgg cgccgaagag     180

cgtaaagcca ttgcccgctt tgctatcgat catgtcgatc gtcgcgtgcc ggtgctgatc     240

ggcaccggcg gcaccaacgc ccgggaaacc atcgaactca gccagcacgc gcagcaggcg     300

ggcgcggacg gcatcgtggt gatcaacccc tactactgga aagtgtcgga agcgaacctg     360

atccgctatt tcgagcaggt ggccgacagc gtcacgctgc cggtgatgct ctataacttc     420

ccggcgctga ccgggcagga tctgactccg gcgctggtga aaccctcgc cgactcgcgc      480

agcaatatta tcggcatcaa agacaccatc gactccgtcg cccacctgcg cagcatgatc     540

cataccgtca aaggtgccca tccgcacttc accgtgctct gcggctacga cgatcatctg     600

ttcaataccc tgctgctcgg cggcgacggg gcgatatcgg cgagcggcaa ctttgccccg     660

caggtgtcgg tgaatcttct gaaagcctgg cgcgacgggg acgtggcgaa agcggccggg     720

tatcatcaga ccttgctgca aattccgcag atgtatcagc tggatacgcc gtttgtgaac     780

gtgattaaag aggcgatcgt gctctgcggt cgtcctgtct ccacgcacgt gctgccgccc     840

gcctcgccgc tggacgagcc gcgcaaggcg cagctgaaaa ccctgctgca acagctcaag     900

ctttgctga                                                             909
```

<210> SEQ ID NO 80
<211> LENGTH: 909
<212> TYPE: DNA
<213> ORGANISM: Escherichia coli

<400> SEQUENCE: 80

```
atgccgcagt ccgcgttgtt cacgggaatc attccccctg tctccaccat ttttaccgcc      60

gacggccagc tcgataagcc gggcaccgcc gcgctgatcg acgatctgat caaagcaggc     120

gttgacggcc tgttcttcct gggcagcggt ggcgagttct cccagctcgg cgccgaagag     180

cgtaaagcca ttgcccgctt tgctatcgat catgtcgatc gtcgcgtgcc ggtgctgatc     240
```

-continued

```
ggcaccggcg gcaccaacgc ccgggaaacc atcgaactca gccagcacgc gcagcaggcg    300

ggcgcggacg gcatcgtggt gatcaacccc tactactgga aagtgtcgga agcgaacctg    360

atccgctatt tcgagcaggt ggccgacagc gtcacgctgc cggtgatgct ctataacttc    420

ccggcgctga ccgggcagga tctgactccg gcgctggtga aaccctcgc cgactcgcgc     480

agcaatatta tcggcatcaa agacaccatc gactccgtcg cccacctgcg cagcatgatc    540

cataccgtca aaggtgccca tccgcacttc accgtgctct gcggctacga cgatcatctg    600

ttcaataccc tgctgctcgg cggcgacggg gcgatatcgg cgagcggcaa ctttgccccg    660

caggtgtcgg tgaatcttct gaaagcctgg cgcgacgggg acgtggcgaa agcggccggg    720

tatcatcaga ccttgctgca aattccgcag atgtatcagc tggatacgcc gtttgtgaac    780

gtgattaaag aggcgatcgt gctctgcggt cgtcctgtct ccacgcacgt gctgccgccc    840

gcctcgccgc tggacgagcc gcgcaaggcg cagctgaaaa ccctgctgca acagctcaag    900

ctttgctga                                                            909
```

```
<210> SEQ ID NO 81
<211> LENGTH: 302
<212> TYPE: PRT
<213> ORGANISM: Escherichia coli

<400> SEQUENCE: 81

Met Pro Gln Ser Ala Leu Phe Thr Gly Ile Ile Pro Pro Val Ser Thr
1               5                   10                  15

Ile Phe Thr Ala Asp Gly Gln Leu Asp Lys Pro Gly Thr Ala Ala Leu
            20                  25                  30

Ile Asp Asp Leu Ile Lys Ala Gly Val Asp Gly Leu Phe Phe Leu Gly
        35                  40                  45

Ser Gly Gly Glu Phe Ser Gln Leu Gly Ala Glu Glu Arg Lys Ala Ile
    50                  55                  60

Ala Arg Phe Ala Ile Asp His Val Asp Arg Arg Val Pro Val Leu Ile
65                  70                  75                  80

Gly Thr Gly Gly Thr Asn Ala Arg Glu Thr Ile Glu Leu Ser Gln His
                85                  90                  95

Ala Gln Gln Ala Gly Ala Asp Gly Ile Val Val Ile Asn Pro Tyr Tyr
            100                 105                 110

Trp Lys Val Ser Glu Ala Asn Leu Ile Arg Tyr Phe Glu Gln Val Ala
        115                 120                 125

Asp Ser Val Thr Leu Pro Val Met Leu Tyr Asn Phe Pro Ala Leu Thr
    130                 135                 140

Gly Gln Asp Leu Thr Pro Ala Leu Val Lys Thr Leu Ala Asp Ser Arg
145                 150                 155                 160

Ser Asn Ile Ile Gly Ile Lys Asp Thr Ile Asp Ser Val Ala His Leu
                165                 170                 175

Arg Ser Met Ile His Thr Val Lys Gly Ala His Pro His Phe Thr Val
            180                 185                 190

Leu Cys Gly Tyr Asp Asp His Leu Phe Asn Thr Leu Leu Leu Gly Gly
        195                 200                 205

Asp Gly Ala Ile Ser Ala Ser Gly Asn Phe Ala Pro Gln Val Ser Val
    210                 215                 220

Asn Leu Leu Lys Ala Trp Arg Asp Gly Asp Val Ala Lys Ala Ala Gly
225                 230                 235                 240

Tyr His Gln Thr Leu Leu Gln Ile Pro Gln Met Tyr Gln Leu Asp Thr
                245                 250                 255
```

-continued

```
Pro Phe Val Asn Val Ile Lys Glu Ala Ile Val Leu Cys Gly Arg Pro
            260                 265                 270

Val Ser Thr His Val Leu Pro Pro Ala Ser Pro Leu Asp Glu Pro Arg
        275                 280                 285

Lys Ala Gln Leu Lys Thr Leu Leu Gln Gln Leu Lys Leu Cys
    290                 295                 300
```

<210> SEQ ID NO 82
<211> LENGTH: 957
<212> TYPE: DNA
<213> ORGANISM: Scheffersomyces stipitis

<400> SEQUENCE: 82

```
atgccttcta ttaagttgaa ctctggttac gacatgccag ccgtcggttt cggctgttgg     60

aaagtcgacg tcgacacctg ttctgaacag atctaccgtg ctatcaagac cggttacaga    120

ttgttcgacg gtgccgaaga ttacgccaac gaaaagttag ttggtgccgg tgtcaagaag    180

gccattgacg aaggtatcgt caagcgtgaa gatttgttcc ttacctccaa gttgtggaac    240

aactaccacc acccagacaa cgtcgaaaag gccttgaaca gaaccctttc tgacttgcaa    300

gttgactacg ttgacttgtt cttgatccac ttcccagtca ccttcaagtt cgttccatta    360

gaagaaaagt acccaccagg attctactgt ggtaagggtg acaacttcga ctacgaagat    420

gttccaattt tagagacttg gaaggctctt gaaaagttgg tcaaggccgg taagatcaga    480

tctatcggtg tttctaactt cccaggtgct ttgctcttgg acttgttgag aggtgctacc    540

atcaagccat ctgtcttgca agttgaacac cacccatact tgcaacaacc aagattgatc    600

gaattcgctc aatcccgtgg tattgctgtc accgcttact cttcgttcgg tcctcaatct    660

ttcgttgaat tgaaccaagg tagagctttg aacacttctc cattgttcga gaacgaaact    720

atcaaggcta tcgctgctaa gcacggtaag tctccagctc aagtcttgtt gagatggtca    780

tcccaaagag gcattgccat cattccaaag tccaacactg tcccaagatt gttggaaaac    840

aaggacgtca acagcttcga cttggacgaa caagatttcg ctgacattgc caagttggac    900

atcaacttga gattcaacga cccatgggac tgggacaaga ttcctatctt cgtctaa       957
```

<210> SEQ ID NO 83
<211> LENGTH: 957
<212> TYPE: DNA
<213> ORGANISM: Scheffersomyces stipitis

<400> SEQUENCE: 83

```
atgccatcta tcaagttaaa ttccggttac gacatgcctg ctgttggttt cggttgctgg     60

aaggttgatg tcgatacttg ttccgagcaa atttaccgtg ctatcaagac tggttacaga    120

ttgttcgatg gtgctgaaga ctacgccaac gaaaagttag tcggtgctgg tgttaaaaag    180

gctatcgacg aaggtattgt taaaagagaa gacttgttct tgacttctaa gttgtggaac    240

aactaccacc atcctgataa cgtcgaaaaa gctttgaacc gtaccttgtc cgatttgcaa    300

gtcgattacg ttgatttgtt cttgattcat ttcccagtta ccttcaagtt cgttccattg    360

gaagagaagt atccaccagg tttctactgt ggtaagggtg ataacttcga ttacgaagat    420

gtcccaatct tagaaacctg gaaggcttta gaaaagttgg ttaaggctgg taagatcaga    480

tccatcggtg tttctaactt cccaggtgcc ttattgttag acttattgag aggtgctacc    540

attaagcctt ccgttttgca agttgaacat catccttact tgcaacaacc aagattgatc    600

gaattcgctc aatctagagg tatcgctgtt actgcctact cttccttcgg tccacaatct    660
```

```
ttcgttgagt tgaaccaagg tagagctttg aacacctctc cattgttcga aaacgaaact    720

attaaggcca ttgctgctaa gcatggtaag tctccagccc aagttttgtt gagatggtct    780

tctcaaagag gtatcgctat tatcccaaag tctaatactg tcccaagatt gttggaaaac    840

aaggacgtta actcctttga tttggatgaa caagactttg ctgacatcgc taaattggac    900

atcaacttga gattcaacga cccatgggac tgggacaaga ttccaatttt tgtttaa       957
```

<210> SEQ ID NO 84
<211> LENGTH: 318
<212> TYPE: PRT
<213> ORGANISM: Scheffersomyces stipitis

<400> SEQUENCE: 84

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 85
<211> LENGTH: 984
<212> TYPE: DNA
<213> ORGANISM: Saccharomyces cerevisiae

<400> SEQUENCE: 85
atgtcttcac tggttactct taataacggt ctgaaaatgc ccctagtcgg cttagggtgc 60
tggaaaattg acaaaaaagt ctgtgcgaat caaatttatg aagctatcaa attaggctac 120
cgtttattcg atggtgcttg cgactacggc aacgaaaagg aagttggtga aggtatcagg 180
aaagccatct ccgaaggtct tgtttctaga aaggatatat ttgttgtttc aaagttatgg 240
aacaattttc accatcctga tcatgtaaaa ttagctttaa agaagacctt aagcgatatg 300
ggacttgatt atttagacct gtattatatt cacttcccaa tcgccttcaa atatgttcca 360
tttgaagaga aataccctcc aggattctat acgggcgcag atgacgagaa gaaaggtcac 420
atcaccgaag cacatgtacc aatcatagat acgtaccggg ctctggaaga atgtgttgat 480
gaaggcttga ttaagtctat tggtgtttcc aactttcagg gaagcttgat tcaagattta 540
ttacgtggtt gtagaatcaa gcccgtggct ttgcaaattg aacaccatcc ttatttgact 600
caagaacacc tagttgagtt ttgtaaatta cacgatatcc aagtagttgc ttactcctcc 660
ttcggtcctc aatcattcat tgagatggac ttacagttgg caaaaaccac gccaactctg 720
ttcgagaatg atgtaatcaa gaaggtctca caaaaccatc caggcagtac cacttcccaa 780
gtattgctta gatgggcaac tcagagaggc attgccgtca ttccaaaatc ttccaagaag 840
gaaaggttac ttggcaacct agaaatcgaa aaaaagttca ctttaacgga gcaagaattg 900
aaggatattt ctgcactaaa tgccaacatc agatttaatg atccatggac ctggttggat 960
ggtaaattcc ccacttttgc ctga 984

<210> SEQ ID NO 86
<211> LENGTH: 984
<212> TYPE: DNA
<213> ORGANISM: Saccharomyces cerevisiae

<400> SEQUENCE: 86
atgtcttcac tggttactct taataacggt ctgaaaatgc ccctagtcgg cttagggtgc 60
tggaaaattg acaaaaaagt ctgtgcgaat caaatttatg aagctatcaa attaggctac 120
cgtttattcg atggtgcttg cgactacggc aacgaaaagg aagttggtga aggtatcagg 180
aaagccatct ccgaaggtct tgtttctaga aaggatatat ttgttgtttc aaagttatgg 240
aacaattttc accatcctga tcatgtaaaa ttagctttaa agaagacctt aagcgatatg 300
ggacttgatt atttagacct gtattatatt cacttcccaa tcgccttcaa atatgttcca 360
tttgaagaga aataccctcc aggattctat acgggcgcag atgacgagaa gaaaggtcac 420
atcaccgaag cacatgtacc aatcatagat acgtaccggg ctctggaaga atgtgttgat 480
gaaggcttga ttaagtctat tggtgtttcc aactttcagg gaagcttgat tcaagattta 540
ttacgtggtt gtagaatcaa gcccgtggct ttgcaaattg aacaccatcc ttatttgact 600
caagaacacc tagttgagtt ttgtaaatta cacgatatcc aagtagttgc ttactcctcc 660
ttcggtcctc aatcattcat tgagatggac ttacagttgg caaaaaccac gccaactctg 720
ttcgagaatg atgtaatcaa gaaggtctca caaaaccatc caggcagtac cacttcccaa 780
gtattgctta gatgggcaac tcagagaggc attgccgtca ttccaaaatc ttccaagaag 840
gaaaggttac ttggcaacct agaaatcgaa aaaaagttca ctttaacgga gcaagaattg 900
aaggatattt ctgcactaaa tgccaacatc agatttaatg atccatggac ctggttggat 960
ggtaaattcc ccacttttgc ctga 984

<210> SEQ ID NO 87
<211> LENGTH: 327
<212> TYPE: PRT
<213> ORGANISM: Saccharomyces cerevisiae

<400> SEQUENCE: 87

```
Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
    210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
                325
```

<210> SEQ ID NO 88
<211> LENGTH: 1092

<212> TYPE: DNA
<213> ORGANISM: Scheffersomyces stipitis

<400> SEQUENCE: 88
atgactgcta acccttcctt ggtgttgaac aagatcgacg acatttcgtt cgaaacttac 60
gatgccccag aaatctctga acctaccgat gtcctcgtcc aggtcaagaa aaccggtatc 120
tgtggttccg acatccactt ctacgcccat ggtagaatcg gtaacttcgt tttgaccaag 180
ccaatggtct tgggtcacga atccgccggt actgttgtcc aggttggtaa gggtgtcacc 240
tctcttaagg ttggtgacaa cgtcgctatc gaaccaggta ttccatccag attctccgac 300
gaatacaaga gcggtcacta caacttgtgt cctcacatgg ccttcgccgc tactcctaac 360
tccaaggaag gcgaaccaaa cccaccaggt accttatgta agtacttcaa gtcgccagaa 420
gacttcttgg tcaagttgcc agaccacgtc agcttggaac tcggtgctct tgttgagcca 480
ttgtctgttg gtgtccacgc ctctaagttg ggttccgttg ctttcggcga ctacgttgcc 540
gtctttggtg ctggtcctgt tggtcttttg gctgctgctg tcgccaagac cttcggtgct 600
aagggtgtca tcgtcgttga cattttcgac aacaagttga agatggccaa ggacattggt 660
gctgctactc acaccttcaa ctccaagacc ggtggttctg aagaattgat caaggctttc 720
ggtggtaacg tgccaaacgt cgttttggaa tgtactggtg ctgaaccttg tatcaagttg 780
ggtgttgacg ccattgcccc aggtggtcgt ttcgttcaag tcggtaacgc tgctggtcca 840
gtcagcttcc caatcaccgt tttcgccatg aaggaattga ctttgttcgg ttctttcaga 900
tacggattca acgactacaa gactgctgtt ggaatctttg acactaacta ccaaaacggt 960
agagaaaatg ctccaattga ctttgaacaa ttgatcaccc acagatacaa gttcaaggac 1020
gctattgaag cctacgactt ggtcagagcc ggtaagggtg ctgtcaagtg tctcattgac 1080
ggccctgagt aa 1092

<210> SEQ ID NO 89
<211> LENGTH: 1092
<212> TYPE: DNA
<213> ORGANISM: Scheffersomyces stipitis

<400> SEQUENCE: 89
atgactgcta acccttcctt ggtgttgaac aagatcgacg acatttcgtt cgaaacttac 60
gatgccccag aaatctctga acctaccgat gtcctcgtcc aggtcaagaa aaccggtatc 120
tgtggttccg acatccactt ctacgcccat ggtagaatcg gtaacttcgt tttgaccaag 180
ccaatggtct tgggtcacga atccgccggt actgttgtcc aggttggtaa gggtgtcacc 240
tctcttaagg ttggtgacaa cgtcgctatc gaaccaggta ttccatccag attctccgac 300
gaatacaaga gcggtcacta caacttgtgt cctcacatgg ccttcgccgc tactcctaac 360
tccaaggaag gcgaaccaaa cccaccaggt accttatgta agtacttcaa gtcgccagaa 420
gatttcttgg tcaagttgcc agaccacgtc agcttggaac tcggtgctct tgttgagcca 480
ttgtctgttg gtgtccacgc ctctaagttg ggttccgttg ctttcggcga ctacgttgcc 540
gtctttggag caggtcctgt tggtcttttg gctgctgctg tcgccaagac cttcggtgct 600
aagggtgtca tcgtcgttga cattttcgac aacaagttga agatggccaa ggacattgga 660
gctgctactc acaccttcaa ctccaagacc ggtggttctg aagaattgat caaggctttc 720
ggtggtaacg tgccaaacgt cgttttggaa tgtacaggtg cagaaccttg tatcaagttg 780
ggtgttgacg ccattgcccc aggtggtcgt ttcgttcaag tcggtaacgc tgctggtcca 840

-continued

```
gtcagcttcc caatcaccgt tttcgccatg aaggaattga ctttgttcgg ttctttcaga    900

tacggattca acgactacaa gactgctgtt ggaatctttg acactaacta ccaaaacggt    960

agagaaaatg ctccaattga ctttgaacaa ttgatcaccc acagatacaa gttcaaggac   1020

gctattgaag cctacgactt ggtcagagcc ggtaagggtg ctgtcaagtg tctcattgac   1080

ggccctgagt aa                                                        1092


<210> SEQ ID NO 90
<211> LENGTH: 363
<212> TYPE: PRT
<213> ORGANISM: Scheffersomyces stipitis

<400> SEQUENCE: 90

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Phe Asp Asn Lys Leu Lys Met Ala Lys Asp Ile Gly Ala Ala Thr His
    210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
    290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
```

-continued

```
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360
```

<210> SEQ ID NO 91
<211> LENGTH: 1092
<212> TYPE: DNA
<213> ORGANISM: Trichoderma reesei

<400> SEQUENCE: 91

```
atggcgactc aaacgatcaa caaggatgcg atcagcaacc tctccttcgt cctcaacaag     60

cccggcgacg tgacctttga ggagcggccg aagccgacca tcacggaccc caacgacgtc    120

ctcgtcgccg tcaactacac gggcatctgc ggctccgacg tgcactactg ggtgcacggc    180

gccatcgggc acttcgtcgt caaggacccg atggtgctgg gccacgagtc ggccggcacc    240

gtcgtcgagg tcggcccggc cgtcaagagc ctcaagcccg gcgaccgcgt cgccctcgag    300

cccggctacc cgtgccggcg gtgctccttc tgccgcgccg gcaaatacaa cctgtgcccg    360

gacatggtct tcgccgccac gccgccgtac cacggcaccc tgacgggcct gtgggcggcg    420

cccgccgact tctgctacaa gctgccggac ggcgtgtcgc tgcaggaggg cgcgctgatc    480

gagccgctgg ccgtggccgt ccacattgtc aagcaggccc gcgtccagcc gggccagtcc    540

gtcgtcgtca tgggcgccgg ccccgtcggc ctgctgtgcg ccgccgtggc caaggcgtac    600

ggcgcctcca ccattgtcag cgtcgacatc gtgcagtcca agctcgactt tgcgcgcggc    660

ttctgctcga cgcacacgta cgtctcgcag cgcatctcgg ctgaggacaa cgcaaaggcc    720

atcaaggagc tggcgggcct gcccggcggc gccgacgtcg tgattgacgc cagcggcgcg    780

gagccgtcga tccagacgag cattcacgtc gtccgcatgg gcggcacgta cgtccagggc    840

ggcatgggca agagcgacat cacgttcccc atcatggcca tgtgcctcaa ggaggtgacg    900

gtccggggct cgttccgcta cggcgccggc gactacgagc tggcggtcga gctggtccgg    960

acggggcggg tggacgtcaa gaagctgatt acgggcaccg tcagcttcaa gcaggcggag   1020

gaggcgttcc aaaaggtcaa gtctggggag gccatcaaga ttctgattgc cgggcccaac   1080

gagaaggtgt aa                                                       1092
```

<210> SEQ ID NO 92
<211> LENGTH: 363
<212> TYPE: PRT
<213> ORGANISM: Trichoderma reesei

<400> SEQUENCE: 92

```
Met Ala Thr Gln Thr Ile Asn Lys Asp Ala Ile Ser Asn Leu Ser Phe
1               5                   10                  15

Val Leu Asn Lys Pro Gly Asp Val Thr Phe Glu Glu Arg Pro Lys Pro
            20                  25                  30

Thr Ile Thr Asp Pro Asn Asp Val Leu Val Ala Val Asn Tyr Thr Gly
        35                  40                  45

Ile Cys Gly Ser Asp Val His Tyr Trp Val His Gly Ala Ile Gly His
    50                  55                  60

Phe Val Val Lys Asp Pro Met Val Leu Gly His Glu Ser Ala Gly Thr
65                  70                  75                  80

Val Val Glu Val Gly Pro Ala Val Lys Ser Leu Lys Pro Gly Asp Arg
                85                  90                  95
```

-continued

```
Val Ala Leu Glu Pro Gly Tyr Pro Cys Arg Arg Cys Ser Phe Cys Arg
            100                 105                 110

Ala Gly Lys Tyr Asn Leu Cys Pro Asp Met Val Phe Ala Ala Thr Pro
        115                 120                 125

Pro Tyr His Gly Thr Leu Thr Gly Leu Trp Ala Ala Pro Ala Asp Phe
    130                 135                 140

Cys Tyr Lys Leu Pro Asp Gly Val Ser Leu Gln Glu Gly Ala Leu Ile
145                 150                 155                 160

Glu Pro Leu Ala Val Ala Val His Ile Val Lys Gln Ala Arg Val Gln
                165                 170                 175

Pro Gly Gln Ser Val Val Val Met Gly Ala Gly Pro Val Gly Leu Leu
            180                 185                 190

Cys Ala Ala Val Ala Lys Ala Tyr Gly Ala Ser Thr Ile Val Ser Val
        195                 200                 205

Asp Ile Val Gln Ser Lys Leu Asp Phe Ala Arg Gly Phe Cys Ser Thr
    210                 215                 220

His Thr Tyr Val Ser Gln Arg Ile Ser Ala Glu Asp Asn Ala Lys Ala
225                 230                 235                 240

Ile Lys Glu Leu Ala Gly Leu Pro Gly Gly Ala Asp Val Val Ile Asp
                245                 250                 255

Ala Ser Gly Ala Glu Pro Ser Ile Gln Thr Ser Ile His Val Val Arg
            260                 265                 270

Met Gly Gly Thr Tyr Val Gln Gly Gly Met Gly Lys Ser Asp Ile Thr
        275                 280                 285

Phe Pro Ile Met Ala Met Cys Leu Lys Glu Val Thr Val Arg Gly Ser
    290                 295                 300

Phe Arg Tyr Gly Ala Gly Asp Tyr Glu Leu Ala Val Glu Leu Val Arg
305                 310                 315                 320

Thr Gly Arg Val Asp Val Lys Lys Leu Ile Thr Gly Thr Val Ser Phe
                325                 330                 335

Lys Gln Ala Glu Glu Ala Phe Gln Lys Val Lys Ser Gly Glu Ala Ile
            340                 345                 350

Lys Ile Leu Ile Ala Gly Pro Asn Glu Lys Val
        355                 360
```

<210> SEQ ID NO 93
<211> LENGTH: 1314
<212> TYPE: DNA
<213> ORGANISM: Pyromyces sp.

<400> SEQUENCE: 93

```
atggctaagg aatatttccc acaaattcaa aagattaagt tcgaaggtaa ggattctaag      60

aatccattag ccttccacta ctacgatgct gaaaaggaag tcatgggtaa gaaaatgaag     120

gattggttac gtttcgccat ggcctggtgg cacactcttt gcgccgaagg tgctgaccaa     180

ttcggtggag gtacaaagtc tttcccatgg aacgaaggta ctgatgctat tgaaattgcc     240

aagcaaaagg ttgatgctgg tttcgaaatc atgcaaaagc ttggtattcc atactactgt     300

ttccacgatg ttgatcttgt ttccgaaggt aactctattg aagaatacga atccaacctt     360

aaggctgtcg ttgcttacct caaggaaaag caaaaggaaa ccggtattaa gcttctctgg     420

agtactgcta acgtcttcgg tcacaagcgt tacatgaacg gtgcctccac taacccagac     480

tttgatgttg tcgcccgtgc tattgttcaa attaagaacg ccatagacgc cggtattgaa     540

cttggtgctg aaaactacgt cttctggggt ggtcgtgaag gttacatgag tctccttaac     600
```

```
actgaccaaa agcgtgaaaa ggaacacatg gccactatgc ttaccatggc tcgtgactac    660

gctcgttcca agggattcaa gggtactttc ctcattgaac caaagccaat ggaaccaacc    720

aagcaccaat acgatgttga cactgaaacc gctattggtt tccttaaggc ccacaactta    780

gacaaggact tcaaggtcaa cattgaagtt aaccacgcta ctcttgctgg tcacactttc    840

gaacacgaac ttgcctgtgc tgttgatgct ggtatgctcg gttccattga tgctaaccgt    900

ggtgactacc aaaacggttg ggatactgat caattcccaa ttgatcaata cgaactcgtc    960

caagcttgga tggaaatcat ccgtggtggt ggtttcgtta ctggtggtac caacttcgat   1020

gccaagactc gtcgtaactc tactgacctc gaagacatca tcattgccca cgtttctggt   1080

atggatgcta tggctcgtgc tcttgaaaac gctgccaagc tcctccaaga atctccatac   1140

accaagatga agaaggaacg ttacgcttcc ttcgacagtg gtattggtaa ggactttgaa   1200

gatggtaagc tcaccctcga acaagtttac gaatacggta agaagaacgg tgaaccaaag   1260

caaacttctg gtaagcaaga actctacgaa gctattgttg ccatgtacca ataa         1314
```

```
<210> SEQ ID NO 94
<211> LENGTH: 1314
<212> TYPE: DNA
<213> ORGANISM: Pyromyces sp.

<400> SEQUENCE: 94

atggccaagg aatacttccc acaaatccaa aagattaaat tcgaaggtaa agattccaag     60

aacccattgg cttttcacta ctacgatgct gagaaggaag ttatgggtaa gaagatgaag    120

gattggttga gattcgctat ggcttggtgg cacactttgt gcgctgaagg tgctgaccaa    180

ttcggtggtg gtactaagtc tttcccatgg aacgaaggta ctgatgctat tgaaatcgct    240

aagcaaaaag tcgatgctgg ttttgagatt atgcaaaaat tgggtatccc atactactgt    300

ttccacgacg tcgacttggt ttctgaaggt aattctatcg aagaatacga atctaatttg    360

aaggctgttg tcgcttactt aaaagaaaag caaaaggaga ctggtattaa gttgttgtgg    420

tccaccgcta acgtctttgg tcataaaaga tacatgaacg gtgcttccac caacccagac    480

ttcgatgtcg tcgccagagc tatcgttcaa attaaaaacg ccatcgacgc tggtattgaa    540

ttgggtgctg aaaattacgt cttttggggt ggtcgtgaag gttacatgtc tttgttgaac    600

actgaccaaa agagagaaaa agaacacatg gccactatgt tgaccatggc cagagattac    660

gccagatcta agggtttcaa gggtaccttc ttaattgaac caaaacctat ggaaccaact    720

aagcaccaat acgacgttga cactgaaact gctatcggtt ttttgaaggc tcacaacttg    780

gataaggatt ttaaagtcaa cattgaagtt aaccatgcta ctttggctgg tcacactttt    840

gaacatgaat tggcctgtgc tgttgatgct ggtatgttgg gttctatcga tgctaataga    900

ggtgactatc aaaacggttg ggacactgat caattcccaa tcgatcaata tgaattagtt    960

caagcttgga tggaaattat cagaggtggt ggtttcgtta ctggtggtac taacttcgat   1020

gctaagacca gaagaaactc tactgatttg gaagatatta tcattgccca cgtttccggt   1080

atggatgcca tggccagagc tttggaaaac gccgccaagt tattgcaaga gtccccatac   1140

accaagatga aaaaggaacg ttacgcttct ttcgactctg gtatcggtaa agacttcgaa   1200

gatggtaagt tgaccttgga acaagtttac gaatacggta agaagaacgg tgaacctaaa   1260

caaacctctg gtaaacaaga attgtatgaa gctattgttg ccatgtacca ataa         1314

<210> SEQ ID NO 95
```

<211> LENGTH: 437
<212> TYPE: PRT
<213> ORGANISM: Pyromyces sp.

<400> SEQUENCE: 95

```
Met Ala Lys Glu Tyr Phe Pro Gln Ile Gln Lys Ile Lys Phe Glu Gly
1               5                   10                  15

Lys Asp Ser Lys Asn Pro Leu Ala Phe His Tyr Tyr Asp Ala Glu Lys
            20                  25                  30

Glu Val Met Gly Lys Lys Met Lys Asp Trp Leu Arg Phe Ala Met Ala
        35                  40                  45

Trp Trp His Thr Leu Cys Ala Glu Gly Ala Asp Gln Phe Gly Gly Gly
    50                  55                  60

Thr Lys Ser Phe Pro Trp Asn Glu Gly Thr Asp Ala Ile Glu Ile Ala
65                  70                  75                  80

Lys Gln Lys Val Asp Ala Gly Phe Glu Ile Met Gln Lys Leu Gly Ile
                85                  90                  95

Pro Tyr Tyr Cys Phe His Asp Val Asp Leu Val Ser Glu Gly Asn Ser
            100                 105                 110

Ile Glu Glu Tyr Glu Ser Asn Leu Lys Ala Val Val Ala Tyr Leu Lys
        115                 120                 125

Glu Lys Gln Lys Glu Thr Gly Ile Lys Leu Leu Trp Ser Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Glu Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Ala Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Gly Phe Val Thr Gly Gly
                325                 330                 335

Thr Asn Phe Asp Ala Lys Thr Arg Arg Asn Ser Thr Asp Leu Glu Asp
            340                 345                 350

Ile Ile Ile Ala His Val Ser Gly Met Asp Ala Met Ala Arg Ala Leu
        355                 360                 365

Glu Asn Ala Ala Lys Leu Leu Gln Glu Ser Pro Tyr Thr Lys Met Lys
    370                 375                 380

Lys Glu Arg Tyr Ala Ser Phe Asp Ser Gly Ile Gly Lys Asp Phe Glu
```

```
385                 390                 395                 400

Asp Gly Lys Leu Thr Leu Glu Gln Val Tyr Glu Tyr Gly Lys Lys Asn
                405                 410                 415

Gly Glu Pro Lys Gln Thr Ser Gly Lys Gln Glu Leu Tyr Glu Ala Ile
            420                 425                 430

Val Ala Met Tyr Gln
        435


<210> SEQ ID NO 96
<211> LENGTH: 657
<212> TYPE: DNA
<213> ORGANISM: Clostridium acetobutylicum

<400> SEQUENCE: 96

atgaactcta aaataattag atttgaaaat ttaaggtcat tctttaaaga tgggatgaca      60

attatgattg gaggtttttt aaactgtggc actccaacca aattaattga tttttttagtt    120

aatttaaata taaagaattt aacgattata agtaatgata catgttatcc taatacaggt     180

attggtaagt taatatcaaa taatcaagta aaaaagctta ttgcttcata tataggcagc     240

aacccagata ctggcaaaaa actttttaat aatgaacttg aagtagagct ctctccccaa     300

ggaactctag tggaaagaat acgtgcaggc ggatctggct taggtggtgt actaactaaa     360

acaggtttag gaactttgat tgaaaaagga aagaaaaaaa tatctataaa tggaacggaa     420

tatttgttag agctacctct tacagccgat gtagcattaa ttaaaggtag tattgtagat     480

gaggccggaa acaccttcta taaaggtact actaaaaact ttaatcccta tatggcaatg     540

gcagctaaaa ccgtaatagt tgaagctgaa aatttagtta gctgtgaaaa actagaaaag     600

gaaaaagcaa tgacccccgg agttcttata aattatatag taaaggagcc tgcataa        657


<210> SEQ ID NO 97
<211> LENGTH: 218
<212> TYPE: PRT
<213> ORGANISM: Clostridium acetobutylicum

<400> SEQUENCE: 97

Met Asn Ser Lys Ile Ile Arg Phe Glu Asn Leu Arg Ser Phe Phe Lys
1               5                   10                  15

Asp Gly Met Thr Ile Met Ile Gly Gly Phe Leu Asn Cys Gly Thr Pro
            20                  25                  30

Thr Lys Leu Ile Asp Phe Leu Val Asn Leu Asn Ile Lys Asn Leu Thr
        35                  40                  45

Ile Ile Ser Asn Asp Thr Cys Tyr Pro Asn Thr Gly Ile Gly Lys Leu
    50                  55                  60

Ile Ser Asn Asn Gln Val Lys Lys Leu Ile Ala Ser Tyr Ile Gly Ser
65                  70                  75                  80

Asn Pro Asp Thr Gly Lys Lys Leu Phe Asn Asn Glu Leu Glu Val Glu
                85                  90                  95

Leu Ser Pro Gln Gly Thr Leu Val Glu Arg Ile Arg Ala Gly Gly Ser
            100                 105                 110

Gly Leu Gly Gly Val Leu Thr Lys Thr Gly Leu Gly Thr Leu Ile Glu
        115                 120                 125

Lys Gly Lys Lys Lys Ile Ser Ile Asn Gly Thr Glu Tyr Leu Leu Glu
    130                 135                 140

Leu Pro Leu Thr Ala Asp Val Ala Leu Ile Lys Gly Ser Ile Val Asp
145                 150                 155                 160
```

```
Glu Ala Gly Asn Thr Phe Tyr Lys Gly Thr Thr Lys Asn Phe Asn Pro
                165                 170                 175

Tyr Met Ala Met Ala Ala Lys Thr Val Ile Val Glu Ala Glu Asn Leu
            180                 185                 190

Val Ser Cys Glu Lys Leu Glu Lys Glu Lys Ala Met Thr Pro Gly Val
        195                 200                 205

Leu Ile Asn Tyr Ile Val Lys Glu Pro Ala
    210                 215


<210> SEQ ID NO 98
<211> LENGTH: 666
<212> TYPE: DNA
<213> ORGANISM: Clostridium acetobutylicum

<400> SEQUENCE: 98

atgattaatg ataaaaacct agcgaaagaa ataatagcca aaagagttgc aagagaatta      60

aaaaatggtc aacttgtaaa cttaggtgta ggtcttccta ccatggttgc agattatata     120

ccaaaaaatt tcaaaattac tttccaatca gaaaacggaa tagttggaat gggcgctagt     180

cctaaaataa atgaggcaga taaagatgta gtaaatgcag gaggagacta tacaacagta     240

cttcctgacg gcacattttt cgatagctca gtttcgtttt cactaatccg tggtggtcac     300

gtagatgtta ctgttttagg ggctctccag gtagatgaaa agggtaatat agccaattgg     360

attgttcctg gaaaaatgct ctctggtatg ggtggagcta tggatttagt aaatggagct     420

aagaaagtaa taattgcaat gagacataca aataaaggtc aacctaaaat tttaaaaaaa     480

tgtacacttc ccctcacggc aaagtctcaa gcaaatctaa ttgtaacaga acttggagta     540

attgaggtta ttaatgatgg tttacttctc actgaaatta ataaaaacac aaccattgat     600

gaaataaggt ctttaactgc tgcagattta ctcatatcca atgaacttag acccatggct     660

gtttag                                                                666


<210> SEQ ID NO 99
<211> LENGTH: 221
<212> TYPE: PRT
<213> ORGANISM: Clostridium acetobutylicum

<400> SEQUENCE: 99

Met Ile Asn Asp Lys Asn Leu Ala Lys Glu Ile Ile Ala Lys Arg Val
1               5                   10                  15

Ala Arg Glu Leu Lys Asn Gly Gln Leu Val Asn Leu Gly Val Gly Leu
            20                  25                  30

Pro Thr Met Val Ala Asp Tyr Ile Pro Lys Asn Phe Lys Ile Thr Phe
        35                  40                  45

Gln Ser Glu Asn Gly Ile Val Gly Met Gly Ala Ser Pro Lys Ile Asn
    50                  55                  60

Glu Ala Asp Lys Asp Val Val Asn Ala Gly Gly Asp Tyr Thr Thr Val
65                  70                  75                  80

Leu Pro Asp Gly Thr Phe Phe Asp Ser Ser Val Ser Phe Ser Leu Ile
                85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
    130                 135                 140
```

-continued

Ile Ala Met Arg His Thr Asn Lys Gly Gln Pro Lys Ile Leu Lys Lys
145 150 155 160

Cys Thr Leu Pro Leu Thr Ala Lys Ser Gln Ala Asn Leu Ile Val Thr
165 170 175

Glu Leu Gly Val Ile Glu Val Ile Asn Asp Gly Leu Leu Leu Thr Glu
180 185 190

Ile Asn Lys Asn Thr Thr Ile Asp Glu Ile Arg Ser Leu Thr Ala Ala
195 200 205

Asp Leu Leu Ile Ser Asn Glu Leu Arg Pro Met Ala Val
210 215 220

<210> SEQ ID NO 100
<211> LENGTH: 651
<212> TYPE: DNA
<213> ORGANISM: Escherichia coli

<400> SEQUENCE: 100
atggatgcga aacaacgtat tgcgcgccgt gtggcgcaag agcttcgtga tggtgacatc 60
gttaacttag ggatcggttt acccacaatg gtcgccaatt atttaccgga gggtattcat 120
atcactctgc aatcggaaaa cggcttcctc ggtttaggcc cggtcacgac agcgcatcca 180
gatctggtga acgctggcgg gcaaccgtgc ggtgttttac ccggtgcagc catgtttgat 240
agcgccatgt catttgcgct aatccgtggc ggtcatattg atgcctgcgt gctcggcggt 300
ttgcaagtag acgaagaagc aaacctcgcg aactgggtag tgcctgggaa aatggtgccc 360
ggtatgggtg gcgcgatgga tctggtgacc gggtcgcgca aagtgatcat cgccatggaa 420
cattgcgcca aagatggttc agcaaaaatt ttgcgccgct gcaccatgcc actcactgcg 480
caacatgcgg tgcatatgct ggttactgaa ctggctgtct ttcgttttat tgacggcaaa 540
atgtggctca ccgaaattgc cgacgggtgt gatttagcca ccgtgcgtgc caaaacagaa 600
gctcggtttg aagtcgccgc cgatctgaat acgcaacggg gtgatttatg a 651

<210> SEQ ID NO 101
<211> LENGTH: 216
<212> TYPE: PRT
<213> ORGANISM: Escherichia coli

<400> SEQUENCE: 101

Met Asp Ala Lys Gln Arg Ile Ala Arg Arg Val Ala Gln Glu Leu Arg
1 5 10 15

Asp Gly Asp Ile Val Asn Leu Gly Ile Gly Leu Pro Thr Met Val Ala
20 25 30

Asn Tyr Leu Pro Glu Gly Ile His Ile Thr Leu Gln Ser Glu Asn Gly
35 40 45

Phe Leu Gly Leu Gly Pro Val Thr Thr Ala His Pro Asp Leu Val Asn
50 55 60

Ala Gly Gly Gln Pro Cys Gly Val Leu Pro Gly Ala Ala Met Phe Asp
65 70 75 80

Ser Ala Met Ser Phe Ala Leu Ile Arg Gly Gly His Ile Asp Ala Cys
85 90 95

Val Leu Gly Gly Leu Gln Val Asp Glu Glu Ala Asn Leu Ala Asn Trp
100 105 110

Val Val Pro Gly Lys Met Val Pro Gly Met Gly Gly Ala Met Asp Leu
115 120 125

Val Thr Gly Ser Arg Lys Val Ile Ile Ala Met Glu His Cys Ala Lys
130 135 140

-continued

Asp Gly Ser Ala Lys Ile Leu Arg Arg Cys Thr Met Pro Leu Thr Ala
145 150 155 160

Gln His Ala Val His Met Leu Val Thr Glu Leu Ala Val Phe Arg Phe
165 170 175

Ile Asp Gly Lys Met Trp Leu Thr Glu Ile Ala Asp Gly Cys Asp Leu
180 185 190

Ala Thr Val Arg Ala Lys Thr Glu Ala Arg Phe Glu Val Ala Ala Asp
195 200 205

Leu Asn Thr Gln Arg Gly Asp Leu
210 215

<210> SEQ ID NO 102
<211> LENGTH: 663
<212> TYPE: DNA
<213> ORGANISM: Escherichia coli

<400> SEQUENCE: 102
atgaaaacaa aattgatgac attacaagac gccaccggct tctttcgtga cggcatgacc 60
atcatggtgg gcggatttat ggggattggc actccatccc gcctggttga agcattactg 120
gaatctggtg ttcgcgacct gacattgata gccaatgata ccgcgtttgt tgataccggc 180
atcggtccgc tcatcgtcaa tggtcgagtc cgcaaagtga ttgcttcaca tatcggcacc 240
aacccggaaa caggtcggcg catgatatct ggtgagatgg acgtcgttct ggtgccgcaa 300
ggtacgctaa tcgagcaaat tcgctgtggt ggagctggac ttggtggttt tctcacccca 360
acgggtgtcg gcaccgtcgt agaggaaggc aaacagacac tgacactcga cggtaaaacc 420
tggctgctcg aacgcccact gcgcgccgac ctggcgctaa ttcgcgctca tcgttgcgac 480
acacttggca acctgaccta tcaacttagc gcccgcaact ttaacccccct gatagccctt 540 gcggctgata tcacgctggt agagccagat gaactggtcg aaaccggcga gctgcaacct 600
gaccatattg tcacccctgg tgccgttatc gaccacatca tcgtttcaca ggagagcaaa 660
taa 663

<210> SEQ ID NO 103
<211> LENGTH: 220
<212> TYPE: PRT
<213> ORGANISM: Escherichia coli

<400> SEQUENCE: 103

Met Lys Thr Lys Leu Met Thr Leu Gln Asp Ala Thr Gly Phe Phe Arg
1 5 10 15

Asp Gly Met Thr Ile Met Val Gly Gly Phe Met Gly Ile Gly Thr Pro
20 25 30

Ser Arg Leu Val Glu Ala Leu Leu Glu Ser Gly Val Arg Asp Leu Thr
35 40 45

Leu Ile Ala Asn Asp Thr Ala Phe Val Asp Thr Gly Ile Gly Pro Leu
50 55 60

Ile Val Asn Gly Arg Val Arg Lys Val Ile Ala Ser His Ile Gly Thr
65 70 75 80

Asn Pro Glu Thr Gly Arg Arg Met Ile Ser Gly Glu Met Asp Val Val
85 90 95

Leu Val Pro Gln Gly Thr Leu Ile Glu Gln Ile Arg Cys Gly Gly Ala
100 105 110

Gly Leu Gly Gly Phe Leu Thr Pro Thr Gly Val Gly Thr Val Val Glu
115 120 125

```
Glu Gly Lys Gln Thr Leu Thr Leu Asp Gly Lys Thr Trp Leu Leu Glu
    130                 135                 140

Arg Pro Leu Arg Ala Asp Leu Ala Leu Ile Arg Ala His Arg Cys Asp
145                 150                 155                 160

Thr Leu Gly Asn Leu Thr Tyr Gln Leu Ser Ala Arg Asn Phe Asn Pro
                165                 170                 175

Leu Ile Ala Leu Ala Ala Asp Ile Thr Leu Val Glu Pro Asp Glu Leu
            180                 185                 190

Val Glu Thr Gly Glu Leu Gln Pro Asp His Ile Val Thr Pro Gly Ala
        195                 200                 205

Val Ile Asp His Ile Ile Val Ser Gln Glu Ser Lys
    210                 215                 220
```

<210> SEQ ID NO 104
<211> LENGTH: 1056
<212> TYPE: DNA
<213> ORGANISM: Clostridium beijerinckii

<400> SEQUENCE: 104

```
atgaaaggtt ttgcaatgct aggtattaat aagttaggat ggatcgaaaa agaaaggcca     60

gttgcgggtt catatgatgc tattgtacgc ccattagcag tatctccgtg tacatcagat    120

atacatactg tttttgaggg agctcttgga gataggaaga atatgatttt agggcatgaa    180

gctgtaggtg aagttgttga agtaggaagt gaagtgaagg attttaaacc tggtgacaga    240

gttatagttc cttgtacaac tccagattgg agatctttgg aagttcaagc tggttttcaa    300

cagcactcaa acggtatgct cgcaggatgg aaattttcaa atttcaagga tggagttttt    360

ggtgaatatt ttcatgtaaa tgatgcggat atgaatcttg cgattctacc taaagacatg    420

ccattagaaa atgctgttat gataacagat atgatgacta ctggatttca tggagcagaa    480

cttgcagata ttcaaatggg ttcaagtgtt gtggtaattg gcattggagc tgttggctta    540

atgggaatag caggtgctaa attacgtgga gcaggtagaa taattggagt ggggagcagg    600

ccgatttgtg ttgaggctgc aaaattttat ggagcaacag atattctaaa ttataaaaat    660

ggtcatatag ttgatcaagt tatgaaatta acgaatggaa aaggcgttga ccgcgtaatt    720

atggcaggcg gtggttctga aacattatcc caagcagtat ctatggttaa accaggagga    780

ataatttcta atataaatta tcatggaagt ggagatgctt tactaatacc acgtgtagaa    840

tggggatgtg gaatggctca caagactata aaaggaggtc tttgtcctgg gggacgtttg    900

agagcagaaa tgttaagaga tatggtagta tataatcgtg ttgatctaag taaattagtt    960

acacatgtat atcatggatt tgatcacata gaagaagcac tgttattaat gaaagacaag   1020

ccaaaagact taattaaagc agtagttata ttataa                             1056
```

<210> SEQ ID NO 105
<211> LENGTH: 1056
<212> TYPE: DNA
<213> ORGANISM: Clostridium beijerinckii

<400> SEQUENCE: 105

```
atgaaagggt ttgccatgtt aggtatcaat aaactgggct ggattgaaaa agagcgcccg     60

gtggcgggtt catacgatgc aattgttcgt ccgctggccg tcagtccgtg caccagcgac    120

atccatacag tctttgaagg tgccctgggt gatcggaaaa acatgattct gggccatgaa    180

gccgtaggcg aagtagtgga agtgggcagc gaggtaaagg atttcaaacc gggtgatcgc    240
```

```
gtaattgttc cttgcacgac cccagattgg cgctcactgg aagttcaggc tggttttcag    300

cagcatagta acggtatgtt agcaggctgg aagtttagca attttaaaga cggggtgttc    360

ggggagtatt ttcatgtcaa cgatgcggac atgaatctgg ctattttacc taaagatatg    420

ccgctggaga acgcagtgat gattaccgac atgatgacga caggctttca cggtgcagaa    480

ctggctgaca tccaaatggg ctccagtgtg gtggttatcg gtattggtgc ggtcgggctg    540

atgggtatcg cgggcgcgaa attacggggc gctggtcgca tcatcggtgt cggcagccgt    600

ccaatttgcg ttgaagcagc taaattctat ggtgccacgg acattctgaa ctataaaaat    660

ggtcacatcg tcgatcaggt gatgaaactg accaatggca aaggtgtgga ccgcgtgatc    720

atggcgggcg gcggctcaga gactttatct caagcggtgt ctatggttaa acctgggggc    780

atcatttcta atattaacta tcatggctcc ggcgacgcat tactgatccc gcgtgttgaa    840

tggggctgtg ggatggccca caaaaccatt aaagggggt tatgtccggg tggtcgcctg    900

cgtgccgaaa tgctgcgtga catggtggtt tacaaccgtg tggatctgtc caaactggta    960

actcacgtat accacggttt cgatcacatt gaagaggcgc tgctgctgat gaaggataag   1020

ccaaaggatc tgattaaggc ggttgttatc ctgtaa                             1056
```

<210> SEQ ID NO 106
<211> LENGTH: 351
<212> TYPE: PRT
<213> ORGANISM: Clostridium beijerinckii

<400> SEQUENCE: 106

```
Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Val Ile Gly Ile Gly
                165                 170                 175

Ala Val Gly Leu Met Gly Ile Ala Gly Ala Lys Leu Arg Gly Ala Gly
            180                 185                 190

Arg Ile Ile Gly Val Gly Ser Arg Pro Ile Cys Val Glu Ala Ala Lys
        195                 200                 205

Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
```

-continued

```
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
            260                 265                 270

Ala Leu Leu Ile Pro Arg Val Glu Trp Gly Cys Gly Met Ala His Lys
        275                 280                 285

Thr Ile Lys Gly Gly Leu Cys Pro Gly Gly Arg Leu Arg Ala Glu Met
    290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
            340                 345                 350


<210> SEQ ID NO 107
<211> LENGTH: 2580
<212> TYPE: DNA
<213> ORGANISM: Clostridium carboxidivorans

<400> SEQUENCE: 107

atgaaggtaa ctaatgttga agaactgatg aaaaaaatgc aggaagtgca aaatgctcaa     60

aaaaaatttg ggagttttac tcaggaacaa gtagatgaaa ttttcaggca agcagcacta    120

gcagctaaca gtgccagaat agatctagct aaaatggcag tggaagaaac taaaatggga    180

attgtagagg ataaggttat aaaaaatcat tttgttgcag aatacatata taataagtat    240

aaaaatgaaa aaacttgtgg gattttggaa gaagatgaag gctttggaat ggttaaaatt    300

gcagaacctg taggtgtgat tgcagcagta attccaacaa caaatccaac atctacagca    360

atatttaaag cattattagc tttgaaaaca agaaatggta taattttttc accacatcca    420

agagcaaaaa agtgtactat tgcagcagct aagttagttc ttgatgctgc agttaaagca    480

ggtgctccta aaggaattat aggttggata gatgaacctt ctattgaact ttcacagata    540

gtaatgaaag aagctgatat aatccttgca acaggtggtc caggtatggt taaagcagct    600

tattcttcag gtaaacctgc tataggggtt ggtcctggta acacacctgc tttaattgat    660

gaaagtgctg atattaaaat ggcagtaaat tcaatacttc tttccaaaac ttttgataat    720

ggtatgattt gtgcttcaga gcagtcggta gtagttgtag attcaatata tgaagaagtt    780

aagaaagaat ttgctcatag aggagcttat attttaagta aggatgaaac aactaaagtt    840

ggaaaaatac tcttagttaa tggtacatta aatgctggta tcgttggtca gagtgcttat    900

aaaatagcag aaatggcagg agttaaagtt ccagaagatg ctaaagttct tataggagaa    960

gtaaaatcag tggagcattc agaagagcca ttttcacatg aaaagttatc tccagtttta   1020

gctatgtata gagctaaaaa ttttgatgaa gctcttttaa aagctggaag attagttgaa   1080

ctcggtggaa tgggtcatac atctgtatta tatgtaaatg caataactga aaaagtaaaa   1140

gtagaaaaat ttagagaaac tatgaagact ggtagaacat taataaatat gccttcagca   1200

caaggtgcta taggagacat atataacttt aaactagctc cttcattaac attaggttgt   1260

ggttcatggg gaggaaactc cgtatcagaa aatgttggac ctaaacactt attaaatata   1320

aaaagtgttg ctgagaggag agaaaatatg ctttggttta gagttcctga aaaggtttat   1380

tttaaatatg gtagtcttgg agttgcatta aaagaattag atattttgga taagaaaaaa   1440
```

-continued

```
gtatttatag taacagataa agttctttat caattaggtt atatagatag agttacaaag   1500

attcttgaag aattgaaaat ttcatataaa atatttacag atgtagaacc agatccaacc   1560

ctagctacag ctaaaaaagg tgcagaagaa ttgttatcat ttaatccaga tactattata   1620

gcagttggtg gtggttcagc aatggatgct gctaagatta tgtgggtaat gtatgaacat   1680

ccggaagtaa gatttgaaga tttagctatg agatttatgg atataagaaa gagagtatat   1740

acttttccta agatgggtga aaaagcaatg atgatttctg ttgcaacatc agcaggaaca   1800

ggatcagaag taacaccttt tgcagtaatt actgatgaaa aaacaggagc taaatatcca   1860

ttagctgatt atgaattaac tccaaatatg gctataattg atgctgaact tatgatgggt   1920

atgccaaaag gattaacagc agcttcagga atagatgcac taactcatgc aatagaagct   1980

tatgtatcaa taatggcttc agaatatact aatggattag cgttagaagc aataagattg   2040

atatttaagt atttaccaat agcttacagt gaaggaacaa caagtataaa ggcaagagaa   2100

aaaatggcgc atgcttcaac aatagctggt atggcatttg ctaatgcatt tttaggagta   2160

tgtcattcaa tggcacataa attaggatca actcatcacg taccacatgg cattgccaat   2220

gcactactta taaatgaagt tataaaattt aatgcagtag aaaatccaag aaaacaagct   2280

gcatttccac aatataagta tccaaatata aaaaagagat atgctagaat agcagattac   2340

cttaacttag gtgggtcaac agacgatgaa aaagtacaat tattaataaa tgctatagat   2400

gaattaaaag ctaagataaa tattccagaa agtattaaag aagcaggagt aacagaagaa   2460

aaattttatg ctactttaga taaaatgtca gaattagctt ttgatgatca atgtacaggt   2520

gcaaacccta gatatccatt aataagtgaa ataaaacaaa tgtatgtaaa tgcattttaa   2580
```

<210> SEQ ID NO 108
<211> LENGTH: 859
<212> TYPE: PRT
<213> ORGANISM: Clostridium carboxidivorans

<400> SEQUENCE: 108

```
Met Lys Val Thr Asn Val Glu Glu Leu Met Lys Lys Met Gln Glu Val
1               5                   10                  15

Gln Asn Ala Gln Lys Lys Phe Gly Ser Phe Thr Gln Glu Gln Val Asp
            20                  25                  30

Glu Ile Phe Arg Gln Ala Ala Leu Ala Ala Asn Ser Ala Arg Ile Asp
        35                  40                  45

Leu Ala Lys Met Ala Val Glu Glu Thr Lys Met Gly Ile Val Glu Asp
    50                  55                  60

Lys Val Ile Lys Asn His Phe Val Ala Glu Tyr Ile Tyr Asn Lys Tyr
65                  70                  75                  80

Lys Asn Glu Lys Thr Cys Gly Ile Leu Glu Glu Asp Glu Gly Phe Gly
                85                  90                  95

Met Val Lys Ile Ala Glu Pro Val Gly Val Ile Ala Ala Val Ile Pro
            100                 105                 110

Thr Thr Asn Pro Thr Ser Thr Ala Ile Phe Lys Ala Leu Leu Ala Leu
        115                 120                 125

Lys Thr Arg Asn Gly Ile Ile Phe Ser Pro His Pro Arg Ala Lys Lys
    130                 135                 140

Cys Thr Ile Ala Ala Ala Lys Leu Val Leu Asp Ala Ala Val Lys Ala
145                 150                 155                 160

Gly Ala Pro Lys Gly Ile Ile Gly Trp Ile Asp Glu Pro Ser Ile Glu
                165                 170                 175
```

-continued

```
Leu Ser Gln Ile Val Met Lys Glu Ala Asp Ile Ile Leu Ala Thr Gly
            180                 185                 190

Gly Pro Gly Met Val Lys Ala Ala Tyr Ser Ser Gly Lys Pro Ala Ile
        195                 200                 205

Gly Val Gly Pro Gly Asn Thr Pro Ala Leu Ile Asp Glu Ser Ala Asp
    210                 215                 220

Ile Lys Met Ala Val Asn Ser Ile Leu Leu Ser Lys Thr Phe Asp Asn
225                 230                 235                 240

Gly Met Ile Cys Ala Ser Glu Gln Ser Val Val Val Val Asp Ser Ile
                245                 250                 255

Tyr Glu Glu Val Lys Lys Glu Phe Ala His Arg Gly Ala Tyr Ile Leu
            260                 265                 270

Ser Lys Asp Glu Thr Thr Lys Val Gly Lys Ile Leu Leu Val Asn Gly
        275                 280                 285

Thr Leu Asn Ala Gly Ile Val Gly Gln Ser Ala Tyr Lys Ile Ala Glu
    290                 295                 300

Met Ala Gly Val Lys Val Pro Glu Asp Ala Lys Val Leu Ile Gly Glu
305                 310                 315                 320

Val Lys Ser Val Glu His Ser Glu Glu Pro Phe Ser His Glu Lys Leu
                325                 330                 335

Ser Pro Val Leu Ala Met Tyr Arg Ala Lys Asn Phe Asp Glu Ala Leu
            340                 345                 350

Leu Lys Ala Gly Arg Leu Val Glu Leu Gly Gly Met Gly His Thr Ser
        355                 360                 365

Val Leu Tyr Val Asn Ala Ile Thr Glu Lys Val Lys Val Glu Lys Phe
    370                 375                 380

Arg Glu Thr Met Lys Thr Gly Arg Thr Leu Ile Asn Met Pro Ser Ala
385                 390                 395                 400

Gln Gly Ala Ile Gly Asp Ile Tyr Asn Phe Lys Leu Ala Pro Ser Leu
                405                 410                 415

Thr Leu Gly Cys Gly Ser Trp Gly Gly Asn Ser Val Ser Glu Asn Val
            420                 425                 430

Gly Pro Lys His Leu Leu Asn Ile Lys Ser Val Ala Glu Arg Arg Glu
        435                 440                 445

Asn Met Leu Trp Phe Arg Val Pro Glu Lys Val Tyr Phe Lys Tyr Gly
    450                 455                 460

Ser Leu Gly Val Ala Leu Lys Glu Leu Asp Ile Leu Asp Lys Lys Lys
465                 470                 475                 480

Val Phe Ile Val Thr Asp Lys Val Leu Tyr Gln Leu Gly Tyr Ile Asp
                485                 490                 495

Arg Val Thr Lys Ile Leu Glu Glu Leu Lys Ile Ser Tyr Lys Ile Phe
            500                 505                 510

Thr Asp Val Glu Pro Asp Pro Thr Leu Ala Thr Ala Lys Lys Gly Ala
        515                 520                 525

Glu Glu Leu Leu Ser Phe Asn Pro Asp Thr Ile Ile Ala Val Gly Gly
    530                 535                 540

Gly Ser Ala Met Asp Ala Ala Lys Ile Met Trp Val Met Tyr Glu His
545                 550                 555                 560

Pro Glu Val Arg Phe Glu Asp Leu Ala Met Arg Phe Met Asp Ile Arg
                565                 570                 575

Lys Arg Val Tyr Thr Phe Pro Lys Met Gly Glu Lys Ala Met Met Ile
            580                 585                 590

Ser Val Ala Thr Ser Ala Gly Thr Gly Ser Glu Val Thr Pro Phe Ala
```

-continued

```
        595                 600                 605

Val Ile Thr Asp Glu Lys Thr Gly Ala Lys Tyr Pro Leu Ala Asp Tyr
    610                 615                 620

Glu Leu Thr Pro Asn Met Ala Ile Ile Asp Ala Glu Leu Met Met Gly
625                 630                 635                 640

Met Pro Lys Gly Leu Thr Ala Ala Ser Gly Ile Asp Ala Leu Thr His
                645                 650                 655

Ala Ile Glu Ala Tyr Val Ser Ile Met Ala Ser Glu Tyr Thr Asn Gly
            660                 665                 670

Leu Ala Leu Glu Ala Ile Arg Leu Ile Phe Lys Tyr Leu Pro Ile Ala
        675                 680                 685

Tyr Ser Glu Gly Thr Thr Ser Ile Lys Ala Arg Glu Lys Met Ala His
    690                 695                 700

Ala Ser Thr Ile Ala Gly Met Ala Phe Ala Asn Ala Phe Leu Gly Val
705                 710                 715                 720

Cys His Ser Met Ala His Lys Leu Gly Ser Thr His His Val Pro His
                725                 730                 735

Gly Ile Ala Asn Ala Leu Leu Ile Asn Glu Val Ile Lys Phe Asn Ala
            740                 745                 750

Val Glu Asn Pro Arg Lys Gln Ala Ala Phe Pro Gln Tyr Lys Tyr Pro
        755                 760                 765

Asn Ile Lys Lys Arg Tyr Ala Arg Ile Ala Asp Tyr Leu Asn Leu Gly
    770                 775                 780

Gly Ser Thr Asp Asp Glu Lys Val Gln Leu Leu Ile Asn Ala Ile Asp
785                 790                 795                 800

Glu Leu Lys Ala Lys Ile Asn Ile Pro Glu Ser Ile Lys Glu Ala Gly
                805                 810                 815

Val Thr Glu Glu Lys Phe Tyr Ala Thr Leu Asp Lys Met Ser Glu Leu
            820                 825                 830

Ala Phe Asp Asp Gln Cys Thr Gly Ala Asn Pro Arg Tyr Pro Leu Ile
        835                 840                 845

Ser Glu Ile Lys Gln Met Tyr Val Asn Ala Phe
    850                 855
```

<210> SEQ ID NO 109
<211> LENGTH: 1401
<212> TYPE: DNA
<213> ORGANISM: Escherichia coli

<400> SEQUENCE: 109

```
atgccacatt cctacgatta cgatgccata gtaataggtt ccggccccgg cggcgaaggc      60

gctgcaatgg gcctggttaa gcaaggtgcg cgcgtcgcag ttatcgagcg ttatcaaaat     120

gttggcggcg gttgcaccca ctggggcacc atcccgtcga aagctctccg tcacgccgtc     180

agccgcatta tagaattcaa tcaaaaccca ctttacagcg accattcccg actgctccgc     240

tcttcttttg ccgatatcct taaccatgcc gataacgtga ttaatcaaca aacgcgcatg     300

cgtcagggat tttacgaacg taatcactgt gaaatattgc agggaaacgc tcgctttgtt     360

gacgagcata cgttggcgct ggattgcccg gacggcagcg ttgaaacact aaccgctgaa     420

aaatttgtta ttgcctgcgg ctctcgtcca tatcatccaa cagatgttga tttcacccat     480

ccacgcattt acgacagcga ctcaattctc agcatgcacc acgaaccgcg ccatgtactt     540

atctatggtg ctggagtgat cggctgtgaa tatgcgtcga tcttccgcgg tatggatgta     600

aaagtggatc tgatcaacac ccgcgatcgc ctgctggcat ttctcgatca agagatgtca     660
```

```
gattctctct cctatcactt ctggaacagt ggcgtagtga ttcgtcacaa cgaagagtac    720

gagaagatcg aaggctgtga cgatggtgtg atcatgcatc tgaagtcggg taaaaaactg    780

aaagctgact gcctgctcta tgccaacggt cgcaccggta ataccgattc gctggcgtta    840

cagaacattg ggctagaaac tgacagccgc ggacagctga aggtcaacag catgtatcag    900

accgcacagc cacacgttta cgcggtgggc gacgtgattg gttatccgag cctggcgtcg    960

gcggcctatg accaggggcg cattgccgcg caggcgctgg taaaaggcga agccaccgca   1020

catctgattg aagatatccc taccggtatt tacaccatcc cggaaatcag ctctgtgggc   1080

aaaaccgaac agcagctgac cgcaatgaaa gtgccatatg aagtgggccg cgcccagttt   1140

aaacatctgg cacgcgcaca aatcgtcggc atgaacgtgg gcacgctgaa aattttgttc   1200

catcgggaaa caaaagagat tctgggtatt cactgctttg gcgagcgcgc tgccgaaatt   1260

attcatatcg gtcaggcgat tatggaacag aaaggtggcg gcaacactat tgagtacttc   1320

gtcaacacca cctttaacta cccgacgatg gcggaagcct atcgggtagc tgcgttaaac   1380

ggtttaaacc gcctgtttta a                                             1401


<210> SEQ ID NO 110
<211> LENGTH: 466
<212> TYPE: PRT
<213> ORGANISM: Escherichia coli

<400> SEQUENCE: 110

Met Pro His Ser Tyr Asp Tyr Asp Ala Ile Val Ile Gly Ser Gly Pro
1               5                   10                  15

Gly Gly Glu Gly Ala Ala Met Gly Leu Val Lys Gln Gly Ala Arg Val
            20                  25                  30

Ala Val Ile Glu Arg Tyr Gln Asn Val Gly Gly Gly Cys Thr His Trp
        35                  40                  45

Gly Thr Ile Pro Ser Lys Ala Leu Arg His Ala Val Ser Arg Ile Ile
    50                  55                  60

Glu Phe Asn Gln Asn Pro Leu Tyr Ser Asp His Ser Arg Leu Leu Arg
65                  70                  75                  80

Ser Ser Phe Ala Asp Ile Leu Asn His Ala Asp Asn Val Ile Asn Gln
                85                  90                  95

Gln Thr Arg Met Arg Gln Gly Phe Tyr Glu Arg Asn His Cys Glu Ile
            100                 105                 110

Leu Gln Gly Asn Ala Arg Phe Val Asp Glu His Thr Leu Ala Leu Asp
        115                 120                 125

Cys Pro Asp Gly Ser Val Glu Thr Leu Thr Ala Glu Lys Phe Val Ile
    130                 135                 140

Ala Cys Gly Ser Arg Pro Tyr His Pro Thr Asp Val Asp Phe Thr His
145                 150                 155                 160

Pro Arg Ile Tyr Asp Ser Asp Ser Ile Leu Ser Met His His Glu Pro
                165                 170                 175

Arg His Val Leu Ile Tyr Gly Ala Gly Val Ile Gly Cys Glu Tyr Ala
            180                 185                 190

Ser Ile Phe Arg Gly Met Asp Val Lys Val Asp Leu Ile Asn Thr Arg
        195                 200                 205

Asp Arg Leu Leu Ala Phe Leu Asp Gln Glu Met Ser Asp Ser Leu Ser
    210                 215                 220

Tyr His Phe Trp Asn Ser Gly Val Val Ile Arg His Asn Glu Glu Tyr
225                 230                 235                 240
```

```
Glu Lys Ile Glu Gly Cys Asp Asp Gly Val Ile Met His Leu Lys Ser
                245                 250                 255

Gly Lys Lys Leu Lys Ala Asp Cys Leu Leu Tyr Ala Asn Gly Arg Thr
            260                 265                 270

Gly Asn Thr Asp Ser Leu Ala Leu Gln Asn Ile Gly Leu Glu Thr Asp
        275                 280                 285

Ser Arg Gly Gln Leu Lys Val Asn Ser Met Tyr Gln Thr Ala Gln Pro
    290                 295                 300

His Val Tyr Ala Val Gly Asp Val Ile Gly Tyr Pro Ser Leu Ala Ser
305                 310                 315                 320

Ala Ala Tyr Asp Gln Gly Arg Ile Ala Ala Gln Ala Leu Val Lys Gly
                325                 330                 335

Glu Ala Thr Ala His Leu Ile Glu Asp Ile Pro Thr Gly Ile Tyr Thr
            340                 345                 350

Ile Pro Glu Ile Ser Ser Val Gly Lys Thr Glu Gln Gln Leu Thr Ala
        355                 360                 365

Met Lys Val Pro Tyr Glu Val Gly Arg Ala Gln Phe Lys His Leu Ala
    370                 375                 380

Arg Ala Gln Ile Val Gly Met Asn Val Gly Thr Leu Lys Ile Leu Phe
385                 390                 395                 400

His Arg Glu Thr Lys Glu Ile Leu Gly Ile His Cys Phe Gly Glu Arg
                405                 410                 415

Ala Ala Glu Ile Ile His Ile Gly Gln Ala Ile Met Glu Gln Lys Gly
            420                 425                 430

Gly Gly Asn Thr Ile Glu Tyr Phe Val Asn Thr Thr Phe Asn Tyr Pro
        435                 440                 445

Thr Met Ala Glu Ala Tyr Arg Val Ala Ala Leu Asn Gly Leu Asn Arg
    450                 455                 460

Leu Phe
465
```

<210> SEQ ID NO 111
<211> LENGTH: 41
<212> TYPE: DNA
<213> ORGANISM: artificial
<220> FEATURE:
<223> OTHER INFORMATION: Forward primer to amplify fucA and fucO

<400> SEQUENCE: 111
cctttaataa ggagatatac catggaacga aataaacttg c 41

<210> SEQ ID NO 112
<211> LENGTH: 56
<212> TYPE: DNA
<213> ORGANISM: artificial
<220> FEATURE:
<223> OTHER INFORMATION: Reverse primer to amplify fucA and fucO

<400> SEQUENCE: 112
ggttattcct ccttatttag agctctaaac gaattcttac caggcggtat ggtaaa 56

<210> SEQ ID NO 113
<211> LENGTH: 56
<212> TYPE: DNA
<213> ORGANISM: artificial
<220> FEATURE:
<223> OTHER INFORMATION: Forward primer to amplify fucK

<400> SEQUENCE: 113
gaattcgttt agagctctaa ataaggagga ataaccatga tgaaacaaga agttat 56

<210> SEQ ID NO 114
<211> LENGTH: 40
<212> TYPE: DNA
<213> ORGANISM: artificial
<220> FEATURE:
<223> OTHER INFORMATION: Reverse primer to amplify fucK

<400> SEQUENCE: 114
gagctcggta cccggggatc caaaaaaccc ctcaagaccc 40

<210> SEQ ID NO 115
<211> LENGTH: 39
<212> TYPE: DNA
<213> ORGANISM: artificial
<220> FEATURE:
<223> OTHER INFORMATION: Forward primer to amplify thl

<400> SEQUENCE: 115
ctgttgttat attgtaatga tgtatgcaag agggataaa 39

<210> SEQ ID NO 116
<211> LENGTH: 38
<212> TYPE: DNA
<213> ORGANISM: artificial
<220> FEATURE:
<223> OTHER INFORMATION: Reverse primer to amplify thl

<400> SEQUENCE: 116
tatatctcct tcttaaagtt cataaatcac cccgttgc 38

<210> SEQ ID NO 117
<211> LENGTH: 21
<212> TYPE: DNA
<213> ORGANISM: artificial
<220> FEATURE:
<223> OTHER INFORMATION: Forward primer to amplify fucO

<400> SEQUENCE: 117
atggctaaca gaatgattct g 21

<210> SEQ ID NO 118
<211> LENGTH: 23
<212> TYPE: DNA
<213> ORGANISM: artificial
<220> FEATURE:
<223> OTHER INFORMATION: Reverse primer to amplify fucO

<400> SEQUENCE: 118
ttaccaggcg gtatggtaaa gct 23

<210> SEQ ID NO 119
<211> LENGTH: 39
<212> TYPE: DNA
<213> ORGANISM: artificial
<220> FEATURE:
<223> OTHER INFORMATION: Forward primer to amplify atoA/D

<400> SEQUENCE: 119
ctgttgttat attgtaatga tgtatgcaag agggataaa 39

<210> SEQ ID NO 120
<211> LENGTH: 38
<212> TYPE: DNA

-continued

```
<213> ORGANISM: artificial
<220> FEATURE:
<223> OTHER INFORMATION: Reverse primer to amplify atoA/D

<400> SEQUENCE: 120

tatatctcct tcttaaagtt cataaatcac cccgttgc                    38
```

MODULATION OF CARBON FLUX THROUGH THE MEG AND C3 PATHWAYS FOR THE IMPROVED PRODUCTION OF MONOETHYLENE GLYCOL AND C3 COMPOUNDS

CROSS-REFERENCE TO RELATED APPLICATION

This application claims priority to U.S. Provisional Application No. 62/786,294 filed Dec. 28, 2018, entitled "METABOLIC ENGINEERING FOR THE IMPROVED PRODUCTION OF MONOETHYLENE GLYCOL AND C3 COMPOUNDS"; U.S. Provisional Application No. 62/786,298 filed Dec. 28, 2018, entitled "METABOLIC ENGINEERING OF THE ACETATE PATHWAY FOR THE IMPROVED PRODUCTION OF MONOETHYLENE GLYCOL AND C3 COMPOUNDS"; U.S. Provisional Application No. 62/786,282 filed Dec. 28, 2018, entitled "METABOLIC ENGINEERING OF XYLONATE PATHWAY FOR THE IMPROVED PRODUCTION OF MONOETHYLENE GLYCOL AND C3 COMPOUNDS"; U.S. Provisional Application No. 62/786,283 filed Dec. 28, 2018, entitled "MODULATION OF ENZYMES FOR IMPROVED FLUX THROUGH THE C3 PATHWAY FOR THE IMPROVED PRODUCTION OF MONOETHYLENE GLYCOL AND C3 COMPOUNDS"; U.S. Provisional Application No. 62/786,304 filed Dec. 28, 2018, entitled "MODULATION OF CARBON FLUX THROUGH THE MEG AND C3 PATHWAYS FOR THE IMPROVED PRODUCTION OF MONOETHYLENE GLYCOL AND C3 COMPOUNDS", the disclosures of which are incorporated by reference herein.

FIELD

The present disclosure relates to recombinant microorganisms useful in the biosynthesis of monoethylene glycol (MEG) and one or more three-carbon (C3) compounds. The application further relates to the methods of producing MEG and one or more C3 compounds using the recombinant microorganisms, as well as compositions comprising MEG, one or more C3 compound, and/or the recombinant microorganisms.

STATEMENT REGARDING SEQUENCE LISTING

The sequence listing associated with this application is provided in text format in lieu of a paper copy, and is hereby incorporated by reference into the specification. The name of the text file containing the sequence listing is BRSK_018_01US ST25.txt. The text file is about 232 kilobytes, was created on Dec. 17, 2019, and is being submitted electronically via EFS-Web.

BACKGROUND OF THE DISCLOSURE

The expression of enzymes corresponding to the complete monoethylene glycol (MEG) and C3 pathways and their corresponding products is not enough to reach yields and productivities of MEG and C3 compounds needed for an advantageous industrial process.

There exists a need for improved biosynthesis pathways for the production of MEG and other chemical compounds useful in industrial and pharmaceutical applications.

SUMMARY OF THE DISCLOSURE

The present application generally relates to metabolic engineering strategies to improve carbon flux through MEG and C3 pathways, thus increasing yield, titer and/or productivity (rate of production) of MEG, C3 compounds, and the co-production of MEG and C3 compounds. The present application relates to recombinant microorganisms having one or more biosynthesis pathways for the production of monoethylene glycol (MEG) and one or more C3 compound biosynthesis pathways modified such that the MEG and/or the one or more C3 compounds are produced at a faster rate and/or exhibits an increased yield or titer as compared to a microbe lacking the genetic modification (disruption and/or the overexpression of the endogenous or exogenous polynucleotides).

In some aspects of the present disclosure, the subject matter is drawn to a recombinant method of modulating the flux of carbon through the monoethylene glycol (MEG) biosynthesis pathway and one or more C3 compound biosynthesis pathways, the method comprising: modifying a microbe capable of coproducing MEG and one or more C3 compounds, wherein the microbe comprises (i) a disruption of one or more nucleic acid sequences encoding methylglyoxal synthase (mgsA), and/or (ii) a disruption of one or more nucleic acid sequences encoding glyoxylate carboligase (gcl); wherein the MEG and/or the one or more C3 compounds is produced at a faster rate and/or exhibits an increased yield or titer; as compared to a microbe lacking a disruption of one or more nucleic acid sequences encoding methylglyoxal synthases and/or glyoxylate carboligases.

In some aspects of the present disclosure, the subject matter is drawn to a recombinant microbe capable of coproducing MEG and one or more C3 compounds, wherein the microbe comprises one or more of the following (i) a disruption of one or more exogenous polynucleotide sequences encoding a phosphate acetyltransferase, (ii) a disruption of one or more endogenous polynucleotide sequences encoding an acetate kinase, (iii) a disruption of one or more endogenous polynucleotide sequences encoding a pyruvate oxidase, (iv) a disruption of one or more endogenous polynucleotide sequences encoding an ArcA regulator, (v) a disruption of one or more endogenous polynucleotide sequences encoding a lysine acetyltransferase, (vi) one or more overexpressed endogenous or exogenous polynucleotide sequences encoding a CobB regulator, and (vii) one or more overexpressed endogenous or exogenous polynucleotide sequences encoding an acetyl-CoA synthetase; wherein the MEG and/or the one or more C3 compounds are produced at a faster rate and/or exhibit an increased yield and/or titer; as compared to a microbe lacking the disruption and/or the overexpression of the endogenous or exogenous polynucleotides of any one or more of i-vii.

In some aspects of the present disclosure, the subject matter is drawn to a recombinant microbe capable of coproducing MEG and one or more C3 compounds, wherein the microbe comprises one or more of the following: (i) one or more exogenous polynucleotide sequences encoding a xylose dehydrogenase, (ii) one or more endogenous or exogenous polynucleotide sequences encoding a xylonolactonase, (iii) one or more endogenous or exogenous polynucleotide sequences encoding a xylonate dehydratase, (iv) one or more endogenous or exogenous polynucleotide sequences encoding a 3-deoxy-D-glycerol pentanone sugar acid aldolase, (v) one or more overexpressed endogenous or exogenous polynucleotide sequences encoding a xylonate dehydratase, (vi) one or more overexpressed endogenous or exogenous polynucleotide sequences encoding a 3-deoxy-D-glycerol pentanone sugar acid aldolase, and (vii) one or more overexpressed endogenous or exogenous polynucleotide sequences encoding a glycoaldehyde reductase; wherein the MEG and/or the one or more C3 compounds are produced at a faster rate and/or exhibit an increased yield or titer; as compared to a microbe lacking the endogenous or exogenous introduced enzymes and/or the overexpression of the endogenous or exogenous enzymes of any one or more of i-vii.

In some aspects of the present disclosure, the subject matter is drawn to a recombinant microbe capable of coproducing MEG and one or more C3 compounds, wherein the microbe comprises: (i) introducing one or more polynucleotide sequences encoding acetoacetyl CoA synthase, and/or (ii) introducing one or more polynucleotide sequences encoding hydroxymethylglutaryl-CoA synthase and hydroxymethylglutaryl-CoA lyase; wherein the MEG and/or the one or more C3 compounds is produced at a faster rate and/or exhibits an increased yield or titer; as compared to a microbe not having been introduced an acetoacetyl CoA synthase, hydroxymethylglutaryl-CoA synthase, and/or hydroxymethylglutaryl-CoA lyase.

In some aspects, the recombinant microbe further comprises any one or more modifications described herein.

In some aspects of the present disclosure, the subject matter is drawn to a recombinant microbe capable of coproducing MEG and one or more C3 compounds wherein the microbe comprises one or more of the following: (i) one or more disrupted nucleic acid sequences encoding methylglyoxal synthase (mgsA), (ii) one or more disrupted nucleic acid sequences encoding glyoxylate carboligase (gel), (iii) one or more disrupted polynucleotide sequences encoding a phosphate acetyltransferase, (iv) one or more disrupted polynucleotide sequences encoding an acetate kinase, (v) one or more disrupted polynucleotide sequences encoding a pyruvate oxidase, (vi) one or more disrupted endogenous polynucleotide sequences encoding an ArcA regulator, (vii) one or more disrupted endogenous polynucleotide sequences encoding a lysine acetyltransferase, (viii) one or more overexpressed endogenous or exogenous polynucleotide sequences encoding a CobB regulator, (ix) one or more overexpressed endogenous or exogenous polynucleotide sequences encoding an acetyl-CoA synthetase, (x) one or more exogenous polynucleotide sequences encoding a xylose dehydrogenase, (xi) one or more endogenous or exogenous polynucleotide sequences encoding a xylonolactonase, (xii) one or more endogenous or exogenous polynucleotide sequences encoding a xylonate dehydratase, (xiii) one or more endogenous or exogenous polynucleotide sequences encoding a 3-deoxy-D-glycerol pentanone sugar acid aldolase, (xiv) one or more overexpressed endogenous or exogenous polynucleotide sequences encoding a xylonate dehydratase, (xv) one or more overexpressed endogenous or exogenous polynucleotide sequences encoding a 3-deoxy-D-glycerol pentanone sugar acid aldolase, (xvi) one or more overexpressed endogenous or exogenous polynucleotide sequences encoding a glycoaldehyde reductase, (xvii) one or more polynucleotide sequences encoding acetoacetyl CoA synthase, and (xviii) one or more polynucleotide sequences encoding hydroxymethylglutaryl-CoA synthase and hydroxymethylglutaryl-CoA lyase; wherein the MEG and/or the one or more C3 compounds is produced at a faster rate and/or exhibits an increased yield or titer; as compared to a microbe lacking the modification.

In some aspects of the present disclosure, the subject matter is drawn to a recombinant microbe capable of coproducing MEG and one or more C3 compounds, wherein the microbe comprises one or more of the following: one or more disrupted nucleic acid sequences encoding methylglyoxal synthase (mgsA), and one or more disrupted nucleic acid sequences encoding glyoxylate carboligase (gcl) and/or; one or more disrupted polynucleotide sequences encoding a phosphate acetyltransferase, and/or one or more disrupted polynucleotide sequences encoding an acetate kinase, and/or one or more endogenous or exogenous polynucleotide sequences encoding a xylolactonase, and/or one or more endogenous or exogenous polynucleotide sequences encoding a xylonate dehydratase, and/or one or more endogenous or exogenous a deletion of one or more polynucleotide sequences encoding acetoacetyl CoA synthase, and/or transferase (AtoDA). In some aspects, the microbe comprises a functional acetoacetyl-CoA transferase (AtoDA).

In some aspects, the deletion comprises the deletion of the one or more endogenous or exogenous polynucleotide sequences encoding hydroxymethylglutaryl-CoA synthase and hydroxymethylglutaryl-CoA lyase; wherein.

In some aspects, the MEG and/or the one or more C3 compounds is produced at a faster rate and/or exhibits an increased yield or titer; as compared to a microbe lacking a disruption of one or more nucleic acid sequences encoding methylglyoxal synthases and any of the modifications above.

In some aspects of the present disclosure, the subject matter is drawn to a recombinant microbe capable of coproducing MEG and one or more C3 compounds, the microbe comprising one or more of the following: one or more disrupted nucleic acid sequences encoding glyoxylate carboligase (gcl); and one or more disrupted polynucleotide sequences encoding a phosphate acetyltransferase, and/or one or more disrupted polynucleotide sequences encoding an acetate kinase, and/or one or more endogenous or exogenous polynucleotide sequences encoding a xylolactonase, and/or one or more endogenous or exogenous polynucleotide sequences or overexpressing an endogenous polynucleotide o sequences encoding a xylonate dehydratase, and/or one or more polynucleotide sequences encoding acetoacetyl CoA synthase, and/or one or more polynucleotide sequences encoding hydroxymethylglutaryl-CoA synthase and hydroxymethylglutaryl-CoA lyase; wherein the MEG and/or the one or more C3 compounds is produced at a faster rate and/or exhibits an increased yield or titer; as compared to a microbe lacking a disruption of one or more nucleic acid sequences encoding glyoxylate carboligase (gcl) and any of the modifications above.

In some aspects of the present disclosure, the subject matter is drawn to a recombinant microbe capable of coproducing MEG and one or more C3 compounds, the microbe comprising one or more of the following: one or more disrupted polynucleotide sequences encoding a phosphate acetyltransferase and disrupting one or more endogenous polynucleotide sequences encoding an acetate kinase, and/or introducing one or more endogenous or exogenous polynucleotide sequences encoding a xylolactonase, and/or introducing one or more endogenous or exogenous polynucleotide sequences or overexpressing an endogenous polynucleotide o sequence encoding a xylonate dehydratase, and/or introducing one or more polynucleotide sequences encoding acetoacetyl CoA synthase, and/or introducing one or more polynucleotide sequences encoding hydroxymethylglutaryl-CoA synthase and hydroxymethylglutaryl-CoA lyase, and/or; disrupting one or more endogenous polynucleotide sequences encoding an ArcA regulator, and/or, disrupting one or more endogenous polynucleotide sequences encoding a lysine acetyltransferase, and/or overexpressing one or more endogenous or exogenous polynucleotide sequences encoding an acetyl-CoA synthetase; wherein the MEG and/or the one or more C3 compounds is produced at a faster rate and/or exhibits an increased yield or titer; as compared to a microbe lacking a disruption of one or more nucleic acid sequences encoding a phosphate acetyltransferase and any of the modifications above.

In some aspects of the present disclosure, the subject matter is drawn to a recombinant microbe capable of coproducing MEG and one or more C3 compounds by: modifying a microbe coproducing MEG and one or more C3 compounds by: disrupting one or more endogenous polynucleotide sequences encoding an acetate kinase and introducing one or more endogenous or exogenous polynucleotide sequences encoding a xylolactonase, and/or one or more endogenous or exogenous polynucleotide sequence or overexpressing an endogenous polynucleotide sequence encoding a xylonate dehydratase, and/or one or more polynucleotide sequences encoding acetoacetyl CoA synthase, and/or one or more polynucleotide sequences encoding hydroxymethylglutaryl-CoA synthase and hydroxymethylglutaryl-CoA lyase; wherein the MEG and/or the one or more C3 compounds is produced at a faster rate and/or exhibits an increased yield or titer; as compared to a microbe lacking a disruption of one or more nucleic acid sequences encoding acetate kinase and any of the modifications above.

In some aspects of the present disclosure, the subject matter is drawn to a recombinant microbe capable of coproducing MEG and one or more C3 compounds, the microbe comprising one or more of the following: one or more endogenous or exogenous polynucleotide sequences encoding a xylolactonase and one or more endogenous or exogenous polynucleotide sequence or overexpressing an endogenous polynucleotide sequence encoding a xylonate dehydratase, and/or one or more polynucleotide sequences encoding acetoacetyl CoA synthase, and/or one or more polynucleotide sequences encoding hydroxymethylglutaryl-CoA synthase and hydroxymethylglutaryl-CoA lyase; wherein the MEG and/or the one or more C3 compounds is produced at a faster rate and/or exhibits an increased yield or titer; as compared to a microbe lacking the exogenous introduced or endogenous overexpressed xylolactonase, and any of the modifications above.

In some aspects of the present disclosure, the subject matter is drawn to a recombinant microbe capable of coproducing MEG and one or more C3 compounds, the microbe comprising one or more of the following: one or more endogenous or exogenous polynucleotide sequence or overexpressing an endogenous polynucleotide sequence encoding a xylonate dehydratase and one or more polynucleotide sequences encoding acetoacetyl CoA synthase, and/or one or more polynucleotide sequences encoding hydroxymethylglutaryl-CoA synthase and hydroxymethylglutaryl-CoA lyase; wherein the MEG and/or the one or more C3 compounds is produced at a faster rate and/or exhibits an increased yield or titer; as compared to a microbe lacking the exogenous introduced or endogenous overexpressed xylonate dehydratase, any of the modifications above.

In some aspects of the present disclosure, the subject matter is drawn to a recombinant microbe capable of coproducing MEG and one or more C3 compounds, the microbe comprising one or more of the following: one or more overexpressed endogenous or exogenous polynucleotide sequences encoding an acetyl-CoA synthetase; and one or more disrupted nucleic acid sequences encoding methylglyoxal synthase (mgsA), one or more disrupted nucleic acid sequences encoding glyoxylate carboligase (gcl) and/or; one or more disrupted polynucleotide sequences encoding an acetate kinase, and/or one or more endogenous or exogenous polynucleotide sequences encoding a xylolactonase, and/or one or more endogenous or exogenous polynucleotide sequences or overexpressing an endogenous polynucleotidesequences encoding a xylonate dehydratase, and/or one or more polynucleotide sequences encoding acetoacetyl CoA synthase, and/or one or more polynucleotide sequences encoding hydroxymethylglutaryl-CoA synthase and hydroxymethylglutaryl-CoA lyase; one or more disrupted polynucleotide sequences encoding an ArcA regulator, and/or, one or more disrupted polynucleotide sequences encoding a lysine acetyltransferase, and/or wherein the MEG and/or the one or more C3 compounds is produced at a faster rate and/or exhibits an increased yield or titer; as compared to a microbe lacking the endogenous overexpressed acetyl-CoA synthetase and any of the modifications above.

In some aspects of the present disclosure, the subject matter is drawn to a method of making a recombinant microbe capable of coproducing MEG and one or more C3 compounds by: modifying a microbe coproducing MEG and one or more C3 compounds by: (i) disrupting one or more nucleic acid sequences encoding methylglyoxal synthase (mgsA), and/or (ii) disrupting one or more nucleic acid sequences encoding glyoxylate carboligase (gcl); wherein the MEG and/or the one or more C3 compounds is produced at a faster rate and/or exhibits an increased yield or titer; as compared to a microbe lacking a disruption of one or more nucleic acid sequences encoding methylglyoxal synthases and/or glyoxylate carboligases.

In some aspects of the present disclosure, the subject matter is drawn to a method of making a recombinant microbe capable of coproducing MEG and one or more C3 compounds by: modifying a microbe coproducing MEG and one or more C3 compounds by performing one or more of the following: (i) disrupting one or more polynucleotide sequences encoding a phosphate acetyltransferase, (ii) disrupting one or more polynucleotide sequences encoding an acetate kinase, (iii) disrupting one or more polynucleotide sequences encoding a pyruvate oxidase, (iv) disrupting one or more polynucleotide sequences encoding an ArcA regulator, (v) disrupting one or more polynucleotide sequences encoding a lysine acetyltransferase, (vi) overexpressing one or more endogenous or exogenous polynucleotide sequences encoding a CobB regulator, and (vii) overexpressing one or more endogenous or exogenous polynucleotide sequences encoding an acetyl-CoA synthetase; wherein the MEG and/or the one or more C3 compounds are produced at a faster rate and/or exhibit an increased yield or titer; as compared to a microbe lacking the disruption and/or the overexpression of the endogenous or exogenous polynucleotides of any one or more of i-vii.

In some aspects of the present disclosure, the subject matter is drawn to a method of making a recombinant microbe capable of coproducing MEG and one or more C3 compounds by: modifying a microbe coproducing MEG and one or more C3 compounds by performing one or more of the following: (i) introducing one or more endogenous or exogenous polynucleotide sequences encoding a xylose dehydrogenase, (ii) introducing one or more exogenous polynucleotide sequences encoding a xylolactonase, (iii) introducing one or more endogenous or exogenous polynucleotide sequences encoding a xylonate dehydratase, (iv) introducing one or more endogenous or exogenous polynucleotide sequences encoding a 3-deoxy-D-glycerol pentanone sugar acid aldolase, (v) overexpressing one or more endogenous or exogenous polynucleotide sequences encoding a xylonate dehydratase, (vi) overexpressing one or more endogenous or exogenous polynucleotide sequences encoding a 3-deoxy-D-glycerol pentanone sugar acid aldolase, and (vii) overexpressing one or more endogenous or exogenous polynucleotide sequences encoding a glycoaldehyde reductase; wherein the MEG and/or the one or more C3 compounds are produced at a faster rate and/or exhibit an increased yield or titer; as compared to a microbe lacking the exogenous introduced enzymes and/or the overexpression of the endogenous or exogenous enzymes of any one or more of i-vii.

In some aspects of the present disclosure, the subject matter is drawn to a method of making a recombinant microbe capable of coproducing MEG and one or more C3 compounds by: modifying a microbe coproducing MEG and one or more C3 compounds by: (i) introducing one or more polynucleotide sequences encoding acetoacetyl CoA synthase, and/or (ii) introducing one or more polynucleotide sequences encoding hydroxymethylglutaryl-CoA synthase and hydroxymethylglutaryl-CoA lyase; wherein the MEG and/or the one or more C3 compounds is produced at a faster rate and/or exhibits an increased yield or titer; as compared to a microbe not having been introduced an acetoacetyl CoA, hydroxymethylglutaryl-CoA synthase, or hydroxymethylglutaryl-CoA lyase.

In some aspects the microbe comprises any one or more modifications set forth herein.

In some aspects of the present disclosure, the subject matter is drawn to a method of making a recombinant microbe capable of coproducing MEG and one or more C3 compounds by: modifying a microbe coproducing MEG and one or more C3 compounds by performing one or more of the following: (i) disrupting one or more nucleic acid sequences encoding methylglyoxal synthase (mgsA), (ii) disrupting one or more nucleic acid sequences encoding glyoxylate carboligase (gel), (iii) disrupting one or more exogenous polynucleotide sequences encoding a phosphate acetyltransferase, (iv) disrupting one or more polynucleotide sequences encoding an acetate kinase, (v) disrupting one or more polynucleotide sequences encoding a pyruvate oxidase, (vi) disrupting one or more polynucleotide sequences encoding an ArcA regulator, (vii) disrupting one or more polynucleotide sequences encoding a lysine acetyltransferase, (viii) overexpressing one or more endogenous or exogenous polynucleotide sequences encoding a CobB regulator, (ix) overexpressing one or more endogenous or exogenous polynucleotide sequences encoding an acetyl-CoA synthetase, (x) introducing one or more exogenous polynucleotide sequences encoding a xylose dehydrogenase, (xi) introducing one or more endogenous or exogenous polynucleotide sequences encoding a xylolactonase, (xii) introducing one or more endogenous or exogenous polynucleotide sequences encoding a xylonate dehydratase, (xiii) introducing one or more endogenous or exogenous polynucleotide sequences encoding a 3-deoxy-D-glycerol pentanone sugar acid aldolase, (xiv) overexpressing one or more endogenous or exogenous polynucleotide sequences encoding a xylonate dehydratase, (xv) overexpressing one or more endogenous or exogenous polynucleotide sequences encoding a 3-deoxy-D-glycerol pentanone sugar acid aldolase, (xvi) overexpressing one or more endogenous or exogenous polynucleotide sequences encoding a glycoaldehyde reductase, (xvii) introducing one or more endogenous or exogenous polynucleotide sequences encoding acetoacetyl CoA synthase, and (xviii) introducing one or more endogenous or exogenous polynucleotide sequences encoding hydroxymethylglutaryl-CoA synthase and hydroxymethylglutaryl-CoA lyase; wherein the MEG and/or the one or more C3 compounds is produced at a faster rate and/or exhibits an increased yield or titer; as compared to a microbe lacking the modification.

In some aspects, the microbe is a bacterium or a fungus. In some aspects, the bacterium is an *Escherichia coli*. In some aspects, the MEG exhibits an increased yield or titer. In some aspects, the increased yield or titer is an increase of at least 2%. In some aspects, the increased yield or titer is an increase of at least 15%.

In some aspects, the one or more C3 compounds is acetone. In some aspects, the acetone exhibits an increased yield or titer. In some aspects, the increased yield or titer is an increase of at least 2%. In some aspects, the increased yield or titer is an increase of at least 15%.

In some aspects, the microbe utilizes xylose, cellobiose, arabinose, mannose, and/or glucose in the coproduction of the MEG and the one or more C3 compounds. In some aspects, the C3 compounds are selected from acetone, isopropanol, and propene.

In some aspects of the present disclosure, the subject matter is drawn to a method of modulating the flux of carbon through the monoethylene glycol (MEG) biosynthesis pathway and one or more C3 compound biosynthesis pathways, the method comprising: modifying a microbe coproducing MEG and one or more C3 compounds by: (i) introducing one or more polynucleotide sequences encoding acetoacetyl CoA synthase, and/or (ii) introducing one or more polynucleotide sequences encoding hydroxymethylglutaryl-CoA synthase and hydroxymethylglutaryl-CoA lyase; wherein the MEG and/or the one or more C3 compounds is produced at a faster rate and/or exhibits an increased yield and/or titer; as compared to a microbe not having been introduced an acetoacetyl CoA, hydroxymethylglutaryl-CoA synthase, or hydroxymethylglutaryl-CoA lyase.

In some aspects, the microbe comprises a deletion of one or more polynucleotide sequences encoding acetoacetyl-CoA thiolase. In some aspects, the microbe lacks a functional acetoacetyl-CoA thiolase. In some aspects, the microbe comprises a functional acetoacetyl-CoA thiolase.

In some aspects, the microbe comprises a deletion of one or more polynucleotide sequences encoding acetoacetyl-CoA transferase (AtoDA). In some aspects, the microbe comprises a functional acetoacetyl-CoA transferase (AtoDA).

In some aspects, the deletion comprises the deletion of the one or more polynucleotide sequences.

In some aspects, the MEG and/or the one or more C3 compounds is produced at a faster rate and/or an increased yield and/or titer. In some aspects, the microbe is a bacterium or a fungus. In some aspects, the bacterium is an *Escherichia coli*. In some aspects, the MEG exhibits an increased yield or titer. In some aspects, the increased yield or titer is an increase of at least 2%. In some aspects, the increased yield or titer is an increase of at least 15%. In some aspects, the one or more C3 compounds is acetone. In some aspects, the acetone exhibits an increased yield or titer. In some aspects, the increased yield or titer is an increase of at least 2%. In some aspects, the increased yield or titer is an increase of at least 15%.

In some aspects, the one or more C3 compounds is acetone. In some aspects, the acetone exhibits an increased yield and/or titer. In some aspects, the increased yield and/or titer is an increase of at least 2%. In some aspects, the increased yield and/or titer is an increase of at least 15%. In some aspects, the acetone is produced at a faster rate. In some aspects, the faster rate is an increase of at least 2%. In some aspects, the faster rate is an increase of at least 15%. In some aspects, (i) the MEG exhibits an increased yield and/or titer of at least 2%, and/or (ii) the one or more C3 compounds exhibits an increased yield and/or titer of at least 2%. In some aspects, (i) the MEG exhibits an increased yield and/or titer of at least 15%, and/or (ii) the one or more C3 compounds exhibits an increased yield and/or titer of at least 15%. In some aspects, (i) the rate of MEG production exhibits an increase of at least 2%, and/or (ii) the rate of the one or more C3 compound production exhibits an increase of at least 2%. In some aspects, (i) the rate of MEG production exhibits an increase of at least 15%, and/or (ii) the rate of the one or more C3 compound production exhibits an increase of at least 15%.

In some aspects, the microbe utilizes xylose, cellobiose, arabinose, mannose, and/or glucose in the coproduction of the MEG and the one or more C3 compounds, wherein the C3 compounds are selected from acetone, isopropanol, and propene.

BRIEF DESCRIPTION OF THE FIGURES

Illustrative embodiments of the disclosure are illustrated in the drawings, in which.

DETAILED DESCRIPTION OF THE DISCLOSURE

Figure 1:
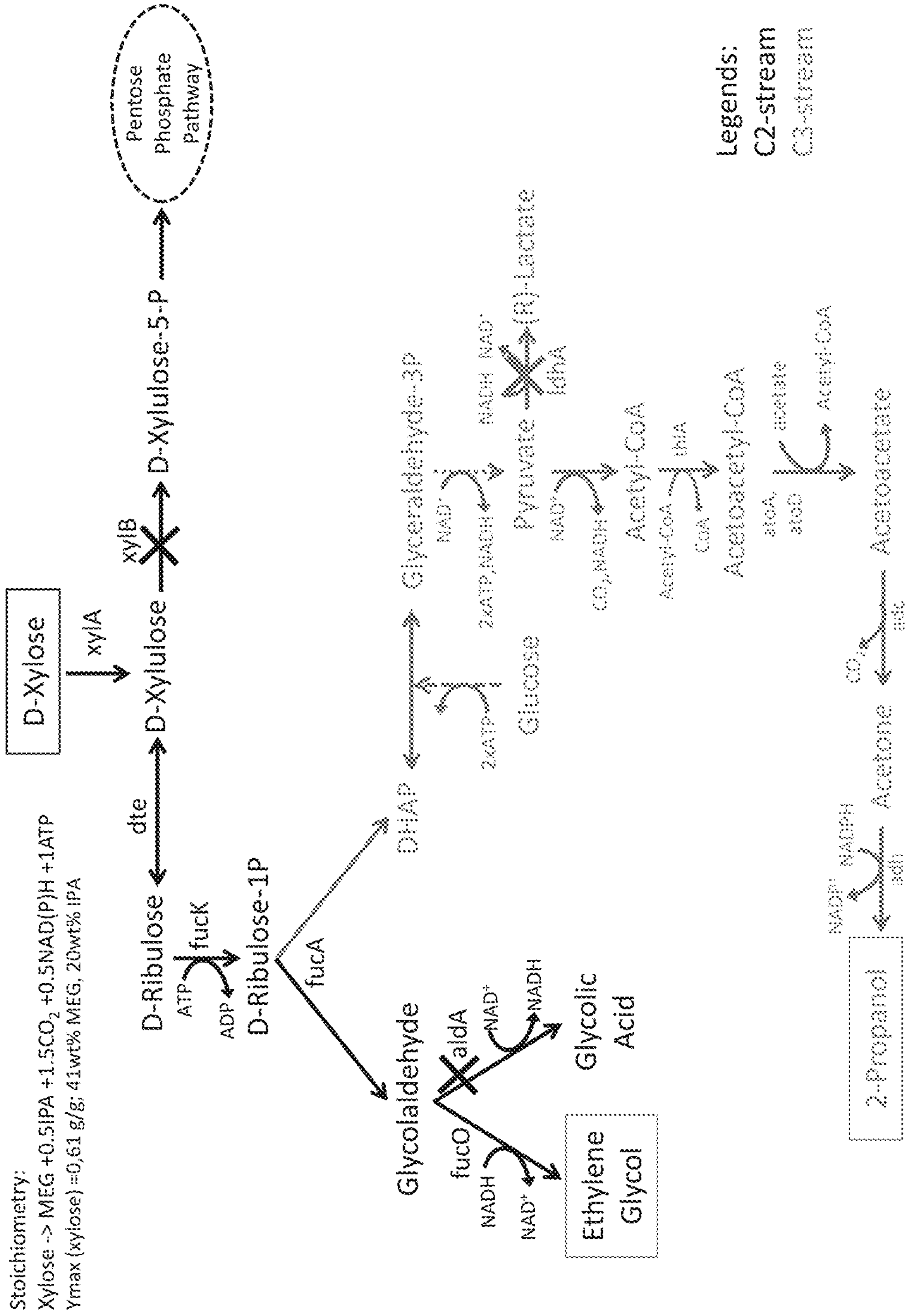
FIG. 1 illustrates MEG and isopropanol co-production pathway via xylulose-1-phosphate.

The following definitions and abbreviations are to be used for the interpretation of the disclosure.

As used herein and in the appended claims, the singular forms "a," "an," and "the" include plural referents unless the context clearly dictates otherwise. Thus, for example, reference to "an enzyme" includes a plurality of such enzymes and reference to "the microorganism" includes reference to one or more microorganisms, and so forth.

As used herein, the terms "comprises," "comprising," "includes," "including," "has," "having, "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss water/nucleotide.html, optionally with default settings). Optimal alignment may be assessed using any suitable parameters of a chosen algorithm, including default parameters.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "about" is used synonymously with the term "approximately." Illustratively, the use of the term "about" with regard to an amount indicates that values slightly outside the cited values, e.g., plus or minus 0.1% to 10%.

The term "biologically pure culture" or "substantially pure culture" refers to a culture of a bacterial species described herein containing no other bacterial species in quantities sufficient to interfere with the replication of the culture or be detected by normal bacteriological techniques.

As used herein, a "parent strain" or "base strain" is the strain which has been modified to produce a new resulting strain. For example, if *Escherichia coli* strain XL1-Blue were genetically modified to disrupt a genomic polynucleotide sequences, the *E. coli* strain XL1-Blue is the parent strain or base strain to the subsequent genetically modified strain. In some aspects, a parent or base strain may be naturally occurring. In other aspects, a parent or base strain may be non-naturally occurring.

As used herein, a "control sequence" refers to an operator, promoter, silencer, or terminator.

As used herein, "introduced" refers to the introduction by means of modern biotechnology, and not a naturally occurring introduction.

As used herein, a "constitutive promoter" is a promoter, which is active under most conditions and/or during most development stages. There are several advantages to using constitutive promoters in expression vectors used in biotechnology, such as: high level of production of proteins used to select transgenic cells or organisms; high level of expression of reporter proteins or scorable markers, allowing easy detection and quantification; high level of production of a transcription factor that is part of a regulatory transcription system; production of compounds that requires ubiquitous activity in the organism; and production of compounds that are required during all stages of development.

As used herein, a "non-constitutive promoter" is a promoter which is active under certain conditions, in certain types of cells, and/or during certain development stages. For example, inducible promoters, and promoters under development control are non-constitutive promoters.

As used herein, "inducible" or "repressible" promoter is a promoter which is under chemical or environmental factors control. Examples of environmental conditions that may affect transcription by inducible promoters include anaerobic conditions, certain chemicals, the presence of light, acidic or basic conditions, etc.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

The term "signal sequence" as used herein refers to an amino acid sequence that targets peptides and polypeptides to cellular locations or to the extracellular environment. Signal sequences are typically at the N-terminal portion of a polypeptide and are typically removed enzymatically. Polypeptides that have their signal sequences are referred to as being full-length and/or unprocessed. Polypeptides that have had their signal sequences removed are referred to as being mature and/or processed.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution. The terms "homologous sequences" or "homologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Michigan), AlignX, and Vector NTI (Invitrogen, Carlsbad, CA). A similar biological function may include, but is not limited to: catalyzing the same or similar enzymatic reaction; having the same or similar selectivity for a substrate or co-factor; having the same or similar stability; having the same or similar tolerance to various fermentation conditions (temperature, pH, etc.); and/or having the same or similar tolerance to various metabolic substrates, products, by-products, intermediates, etc. The degree of similarity in biological function may vary, but in one embodiment, is at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%, according to one or more assays known to one skilled in the art to determine a given biological function.

The term "variant" refers to any polypeptide or enzyme described herein. A variant also encompasses one or more components of a multimer, multimers comprising an individual component, multimers comprising multiples of an individual component (e.g., multimers of a reference molecule), a chemical breakdown product, and a biological breakdown product. In particular, non-limiting embodiments, an enzyme may be a "variant" relative to a reference enzyme by virtue of alteration(s) in any part of the polypeptide sequence encoding the reference enzyme. A variant of a reference enzyme can have enzyme activity of at least 10%, at least 30%, at least 50%, at least 80%, at least 90%, at least 100%, at least 105%, at least 110%, at least 120%, at least 130% or more in a standard assay used to measure enzyme activity of a preparation of the reference enzyme. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the full-length, or unprocessed enzymes of the present disclosure. In some embodiments, a variant may also refer to polypeptides having at least 50%, at least 60%, at least 70%, at least 80%, at least 90%, at least 91%, at least 92%, at least 93%, at least 94%, at least 95%, at least 96%, at least 97%, at least 98%, or at least 99% sequence identity to the mature, or processed enzymes of the present disclosure.

As used herein, the term "non-naturally occurring," when used in reference to a microorganism, organism, or enzyme activity of the disclosure, is intended to mean that the microorganism, organism, or enzyme has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganism or enzyme activity includes the hydroxylation activity described above.

As used herein the terms "microorganism" or "microbe" should be taken broadly. These terms, used interchangeably, include but are not limited to, the two prokaryotic domains, Bacteria and Archaea.

As used herein, "isolate," "isolated," "isolated microbe," and like terms, are intended to mean that the one or more microorganisms has been separated from at least one of the materials with which it is associated in a particular environment (for example media, water, reaction chamber, etc.). Thus, an "isolated microbe" does not exist in its naturally occurring environment; rather, it is through the various techniques described herein that the microbe has been removed from its natural setting and placed into a non-naturally occurring state of existence. Thus, the isolated strain or isolated microbe may exist as, for example, a biologically pure culture, or as spores (or other forms of the strain). In aspects, the isolated microbe may be in association with an acceptable carrier, which may be a commercially or industrial acceptable carrier.

In certain aspects of the disclosure, the isolated microbes exist as "isolated and biologically pure cultures." It will be appreciated by one of skill in the art that an isolated and biologically pure culture of a particular microbe, denotes that said culture is substantially free of other living organisms and contains only the individual microbe in question. The culture can contain varying concentrations of said microbe. The present disclosure notes that isolated and biologically pure microbes often "necessarily differ from less pure or impure materials." See, e.g. In re Bergstrom, 427 F.2d 1394, (CCPA 1970) (discussing purified prostaglandins), see also, In re Bergy, 596 F.2d 952 (CCPA 1979) (discussing purified microbes), see also, Parke-Davis & Co. v. H. K. Mulford & Co., 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., Merck & Co. v. Olin Mathieson Chemical Corp., 253 F.2d 156 (4th Cir. 1958) (discussing purity limitations for vitamin B12 produced by microbes), incorporated herein by reference.

As used herein, "individual isolates" should be taken to mean a composition, or culture, comprising a predominance of a single genera, species, or strain, of microorganism, following separation from one or more other microorganisms.

Microbes of the present disclosure may include spores and/or vegetative cells. In some embodiments, microbes of the present disclosure include microbes in a viable but non-culturable (VBNC) state. As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and in some cases are necessary structures in fungal life cycles. Bacterial spores are structures for surviving conditions that may ordinarily be nonconducive to the survival or growth of vegetative cells.

As used herein, "microbial composition" refers to a composition comprising one or more microbes of the present disclosure.

As used herein, "carrier," "acceptable carrier," "commercially acceptable carrier," or "industrial acceptable carrier" refers to a diluent, adjuvant, excipient, or vehicle with which the microbe can be administered, which does not detrimentally effect the microbe.

The term "yield potential" as used herein refers to a yield of a product from a biosynthetic pathway. In one embodiment, the yield potential may be expressed as a percent by weight of end product per weight of starting compound.

The term "thermodynamic maximum yield" as used herein refers to the maximum yield of a product obtained from fermentation of a given feedstock, such as glucose, based on the energetic value of the product compared to the feedstock. In a normal fermentation, without use of additional energy sources such as light, hydrogen gas or methane or electricity, for instance, the product cannot contain more energy than the feedstock. The thermodynamic maximum yield signifies a product yield at which all energy and mass from the feedstock is converted to the product. This yield can be calculated and is independent of a specific pathway. If a specific pathway towards a product has a lower yield than the thermodynamic maximum yield, then it loses mass and can most likely be improved upon or substituted with a more efficient pathway towards the product.

The term "redox balanced" refers to a set of reactions, which taken together produce as much redox cofactors as they consume. Designing metabolic pathways and engineering an organism such that the redox cofactors are balanced or close to being balanced usually results in a more efficient, higher yield production of the desired compounds. Redox reactions always occur together as two half-reactions happening simultaneously, one being an oxidation reaction and the other a reduction reaction. In redox processes, the reductant transfers electrons to the oxidant. Thus, in the reaction, the reductant or reducing agent loses electrons and is oxidized, and the oxidant or oxidizing agent gains electrons and is reduced. In one embodiment, the redox reactions take place in a biological system. Biological energy is frequently stored and released by means of redox reactions. Photosynthesis involves the reduction of carbon dioxide into sugars and the oxidation of water into molecular oxygen. The reverse reaction, respiration, oxidizes sugars to produce carbon dioxide and water. As intermediate steps, the reduced carbon compounds are used to reduce nicotinamide adenine dinucleotide ($NAD^+$), which then contributes to the creation of a proton gradient, which drives the synthesis of adenosine triphosphate (ATP) and is maintained by the reduction of oxygen. The term redox state is often used to describe the balance of GSH/GSSG, $NAD^+$/NADH and $NADP^+$/NADPH in a biological system such as a cell or organ. The redox state is reflected in the balance of several sets of metabolites (e.g., lactate and pyruvate, beta-hydroxybutyrate, and acetoacetate), whose interconversion is dependent on these ratios. An abnormal redox state can develop in a variety of deleterious situations, such as hypoxia, shock, and sepsis.

As used herein, the term “productivity” refers to the total amount of bioproduct produced per liter per hour.

The terms “C2 pathway”, “C2 branch pathway”, “C2 biochemical pathway” or “C2 stream” as used herein refers to a biochemical pathway wherein MEG can be produced via glycolaldehyde.

The terms “C3 pathway”, “C3 branch pathway”, “C3 biochemical pathway” or “C3 stream” as used herein refers to a biochemical pathway wherein MEG and/or one or more co-product such as acetone, isopropanol, propene, isobutene and/or serine pathway compounds can be produced via pyruvate, acetyl-CoA or dihydroxyacetonephosphate (DHAP).

The strategies described herein were evaluated for the potential of improvement considering the overall carbon flux of the MEG+C3 compound co-production pathways. The methods described herein deliver gains that are not only specific to a single pathway but have a synergistic effect on the global carbon, energy and co-factor balances. These synergistic or antagonistic results can only be predict when focusing on the metabolic complexity of the MEG+C3 co-production pathway.

The present disclosure combines the production of monoethylene glycol (MEG) and one or more three carbon compounds in different hosts. In some embodiments, the three carbon compound is isopropanol (IPA). The present disclosure thereby avoids some of the biggest pathway engineering challenges for known MEG and IPA pathways demonstrated so far. Surprisingly, the combination of a pathway for MEG production and a pathway for production of a three carbon compound complements each other and is highly synergistic, avoiding or overcoming the biggest challenges and shortcomings of each pathway alone, establishing a good redox balance but also delivering required ATP, without production of excess ATP.

A demonstrated fermentative production of MEG from xylose (WO2013126721A1, which is herein referenced in its entirety), via ribulose-1-phosphate, has a high yield potential (79 wt %=0.79 g MEG/g xylose). MEG is produced via two different pathways which are active in parallel, a 2-carbon (C2) stream (via glycolaldehyde) and a 3-carbon (C3) stream (via dihydroxyacetonephosphate (DHAP)). The C2 stream is easy to implement at high efficiency, but the C3 stream is very difficult to implement at high efficiency via metabolic engineering. Several pathway options for DHAP→MEG exist, all of which are difficult to implement. Furthermore, the overall process is ATP neutral. Thus, some xylose and therefore yield will be lost in order to obtain some surplus ATP required for cell growth and maintenance.

A further demonstrated fermentative production of MEG from xylose (Alkim et al., Microb Cell Fact (2015) 14:127), via xylulose-1-phosphate, is very similar to the route described by WO2013126721A1. It has the same high yield potential (79 wt %), but the C3 stream for MEG production via DHAP is difficult to implement and there is an ATP shortage.

A further fermentative production of MEG was demonstrated from glucose (Chen et al., Met. Eng. (2016) 33:12-18). It uses exclusively a pathway identical to one of the C3 stream solutions of WO2013126721A1, going via DHAP and then ethanolamine to glyceraldehyde to MEG. Only in this case, DHAP is derived from glucose, not from xylose. Thus it suffers even more from the technical difficulty to implement a high productivity and high yield pathway from DHAP to MEG. It furthermore has a reduced total yield potential of 69 wt % versus the thermodynamic maximum yield for the product MEG derived from glucose (82 wt %). The pathway is furthermore ATP neutral, not generating any ATP that the cells need for growth and maintenance. This pathway is also not redox balanced and has a high excess of 2 mol NADH per mol of consumed glucose, all of which needs to be re-oxidized for the cell to be viable. In an aerobic fermentation, this NADH can be used to generate ATP, which however would be in high excess (2 NADH→6 ATP), leading to excess biomass formation during the production phase and therefore reduced product formation and yield. The only described solution for the loss of yield potential for MEG production from glucose is the production of MEG from xylose with a high yield potential. The only described solution for the excess NADH production in the MEG from glucose process is the production of MEG from xylose which can be redox neutral.

A demonstrated fermentative production of IPA via acetoacetyl-CoA (US 2010/0311135, which is herein referenced in its entirety) has excess NADH (2 mol per mol of consumed glucose) and low yield potential (34 wt %). This pathway has excess ATP (2 mol per mol of consumed glucose), more than is required for cell maintenance during the production phase, thereby favoring biomass formation over production. If the NADH is not utilized via carbon fixation, it needs to be re-oxidized for the cell to stay viable, further losing glucose in this process. Alternatively, NADH can be oxidized through ATP production, which would lead to even more unwanted excess ATP.

Other potential solutions exist for reducing NADH excess and increasing IPA yield potential (thermodynamic max yield=47 wt %): re-capturing $CO_2$ produced in excess during the fermentation and in doing so also re-oxidizing excess NADH ($CO_2$ fixation). Or avoid excess $CO_2$ and NADH release altogether by diverting some flux from glycolysis to a phosphoketolase (PK)/phosphotransacetylase (PTA) pathway to generate more acetyl-CoA and less $CO_2$ and NADH. However, so far none of these options have been technically demonstrated in the context of IPA production and are generally known to be very challenging.

The present disclosure combines one of three easy to implement high yield C2-streams for MEG production from xylose with an easy to implement IPA production stream via the DHAP pathway. Surprisingly, the problem of the IPA pathway, excess NADH production, complements the NADH requiring C2 part of MEG production. The combination of these pathways leads to a high total yield potential of 61 wt %, which is close to the maximum energetic yield of 65 wt % for degradation of xylose into MEG and IPA, assuming these products are produced in a 2:1 ratio. This high yield potential stems from the synergies of coupling the IPA pathway with the C2-branch of MEG production from xylose.

The proposed pathway in its basic form is not redox neutral, but has a small excess of 0.5 mol NADH per mol of consumed xylose. In an aerobic fermentation, oxidation of NADH can deliver just enough ATP to obtain sufficient, but not excessive, ATP required for growth and maintenance during the production phase without having a significantly negative impact on product formation.

The present disclosure solves a number of problems associated with MEG and/or IPA production. In one embodiment, the problem of a difficult to implement C3 pathway in production of MEG from xylose is solved. In another embodiment, the problem of ATP shortage in production of MEG from xylose is solved. In another embodiment, the problem of loss of yield potential in production of MEG from glucose is solved. In another embodiment, the problem of ATP shortage in production of MEG from glucose is solved. In another embodiment, the problem of excess NADH production in production of MEG from glucose is solved. In another embodiment, the problem of loss of yield potential in production of IPA from glucose is solved. In another embodiment, the problem of excess NADH production in production of IPA from glucose is solved.

In one embodiment, the pathway for MEG+IPA co-production in *E. coli* comprises the following enzymes for IPA production: thiolase, acetate:acetoacetyl-CoA transferase or hydrolase, acetoacetate decarboxylase and secondary alcohol dehydrogenase. The MEG pathway via ribulose-1-phosphate comprises the following enzymes: D-tagatose 3-epimerase, D-ribulokinase, D-ribulose-phosphate aldolase and glycolaldehyde reductase. In order to increase carbon flux to the desired pathway, three specific genes that could divert carbon flux were identified and deleted: xylB gene coding for a xylulokinase (this enzyme can divert carbon flux into the pentose phosphate pathway), the aldA gene coding for aldehyde dehydrogenase A (can divert carbon flux from glycolaldehyde to glycolate instead of to MEG) and the ldhA gene coding for lactate dehydrogenase (this enzyme can divert carbon flux from pyruvate to lactate instead of to acetyl-CoA).

The first step of the pathway (FIG. 1) is the natural conversion of D-xylose into D-xylulose. D-xylulose normally enters the pentose phosphate pathway for energy and biomass generation, which is inhibited by the deletion of the xylB gene. In the engineered pathway, all carbon will be re-directed to D-ribulose by the D-tagatose 3-epimerase enzyme. D-ribulose is them converted to D-Ribulose-1-phosphate by the native *E. coli* enzyme D-ribulokinase. D-Ribulose-1-phosphate is cleaved into glycolaldehyde and dihydroxy acetone phosphate (DHAP) by D-ribulose-phosphate aldolase. The further degradation of DHAP is termed the C3 branch, leading to IPA production. Degradation of glycolaldehyde, termed the C2-branch, can lead to ethylene glycol or glycolate formation. Glycolate is the undesired by-product that can be produced by the aldA gene product. Ethylene glycol can be produced from glycolaldehyde using the enzyme glycolaldehyde reductase. The conversion of DHAP to acetyl-CoA (through glyceraldehyde-3-phosphate and pyruvate) is part of natural *E. coli* metabolism. One molecule of acetyl-CoA is condensed to another molecule of acetyl-CoA by the enzyme thiolase to produce acetoacetyl-CoA. The CoA from acetoacetyl-CoA is recycled to a molecule of acetate by acetate:acetoacetyl-CoA transferase or hydrolase, generating acetyl-CoA and acetoacetate. Acetoacetate is decarboxylated by acetoacetate decarboxylase to acetone which is further reduced to IPA by a secondary alcohol dehydrogenase enzyme. IPA can further be converted to propene by a dehydratase.

In another embodiment, the pathway for MEG+IPA co-production in *E. coli* comprises the following enzymes for IPA production: thiolase, acetate:acetoacetyl-CoA transferase or hydrolase, acetoacetate decarboxylase and secondary alcohol dehydrogenase. The MEG pathway via D-xylulose-1-phosphate comprises the following enzymes: D-xylulose 1-kinase, D-xylulose-1-phosphate aldolase and glycolaldehyde reductase. In order to increase carbon flux to the desired pathway, three specific genes that could divert carbon flux were identified and deleted: xylB gene coding for a xylulokinase (this enzyme can divert carbon flux into the pentose phosphate pathway), the aldA gene coding for aldehyde dehydrogenase A (can divert carbon flux from glycolaldehyde to glycolate instead of to MEG) and the ldhA gene coding for lactate dehydrogenase (this enzyme can divert carbon flux from pyruvate to lactate instead of to acetyl-CoA).

Figure 2:
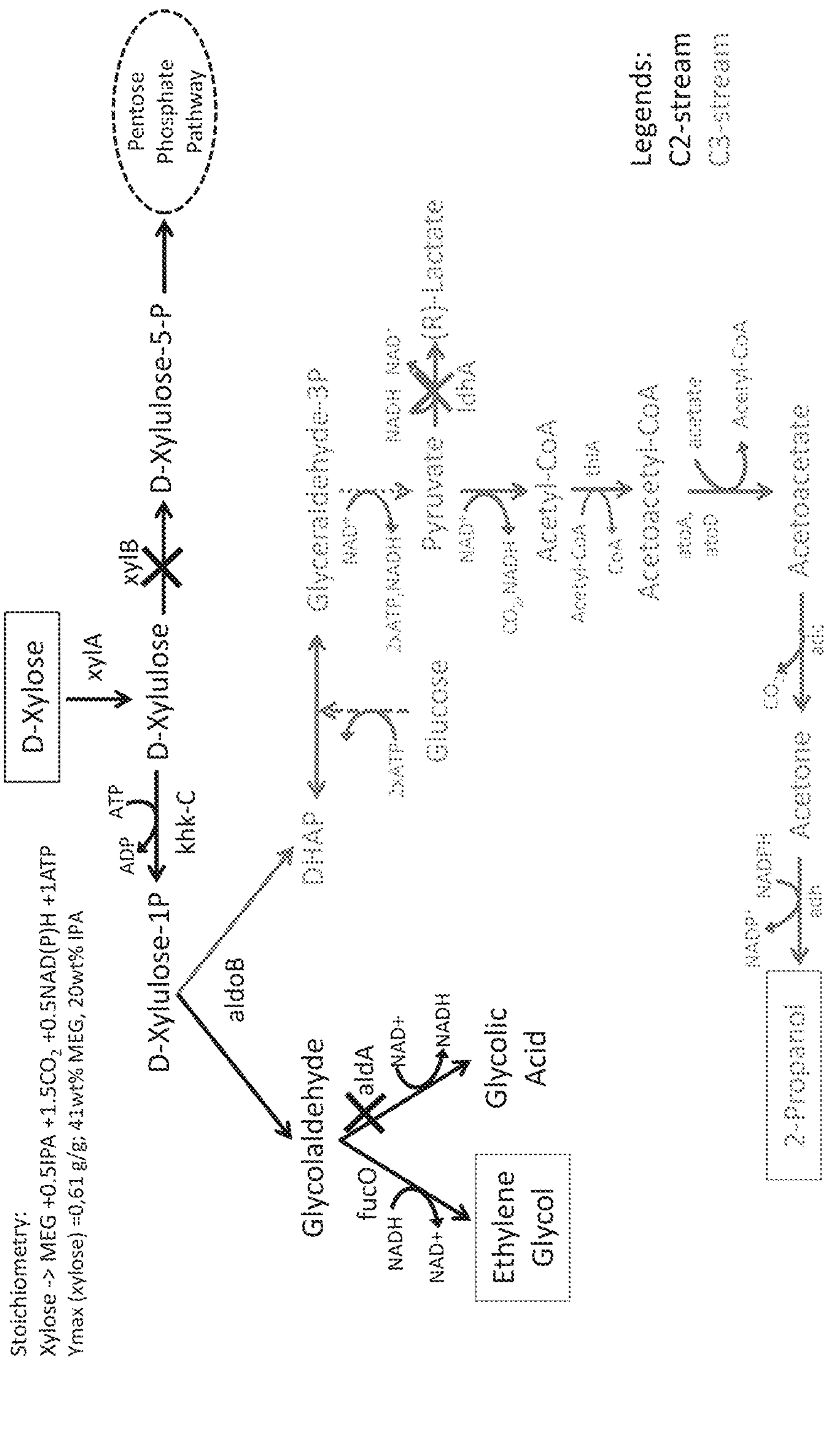
FIG. 2 illustrates MEG and isopropanol co-production pathway via xylonate.

The first step of the pathway (FIG. 2) is the natural conversion of D-xylose into D-xylulose. D-xylulose normally enters the pentose phosphate pathway for energy and biomass generation, which is inhibited by the deletion of the xylB gene. In the engineered pathway, all carbon will be re-directed to D-xylulose-1-phosphate by the D-xylulose 1-kinase enzyme. D-xylulose-1-phosphate is then cleaved into glycolaldehyde and dihydroxy acetone phosphate (DHAP) by D-xylulose-1-phosphate aldolase. Production of MEG from glycolaldehyde and a three carbon compound from DHAP (for example, acetone, IPA and/or propene) proceeds as described for FIG. 1.

In another embodiment, the pathway for MEG+IPA co-production in *E. coli* comprises the following enzymes for IPA production: thiolase, acetate:acetoacetyl-CoA transferase or hydrolase, acetoacetate decarboxylase and secondary alcohol dehydrogenase. The MEG pathway via D-xylonate comprises the following enzymes: xylose dehydrogenase, optionally xylonolactonase, xylonate dehydratase, 2-keto-3-deoxy-D-xylonate aldolase and glycolaldehyde reductase. In order to increase carbon flux to the desired pathway, three specific genes that could divert carbon flux were identified and deleted: xylA gene coding for a D-xylose isomerase (this enzyme can divert carbon flux from D-xylose to D-xylulose instead of to D-xylonate or D-xylonolactone), the aldA gene coding for aldehyde dehydrogenase A (can divert carbon flux from glycolaldehyde to glycolate instead of to MEG) and the ldhA gene coding for lactate dehydrogenase (this enzyme can divert carbon flux from pyruvate to lactate instead of to acetyl-CoA).

Figure 3:
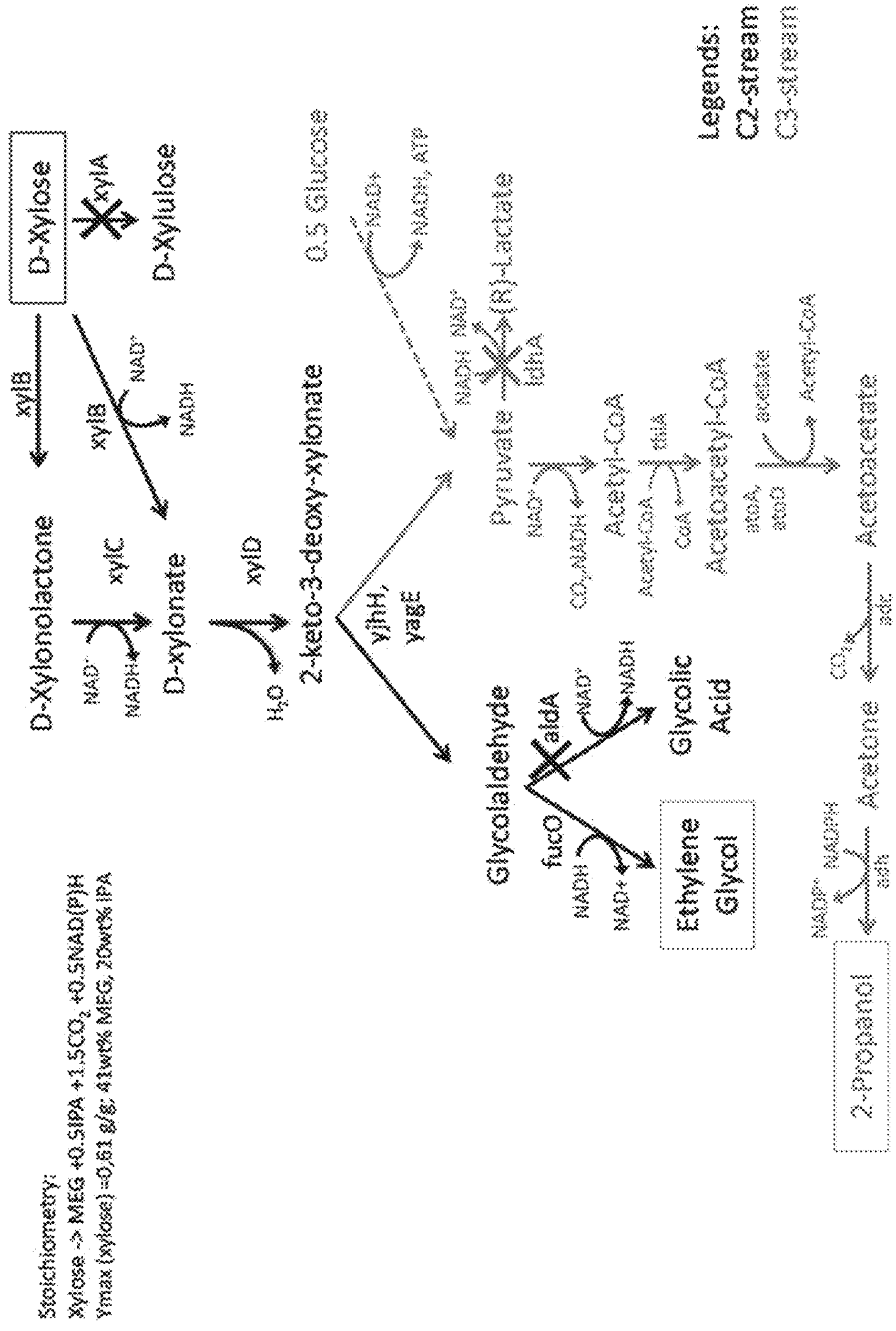
FIG. 3 illustrates possible three carbon co-products for MEG.

The first step of the pathway (FIG. 3) is the conversion of D-xylose into D-xylonate, either by a two-step process using a xylose dehydrogenase to convert D-xylose to D-xylonolactone followed by conversion of D-xylonolactone to D-xylonate with a xylonolactonase enzyme, or by a one-step process using a xylose dehydrogenase to convert D-xylose directly to D-xylonate. The conversion of D-xylose to D-xylulose is inhibited by the deletion of the xylA gene. D-xylonate is then converted to 2-keto-3-deoxy-xylonate by a xylonate dehydratase. 2-keto-3-deoxy-xylonate is then cleaved into glycolaldehyde and pyruvate by 2-keto-3-deoxy-D-xylonate aldolase. Production of MEG from glycolaldehyde and a three carbon compound from pyruvate (for example, acetone, IPA and/or propene) proceeds as described for FIG. 1.

Figure 5:
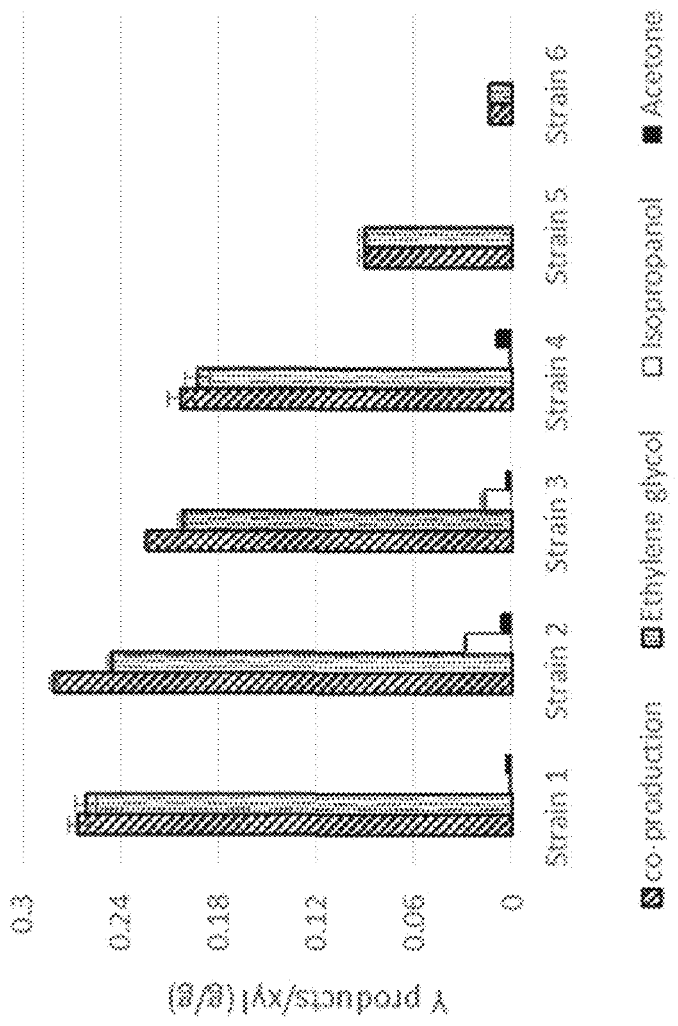
FIG. 5 illustrates overall yield (g products/g xylose) of ethylene glycol, isopropanol and acetone produced using a xylulose-1-phosphate pathway.
Figure 6:
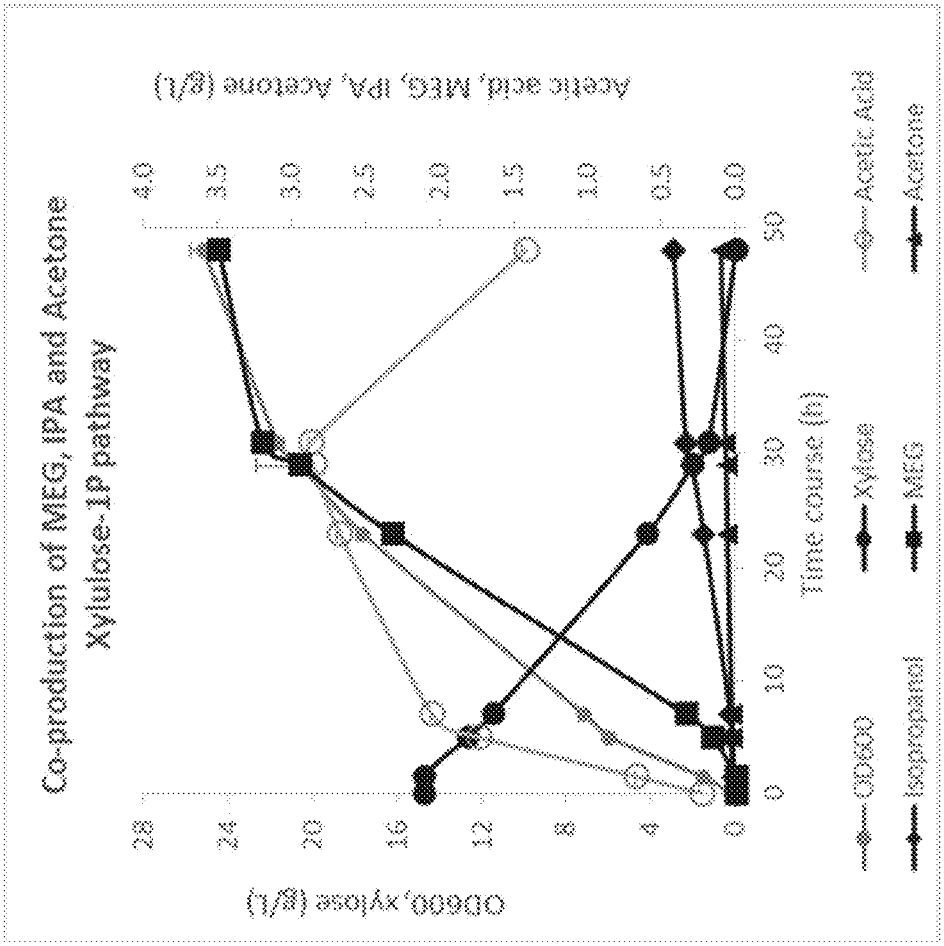
FIG. 6 illustrates co-production of MEG, isopropanol and acetone using a xylulose-1-phosphate pathway in *E. coli.*

The pathway for MEG+IPA co-production in *S. cerevisiae* (FIG. 5) comprises the following enzymes for IPA production: thiolase, acetate: acetoacetyl-CoA transferase or hydrolase, acetoacetate decarboxylase and secondary alcohol dehydrogenase. The MEG pathway via D-ribulose-1-phosphate comprises the following enzymes: D-tagatose 3-epimerase, D-ribulokinase, D-ribulose-phosphate aldolase and glycolaldehyde reductase. Besides the two main pathways, *S. cerevisiae* is not capable of consuming xylose, so two different pathways were tested for xylose consumption. Pathway 1 comprises 2 genes: Xyl1 converts D-Xylose to xylitol, and Xyl2 converts Xylitol to D-xylulose. Pathway 2 comprises only one gene: XylA that directly converts D-xylose to D-xylulose. In order to increase carbon flux to the desired pathway, two specific genes that could divert carbon flux were identified and deleted: XKS1 gene coding for a xylulokinase (this enzyme can divert carbon flux into the pentose phosphate pathway) and PHO13 gene coding for alkaline phosphatase (can divert carbon from pentose phosphate pathway).

The first step of the pathway is the conversion of D-xylose into D-xylulose, directly or via the intermediate xylitol. D-xylulose is converted to D-ribulose by the D-tagatose 3-epimerase enzyme. D-ribulose is then converted to D-Ribulose-1-phosphate by D-ribulokinase. D-Ribulose-1-phosphate is cleaved into glycolaldehyde and DHAP by D-ribulose-phosphate aldolase. DHAP enters the C3 branch for IPA production and glycolaldehyde can be converted to ethylene glycol using glycolaldehyde reductase. The conversion of DHAP to acetyl-CoA (through glyceraldehyde-3-phosphate and pyruvate) is part of the natural *S. cerevisiae* metabolism. One molecule of acetyl-CoA is condensed to another molecule of acetyl-CoA by thiolase, producing acetoacetyl-CoA. The CoA from acetoacetyl-CoA is recycled to a molecule of acetate by acetate:acetoacetyl-CoA transferase or hydrolase, generating one molecule of acetyl-CoA and one of acetoacetate. Acetoacetate is further decarboxylated by acetoacetate decarboxylase to acetone, which is further converted to IPA by a secondary alcohol dehydrogenase enzyme. IPA can further be converted to propene by a dehydratase-isomerase.

Surprisingly, the main problem of the IPA pathway, excess NADH production, is highly synergistic with a C2-stream for MEG production by complementing the NADH requirement of the C2 branch, while leaving just enough NADH to generate required ATP in an aerobic process, without excess ATP production.

The described IPA process of US 2010/0311135 and other applications, without carbon fixation, can only achieve 34 wt % versus the energetic maximum yield potential of 47 wt %. Thus, this IPA pathway, even if implemented perfectly, can only achieve 72% of the energetic maximum yield. In the present disclosure, the synergy of coupling IPA with MEG production is such that, without necessity of $CO_2$ fixation, the combined products' yield potential of 61 wt % is very close (94%) to the energetic (=theoretic, pathway independent) maximum yield potential of 65 wt %.

In a further embodiment, the inventive co-production pathway from xylose is implemented in an organism with natural or added capability to fix $CO_2$ using excess reducing agents, thereby providing even higher yield potential. Various $CO_2$ fixation pathways are known and have been implemented in *E. coli* or other hosts. Acetogens, such as *Clostridium ljungdahlii*, can naturally utilize excess NADH generated in the presented xylose fermentation pathway especially efficient to re-capture released $CO_2$ in the Wood-Ljungdahl pathway to produce the intermediate acetyl-CoA, which can then be used to produce more acetone or related products. $CO_2$ is released for instance in the pyruvate+CoA+$NAD^+$→acetyl-CoA+$CO_2$+2 NADH or acetoacetone→acetone+$CO_2$ reactions. Furthermore, adding a second feedstock, such as hydrogen gas ($H_2$) or syngas (a composition of $H_2$, CO, $CO_2$) or methanol, can provide more reducing agents and even allow acetogens or similarly enabled organisms to re-capture all $CO_2$ released in the xylose fermentation pathway or $CO_2$ present in the second feedstock. Such a mixotrophic fermentation can thus further increase yield potential. In the case of MEG+acetone from xylose, $CO_2$ fixation can lead to an increase of 25% relative acetone or 8% total MEG+acetone product yield. With externally added reducing agents, calculated for full capture of all xylose carbon, the yield potential is +100% for acetone which equals +32% total product yield.

Yield potentials without $CO_2$ fixation:

1 xylose→1 MEG+½ acetone+3/2 $CO_2$+1 NADH 1 xylose→1 MEG+½ IPA+3/2 $CO_2$+½ NADH Yield potentials with $CO_2$ fixation:

1 xylose→1 MEG+⅝ acetone+9/8 $CO_2$ 1 xylose→1 MEG+10/18 IPA+4/3 $CO_2$

Yield potentials with externally added reducing agents, calculated for fixation of $CO_2$ equivalent to all $CO_2$ released during xylose fermentation:

1 xylose→1 MEG+1 acetone 1 xylose→1 MEG+1 IPA

While this present disclosure is theoretically sound and synergistic, it surprisingly also avoids the biggest metabolic engineering and technical challenges of both MEG and IPA fermentation processes: C3-stream MEG fermentation and carbon fixation for IPA process.

In one embodiment, MEG is produced through the conversion of glycolaldehyde in a C-2 branch pathway and acetone is produced through the conversion of DHAP or pyruvate in a C-3 branch pathway. In another embodiment, MEG is produced through the conversion of glycolaldehyde in a C-2 branch pathway and IPA is produced through the conversion of DHAP or pyruvate in a C-3 branch pathway. In a further embodiment, MEG is produced through the conversion of glycolaldehyde in a C-2 branch pathway and propene is produced through the conversion of DHAP or pyruvate in a C-3 branch pathway.

In one embodiment, at least a portion of the excess NADH produced in the C-3 branch is used as a source of reducing equivalents in the C-2 branch. In another embodiment, at least a portion of the excess NADH produced in the C-3 branch is used to produce ATP.

In one embodiment, the co-produced MEG and acetone comprise a yield potential greater than 90% of the theoretical maximum yield potential without carbon fixation. In another embodiment, the co-produced MEG and IPA comprise a yield potential greater than 90% of the theoretical maximum yield potential without carbon fixation. In a further embodiment, the co-produced MEG and propene comprise a yield potential greater than 90% of the theoretical maximum yield potential without carbon fixation.

In one embodiment, excess biomass formation is minimized and production of MEG and acetone is maximized. In another embodiment, excess biomass formation is minimized and production of MEG and IPA is maximized. In a further embodiment, excess biomass formation is minimized and production of MEG and propene is maximized.

Production Compounds

Monoethylene Glycol

Monoethylene glycol (MEG) is an important raw material for industrial applications. A primary use of MEG is in the manufacture of polyethylene terephthalate (PET) resins, films and fibers. In addition, MEG is important in the production of antifreezes, coolants, aircraft anti-icer and deicers and solvents. MEG is also known as ethane-1,2-diol or ethylene glycol.

Ethylene glycol is also used as a medium for convective heat transfer in, for example, automobiles and liquid cooled computers.

Because of its high boiling point and affinity for water, ethylene glycol is a useful desiccant. Ethylene glycol is widely used to inhibit the formation of natural gas clathrates (hydrates) in long multiphase pipelines that convey natural gas from remote gas fields to a gas processing facility. Ethylene glycol can be recovered from the natural gas and reused as an inhibitor after purification treatment that removes water and inorganic salts.

Minor uses of ethylene glycol include in the manufacture of capacitors, as a chemical intermediate in the manufacture of 1,4-dioxane, and as an additive to prevent corrosion in liquid cooling systems for personal computers. Ethylene glycol is also used in the manufacture of some vaccines; as a minor ingredient in shoe polish, inks and dyes; as a rot and fungal treatment for wood; and as a preservative for biological specimens.

Acetone

Acetone (also known as propanone) is an organic compound with the formula (CH3)2CO. It is a colorless, volatile, flammable liquid, and is the simplest ketone.

Acetone is miscible with water and serves as an important solvent, typically for cleaning purposes in the laboratory. Over 6.7 million tonnes are produced worldwide, mainly for use as a solvent and production of methyl methacrylate and bisphenol A. It is a common building block in organic chemistry. Familiar household uses of acetone are as the active ingredient in nail polish remover and as paint thinner.

Isopropanol

Isopropyl alcohol (IUPAC name 2-propanol), also called isopropanol, is a compound with the chemical formula C3H8O or C3H7OH or CH3CHOHCH3. It is a colorless, flammable chemical compound with a strong odor. It is the simplest example of a secondary alcohol, where the alcohol carbon atom is attached to two other carbon atoms sometimes shown as (CH3)2CHOH. It is a structural isomer of propanol. It has a wide variety of industrial and household uses.

Propene

Propene, also known as propylene or methyl ethylene, is an unsaturated organic compound having the chemical formula $C3H_6$. It has one double bond, and is the second simplest member of the alkene class of hydrocarbons.

Propene is produced from fossil fuels—petroleum, natural gas, and, to a much lesser extent, coal. Propene is a byproduct of oil refining and natural gas processing.

In some aspects, the microbes of the present disclosure produce monoethylene glycol (MEG). In some aspects, the microbes of the present disclosure produce MEG and one or more C3 compounds. In some aspects, the microbes of the present disclosure produce MEG and one or more C3 compounds. In some aspects, the microbes of the present disclosure produce one or more of the following C3 compounds: acetone, isopropanol, and propene. In some aspects, the microbes of the present disclosure produce MEG and acetone. In some aspects, the microbes of the present disclosure produce MEG and isopropanol. In some aspects, the microbes of the present disclosure produce MEG and propene. In some aspects, the microbes of the present disclosure produce MEG, acetone, and isopropanol. In some aspects, the microbes of the present disclosure produce MEG, acetone, and propene. In some aspects, the microbes of the present disclosure produce MEG, isopropanol and propene. In some aspects, the microbes of the present disclosure produce MEG, acetone, isopropanol, and propene.

Generation of Microbial Populations

Isolation of Microbes

Microbes useful in methods and compositions disclosed herein can be obtained from microbial deposits of microbes, bacteria and/or fungi, that produce or are capable of producing MEG and/or C3 compounds. A method of obtaining microbes may be through the isolation of microbes from any number of environmental samples. Microbes can be obtained from global strain banks.

Genetic Modification

The genetic modification introduced into one or more microbes of the methods disclosed herein may be a knockout mutation (e.g. deletion of a promoter, insertion or deletion to produce a premature stop codon, deletion of an entire gene), or it may be elimination or abolishment of activity of a protein domain (e.g. point mutation affecting an active site, or deletion of a portion of a gene encoding the relevant portion of the protein product), or it may alter or abolish a regulatory sequence of a target gene. One or more regulatory sequences may also be inserted, including heterologous regulatory sequences and regulatory sequences found within a genome of a microbial species or genus corresponding to the microbe into which the genetic variation is introduced. Moreover, regulatory sequences may be selected based on the expression level of a gene in a microbial culture. The genetic variation may be a predetermined genetic variation that is specifically introduced to a target site. The genetic variation may be a random mutation within the target site. The genetic variation may be an insertion or deletion of one or more nucleotides. In some cases, a plurality of different genetic variations (e.g. 2, 3, 4, 5, 10, or more) are introduced into one or more of the isolated bacteria before assessing trait improvement. The plurality of genetic variations can be any of the above types, the same or different types, and in any combination. In some cases, a plurality of different genetic variations are introduced serially, introducing a first genetic variation after a first isolation step, a second genetic variation after a second isolation step, and so forth so as to accumulate a plurality of desired modifications in the microbes.

In general, the term "genetic variation" refers to any change introduced into a polynucleotide sequence relative to a reference polynucleotide, such as a reference genome or portion thereof, or reference gene or portion thereof. A genetic variation may be referred to as a "mutation," and a sequence or organism comprising a genetic variation may be referred to as a "genetic variant" or "mutant". Genetic variations can have any number of effects, such as the increase or decrease of some biological activity, including gene expression, metabolism, and cell signaling. Genetic variations can be specifically introduced to a target site, or introduced randomly. A variety of molecular tools and methods are available for introducing genetic variation. For example, genetic variation can be introduced via polymerase chain reaction mutagenesis, oligonucleotide-directed mutagenesis, saturation mutagenesis, fragment shuffling mutagenesis, homologous recombination, recombineering, lambda red mediated recombination, CRISPR/Cas9 systems, chemical mutagenesis, and combinations thereof. Chemical methods of introducing genetic variation include exposure of DNA to a chemical mutagen, e.g., ethyl methanesulfonate (EMS), methyl methanesulfonate (MMS), N-nitrosourea (EN U), N-methyl-N-nitro-N'-nitrosoguanidine, 4-nitroquinoline N-oxide, di ethyl sulfate, benzopyrene, cyclophosphamide, bleomycin, triethylmelamine, acrylamide monomer, nitrogen mustard, vincristine, diepoxyalkanes (for example, diepoxybutane), ICR-170, formaldehyde, procarbazine hydrochloride, ethylene oxide, dimethylnitrosamine, 7,12 dimethylbenz(a)anthracene, chlorambucil, hexamethylphosphoramide, bisulfan, and the like. Radiation mutation-inducing agents include ultraviolet radiation, γ-irradiation, X-rays, and fast neutron bombardment. Genetic variation can also be introduced into a nucleic acid using, e.g., trimethylpsoralen with ultraviolet light. Random or targeted insertion of a mobile DNA element, e.g., a transposable element, is another suitable method for generating genetic variation. Genetic variations can be introduced into a nucleic acid during amplification in a cell-free in vitro system, e.g., using a polymerase chain reaction (PCR) technique such as error-prone PCR. Genetic variations can be introduced into a nucleic acid in vitro using DNA shuffling techniques (e.g., exon shuffling, domain swapping, and the like). Genetic variations can also be introduced into a nucleic acid as a result of a deficiency in a DNA repair enzyme in a cell, e.g., the presence in a cell of a mutant gene encoding a mutant DNA repair enzyme is expected to generate a high frequency of mutations (i.e., about 1 mutation/100 genes-1 mutation/10,000 genes) in the genome of the cell. Examples of genes encoding DNA repair enzymes include but are not limited to Mut H, Mut S, Mut L, and Mut U, and the homologs thereof in other species (e.g., MSH 1 6, PMS 1 2, MLH 1, GTBP, ERCC-1, and the like). Example descriptions of various methods for introducing genetic variations are provided in e.g., Stemple (2004) Nature 5:1-7; Chiang et al. (1993) PCR Methods Appl 2(3): 210-217; Stemmer (1994) Proc. Natl. Acad. Sci. USA 91:10747-10751; and U.S. Pat. Nos. 6,033,861, and 6,773,900.

Genetic variations introduced into microbes may be classified as transgenic, cisgenic, intragenomic, intrageneric, intergeneric, synthetic, evolved, rearranged, or SNPs.

CRISPR/Cas9 (Clustered regularly interspaced short palindromic repeats)/CRISPR-associated (Cas) systems can be used to introduce desired mutations. CRISPR/Cas9 provide bacteria and archaea with adaptive immunity against viruses and plasmids by using CRISPR RNAs (crRNAs) to guide the silencing of invading nucleic acids. The Cas9 protein (or functional equivalent and/or variant thereof, i.e., Cas9-like protein) naturally contains DNA endonuclease activity that depends on the association of the protein with two naturally occurring or synthetic RNA molecules called crRNA and tracrRNA (also called guide RNAs). In some cases, the two molecules are covalently link to form a single molecule (also called a single guide RNA ("sgRNA"). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-stranded break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Further exemplary descriptions of CRISPR systems for introducing genetic variation can be found in, e.g. U.S. Pat. No. 8,795,965.

As a cyclic amplification technique, polymerase chain reaction (PCR) mutagenesis uses mutagenic primers to introduce desired mutations. PCR is performed by cycles of denaturation, annealing, and extension. After amplification by PCR, selection of mutated DNA and removal of parental plasmid DNA can be accomplished by: 1) replacement of dCTP by hydroxymethylated-dCTP during PCR, followed by digestion with restriction enzymes to remove non-hydroxymethylated parent DNA only; 2) simultaneous mutagenesis of both an antibiotic resistance gene and the studied gene changing the plasmid to a different antibiotic resistance, the new antibiotic resistance facilitating the selection of the desired mutation thereafter; 3) after introducing a desired mutation, digestion of the parent methylated template DNA by restriction enzyme Dpnl which cleaves only methylated DNA, by which the mutagenized unmethylated chains are recovered; or 4) circularization of the mutated PCR products in an additional ligation reaction to increase the transformation efficiency of mutated DNA. Further description of exemplary methods can be found in e.g. U.S. Pat. Nos. 7,132,265, 6,713,285, 6,673,610, 6,391,548, 5,789,166, 5,780,270, 5,354,670, 5,071,743, and US20100267147.

Oligonucleotide-directed mutagenesis, also called site-directed mutagenesis, typically utilizes a synthetic DNA primer. This synthetic primer contains the desired mutation and is complementary to the template DNA around the mutation site so that it can hybridize with the DNA in the gene of interest. The mutation may be a single base change (a point mutation), multiple base changes, deletion, or insertion, or a combination of these. The single-strand primer is then extended using a DNA polymerase, which copies the rest of the gene. The gene thus copied contains the mutated site, and may then be introduced into a host cell as a vector and cloned. Finally, mutants can be selected by DNA sequencing to check that they contain the desired mutation.

Genetic variations can be introduced using error-prone PCR. In this technique the gene of interest is amplified using a DNA polymerase under conditions that are deficient in the fidelity of replication of sequence. The result is that the amplification products contain at least one error in the sequence. When a gene is amplified and the resulting product(s) of the reaction contain one or more alterations in sequence when compared to the template molecule, the resulting products are mutagenized as compared to the template. Another means of introducing random mutations is exposing cells to a chemical mutagen, such as nitrosoguanidine or ethyl methanesulfonate (Nestmann, Mutat Res 1975 June; 28(3):323-30), and the vector containing the gene is then isolated from the host.

Saturation mutagenesis is another form of random mutagenesis, in which one tries to generate all or nearly all possible mutations at a specific site, or narrow region of a gene. In a general sense, saturation mutagenesis is comprised of mutagenizing a complete set of mutagenic cassettes (wherein each cassette is, for example, 1-500 bases in length) in defined polynucleotide sequence to be mutagenized (wherein the sequence to be mutagenized is, for example, from 15 to 100,000 bases in length). Therefore, a group of mutations (e.g. ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Fragment shuffling mutagenesis, also called DNA shuffling, is a way to rapidly propagate beneficial mutations. In an example of a shuffling process, DNAse is used to fragment a set of parent genes into pieces of e.g. about 50-100 bp in length. This is then followed by a polymerase chain reaction (PCR) without primers—DNA fragments with sufficient overlapping homologous sequence will anneal to each other and are then be extended by DNA polymerase. Several rounds of this PCR extension are allowed to occur, after some of the DNA molecules reach the size of the parental genes. These genes can then be amplified with another PCR, this time with the addition of primers that are designed to complement the ends of the strands. The primers may have additional sequences added to their 5' ends, such as sequences for restriction enzyme recognition sites needed for ligation into a cloning vector. Further examples of shuffling techniques are provided in US20050266541.

Homologous recombination mutagenesis involves recombination between an exogenous DNA fragment and the targeted polynucleotide sequence. After a double-stranded break occurs, sections of DNA around the 5' ends of the break are cut away in a process called resection. In the strand invasion step that follows, an overhanging 3' end of the broken DNA molecule then "invades" a similar or identical DNA molecule that is not broken. The method can be used to delete a gene, remove exons, add a gene, and introduce point mutations. Homologous recombination mutagenesis can be permanent or conditional. Typically, a recombination template is also provided. A recombination template may be a component of another vector, contained in a separate vector, or provided as a separate polynucleotide. In some embodiments, a recombination template is designed to serve as a template in homologous recombination, such as within or near a target sequence nicked or cleaved by a site-specific nuclease. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence. Non-limiting examples of site-directed nucleases useful in methods of homologous recombination include zinc finger nucleases, CRISPR nucleases, TALE nucleases, and meganuclease. For a further description of the use of such nucleases, see e.g. U.S. Pat. No. 8,795,965 and US20140301990.

Introducing genetic variation may be an incomplete process, such that some bacteria in a treated population of bacteria carry a desired mutation while others do not. In some cases, it is desirable to apply a selection pressure so as to enrich for bacteria carrying a desired genetic variation. Traditionally, selection for successful genetic variants involved selection for or against some functionality imparted or abolished by the genetic variation, such as in the case of inserting antibiotic resistance gene or abolishing a metabolic activity capable of converting a non-lethal compound into a lethal metabolite. It is also possible to apply a selection pressure based on a polynucleotide sequence itself, such that only a desired genetic variation need be introduced (e.g. without also requiring a selectable marker). In this case, the selection pressure can comprise cleaving genomes lacking the genetic variation introduced to a target site, such that selection is effectively directed against the reference sequence into which the genetic variation is sought to be introduced. Typically, cleavage occurs within 100 nucleotides of the target site (e.g. within 75, 50, 25, 10, or fewer nucleotides from the target site, including cleavage at or within the target site). Cleaving may be directed by a site-specific nuclease selected from the group consisting of a Zinc Finger nuclease, a CRISPR nuclease, a TALE nuclease (TALEN), or a meganuclease. Such a process is similar to processes for enhancing homologous recombination at a target site, except that no template for homologous recombination is provided. As a result, bacteria lacking the desired genetic variation are more likely to undergo cleavage that, left unrepaired, results in cell death. Bacteria surviving selection may then be isolated for assessing conferral of an improved trait.

A CRISPR nuclease may be used as the site-specific nuclease to direct cleavage to a target site. An improved selection of mutated microbes can be obtained by using Cas9 to kill non-mutated cells. CRISPR nuclease systems employed for selection against non-variants can employ similar elements to those described above with respect to introducing genetic variation, except that no template for homologous recombination is provided. Cleavage directed to the target site thus enhances death of affected cells.

Other options for specifically inducing cleavage at a target site are available, such as zinc finger nucleases, TALE nuclease (TALEN) systems, and meganuclease. Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double stranded breaks. Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. Meganucleases (homing endonuclease) are endodeoxyribonucleases characterized by a large recognition site (double-stranded DNA sequences of 12 to 40 base pairs. Meganucleases can be used to replace, eliminate or modify sequences in a highly targeted way. By modifying their recognition sequence through protein engineering, the targeted sequence can be changed. Meganucleases can be used to modify all genome types, whether bacterial, plant or animal and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

In some aspects, the disclosure provides for a sequence which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any sequence described herein.

In some aspects, the disclosure provides for a microbe that comprises a sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any sequence described herein.

In some aspects, the disclosure provides for a microbe that comprises a nucleic acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any sequence described herein.

In some aspects, the disclosure provides for a microbe that comprises, or primer that comprises, or probe that comprises, or non-native junction sequence that comprises, a nucleic acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any sequence described herein.

In some aspects, the disclosure provides for a microbe that comprises a non-native junction sequence that shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any sequence described herein.

In some aspects, the disclosure provides for a microbe that comprises an amino acid sequence, which shares at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any sequence described herein.

Methods of Detecting Genetic Modification

The present disclosure teaches primers, probes, and assays that are useful for detecting the microbes taught herein. In some aspects, the disclosure provides for methods of detecting the WT parental strains. In other aspects, the disclosure provides for methods of detecting the engineered or modified microbes derived from parent strains or WT strains. In aspects, the present disclosure provides methods of identifying genetic alterations in a microbe.

In some aspects, the genomic engineering methods of the present disclosure lead to the creation of non-natural nucleotide "junction" sequences in the modified microbes. These non-naturally occurring nucleotide junctions can be used as a type of diagnostic that is indicative of the presence of a particular genetic alteration in a microbe taught herein.

The present techniques are able to detect these non-naturally occurring nucleotide junctions via the utilization of specialized quantitative PCR methods, including uniquely designed primers and probes. In some aspects, the probes of the disclosure bind to the non-naturally occurring nucleotide junction sequences. In some aspects, traditional PCR is utilized. In other aspects, real-time PCR is utilized. In some aspects, quantitative PCR (qPCR) is utilized. In some aspects, the PCR methods are used to identify heterologous sequences that have been inserted into the genomic DNA or extra-genomic DNA of the microbes.

Thus, the disclosure can cover the utilization of two common methods for the detection of PCR products in real-time: (1) non-specific fluorescent dyes that intercalate with any double-stranded DNA, and (2) sequence-specific DNA probes consisting of oligonucleotides that are labelled with a fluorescent reporter which permits detection only after hybridization of the probe with its complementary sequence. In some aspects, only the non-naturally occurring nucleotide junction will be amplified via the taught primers, and consequently can be detected via either a non-specific dye, or via the utilization of a specific hybridization probe. In other aspects, the primers of the disclosure are chosen such that the primers flank either side of a junction sequence, such that if an amplification reaction occurs, then said junction sequence is present.

Aspects of the disclosure involve non-naturally occurring nucleotide junction sequence molecules per se, along with other nucleotide molecules that are capable of binding to said non-naturally occurring nucleotide junction sequences under mild to stringent hybridization conditions. In some aspects, the nucleotide molecules that are capable of binding to said non-naturally occurring nucleotide junction sequences under mild to stringent hybridization conditions are termed "nucleotide probes."

In some aspects, genomic DNA can be extracted from samples and used to quantify the presence of microbes of the disclosure by using qPCR. The primers utilized in the qPCR reaction can be primers designed by Primer Blast (https://www.ncbi.nlm.nih.gov/tools/primer-blast/) to amplify unique regions of the wild-type genome or unique regions of the engineered non-intergeneric mutant strains. The qPCR reaction can be carried out using the SYBR GreenER qPCR SuperMix Universal (Thermo Fisher P/N 11762100) kit, using only forward and reverse amplification primers; alternatively, the Kapa Probe Force kit (Kapa Biosystems P/N KK4301) can be used with amplification primers and a TaqMan probe containing a FAM dye label at the 5' end, an internal ZEN quencher, and a minor groove binder and fluorescent quencher at the 3' end (Integrated DNA Technologies).

Quantitative polymerase chain reaction (qPCR) is a method of quantifying, in real time, the amplification of one or more nucleic acid sequences. The real time quantification of the PCR assay permits determination of the quantity of nucleic acids being generated by the PCR amplification steps by comparing the amplifying nucleic acids of interest and an appropriate control nucleic acid sequence, which may act as a calibration standard.

TaqMan probes are often utilized in qPCR assays that require an increased specificity for quantifying target nucleic acid sequences. TaqMan probes comprise a oligonucleotide probe with a fluorophore attached to the 5' end and a quencher attached to the 3' end of the probe. When the TaqMan probes remain as is with the 5' and 3' ends of the probe in close contact with each other, the quencher prevents fluorescent signal transmission from the fluorophore. TaqMan probes are designed to anneal within a nucleic acid region amplified by a specific set of primers. As the Taq polymerase extends the primer and synthesizes the nascent strand, the 5' to 3' exonuclease activity of the Taq polymerase degrades the probe that annealed to the template. This probe degradation releases the fluorophore, thus breaking the close proximity to the quencher and allowing fluorescence of the fluorophore. Fluorescence detected in the qPCR assay is directly proportional to the fluorophore released and the amount of DNA template present in the reaction.

The features of qPCR allow the practitioner to eliminate the labor-intensive post-amplification step of gel electrophoresis preparation, which is generally required for observation of the amplified products of traditional PCR assays. The benefits of qPCR over conventional PCR are considerable, and include increased speed, ease of use, reproducibility, and quantitative ability Microbes As described herein, in some embodiments, the recombinant microorganisms are prokaryotic microorganism. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus*, Staphylococci, Streptococci, Mycoplasmas); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and Thermosipho thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium.*

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces.*

In some aspects, the microorganisms of the present disclosure are fungi.

In some aspects, the recombinant microorganism is a eukaryotic microorganism. In some embodiments, the eukaryotic microorganism is a yeast. In exemplary embodiments, the yeast is a member of a genus selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula*, and *Myxozyma.*

In some aspects, the recombinant microorganism is a prokaryotic microorganism. In exemplary embodiments, the prokaryotic microorganism is a member of a genus selected from the group consisting of *Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium*, and *Brevibacterium.*

In some aspects, microorganism for use in the methods of the present disclosure can be selected from the group consisting of *Yarrowia, Candida, Saccharomyces, Pichia, Hansenula, Kluyveromyces, Issatchenkia, Zygosaccharomyces, Debaryomyces, Schizosaccharomyces, Pachysolen, Cryptococcus, Trichosporon, Rhodotorula, Myxozyma, Escherichia, Clostridium, Zymomonas, Salmonella, Rhodococcus, Pseudomonas, Bacillus, Lactobacillus, Enterococcus, Alcaligenes, Klebsiella, Paenibacillus, Arthrobacter, Corynebacterium*, and *Brevibacterium.*

In some aspects, a microbe resulting from the methods described herein may be a species selected from any of the following genera: *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema, Fusobacterium, Actinomyces, Bacillus, Clostridium, Corynebacterium, Erysipelothrix, Lactobacillus, Listeria, Mycobacterium, Myxococcus, Nocardia, Staphylococcus, Streptococcus, Streptomyces, Saccharomyces, Pichia*, and *Aspergillus.*

In some aspects, microorganisms for use in the methods of the present disclosure include *Clostridium* sp., *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Clostridium acetobutylicum, Clostridium beijerinckii, Oxobacter pfennigii, Thermoanaerobacter kivui, Sporomusa ovata, Thermoacetogenium phaeum, Acetobacterium carbinolicum, Sporomusa termitida, Moorella glycerini, Eubacterium aggregans, Treponema azotonutricium, Escherichia coli, Saccharomyces cerevisiae, Pseudomonas putida, Bacillus* sp, *Corynebacterium* sp., *Yarrowia lipolytica, Scheffersomyces stipitis*, and *Terrisporobacter glycolicus.*

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

Culturing of the microorganisms used in the methods of the disclosure may be conducted using any number of processes known in the art for culturing and fermenting substrates using the microorganisms. By way of example, those processes generally described in the following articles using gaseous substrates for fermentation may be utilized: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (v) J. L. Vega, et al. (1989). Study of gaseous substrate fermentations: Carbon monoxide conversion to acetate. 1. Batch culture. Biotechnology and Bioengineering. 34. 6. 774-784; (vi) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactor, such as Continuous Stirred Tank Bioreactor, Bubble Column Bioreactor, Airlift Bioreactor, Fluidized Bed Bioreactor, Packed Bed Bioractor, Photo-Bioreactor, Immobilized Cell Reactor, Trickle Bed Reactor, Moving Bed Biofilm Reactor, Bubble Column, Gas Lift Fermenter, Membrane Reactors such as Hollow Fiber Membrane Bioreactor. Also, in some embodiments, the bioreactor comprises a first, growth reactor in which the microorganisms are cultured, and a second, fermentation reactor, to which fermentation broth from the growth reactor is fed and in which most of the fermentation product (e.g. MEG, acetone, isopropanol, and propene) is produced. In some embodiments, the bioreactor simultaneously accomplishes the culturing of microorganism and the producing the fermentation product (e.g. MEG, acetone, isopropanol, and propene) from carbon sources such substrates and/or feedstocks provided.

Methods of Producing a Recombinant Microorganism that Produces or Accumulates MEG and One or More Three-Carbon Compounds As discussed above, the present application provides a method of producing a recombinant microorganism that produces or accumulates MEG and one or more three-carbon compounds. In one embodiment, the MEG and one or more three-carbon compounds are co-produced from xylose. In another embodiment, a method of producing a recombinant microorganism that produces or accumulates MEG and one or more three-carbon compounds from exogenous D-xylose comprises introducing into the recombinant microorganism a deletion, insertion, or loss of function mutation in a gene encoding a D-xylulose-5-kinase and/or in a gene encoding a glycoaldehyde dehydrogenase. In some embodiments, the gene encoding the D-xylulose-5-kinase is xylB. In some embodiments, the gene encoding the glycoaldehyde dehydrogenase is aldA.

In one embodiment, MEG is produced from xylose via ribulose-1-phosphate. In another embodiment, MEG is produced from xylose via xylulose-1-phosphate. In a further embodiment, MEG is produced from xylose via xylonate.

In one embodiment, one or more three-carbon compounds is produced from DHAP or pyruvate. In one embodiment, the one or more three-carbon compounds is acetone. In another embodiment, the one or more three-carbon compounds is isopropanol. In a further embodiment, the one or more three-carbon compounds is propene.

As discussed above, in one aspect, the present disclosure provides a method of producing a recombinant microorganism that produces or accumulates MEG and acetone from exogenous D-xylose, comprising introducing into the recombinant microorganism and/or overexpressing one or more of the following:

at least one endogenous or exogenous nucleic acid molecule encoding a D-tagatose 3-epimerase that catalyzes the conversion of D-xylulose to D-ribulose;

at least one endogenous or exogenous nucleic acid molecule encoding a D-ribulokinase that catalyzes the conversion of D-ribulose from (a) to D-ribulose-1-phosphate;

at least one endogenous or exogenous nucleic acid molecule encoding a D-ribulose-1-phosphate aldolase that catalyzes the conversion of D-ribulose-1-phosphate from (b) to glycolaldehyde and dihydroxyacetonephosphate (DHAP);

at least one endogenous or exogenous nucleic acid molecule encoding a glycolaldehyde reductase that catalyzes the conversion of glycolaldehyde from (c) to MEG;

at least one exogenous nucleic acid molecule encoding a thiolase that catalyzes the conversion of acetyl-CoA to acetoacetyl-CoA;

at least one endogenous or exogenous nucleic acid molecule encoding an acetate:acetoacetyl-CoA transferase or hydrolase that catalyzes the conversion of acetoacetyl-CoA from (e) to acetoacetate; and/or at least one endogenous or exogenous nucleic acid molecule encoding an acetoacetate decarboxylase that catalyzes the conversion of acetoacetate from (f) to acetone;

wherein the produced intermediate DHAP is converted to acetyl-CoA through the endogenous glycolysis pathway in the microorganism, and wherein MEG and acetone are co-produced.

In one embodiment, the D-tagatose 3-epimerase is encoded by one or more nucleic acid molecules obtained from a microorganism selected from the group consisting of *Pseudomonas* sp., *Mesorhizobium* sp. and *Rhodobacter* sp. In some embodiments, the D-tagatose 3-epimerase is encoded by one or more nucleic acid molecules obtained from a microorganism selected from the group consisting of *Pseudomonas cichorii, Pseudomonas* sp. ST-24, *Mesorhizobium loti* and *Rhodobacter sphaeroides*. In some embodiments, the one or more nucleic acid molecules is dte and/or FJ851309.1, or homolog thereof. In a further embodiment, the D-tagatose 3-epimerase comprises an amino acid sequence selected from the group consisting of SEQ ID NOs: 3 and 5. In yet a further embodiment, the D-tagatose 3-epimerase is encoded by a nucleic acid sequence selected from the group consisting of SEQ ID NOs: 1, 2 and 4.

In one embodiment, the D-ribulokinase is encoded by one or more nucleic acid molecules obtained from *E. coli*. In some embodiments, the one or more nucleic acid molecules is fucK, or homolog thereof. In a further embodiment, the D-ribulokinase comprises an amino acid sequence set forth in SEQ ID NO: 8. In yet a further embodiment, the D-ribulokinase is encoded by a nucleic acid sequence selected from the group consisting of SEQ ID NOs: 6 and 7.

In one embodiment, the D-ribulose-1-phosphate aldolase is encoded by one or more nucleic acid molecules obtained from *E. coli*. In some embodiments, the one or more nucleic acid molecules is fucA, or homolog thereof. In a further embodiment, the D-ribulose-1-phosphate aldolase comprises an amino acid sequence set forth in SEQ ID NO: 11. In yet a further embodiment, the D-ribulose-1-phosphate aldolase is encoded by a nucleic acid sequence selected from the group consisting of SEQ ID NOs: 9 and 10.

In one embodiment, the method further comprises introducing into the recombinant microorganism and/or overexpressing at least one endogenous or exogenous nucleic acid molecule encoding a secondary alcohol dehydrogenase that catalyzes the conversion of acetone from (g) to isopropanol.

In another embodiment, the method further comprises introducing into the recombinant microorganism and/or overexpressing at least one endogenous or exogenous nucleic acid molecule encoding a dehydratase that catalyzes the conversion of isopropanol to propene.

In another embodiment, the method further comprises introducing into the recombinant microorganism one or more modifications selected from the group consisting of:

a deletion, insertion, or loss of function mutation in a gene encoding a D-xylulose-5-kinase that catalyzes the conversion of D-xylulose to D-xylulose-5-phosphate;

a deletion, insertion, or loss of function mutation in a gene encoding a glycolaldehyde dehydrogenase that catalyzes the conversion of glycolaldehyde to glycolic acid; and a deletion, insertion, or loss of function mutation in a gene encoding a lactate dehydrogenase that catalyzes the conversion of pyruvate to lactate.

In one embodiment, an endogenous D-xylose isomerase catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

As discussed above, in another aspect, the present disclosure provides a method of producing a recombinant microorganism that produces or accumulates MEG and acetone from exogenous D-xylose, comprising introducing into the recombinant microorganism and/or overexpressing one or more of the following:

- at least one endogenous or exogenous nucleic acid molecule encoding a D-xylulose 1-kinase that catalyzes the conversion of D-xylulose to D-xylulose-1-phosphate;
- at least one endogenous or exogenous nucleic acid molecule encoding a D-xylulose-1-phosphate aldolase that catalyzes the conversion of D-xylulose-1-phosphate from (a) to glycolaldehyde and dihydroxyacetonephosphate (DHAP);
- at least one endogenous or exogenous nucleic acid molecule encoding a glycolaldehyde reductase that catalyzes the conversion of glycolaldehyde from (b) to MEG;
- at least one endogenous or exogenous nucleic acid molecule encoding a thiolase that catalyzes the conversion of acetyl-CoA to acetoacetyl-CoA;
- at least one endogenous or exogenous nucleic acid molecule encoding an acetate:acetoacetyl-CoA transferase or hydrolase that catalyzes the conversion of acetoacetyl-CoA from (d) to acetoacetate; and/or
- at least one endogenous or exogenous nucleic acid molecule encoding an acetoacetate decarboxylase that catalyzes the conversion of acetoacetate from (e) to acetone;

wherein the produced intermediate DHAP is converted to acetyl-CoA through the endogenous glycolysis pathway in the microorganism, and wherein MEG and acetone are co-produced.

In one embodiment, the D-xylulose 1-kinase is encoded by one or more nucleic acid molecules obtained from *Homo sapiens*. In some embodiments, the one or more nucleic acid molecules encoding the D-xylulose 1-kinase is ketohexokinase C (khk-C), or homolog thereof. In another embodiment, the one or more nucleic acid molecules encoding the D-xylulose 1-kinase comprises an amino acid sequence set forth in SEQ ID NO: 55. In a further embodiment, the one or more nucleic acid molecules encoding the D-xylulose 1-kinase is encoded by a nucleic acid sequence selected from the group consisting of SEQ ID NOs: 53 and 54.

In one embodiment, the D-xylulose-1-phosphate aldolase is encoded by one or more nucleic acid molecules obtained from *Homo sapiens*. In another embodiment, the one or more nucleic acid molecules encoding the D-xylulose-1-phosphate aldolase is aldolase B (ALDOB), or homolog thereof. In some embodiments, the one or more nucleic acid molecules encoding the D-xylulose-1-phosphate aldolase comprises an amino acid sequence set forth in SEQ ID NO: 58. In some embodiments, the one or more nucleic acid molecules encoding the D-xylulose-1-phosphate aldolase is encoded by a nucleic acid sequence selected from the group consisting of SEQ ID NOs: 56 and 57.

In one embodiment, the method further comprises introducing into the recombinant microorganism and/or overexpressing at least one endogenous or exogenous nucleic acid molecule encoding a secondary alcohol dehydrogenase that catalyzes the conversion of acetone from (f) to isopropanol.

In another embodiment, the method further comprises introducing into the recombinant microorganism and/or overexpressing at least one endogenous or exogenous nucleic acid molecule encoding a dehydratase that catalyzes the conversion of isopropanol to propene.

In another embodiment, the method further comprises introducing into the recombinant microorganism one or more modifications selected from the group consisting of:

a deletion, insertion, or loss of function mutation in a gene encoding a D-xylulose-5-kinase that catalyzes the conversion of D-xylulose to D-xylulose-5-phosphate;

a deletion, insertion, or loss of function mutation in a gene encoding a glycolaldehyde dehydrogenase that catalyzes the conversion of glycolaldehyde to glycolic acid; and a deletion, insertion, or loss of function mutation in a gene encoding a lactate dehydrogenase that catalyzes the conversion of pyruvate to lactate.

In one embodiment, an endogenous D-xylose isomerase catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

In some embodiments of any aspect disclosed above, a method of producing a recombinant microorganism that produces or accumulates MEG and one or more three-carbon compounds from exogenous D-xylose comprises introducing into the recombinant microorganism a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate. In some embodiments, the D-xylulose-5-kinase is from *Escherichia coli*. In some embodiments, the D-xylulose-5-kinase is encoded by the xylB gene, or homolog thereof.

In some embodiments of any aspect disclosed above, a method of producing a recombinant microorganism that produces or accumulates MEG and one or more three-carbon compounds from exogenous D-xylose comprises introducing into the recombinant microorganism a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In some embodiments, the glycolaldehyde dehydrogenase is from *Escherichia coli*. In some embodiments, the glycolaldehyde dehydrogenase is encoded by the aldA gene, or homolog thereof.

In some embodiments of any aspect disclosed above, a method of producing a recombinant microorganism that produces or accumulates MEG and one or more three-carbon compounds from exogenous D-xylose comprises introducing into the recombinant microorganism a deletion, insertion, or loss of function mutation in a gene encoding a lactate dehydrogenase to prevent the production of lactate from pyruvate and instead shunt the reaction toward production of one or more three-carbon compounds. In some embodiments, the lactate dehydrogenase is from *Escherichia coli*. In some embodiments, the lactate dehydrogenase is encoded by the ldhA gene, or homolog thereof.

As discussed above, in another aspect, the present disclosure provides a method of producing a recombinant microorganism that produces or accumulates MEG and acetone from exogenous D-xylose and glucose, comprising introducing into the recombinant microorganism and/or overexpressing one or more of the following:

at least one exogenous nucleic acid molecule encoding a xylose reductase or aldose reductase that catalyzes the conversion of D-xylose to xylitol and at least one exogenous nucleic acid molecule encoding a xylitol dehydrogenase that catalyzes the conversion of xylitol to D-xylulose;

at least one exogenous nucleic acid molecule encoding a D-xylose isomerase that catalyzes the conversion of D-xylose to D-xylulose, and wherein the method further comprises introducing into the recombinant microorganism and/or overexpressing one or more of the following:

at least one endogenous or exogenous nucleic acid molecule encoding a D-tagatose 3-epimerase that catalyzes the conversion of D-xylulose from (a) or (b) to D-ribulose;

at least one endogenous or exogenous nucleic acid molecule encoding a D-ribulokinase that catalyzes the conversion of D-ribulose from (c) to D-ribulose-1-phosphate;

at least one endogenous or exogenous nucleic acid molecule encoding a D-ribulose-1-phosphate aldolase that catalyzes the conversion of D-ribulose-1-phosphate from (d) to glycolaldehyde and dihydroxyacetonephosphate (DHAP);

at least one endogenous or exogenous nucleic acid molecule encoding a glycolaldehyde reductase or methylglyoxal reductase that catalyzes the conversion of glycolaldehyde from (e) to MEG;

at least one endogenous or exogenous nucleic acid molecule encoding a thiolase that catalyzes the conversion of acetyl-CoA to acetoacetyl-CoA;

at least one endogenous or exogenous nucleic acid molecule encoding an acetate:acetoacetyl-CoA transferase or hydrolase that catalyzes the conversion of acetoacetyl-CoA from (g) to acetoacetate; and/or at least one endogenous or exogenous nucleic acid molecule encoding an acetoacetate decarboxylase that catalyzes the conversion of acetoacetate from (h) to acetone;

wherein the produced intermediate DHAP is converted to acetyl-CoA through the endogenous glycolysis pathway in the microorganism, and wherein MEG and acetone are co-produced.

In some embodiments, the xylose reductase or aldose reductase is encoded by one or more nucleic acid molecules obtained from a microorganism selected from the group consisting of *Hypocrea* sp., *Scheffersomyces* sp., *Saccharomyces* sp., *Pachysolen* sp., *Pichia* sp., *Candida* sp., *Aspergillus* sp., *Neurospora* sp., and *Cryptococcus* sp. In some embodiments, the xylose reductase or aldose reductase is encoded by one or more nucleic acid molecules obtained from a microorganism selected from the group consisting of *Hypocrea jecorina, Scheffersomyces stipitis, Saccharomyces cerevisiae, Pachysolen tannophilus, Pichia stipitis, Pichia quercuum, Candida shehatae, Candida tenuis, Candida tropicalis, Aspergillus niger, Neurospora crassa* and *Cryptococcus lactativorus*. In another embodiment, the one or more nucleic acid molecules encoding the xylose reductase or aldose reductase is xyl1 and/or GRE3 or homolog thereof. In some embodiments, the one or more nucleic acid molecules encoding the xylose reductase or aldose reductase comprises an amino acid sequence selected from the group consisting of SEQ ID NOs: 84 and 87. In some embodiments, the one or more nucleic acid molecules encoding the xylose reductase or aldose reductase is encoded by a nucleic acid sequence selected from the group consisting of SEQ ID NOs: 82, 83, 85 and 86.

In one embodiment of any aspect disclosed above, the xylitol dehydrogenase is encoded by one or more nucleic acid molecules obtained from a microorganism selected from the group consisting of *Scheffersomyces* sp., *Trichoderma* sp., *Pichia* sp., *Saccharomyces* sp., *Gluconobacter* sp., *Galactocandida* sp., *Neurospora* sp., and *Serratia* sp. In another embodiment, the xylitol dehydrogenase is encoded by one or more nucleic acid molecules obtained from a microorganism selected from the group consisting of *Scheffersomyces stipitis, Trichoderma reesei, Pichia stipitis, Saccharomyces cerevisiae, Gluconobacter oxydans, Galactocandida mastotermitis, Neurospora crassa* and *Serratia marcescens*. In another embodiment, the one or more nucleic acid molecules encoding the xylitol dehydrogenase is xyl2 and/or xdh1, or homolog thereof. In some embodiments, the one or more nucleic acid molecules encoding the xylitol dehydrogenase comprises an amino acid sequence selected from the group consisting of SEQ ID NOs: 90 and 92. In some embodiments, the one or more nucleic acid molecules encoding the xylitol dehydrogenase is encoded by a nucleic acid sequence selected from the group consisting of SEQ ID NOs: 88, 89 and 91.

In one embodiment, an endogenous D-xylose isomerase catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

In one embodiment, the method further comprises introducing into the recombinant microorganism and/or overexpressing at least one endogenous or exogenous nucleic acid molecule encoding a secondary alcohol dehydrogenase that catalyzes the conversion of acetone from (i) to isopropanol.

In another embodiment, the method further comprises introducing into the recombinant microorganism and/or overexpressing at least one endogenous or exogenous nucleic acid molecule encoding a dehydratase that catalyzes the conversion of isopropanol to propene.

In another embodiment, the method further comprises introducing into the recombinant microorganism one or more modifications selected from the group consisting of:

- a deletion, insertion, or loss of function mutation in a gene encoding a D-xylulose-5-kinase that catalyzes the conversion of D-xylulose to D-xylulose-5-phosphate; and
- a deletion, insertion, or loss of function mutation in a gene encoding an alkaline phosphatase that catalyzes the conversion of D-xylulose-5-phosphate to D-xylulose.

In one embodiment, the enzyme that catalyzes the conversion of D-xylulose to D-xylulose-5-phosphate is a D-xylulose-5-kinase. In some embodiments, the D-xylulose-5-kinase is from *Saccharomyces cerevisiae*. In some embodiments the D-xylulose-5-kinase is encoded by the XKS1 gene, or homolog thereof. In some embodiments, the D-xylulose-5-kinase is from *Pichia stipitis*. In some embodiments the D-xylulose-5-kinase is encoded by the XYL3 gene, or homolog thereof.

In a further embodiment, the microorganism is a fungus.

As discussed above, in another aspect, the present application provides a method of producing a recombinant microorganism that produces or accumulates MEG and acetone from exogenous D-xylose, comprising introducing into the recombinant microorganism and/or overexpressing one or more of the following:

- at least one endogenous or exogenous nucleic acid molecule encoding a xylose dehydrogenase that catalyzes the conversion of D-xylose to D-xylonolactone;
- at least one endogenous or exogenous nucleic acid molecule encoding a xylonolactonase that catalyzes the conversion of D-xylonolactone from (a) to D-xylonate;
- at least one endogenous or exogenous nucleic acid molecule encoding a xylonate dehydratase that catalyzes the conversion of D-xylonate from (b) to 2-keto-3-deoxy-xylonate;
- at least one endogenous or exogenous nucleic acid molecule encoding a 2-keto-3-deoxy-D-pentonate aldolase that catalyzes the conversion of 2-keto-3-deoxy-xylonate from (c) to glycolaldehyde and pyruvate;
- at least one endogenous or exogenous nucleic acid molecule encoding a glycolaldehyde reductase that catalyzes the conversion of glycolaldehyde from (d) to MEG;
- at least one exogenous nucleic acid molecule encoding a thiolase that catalyzes the conversion of acetyl-CoA to acetoacetyl-CoA;
- at least one endogenous or exogenous nucleic acid molecule encoding an acetate:acetoacetyl-CoA transferase or hydrolase that catalyzes the conversion of acetoacetyl-CoA from (f) to acetoacetate; and/or
- at least one exogenous nucleic acid molecule encoding an acetoacetate decarboxylase that catalyzes the conversion of acetoacetate from (g) to acetone;
- wherein the produced intermediate pyruvate is converted to acetyl-CoA through the endogenous glycolysis pathway in the microorganism, and wherein MEG and acetone are co-produced.

In one embodiment, the xylose dehydrogenase is encoded by one or more nucleic acid molecules obtained from a microorganism selected from the group consisting of *Caulobacter* sp., *Haloarcula* sp., *Haloferax* sp., *Halorubrum* sp. and *Trichoderma* sp. In another embodiment, the xylose dehydrogenase is encoded by one or more nucleic acid molecules obtained from a microorganism selected from the group consisting of *Caulobacter crescentus, Haloarcula marismortui, Haloferax volcanii, Halorubrum lacusprofundi* and *Trichoderma reesei*. In some embodiments, the one or more nucleic acid molecules encoding the xylose dehydrogenase is selected from xylB, xdh1 (HVO_B0028) and/or xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

In one embodiment, the xylonolactonase is encoded by one or more nucleic acid molecules obtained from a microorganism selected from *Caulobacter* sp. and *Haloferax* sp. In another embodiment, the xylonolactonase is encoded by one or more nucleic acid molecules obtained from a microorganism selected from the group consisting of *Caulobacter crescentus, Haloferax volcanii* and *Haloferax gibbonsii*. In some embodiments, the one or more nucleic acid molecules encoding the xylonolactonase is xylC, or homolog thereof. In a further embodiment, the one or more nucleic acid molecules encoding the xylonolactonase comprises an amino acid sequence set forth in SEQ ID NO: 67. In yet another embodiment, the one or more nucleic acid molecules encoding the xylonolactonase is encoded by a nucleic acid sequence set forth in SEQ ID NO: 66.

In one embodiment, the xylonate dehydratase is encoded by one or more nucleic acid molecules obtained from a microorganism selected from the group consisting of *Caulobacter* sp., *Sulfolobus* sp. and *E. coli*. In another embodiment, the xylonate dehydratase is encoded by one or more nucleic acid molecules obtained from a microorganism selected from the group consisting of *Caulobacter crescentus, Sulfolobus solfataricus* and *E. coli*. In some embodiments, the one or more nucleic acid molecules encoding the xylonate dehydratase is selected from xylD, yjhG and/or yagF, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

In one embodiment, the 2-keto-3-deoxy-D-pentonate aldolase is encoded by one or more nucleic acid molecules obtained from a microorganism selected from *Pseudomonas* sp. and *E. coli*. In another embodiment, the 2-keto-3-deoxy-D-pentonate aldolase is encoded by one or more nucleic acid molecules obtained from *E. coli*. In some embodiments, the one or more nucleic acid molecules encoding the 2-keto-3-deoxy-D-pentonate aldolase is selected from yjhH and/or yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

In one embodiment, the method further comprises introducing into the recombinant microorganism and/or overexpressing at least one endogenous or exogenous nucleic acid molecule encoding a secondary alcohol dehydrogenase that catalyzes the conversion of acetone from (h) to isopropanol.

In another embodiment, the method further comprises introducing into the recombinant microorganism and/or overexpressing at least one endogenous or exogenous nucleic acid molecule encoding a dehydratase that catalyzes the conversion of isopropanol to propene.

In another embodiment, the method further comprises introducing into the recombinant microorganism one or more modifications selected from the group consisting of:

- a deletion, insertion, or loss of function mutation in a gene encoding a D-xylose isomerase that catalyzes the conversion of D-xylose to D-xylulose;
- a deletion, insertion, or loss of function mutation in a gene encoding a glycolaldehyde dehydrogenase that catalyzes the conversion of glycolaldehyde to glycolic acid; and
- a deletion, insertion, or loss of function mutation in a gene encoding a lactate dehydrogenase that catalyzes the conversion of pyruvate to lactate.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a D-xylose isomerase to prevent conversion of D-xylose to D-xylulose and instead shunt the reaction toward the conversion of D-xylose to D-xylonate. In one embodiment, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In one embodiment, the glycolaldehyde dehydrogenase is from *Escherichia coli*. In some embodiments, the glycolaldehyde dehydrogenase is encoded by the aldA gene, or homolog thereof.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a lactate dehydrogenase to prevent the production of lactate from pyruvate and instead shunt the reaction toward production of one or more three-carbon compounds. In one embodiment, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the ldhA gene, or homolog thereof.

As discussed above, in another aspect, the present application provides a method of producing a recombinant microorganism that produces or accumulates MEG and acetone from exogenous D-xylose, comprising introducing into the recombinant microorganism and/or overexpressing one or more of the following:

- at least one endogenous or exogenous nucleic acid molecule encoding a xylose dehydrogenase that catalyzes the conversion of D-xylose to D-xylonate;
- at least one endogenous or exogenous nucleic acid molecule encoding a xylonate dehydratase that catalyzes the conversion of D-xylonate from (a) to 2-keto-3-deoxy-xylonate;
- at least one endogenous or exogenous nucleic acid molecule encoding a 2-keto-3-deoxy-D-pentonate aldolase that catalyzes the conversion of 2-keto-3-deoxy-xylonate from (b) to glycolaldehyde and pyruvate;
- at least one exogenous nucleic acid molecule encoding a glycolaldehyde reductase that catalyzes the conversion of glycolaldehyde from (c) to MEG;
- at least one exogenous nucleic acid molecule encoding a thiolase that catalyzes the conversion of acetyl-CoA to acetoacetyl-CoA;
- at least one endogenous or exogenous nucleic acid molecule encoding an acetate:acetoacetyl-CoA transferase or hydrolase that catalyzes the conversion of acetoacetyl-CoA from (e) to acetoacetate; and/or
- at least one exogenous nucleic acid molecule encoding an acetoacetate decarboxylase that catalyzes the conversion of acetoacetate from (f) to acetone;
- wherein the produced intermediate pyruvate is converted to acetyl-CoA through the endogenous glycolysis pathway in the microorganism, and wherein MEG and acetone are co-produced.

In one embodiment, the xylose dehydrogenase is encoded by one or more nucleic acid molecules obtained from a microorganism selected from the group consisting of *Caulobacter* sp., *Haloarcula* sp., *Haloferax* sp., *Halorubrum* sp. and *Trichoderma* sp. In another embodiment, the xylose dehydrogenase is encoded by one or more nucleic acid molecules obtained from a microorganism selected from the group consisting of *Caulobacter crescentus, Haloarcula marismortui, Haloferax volcanii, Halorubrum lacusprofundi* and *Trichoderma reesei*. In some embodiments, the one or more nucleic acid molecules encoding the xylose dehydrogenase is selected from xylB, xdh1 (HVO_B0028) and/or xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

In one embodiment, the xylonate dehydratase is encoded by one or more nucleic acid molecules obtained from a microorganism selected from the group consisting of *Cau-*

*lobacter* sp., *Sulfolobus* sp. and *E. coli*. In another embodiment, the xylonate dehydratase is encoded by one or more nucleic acid molecules obtained from a microorganism selected from the group consisting of *Caulobacter crescentus, Sulfolobus solfataricus* and *E. coli*. In some embodiments, the one or more nucleic acid molecules encoding the xylonate dehydratase is selected from xylD, yjhG and/or yagF, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

In one embodiment, the 2-keto-3-deoxy-D-pentonate aldolase is encoded by one or more nucleic acid molecules obtained from a microorganism selected from *Pseudomonas* sp. and *E. coli*. In another embodiment, the 2-keto-3-deoxy-D-pentonate aldolase is encoded by one or more nucleic acid molecules obtained from *E. coli*. In some embodiments, the one or more nucleic acid molecules encoding the 2-keto-3-deoxy-D-pentonate aldolase is selected from yjhH and/or yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

In one embodiment, the method further comprises introducing into the recombinant microorganism and/or overexpressing at least one endogenous or exogenous nucleic acid molecule encoding a secondary alcohol dehydrogenase that catalyzes the conversion of acetone from (g) to isopropanol.

In another embodiment, the method further comprises introducing into the recombinant microorganism and/or overexpressing at least one endogenous or exogenous nucleic acid molecule encoding a dehydratase that catalyzes the conversion of isopropanol to propene.

In another embodiment, the method further comprises introducing into the recombinant microorganism one or more modifications selected from the group consisting of:

- a deletion, insertion, or loss of function mutation in a gene encoding a D-xylose isomerase that catalyzes the conversion of D-xylose to D-xylulose;
- a deletion, insertion, or loss of function mutation in a gene encoding a glycolaldehyde dehydrogenase that catalyzes the conversion of glycolaldehyde to glycolic acid; and
- a deletion, insertion, or loss of function mutation in a gene encoding a lactate dehydrogenase that catalyzes the conversion of pyruvate to lactate.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a D-xylose isomerase to prevent conversion of D-xylose to D-xylulose and instead shunt the reaction toward the conversion of D-xylose to D-xylonate. In one embodiment, the enzyme that catalyzes the conversion of D-xylose to D-xylulose is a D-xylose isomerase. In some embodiments, the D-xylose isomerase is from *Escherichia coli*. In some embodiments, the D-xylose isomerase is encoded by the xylA gene, or homolog thereof.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG. In one embodiment, the glycolaldehyde dehydrogenase is from *Escherichia coli*. In some embodiments, the glycolaldehyde dehydrogenase is encoded by the aldA gene, or homolog thereof.

In some embodiments, a method of producing a recombinant microorganism that produces or accumulates MEG and one or more three-carbon compounds from exogenous D-xylose comprises introducing into the recombinant microorganism a deletion, insertion, or loss of function mutation in a gene encoding a lactate dehydrogenase to prevent the production of lactate from pyruvate and instead shunt the reaction toward production of one or more three-carbon compounds. In one embodiment, the enzyme that catalyzes the conversion of pyruvate to lactate is a lactate dehydrogenase. In particular embodiments, the enzyme converts pyruvate to lactate. In some embodiments, the lactate dehydrogenase is from *Escherichia coli*. In some embodiments, the lactate dehydrogenase is encoded by the ldhA gene, or homolog thereof.

In one embodiment of any aspect disclosed above, the glycolaldehyde reductase is encoded by one or more nucleic acid molecules obtained from a microorganism selected from *E. coli* and *S. cerevisiae*. In another embodiment, the one or more nucleic acid molecules is selected from gldA, GRE2, GRE3, yqhD, ydjG, fucO, yafB (dkgB), and/or yqhE (dkgA), or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

In one embodiment of any aspect disclosed above, the thiolase or acetyl coenzyme A acetyltransferase is encoded by one or more nucleic acid molecules obtained from a microorganism selected from the group consisting of *Clostridium* sp., *Bacillus* sp., *E. coli, Saccharomyces* sp. and *Marinobacter* sp. In some embodiments, the thiolase or acetyl coenzyme A acetyltransferase is encoded by one or more nucleic acid molecules obtained from a microorganism selected from the group consisting of *Clostridium acetobutylicum, Clostridium thermosaccharolyticum, Bacillus cereus, E. coli, Saccharomyces cerevisiae* and *Marinobacter hydrocarbonoclasticus*. In some embodiments, the one or more nucleic acid molecules is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

In one embodiment of any aspect disclosed above, the acetyl-CoA:acetoacetate-CoA transferase or acetate:acetoacetyl-CoA hydrolase is encoded by one or more nucleic acid molecules obtained from a microorganism selected from *Clostridium* sp. and *E. coli*. In another embodiment, the acetyl-CoA:acetoacetate-CoA transferase or acetate:acetoacetyl-CoA hydrolase is encoded by one or more nucleic acid molecules obtained from *E. coli*. In some embodiments, the one or more nucleic acid molecules encoding the acetyl-CoA:acetoacetate-CoA transferase is atoA and/or atoD, or homolog thereof. In another embodiment, the acetyl-CoA:acetoacetate-CoA transferase or acetate:acetoacetyl-CoA hydrolase is encoded by one or more nucleic acid molecules obtained from *Clostridium acetobutylicum*. In some embodiments, the one or more nucleic acid molecules encoding the acetate:acetoacetyl-CoA hydrolase is ctfA and/or ctfB, or homolog thereof. In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

In one embodiment of any aspect disclosed above, the acetoacetate decarboxylase is encoded by one or more nucleic acid molecules obtained from a microorganism selected from the group consisting of *Clostridium* sp., *Bacillus* sp., *Chromobacterium* sp. and *Pseudomonas* sp. In another embodiment, the acetoacetate decarboxylase is encoded by one or more nucleic acid molecules obtained from a microorganism selected from the group consisting of *Clostridium acetobutylicum, Clostridium beijerinckii, Clostridium cellulolyticum, Bacillus polymyxa, Chromobacterium violaceum* and *Pseudomonas putida*. In some embodiments, the one or more nucleic acid molecules encoding the acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

In one embodiment of any aspect disclosed above, the enzyme that catalyzes the conversion of acetone to isopropanol is a secondary alcohol dehydrogenase (S-ADH). In another embodiment, the enzyme is a secondary alcohol dehydrogenase that is encoded by a nucleic acid molecule obtained from a microorganism selected from *Burkholderia* sp, *Alcaligenes* sp., *Clostridium* sp., *Thermoanaerobacter* sp., *Phytomonas* sp., *Rhodococcus* sp., *Methanobacterium* sp., *Methanogenium* sp., *Entamoeba* sp., *Trichomonas* sp., and *Tritrichomonas* sp. In some embodiments, the nucleic acid molecule encoding the secondary alcohol dehydrogenase is obtained from a microorganism selected from *Burkholderia* sp. AIU 652, *Alcaligenes eutrophus, Clostridium ragsdalei, Clostridium beijerinckii, Clostridium carboxidivorans, Thermoanaerobacter brockii, Thermoanaerobacter ethanolicus* (*Clostridium thermohydrosulfuricum*), *Rhodococcus ruber, Methanobacterium palustre, methanogenic archaea Methanogenium liminatans*, parasitic protist *Entamoeba histolytica*, parasitic protozoan *Tritrichomonas foetus* and human parasite *Trichomonas vaginalis*. In some embodiments, the one or more nucleic acid molecule encoding secondary alcohol dehydrogenase is adh, adhB, EhAdh1, or homolog thereof. In some embodiments, the S-ADH is predicted from homology and can be from *Thermoanaerobacter mathranii, Micrococcus luteus, Nocardiopsis alba, Mycobacterium hassiacum, Helicobacter suis, Candida albicans, Candida parapsilosis, Candida orthopsilosis, Candida metapsilosis, Grosmannia clavigera* and *Scheffersomyces stipitis*. In a further embodiment, the alcohol dehydrogenase comprises an amino acid sequence selected from the group consisting of SEQ ID NOs: 106 and 108. In yet another embodiment, the alcohol dehydrogenase is encoded by a nucleic acid sequence selected from the group consisting of SEQ ID NOs: 104, 105 and 107.

Enzyme Engineering

The enzymes in the recombinant microorganism can be engineered to improve one or more aspects of the substrate to product conversion. Non-limiting examples of enzymes that can be further engineered for use in methods of the disclosure include an aldolase, an aldehyde reductase, an acetoacetyl coenzyme A hydrolase, a xylose isomerase, a xylitol dehydrogenase and combinations thereof. These enzymes can be engineered for improved catalytic activity, improved selectivity, improved stability, improved tolerance to various fermentation conditions (temperature, pH, etc.), or improved tolerance to various metabolic substrates, products, by-products, intermediates, etc. The term "improved catalytic activity" as used herein with respect to a particular enzymatic activity refers to a higher level of enzymatic activity than that measured relative to a comparable non-engineered enzyme.

For example, engineering methods have been used to alter the stability, substrate specificity and stereospecificity of aldolases to produce excellent enzymes for biocatalytic processes. The thermostability and solvent tolerance of fructose-1,6-bisphosphate aldolase (FBP-aldolase) was increased using family DNA shuffling of the fda genes from *Escherichia coli* and *Edwardsiella ictaluri*. A fourth generation variant was identified which displayed an average 280-fold higher half-life at 53° C. than either parent. The same variant also displayed enhanced activity in various polar and non-polar organic solvents (Hao and Berry 2004 Protein Eng Des Sel 17:689-697).

As another example, acetoacetyl coenzyme A hydrolase can convert acetoacetyl-CoA to acetoacetate. However, the hydrolase is unspecific in that it also reacts with the same magnitude of order with acetyl-CoA, which is the substrate required for acetoacetyl-CoA formation by the enzyme thiolase. Thus, to create more efficient acetoacetyl-CoA hydrolases, these enzymes have been engineered to have at least 10× higher activity for the acetoacetyl-CoA substrate than for acetyl-CoA substrate by replacing several glutamic acid residues in the enzyme beta subunit that is important for catalysis (WO 2015/042588).

As another example, the *E. coli* YqhD enzyme is a broad substrate aldehyde reductase with NADPH-dependent reductase activity for more than 10 aldehyde substrates and is a useful enzyme to produce biorenewable fuels and chemicals (Jarboe 2010 Applied Microbiology and Biotechnology 89:249). Though YqhD enzyme activity is beneficial through its scavenging of toxic aldehydes, the enzyme is also NADPH-dependent and contributes to NADPH depletion and growth inhibition of organisms. Error-prone PCR of YqhD was performed in order to improve 1,3-propanediol production from 3-hydroxypropionaldehyde (3-HPA). This directed engineering yielded two mutants, D99QN147H and Q202A, with decreased Km and increased kcat for certain aldehydes, particularly 3-HPA (Li et al. 2008 Prog. Nat. Sci. 18 (12):1519-1524). The improved catalytic activity of the D99QN147H mutant is consistent with what is known about the structure of YqhD (Sulzenbacher et al. 2004 J. Mol. Biol. 342 (2):489-502), as residues Asp99 and Asn147 both interact with NADPH. Use of the D99QN147H mutant increased 1,3-propanediol production from 3-HPA 2-fold. Mutant YqhD enzymes with increased catalytic efficiency (increased Kcat/Km) toward NADPH have also been described in WO 2011012697 A2, which is herein incorporated in its entirety.

As another example, xylose isomerase is a metal-dependent enzyme that catalyzes the interconversion of aldose and ketose sugars, primarily between xylose to xylulose and glucose to fructose. It has lower affinity for lyxose, arabinose and mannose sugars. The hydroxyl groups of sugars may define the substrate preference of sugar isomerases. The aspartate at residue 256 of *Thermus thermophilus* xylose isomerase was replaced with arginine (Patel et al. 2012 Protein Engineering, Design & Selection vol. 25 no. 7 pp. 331-336). This mutant xylose isomerase exhibited an increase in specificity for D-lyxose, L-arabinose and D-mannose. The catalytic efficiency of the D256R xylose isomerase mutant was also higher for these 3 substrates compared to the wild type enzyme. It was hypothesized that the arginine at residue 256 in the mutant enzyme may play a role in the catalytic reaction or influence changes in substrate orientation.

As another example, the enzyme xylitol dehydrogenase plays a role in the utilization of xylose along with xylose reductase. Xylose reductase (XR) reduces xylose to xylitol and then xylitol dehydrogenase (XDH) reoxidizes xylitol to form xylulose. However, since XR prefers NADPH as cosubstrate, while XDH exclusively uses $NAD^+$ as cosubstrate, a cosubstrate recycling problem is encountered. One solution is to engineer XDH such that its cosubstrate specificity is altered from $NAD^+$ to $NADP^+$ (Ehrensberger et al. 2006 Structure 14: 567-575). A crystal structure of the *Gluconobacter oxydans* holoenzyme revealed that Asp38 is largely responsible for the $NAD^+$ specificity of XDH. Asp38 interacts with the hydroxyls of the adenosine ribose, and Met39 stacks under the purine ring and is also located near the 2' hydroxyl. A double mutant (D38S/M39R) XDH was constructed that exclusively used $NADP^+$ without loss of enzyme activity.

TABLE 1

Description of enzymes

| Described Reaction | EC no. | Required enzyme activity | Gene candidate | Source Organism | Natural/annotated function | Gene Identifier (nt) | SEQ ID NO (nt) | Uniprot ID | SEQ ID NO (AA) |
|---|---|---|---|---|---|---|---|---|---|
| Isomerases that may be used in all xylulose dependent MEG pathways | | | | | | | | | |
| D-xylose + NAD(P)H <=> Xylitol + $NAD(P)^+$ | 1.1.1.307 | xylose reductase | xyl1 | *Scheffersomyces stipitis* | D-xylose reductase | GeneID: 4839234 | 82, 83 | P31867 | 84 |
| D-xylose + NAD(P)H <=> Xylitol + $NAD(P)^+$ | 1.1.1.307 | xylose reductase | GRE3 | *Saccharomyces cerevisiae* | aldose reductase | GeneID: 856504 | 85, 86 | P38715 | 87 |
| Xylitol + NAD+ <=> D-xylulose + NADH | 1.1.1.9 | xylitol dehydrogenase | xyl2 | *Scheffersomyces stipitis* | D-xylulose reductase | GeneID: 4852013 | 88, 89 | P22144 | 90 |
| Xylitol + $NAD^+$ <=> D-xylulose + NADH | 1.1.1.9 | xylitol dehydrogenase | xdh1 | Trichoderma reesei | Xylitol dehydrogenase | ENA Nr.: AF428150.1 | 91 | Q876R2 | 92 |
| D-xylopyranose <=> D-xylulose | 5.3.1.5 | xylose isomerase | xylA | *Pyromyces sp.* | xylose isomerase | ENA Nr.: CAB76571.1 | 93, 94 | Q9P8C9 | 95 |
| Glycolaldehyde reductases that may be used in all MEG pathways | | | | | | | | | |
| glycolaldehyde + NAD(P)H <=> monoethylene glycol + $NAD(P)^+$ | 1.1.1.- | glycolaldehyde reductase | gldA | *Escherichia coli* | glycerol dehydrogenase | GeneID: 12933659 | 12 | P0A9S5 | 13 |
| glycolaldehyde + NAD(P)H <=> monoethylene glycol + $NAD(P)^+$ | 1.1.1.- | glycolaldehyde reductase | GRE2 | *Saccharomyces cerevisiae* | methylglyoxal reductase | GeneID: 854014 | 14 | Q12068 | 15 |
| glycolaldehyde + NAD(P)H <=> monoethylene glycol + $NAD(P)^+$ | 1.1.1.- | glycolaldehyde reductase | GRE3 | *Saccharomyces cerevisiae* | aldose reductase | GeneID: 856504 | 16 | P38715 | 17 |
| glycolaldehyde + NAD(P)H <=> monoethylene glycol + $NAD(P)^+$ | 1.1.1.- | glycolaldehyde reductase | yqhD* | *Escherichia coli* | Alcohol dehydrogenase | GeneID: 947493 | 18, 19 | Modified version of Q46856; G149E | 20 |
| glycolaldehyde + NAD(P)H <=> monoethylene glycol + $NAD(P)^+$ | 1.1.1.- | glycolaldehyde reductase | yqhD | *Escherichia coli* | Alcohol dehydrogenase | GeneID: 947493 | 21, 22 | Q46856 | 23 |
| glycolaldehyde + NAD(P)H <=> monoethylene glycol + $NAD(P)^+$ | 1.1.1.- | glycolaldehyde reductase | ydjg | *Escherichia coli* | methylglyoxal reductase | GeneID: 12930149 | 24 | P77256 | 25 |
| glycolaldehyde + NAD(P)H <=> monoethylene glycol + $NAD(P)^+$ | 1.1.1.- | glycolaldehyde reductase | fucO | *Escherichia coli* | lactaldehyde reductase | GeneID: 947273 | 26, 27 | P0A9S1 | 28 |
| glycolaldehyde + NAD(P)H <=> | 1.1.1.- | glycolaldehyde reductase | yafB (dkgB) | *Escherichia coli* | methylglyoxal reductase | 545778205 | 29 | P30863 | 30 |

TABLE 1-continued

| Described Reaction | EC no. | Required enzyme activity | Gene candidate | Source Organism | Natural/ annotated function | Gene Identifier (nt) | SEQ ID NO (nt) | Uniprot ID | SEQ ID NO (AA) |
|---|---|---|---|---|---|---|---|---|---|
| Description of enzymes | | | | | | | | | |
| monoethylene glycol + $NAD(P)^+$ | | | | | [multifunctional] | | | | |
| glycolaldehyde + NAD(P)H <=> monoethylene glycol + $NAD(P)^+$ | 1.1.1.- | glycolaldehyde reductase | yqhE (dkgA) | *Escherichia coli* | 2,5-diketo-D-gluconic acid reductase A | GeneID: 947495 | 31 | Q46857 | 32 |
| Enzymes that may be used in D-ribulose-1-phosphate pathway to MEG | | | | | | | | | |
| D-xylulose <=> D-ribulose | 5.1.3.- | D-ribulose-3-epimerase | DTE | *Pseudomonas cichorii* | D-tagatose 3-epimerase | ENA Nr.: BAA24429.1 | 1, 2 | O50580 | 3 |
| D-xylulose <=> D-ribulose | 5.1.3.- | D-ribulose-3-epimerase | C1KKR1 | *Rhodobacter sphaeroides* | D-tagatose 3-epimerase | ENA Nr.: FJ851309.1 | 4 | C1KKR1 | 5 |
| D-ribulose + ATP <=> D-ribulose-1-phosphate + ADP | 2.7.1.- | D-ribulose-1-kinase | fucK | *Escherichia coli* | L-fuculokinase | GeneID: 946022 | 6, 7 | P11553 | 8 |
| D-ribulose-1-phosphate <=> glyceraldehyde + dihydroxy-acetonephosphate | 4.1.2.- | D-ribulose-1-phosphate aldolase | fucA | *Escherichia coli* | L-fuculose phosphate aldolase | GeneID: 947282 | 9, 10 | P0AB87 | 11 |
| Enzymes that may be used in D-xylulose-1-phosphate pathway to MEG | | | | | | | | | |
| D-xylulose + ATP <=> D-xylulose-1-phosphate + ADP | 2.7.1.- | D-xylulose-1-kinase | khk-C (cDNA) | *Homo sapiens* | ketohexokinase C | GenBank: CR456801.1 | 53, 54 | P50053 | 55 |
| D-xylulose-1-phosphate <=> glyceraldehyde + dihydroxy-acetonephosphate | 4.1.2.- | D-xylulose-1-phosphate aldolase | aldoB (cDNA) | *Homo sapiens* | Fructose-bisphosphate aldolase B | CCDS6756.1 | 56, 57 | P05062 | 58 |
| Enzymes that may be used in xylonate pathway to MEG | | | | | | | | | |
| D-xylose + $NAD^+$ <=> D-xylonolactone + NADH, or D-xylose + $NAD^+$ <=> D-xylonate + NADH | 1.1.1.175 | xylose dehydrogenase | xylB | *Caulobacter crescentus* | D-xylose 1-dehydrogenase | GeneID: 7329904 | 59, 60 | B8H1Z0 | 61 |
| D-xylose + $NADP^+$ <=> D-xylonolactone + NADPH, or D-xylose + $NADP^+$ <=> D-xylonate + NADPH | 1.1.1.179 | xylose dehydrogenase | xdh1, HYO_B0028 | *Haloferax volcanii* | D-xylose 1-dehydrogenase | GeneID: 8919161 | 62 | D4GP29 | 63 |
| D-xylose + $NADP^+$ <=> D-xylonolactone + NADPH, or D-xylose + $NADP^+$ <=> D-xylonate + NADPH | 1.1.1.179 | xylose dehydrogenase | xyd1 | Trichoderma reesei | D-xylose 1-dehydrogenase | ENA Nr.: EF136590.1 | 64 | A0A024 SMV2 | 65 |
| D-xylonolactone + H2O <=> D-xylonate | 3.1.1.68 | xylonolactonase | xylC | *Caulobacter crescentus* | Xylonolactonase | GeneID: 7329903 | 66 | A0A0H3 C6P8 | 67 |
| D-xylonate <=> 2-keto-3-deoxy-xylonate + H2O | 4.2.1.82 | xylonate dehydratase | xylD | *Caulobacter crescentus* | xylonate dehydratase | GeneID: 7329902 | 68 | A0A0H3 C6H6 | 69 |
| D-xylonate <=> 2-keto-3-deoxy-xylonate + H2O | 4.2.1.82 | xylonate dehydratase | yjhG | *Escherichia coli* | xylonate dehydratase | GeneID: 946829 | 70, 71 | P39358 | 72 |
| D-xylonate <=> 2-keto-3-deoxy-xylonate + H2O | 4.2.1.82 | xylonate dehydratase | yagF | *Escherichia coli* | xylonate dehydratase | GeneID: 944928 | 73, 74 | P77596 | 75 |
| 2-keto-3-deoxy-xylonate <=> glycolaldehyde + pyruvate | 4.1.2.- | 2-keto-3-deoxy-D-pentonate aldolase | yjhH | *Escherichia coli* | Uncharacterized lyase | GeneID: 948825 | 76, 77 | P39359 | 78 |
| 2-keto-3-deoxy-xylonate <=> glycolaldehyde + pyruvate | 4.1.2.- | 2-keto-3-deoxy-D-pentonate aldolase | yagE | *Escherichia coli* | Probable 2-keto-3-deoxy-galactonate aldolase | GeneID: 944925 | 79, 80 | P75682 | 81 |

TABLE 1-continued

| Description of enzymes | | | | | | | | | |
|---|---|---|---|---|---|---|---|---|---|
| Described Reaction | EC no. | Required enzyme activity | Gene candidate | Source Organism | Natural/ annotated function | Gene Identifier (nt) | SEQ ID NO (nt) | Uniprot ID | SEQ ID NO (AA) |
| Enzymes that may be used in pathway to produce one or more three-carbon compounds | | | | | | | | | |
| 2 acetyl-Coa -> acetoacetyl-CoA + CoA | 2.3.1.9 | acetyl coenzyme A acetyltransferase | thlA | *Clostridium acetobutylicum* | acetyl coenzyme A acetyltransferase | 3309200 | 33, 34 | P45359 | 35 |
| 2 acetyl-Coa -> acetoacetyl-CoA + CoA | 2.3.1.9 | acetyl coenzyme A acetyltransferase | atoB | *Escherichia coli* | acetyl coenzyme A acetyltransferase | GeneID: 946727 | 36 | P76461 | 37 |
| 2 acetyl-Coa -> acetoacetyl-CoA + CoA | 2.3.1.9 | acetyl coenzyme A acetyltransferase | ERG10 | *Saccharomyces cerevisiae* | acetyl coenzyme A acetyltransferase | 856079 | 38 | P41338 | 39 |
| acetoacetyl-CoA + acetate -> acetoacetate + acetyl-CoA | 2.8.3.8 | Acetyl-CoA:acetoacetate-CoA transferase subunit | atoA | *Escherichia coli* | Acetyl-CoA: acetoacetate-CoA transferase subunit | 48994873 | 41, 42 | P76459 | 43 |
| acetoacetyl-CoA + acetate -> acetoacetate + acetyl-CoA | 2.8.3.8 | Acetyl-CoA:acetoacetate-CoA transferase subunit | atoD | *Escherichia coli* | Acetyl-CoA: acetoacetate-CoA transferase subunit | 48994873 | 44, 45 | P76458 | 46 |
| acetoacetate -> acetone + CO2 | 4.1.1.4 | acetoacetate decarboxylase | adc | *Clostridium acetobutylicum* | acetoacetate decarboxylase | 6466901 | 47, 48 | P23670 | 49 |
| acetoacetate -> acetone + CO2 | 4.1.1.4 | acetoacetate decarboxylase | adc | *Clostridium beijerinckii* | acetoacetate decarboxylase | 149901357 | 50, 51 | A6M020 | 52 |
| acetone + NAD(P)H -> 2-propanol + $NAD(P)^+$ | 1.1.1.2 | secondary alcohol dehydrogenase | adh | *Clostridium beijerinckii* | secondary alcohol dehydrogenase | 60592972 | 104, 105 | P25984 | 106 |
| acetone + NAD(P)H -> 2-propanol + $NAD(P)^+$ | 1.1.1.2 | secondary alcohol dehydrogenase | adh | *Clostridium carboxidivorans* | alcohol dehydrogenase | 308066805 | 107 | C6PZV5 | 108 |
| NADH + $NADP^+$ <--> $NAD^+$ + NADPH | 1.6.1.1. | Soluble pyridine nucleotide transhydrogenase | udhA | *Escherichia coli* | Soluble pyridine nucleotide transhydrogenase | GeneID: 948461 | 109 | P27306 | 110 |
| Hydrolases that may be used in pathway to produce one or more three-carbon compounds | | | | | | | | | |
| Acetoacetyl-CoA + H(2)O <=> CoA + acetoacetate | 3.1.2.11 | acetate:acetoacetyl-CoA hydrolase | ctfA | *Clostridium acetobutylicum* | butyrate-acetoacetate CoA-transferase, complex A | NCBI-GeneID: 1116168 | 96 | P33752 | 97 |
| Acetoacetyl-CoA + H(2)O <=> CoA + acetoacetate | 3.1.2.11 | acetate:acetoacetyl-CoA hydrolase | ctfB | *Clostridium acetobutylicum* | butyrate-acetoacetate CoA-transferase, subunit B | NCBI-GeneID: 1116169 | 98 | P23673 | 99 |
| Acetoacetyl-CoA + H(2)O <=> CoA + acetoacetate | 3.1.2.11 | acetate:acetoacetyl-CoA hydrolase | atoA | *Escherichia coli* (strain K12) | Acetyl-CoA: acetoacetate-CoA transferase subunit | GeneID: 946719 | 100 | P76459 | 101 |
| Acetoacetyl-CoA + H(2)O <=> CoA + acetoacetate | 3.1.2.11 | acetate:acetoacetyl-CoA hydrolase | atoD | *Escherichia coli* (strain K12) | Acetyl-CoA: acetoacetate-CoA transferase subunit | GeneID: 947525 | 102 | P76458 | 103 |

D-tagatose 3-epimerase (EC 5.1.3.31)

The present disclosure describes enzymes that can catalyze the epimerization of various ketoses at the C-3 position, interconverting D-fructose and D-psicose, D-tagatose and D-sorbose, D-ribulose and D-xylulose, and L-ribulose and L-xylulose. The specificity depends on the species. The enzymes from *Pseudomonas cichorii* and *Rhodobacter sphaeroides* require $Mn^{2+}$. In one embodiment, the enzyme is D-tagatose 3-epimerase (dte). In another embodiment, the D-tagatose 3-epimerase catalyzes the conversion of D-xylulose to D-ribulose.

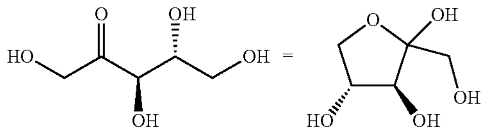

D-ribulose = D-xylulose

In some embodiments, the D-tagatose 3-epimerase is from *Pseudomonas* spp. In another embodiment, the D-tagatose 3-epimerase is from *Pseudomonas cichorii*. In another embodiment, the D-tagatose 3-epimerase is from *Pseudomonas* sp. ST-24. In another embodiment, the D-tagatose 3-epimerase is from *Mesorhizobium loti*. In another embodiment, the D-tagatose 3-epimerase is from *Rhodobacter sphaeroides* (C1KKR1).

In one embodiment, the D-tagatose 3-epimerase is encoded by one or more nucleic acid molecules obtained from a microorganism selected from the group consisting of *Pseudomonas* sp., *Mesorhizobium* sp. and *Rhodobacter* sp. In some embodiments, the D-tagatose 3-epimerase is encoded by one or more nucleic acid molecules obtained from a microorganism selected from the group consisting of *Pseudomonas cichorii, Pseudomonas* sp. ST-24, *Mesorhizobium loti* and *Rhodobacter sphaeroides*. In some embodiments, the one or more nucleic acid molecules is dte and/or FJ851309.1, or homolog thereof. In a further embodiment, the D-tagatose 3-epimerase comprises an amino acid sequence selected from the group consisting of SEQ ID NOs: 3 and 5. In yet a further embodiment, the D-tagatose 3-epimerase is encoded by a nucleic acid sequence selected from the group consisting of SEQ ID NOs: 1, 2 and 4.

D-tagatose 3-epimerase may also be known as L-ribulose 3-epimerase or ketose 3-epimerase.

D-ribulokinase (EC 2.7.1.16)

The present disclosure describes enzymes that can catalyze the following reactions:

L-fuculose+ATP→L-fuculose 1-phosphate+$ADP^+$

D-ribulose+ATP→D-ribulose 1-phosphate+$ADP^+$

D-ribulokinase may also be known as L-fuculokinase, fuculokinase, ATP: L-fuculose 1-phosphotransferase or L-fuculose kinase.

Thus, in some embodiments, the disclosure provides for an enzyme that plays roles in the fucose degradation pathway, the super pathway of fucose and rhamnose degradation and/or the D-arabinose degradation I pathway.

In some embodiments, the enzyme can function as both an L-fucolokinase and a D-ribulokinase, the second enzyme of the L-fucose and D-arabinose degradation pathways, respectively.

In particular embodiments, the enzyme converts D-ribulose to D-ribulose-1-phosphate. In some embodiments, the D-ribulokinase is from *Escherichia coli*. In some embodiments, the D-ribulokinase is encoded by the fucK gene. In one embodiment, the D-ribulokinase is encoded by one or more nucleic acid molecules obtained from *E. coli*. In some embodiments, the one or more nucleic acid molecules is fucK, or homolog thereof. In a further embodiment, the D-ribulokinase comprises an amino acid sequence set forth in SEQ ID NO: 8. In yet a further embodiment, the D-ribulokinase is encoded by a nucleic acid sequence selected from the group consisting of SEQ ID NOs: 6 and 7.

D-ribulose-1-phosphate aldolase (EC 4.1.2.17)

The present disclosure describes enzymes that can catalyze the following reversible reactions:

L-fuculose 1-phosphate⇋(S)-lactaldehyde+dihydroxy acetone phosphate (DHAP)

D-ribulose 1-phosphate⇋glycolaldehyde+dihydroxy acetone phosphate (DHAP)

D-ribulose-1-phosphate aldolase may also be known as L-fuculose-phosphate aldolase, L-fuculose 1-phosphate aldolase or L-fuculose-1-phosphate (S)-lactaldehyde-lyase.

Thus, in some embodiments, the disclosure provides for an enzyme that plays roles in the fucose degradation pathway, the super pathway of fucose and rhamnose degradation and/or the D-arabinose degradation I pathway. In one embodiment, the enzyme may use $Zn^{2+}$ as a cofactor. In another embodiment, an inhibitor of this enzyme may be phosphoglycolohydroxamate.

In some embodiments, the enzyme can function as both an L-fuculose-phosphate aldolase and a D-ribulose-phosphate aldolase, the third enzyme of the L-fucose and D-arabinose degradation pathways, respectively.

The substrate specificity of the enzyme has been tested with a partially purified preparation from an *E. coli* strain.

Crystal structures of the enzyme and a number of point mutants have been solved. The combination of structural data and enzymatic activity of mutants allowed modelling and refinement of the catalytic mechanism of the enzyme. The enantiomeric selectivity of the enzyme has been studied.

In particular embodiments, the enzyme converts D-ribulose-1-phosphate to glycolaldehyde and DHAP. In some embodiments, the D-ribulose-1-phosphate aldolase is from *Escherichia coli*. In some embodiments, the D-ribulose-1-phosphate aldolase is encoded by the fucA gene. In one embodiment, the D-ribulose-1-phosphate aldolase is encoded by one or more nucleic acid molecules obtained from *E. coli*. In some embodiments, the one or more nucleic acid molecules is fucA, or homolog thereof. In a further embodiment, the D-ribulose-1-phosphate aldolase comprises an amino acid sequence set forth in SEQ ID NO: 11. In yet a further embodiment, the D-ribulose-1-phosphate aldolase is encoded by a nucleic acid sequence selected from the group consisting of SEQ ID NOs: 9 and 10.

Glycolaldehyde Reductase (EC 1.1.1.77)

The present disclosure describes enzymes that can catalyze the following reversible reactions:

ethylene glycol+$NAD^+$⇋glycolaldehyde+NADH+$H^+$ (S)-propane-1,2-diol+$NAD^+$⇋(S)-lactaldehyde+NADH+$H^+$ Glycolaldehyde reductase may also be known as lactaldehyde reductase, propanediol oxidoreductase, (R) [or(S)]-propane-1,2-diol:$NAD^+$ oxidoreductase or L-1,2-propanediol oxidoreductase.

Thus, in some embodiments, the disclosure provides for an enzyme that plays roles in the ethylene glycol degradation pathway, the super pathway of glycol metabolism and degradation, the anaerobic L-lactaldehyde degradation pathway and/or the super pathway of fucose and rhamnose degradation. In one embodiment, the enzyme may use $Fe^{2+}$ as a cofactor.

L-1,2-propanediol oxidoreductase is an iron-dependent group III dehydrogenase. It anaerobically reduces L-lactaldehyde, a product of both the L-fucose and L-rhamnose catabolic pathways, to L-1,2-propanediol, which is then excreted from the cell.

Crystal structures of the enzyme have been solved, showing a domain-swapped dimer in which the metal, cofactor and substrate binding sites could be located. An aspartate and three conserved histidine residues are required for $Fe^{2+}$ binding and enzymatic activity.

In vitro, the enzyme can be reactivated by high concentrations of $NAD^+$ and efficiently inactivated by a mixture of $Fe^{3+}$ and ascorbate or $Fe^{2+}$ and $H_2O_2$. Metal-catalyzed oxidation of the conserved His277 residue is proposed to be the cause of the inactivation.

Expression of FucO enables engineered one-turn reversal of the β-oxidation cycle. FucO activity contributes to the conversion of isobutyraldehyde to isobutanol in an engineered strain.

In particular embodiments, the enzyme converts glycolaldehyde to MEG. In some embodiments, the glycolaldehyde reductase is from *Escherichia coli*. In some embodiments, the glycolaldehyde reductase is encoded by the fucO gene. In one embodiment, the glycolaldehyde reductase is encoded by one or more nucleic acid molecules obtained from a microorganism selected from *E. coli* and *S. cerevisiae*. In another embodiment, the one or more nucleic acid molecules is selected from gldA, GRE2, GRE3, yqhD, ydjG, fucO, yafB (dkgB), and/or yqhE (dkgA), or homolog thereof. In another embodiment, the one or more nucleic acid molecules is yqhD. In some embodiments, the yqhD comprises a G149E mutation. In a further embodiment, the glycolaldehyde reductase comprises an amino acid sequence selected from the group consisting of SEQ ID NOs: 13, 15, 17, 20, 23, 25, 28, 30 and 32. In yet a further embodiment, the glycolaldehyde reductase is encoded by a nucleic acid sequence selected from the group consisting of SEQ ID NOs: 12, 14, 16, 18, 19, 21, 22, 24, 26, 27, 29 and 31.

Aldehyde Reductases

A number of aldehyde reductases may be used to convert glycolaldehyde to MEG.

An NADPH-dependent aldehyde reductase (YqhD) can catalyze the following reactions:

acetol+$NADP^+$⇆methylglyoxal+NADPH+$H^+$ (reversible, EC 1.1.1.-)

an alcohol+$NADP^+$⇆an aldehyde+NADPH+$H^+$ (reversibility unspecified, EC 1.1.1.2)

an aldehyde+$NADP^+$+$H_2O$→a carboxylate+NADPH+2$H^+$ (EC 1.2.1.4)

1,3-propanediol+$NADP^+$⇆3-hydroxypropionaldehyde+NADPH+$H^+$ (reversibility unspecified, EC 1.1.1.-)

D-3,4-dihydroxybutanal+NADPH⇆1,3,4-butanetriol+$NADP^+$ (reversibility unspecified)

YqhD is an NADPH-dependent aldehyde reductase that may be involved in glyoxal detoxification and/or be part of a glutathione-independent response to lipid peroxidation.

It has been reported that various alcohols, aldehydes, amino acids, sugars and α-hydroxy acids have been tested as substrates for YqhD. The purified protein only shows NADP-dependent alcohol dehydrogenase activity, with a preference for alcohols longer than C(3), but with Km values in the millimolar range, suggesting that they are not the physiological substrates. In contrast, YqhD does exhibit short-chain aldehyde reductase activity with substrates such as propanaldehyde, acetaldehyde, and butanaldehyde, as well as acrolein and malondialdehyde. In a metabolically engineered strain, phenylacetaldehyde and 4-hydroxyphenylacetaldehyde are reduced to 2-phenylethanol and 2-(4-hydroxyphenyl)ethanol by the endogenous aldehyde reductases YqhD, YjgB, and YahK.

Overexpression of YqhD increases 1,3-propanediol oxidoreductase activity of the cell. *E. coli* has been engineered to express YqhD for the industrial production of 1,3-propanediol. YqhD activity contributes to the production of isobutanol, 1,2-propanediol, 1,2,4-butanetriol and acetol as well. Mutation of yqhD enables production of butanol by an engineered one-turn reversal of the β-oxidation cycle.

YqhD has furfural reductase activity, which appears to cause growth inhibition due to depletion of NADPH in metabolically engineered strains that produce alcohol from lignocellulosic biomass.

The crystal structure of YqhD has been solved at 2 Å resolution. YqhD is an asymmetric dimer of dimers, and the active site contains a $Zn^{2+}$ ion. The NADPH cofactor is modified by hydroxyl groups at positions 5 and 6 in the nicotinamide ring.

Overexpression of yqhD leads to increased resistance to reactive oxygen-generating compounds such as hydrogen peroxide, paraquat, chromate and potassium tellurite. A yqhD deletion mutant shows increased sensitivity to these compounds and to glyoxal, and contains increased levels of reactive aldehydes that are generated during lipid peroxidation. Conversely, yqhD deletion leads to increased furfural tolerance.

In particular embodiments, an NADPH-dependent aldehyde reductase converts glycolaldehyde to MEG. In some embodiments, the NADPH-dependent aldehyde reductase is from *Escherichia coli*. In some embodiments, the NADPH-dependent aldehyde reductase is encoded by the yqhD gene.

A multi-functional methylglyoxal reductase (DkgA) can catalyze the following reactions:

acetol+$NADP^+$⇆methylglyoxal+NADPH+$H^+$ (the reaction is physiologically favored in the opposite direction, EC 1.1.1.-)

isobutanol+$NADP^+$⇆isobutanal+NADPH+$H^+$ (reversibility unspecified, EC 1.1.1.-)

ethyl-(2R)-methyl-(3 S)-hydroxybutanoate+$NADP^+$⇆ethyl-2-methylacetoacetate+NADPH+$H^+$ (reversibility unspecified, EC 1.1.1.-)

2-keto-L-gulonate+$NADP^+$←2,5-didehydro-D-gluconate+NADPH+$H^+$ (the reaction is favored in the opposite direction, EC 1.1.1.346)

DkgA (YqhE) belongs to the aldo-keto reductase (AKR) family and has been shown to have methylglyoxal reductase and beta-keto ester reductase activity.

dkgA is reported to encode a 2,5-diketo-D-gluconate reductase (25DKGR) A, one of two 25DKG reductases in *E. coli*. The enzyme uses NADPH as the preferred electron donor and is thought to be involved in ketogluconate metabolism. The specific activity of the enzyme towards 2,5-diketo-D-gluconate is reported to be almost 1000-fold lower than its activity towards methylglyoxal.

Due to its low Km for NADPH, reduction of furans by DkgA may deplete NADPH pools and thereby limit cellular biosynthesis. A broad survey of aldehyde reductases showed that DkgA was one of several endogenous aldehyde reductases that contribute to the degradation of desired aldehyde end products of metabolic engineering.

A crystal structure of DkgA has been solved at 2.16 Å resolution.

In particular embodiments, a multi-functional methylglyoxal reductase converts glycolaldehyde to MEG. In some embodiments, the multi-functional methylglyoxal reductase is from *Escherichia coli*. In some embodiments, the multi-functional methylglyoxal reductase is encoded by the dkgA gene.

A multi-functional methylglyoxal reductase (DkgB) can catalyze the following reactions:

acetol+$NADP^+$⇆methylglyoxal+NADPH+$H^+$ (the reaction is physiologically favored in the opposite direction, EC 1.1.1.-)

4-nitrobenzyl alcohol+$NADP^+$⇆4-nitrobenzaldehyde+NADPH+$H^+$ (reversibility unspecified, EC 1.1.1.91)

2-keto-L-gulonate+$NADP^+$←2,5-didehydro-D-gluconate+NADPH+$H^+$ (the reaction is favored in the opposite direction, EC 1.1.1.346)

DkgB (YafB) is a member of the aldo-keto reductase (AKR) subfamily 3F. DkgB was shown to have 2,5-diketo-D-gluconate reductase, methylglyoxal reductase and 4-nitrobenzaldehyde reductase activities.

dkgB is reported to encode 2,5-diketo-D-gluconate reductase (25DKGR) B, one of two 25DKG reductases in *E. coli*. The enzyme uses NADPH as the preferred electron donor and is thought to be involved in ketogluconate metabolism. However, the specific activity of the enzyme towards 2,5-diketo-D-gluconate is reported to be almost 1000-fold lower than its activity towards methylglyoxal.

In particular embodiments, a multi-functional methylglyoxal reductase converts glycolaldehyde to MEG. In some embodiments, the multi-functional methylglyoxal reductase is from *Escherichia coli*. In some embodiments, the multi-functional methylglyoxal reductase is encoded by the dkgB gene.

A methylglyoxal reductase (YeaE) can catalyze the following reaction:

acetol+$NADP^+$⇆methylglyoxal+NADPH+$H^+$ (the reaction is physiologically favored in the opposite direction, EC 1.1.1.-)

YeaE has been shown to have methylglyoxal reductase activity.

The subunit structure of YeaE has not been determined, but its amino acid sequence similarity to the aldo-keto reductases DkgA (YqhE) and DkgB (YafB) suggests that it may be monomeric.

In particular embodiments, a methylglyoxal reductase converts glycolaldehyde to MEG. In some embodiments, the methylglyoxal reductase is from *Escherichia coli*. In some embodiments, the methylglyoxal reductase is encoded by the yeaE gene.

A L-glyceraldehyde 3-phosphate reductase (yghZ) can catalyze the following reactions:

L-glyceraldehyde 3-phosphate+NADPH+$H^+$→sn-glycerol 3-phosphate+$NADP^+$ (EC 1.1.1.-)

acetol+$NADP^+$⇆methylglyoxal+NADPH+$H^+$ (the reaction is physiologically favored in the opposite direction, EC 1.1.1.-)

YghZ is an L-glyceraldehyde 3-phosphate (L-GAP) reductase. The enzyme is also able to detoxify methylglyoxal at a low rate. YghZ defines the AKR14 (aldo-keto reductase 14) protein family.

L-GAP is not a natural metabolite and is toxic to *E. coli*. L-GAP is a substrate of both the glycerol-3-phosphate and hexose phosphate transport systems of *E. coli* K-12. It has been postulated that the physiological role of YghZ is the detoxification of L-GAP, which may be formed by non-enzymatic racemization of GAP or by an unknown cellular process.

The crystal structure of the *E. coli* enzyme has been determined and is suggested to be a tetramer. However, others have found that the protein forms an octamer based on gel filtration and electron microscopy studies.

In particular embodiments, a L-glyceraldehyde 3-phosphate reductase converts glycolaldehyde to MEG. In some embodiments, the L-glyceraldehyde 3-phosphate reductase is from *Escherichia coli*. In some embodiments, the L-glyceraldehyde 3-phosphate reductase is encoded by the yghZ gene.

An L-1,2-propanediol dehydrogenase/glycerol dehydrogenase (GldA) can catalyze the following reactions:

(S)-propane-1,2-diol+$NAD^+$⇆acetol+NADH+$H^+$ (reversible reaction)

aminoacetone+NADH+$H^+$→(R)-1-aminopropan-2-ol+$NAD^+$ (EC 1.1.1.75)

glycerol+NAD+⇆dihydroxyacetone+NADH+$H^+$ (reversible reaction, EC 1.1.1.6)

The physiological function of the GldA enzyme has long been unclear. The enzyme was independently isolated as a glycerol dehydrogenase and a D-1-amino-2-propanol:$NAD^+$ oxidoreductase. At that time, D-1-amino-2-propanol was thought to be an intermediate for the biosynthesis of vitamin B12, and although *E. coli* is unable to synthesize vitamin B12 de novo, enzymes catalyzing the synthesis of this compound were sought. It was later found that GldA was responsible for both activities.

The primary in vivo role of GldA was recently proposed to be the removal of dihydroxyacetone by converting it to glycerol. However, a dual role in the fermentation of glycerol has also recently been established. Glycerol dissimilation in *E. coli* can be accomplished by two different pathways. The glycerol and glycerophosphodiester degradation pathway requires the presence of a terminal electron acceptor and utilizes an ATP-dependent kinase of the Glp system, which phosphorylates glycerol to glycerol-3-phosphate. However, upon inactivation of the kinase and selection for growth on glycerol, it was found that an $NAD^+$-linked dehydrogenase, GldA, was able to support glycerol fermentation. Recently, it was shown that GldA was involved in glycerol fermentation both as a glycerol dehydrogenase, producing dihydroxyacetone, and as a 1,2-propanediol dehydrogenase, regenerating $NAD^+$ by producing 1,2-propanediol from acetol.

The enzyme is found in two catalytically active forms, a large form of eight subunits and a small form of two subunits. The large form appears to be the major species.

In particular embodiments, an L-1,2-propanediol dehydrogenase/glycerol dehydrogenase converts glycolaldehyde to MEG. In some embodiments, the L-1,2-propanediol dehydrogenase/glycerol dehydrogenase is from *Escherichia coli*. In some embodiments, the L-1,2-propanediol dehydrogenase/glycerol dehydrogenase is encoded by the gldA gene.

An NADPH-dependent methylglyoxal reductase (GRE2) from *Saccharomyces cerevisiae* can catalyze the following reactions:

(S)-lactaldehyde+$NADP^+$⇆methylglyoxal+NADPH 3-methylbutanol+$NAD(P)^+$⇆3-methylbutanal+NAD(P)H Gre2 is a versatile enzyme that catalyzes the stereoselective reduction of a broad range of substrates including aliphatic and aromatic ketones, diketones, as well as aldehydes, using NADPH as the cofactor.

The crystal structures of Gre2 from *S. cerevisiae* in an apo-form at 2.00 Å and NADPH-complexed form at 2.40 Å resolution have been solved. Gre2 forms a homodimer, each subunit of which contains an N-terminal Rossmann-fold domain and a variable C-terminal domain, which participates in substrate recognition. The induced fit upon binding to the cofactor NADPH makes the two domains shift toward each other, producing an interdomain cleft that better fits the substrate. Computational simulation combined with site-directed mutagenesis and enzymatic activity analysis enabled characterization of a potential substrate-binding pocket that determines the stringent substrate stereo selectivity for catalysis.

Gre2 catalyzes the irreversible reduction of the cytotoxic compound methylglyoxal (MG) to (S)-lactaldehyde as an alternative to detoxification of MG by glyoxalase I GLO1. MG is synthesized via a bypath of glycolysis from dihydroxyacetone phosphate and is believed to play a role in cell cycle regulation and stress adaptation. GRE2 also catalyzes the reduction of isovaleraldehyde to isoamylalcohol. The enzyme serves to suppress isoamylalcohol-induced filamentation by modulating the levels of isovaleraldehyde, the signal to which cells respond by filamentation. GRE2 is also involved in ergosterol metabolism.

In particular embodiments, an NADPH-dependent methylglyoxal reductase converts glycolaldehyde to MEG. In some embodiments, the NADPH-dependent methylglyoxal reductase is from *S. cerevisiae*. In some embodiments, the NADPH-dependent methylglyoxal reductase is encoded by the GRE2 gene.

Thiolase/Acetyl Coenzyme A Acetyltransferase (EC 2.3.1.9)

The present disclosure describes enzymes that can catalyze the following reaction:

2 acetyl-CoA⇆acetoacetyl-CoA+coenzyme A (reversible reaction)

Thiolase/Acetyl coenzyme A acetyltransferase may also be known as acetyl-CoA-C-acetyltransferase, acetoacetyl-CoA thiolase, acetyl-CoA:acetyl-CoA C-acetyltransferase or thiolase II.

Thus, in some embodiments, the disclosure provides for an enzyme that plays a role in acetoacetate degradation (to acetyl CoA). In one embodiment, an inhibitor of this enzyme may be acetoacetyl-CoA.

In particular embodiments, the enzyme converts acetyl-CoA to acetoacetyl-CoA. In some embodiments, the thiolase/acetyl coenzyme A acetyltransferase is from *Clostridium* spp. In some embodiments, the thiolase/acetyl coenzyme A acetyltransferase is from *Clostridium acetobutylicum*. In some embodiments, the thiolase/acetyl coenzyme A acetyltransferase is from *Clostridium thermosaccharolyticum*. In some embodiments, the thiolase/acetyl coenzyme A acetyltransferase is from *Bacillus cereus*. In some embodiments, the thiolase/acetyl coenzyme A acetyltransferase is from *Marinobacter hydrocarbonoclasticus* ATCC 49840. In some embodiments, the thiolase/acetyl coenzyme A acetyltransferase is encoded by the thlA gene. In some embodiments, the thiolase/acetyl coenzyme A acetyltransferase is from *Escherichia coli*. In some embodiments, the thiolase/acetyl coenzyme A acetyltransferase is encoded by the atoB gene.

In one embodiment, the thiolase or acetyl coenzyme A acetyltransferase is encoded by one or more nucleic acid molecules obtained from a microorganism selected from the group consisting of *Clostridium* sp., *Bacillus* sp., *E. coli*, *Saccharomyces* sp. and *Marinobacter* sp. In some embodiments, the thiolase or acetyl coenzyme A acetyltransferase is encoded by one or more nucleic acid molecules obtained from a microorganism selected from the group consisting of *Clostridium acetobutylicum*, *Clostridium thermosaccharolyticum*, *Bacillus cereus*, *E. coli*, *Saccharomyces cerevisiae* and *Marinobacter hydrocarbonoclasticus*. In some embodiments, the one or more nucleic acid molecules is thlA, atoB and/or ERG10, or homolog thereof. In a further embodiment, the thiolase or acetyl coenzyme A acetyltransferase comprises an amino acid sequence selected from the group consisting of SEQ ID NOs: 35, 37 and 40. In yet a further embodiment, the thiolase or acetyl coenzyme A acetyltransferase is encoded by a nucleic acid sequence selected from the group consisting of SEQ ID NOs: 33, 34, 36, 38 and 39.

Acetate:Acetoacetyl-CoA transferase (EC 2.8.3.-)

The present disclosure describes enzymes that can catalyze the following reaction:

acetoacetate+acetyl-CoA⇆acetoacetyl-CoA+acetate (reversible reaction, EC 2.8.3.-)

Acetate:Acetoacetyl-CoA transferase may also be known as acetoacetyl-CoA transferase or acetyl-CoA:acetoacetate-CoA transferase.

Thus, in some embodiments, the disclosure provides for an enzyme that plays a role in acetoacetate degradation (to acetyl CoA). In one embodiment, inhibitors of this enzyme may include acetyl-CoA and coenzyme A.

The growth of *E. coli* on short-chain fatty acids (C3-C6) requires the activation of the acids to their respective thioesters. This activation is catalyzed by acetoacetyl-CoA transferase. The reaction takes place in two half-reactions which involves a covalent enzyme-CoA. The enzyme undergoes two detectable conformational changes during the reaction. It is thought likely that the reaction proceeds by a ping-pong mechanism. The enzyme can utilize a variety of short-chain acyl-CoA and carboxylic acid substrates but exhibits maximal activity with normal and 3-keto substrates.

In particular embodiments, the enzyme converts acetoacetyl-CoA to acetoacetate. In some embodiments, the acetate:acetoacetyl-CoA transferase is from *Clostridium* spp. In some embodiments, the acetate:acetoacetyl-CoA transferase is from *Clostridium acetobutylicum*. In some embodiments, the acetate:acetoacetyl-CoA transferase is from *Escherichia coli*. In some embodiments, the acetate:acetoacetyl-CoA transferase is encoded by the atoA and atoD genes. In another embodiment, the subunit composition of acetoacetyl-CoA transferase is $[(AtoA)_2][(AtoD)_2]$, with $(AtoA)_2$ being the β complex and $(AtoD)_2$ being the α complex. In one embodiment, the acetate:acetoacetyl-CoA transferase is a fused acetate:acetoacetyl-CoA transferase: α subunit/β subunit. In another embodiment, the acetate:acetoacetyl-CoA transferase is encoded by the ydiF gene.

Acetate:Acetoacetyl-CoA Hydrolase (EC 3.1.2.11)

The present disclosure describes enzymes that can catalyze the following reaction:

acetoacetyl-CoA+$H_2O$⇆CoA+acetoacetate

Acetoacetyl-CoA hydrolase may also be known as acetoacetyl coenzyme A hydrolase, acetoacetyl CoA deacylase or acetoacetyl coenzyme A deacylase.

This enzyme belongs to the family of hydrolases, specifically those acting on thioester bonds.

In particular embodiments, the enzyme converts acetoacetyl-CoA to acetoacetate. In some embodiments, the acetate:acetoacetyl-CoA hydrolase is from *Clostridium* spp. In some embodiments, the acetate:acetoacetyl-CoA hydrolase is from *Clostridium acetobutylicum*. In another embodiment, the Acetoacetyl-CoA hydrolase is encoded by the ctfA (subunit A) and/or ctfB (subunit B) genes.

In a further embodiment, the acetyl-CoA:acetoacetate-CoA transferase or acetate:acetoacetyl-CoA hydrolase comprises an amino acid sequence selected from the group consisting of SEQ ID NOs: 43, 46, 97, 99, 101 and 103. In yet a further embodiment, the acetyl-CoA:acetoacetate-CoA transferase or acetate:acetoacetyl-CoA hydrolase is encoded by a nucleic acid sequence selected from the group consisting of SEQ ID NOs: 41, 42, 44, 45, 96, 98, 100 and 102.

Acetoacetate Decarboxylase (EC 4.1.1.4)

The present disclosure describes enzymes that can catalyze the following reaction:

acetoacetate+$H^+$→acetone+$CO_2$

Acetoacetate decarboxylase may also be known as ADC, AADC or acetoacetate carboxy-lyase.

Thus, in some embodiments, the disclosure provides for an enzyme that plays roles in isopropanol biosynthesis, pyruvate fermentation to acetone, the super pathway of *Clostridium acetobutylicum* acidogenic and solventogenic fermentation and/or the super pathway of *Clostridium acetobutylicum* solventogenic fermentation.

Acetoacetate decarboxylase (ADC) plays a key role in solvent production in *Clostridium acetobutylicum*. During the acidogenic phase of growth, acids accumulate causing a metabolic shift to solvent production. In this phase acids are re-assimilated and metabolized to produce acetone, butanol and ethanol.

Preliminary purification and crystallization of the enzyme has revealed that a lysine residue is implicated in the active site. The enzyme is a large complex composed of 12 copies of a single type of subunit.

The enzyme of *Clostridium acetobutylicum* ATCC 824 has been purified and the adc gene encoding it cloned. The enzyme has also been purified from the related strain *Clostridium acetobutylicum* DSM 792 and the gene cloned and sequenced. The decarboxylation reaction proceeds by the formation of a Schiff base intermediate.

ADC is a key enzyme in acid uptake, effectively pulling the CoA-transferase reaction in the direction of acetoacetate formation.

In particular embodiments, the enzyme converts acetoacetate to acetone. In some embodiments, the acetoacetate decarboxylase is from *Clostridium* spp. In some embodiments, the acetoacetate decarboxylase is from *Clostridium acetobutylicum*. In some embodiments, the acetoacetate decarboxylase is from *Clostridium beijerinckii*. In some embodiments, the acetoacetate decarboxylase is from *Clostridium cellulolyticum*. In some embodiments, the acetoacetate decarboxylase is from *Bacillus polymyxa*. In some embodiments, the acetoacetate decarboxylase is from *Chromobacterium violaceum*. In some embodiments, the acetoacetate decarboxylase is from *Pseudomonas putida*. In another embodiment, the acetoacetate decarboxylase is encoded by the adc gene.

In one embodiment, the acetoacetate decarboxylase is encoded by one or more nucleic acid molecules obtained from a microorganism selected from the group consisting of *Clostridium* sp., *Bacillus* sp., *Chromobacterium* sp. and *Pseudomonas* sp. In another embodiment, the acetoacetate decarboxylase is encoded by one or more nucleic acid molecules obtained from a microorganism selected from the group consisting of *Clostridium acetobutylicum, Clostridium beijerinckii, Clostridium cellulolyticum, Bacillus polymyxa, Chromobacterium violaceum* and *Pseudomonas putida*. In some embodiments, the one or more nucleic acid molecules encoding the acetoacetate decarboxylase is adc, or homolog thereof. In a further embodiment, the acetoacetate decarboxylase comprises an amino acid sequence selected from the group consisting of SEQ ID NOs: 49 and 52. In yet another embodiment, the acetoacetate decarboxylase is encoded by a nucleic acid sequence selected from the group consisting of SEQ ID NOs: 47, 48, 50 and 51.

Alcohol Dehydrogenase (EC 1.1.1.-)

The present disclosure describes enzymes that can catalyze the reversible oxidation of primary or secondary alcohols to aldehydes or ketones, respectively. In one embodiment, the enzyme is a secondary alcohol dehydrogenase (S-ADH) and catalyzes the reduction of ketones such as acetone into secondary alcohols such as 2-propanol (isopropanol).

In some embodiments the S-ADH is from *Burkholderia* sp. In some embodiments, the S-ADH is from *Burkholderia* sp. AIU 652. In some embodiments, the S-ADH is from *Alcaligenes* sp. In some embodiments, the S-ADH is from *Alcaligenes eutrophus*. In some embodiments, the S-ADH is from *Clostridium* sp. In some embodiments, the S-ADH is from *Clostridium* ragsdalei. In some embodiments, the S-ADH is from *Clostridium beijerinckii*. In some embodiments, the S-ADH is from *Thermoanaerobacter* sp. In some embodiments, the S-ADH is from *Thermoanaerobacter* brockii. In some embodiments, the S-ADH is from *Thermoanaerobacter* ethanolicus (*Clostridium thermohydrosulfuricum*). In some embodiments, the S-ADH is encoded by the adhB gene. In some embodiments, the S-ADH is from the trypanosomatid *Phytomonas* sp. In some embodiments, the S-ADH is from *Rhodococcus* sp. In some embodiments, the S-ADH is from *Rhodococcus ruber*. In some embodiments, the S-ADH is from *Methanobacterium palustre*. In some embodiments, the S-ADH is from methanogenic archaea *Methanogenium liminatans*. In some embodiments, the S-ADH is from the parasitic protist *Entamoeba histolytica* (EhAdh1). In some embodiments, the S-ADH is from parasitic protozoan *Tritrichomonas foetus*. In some embodiments, the S-ADH is from human parasite *Trichomonas vaginalis*.

In some embodiments, the S-ADH is predicted from homology and can be from *Thermoanaerobacter mathranii, Micrococcus luteus, Nocardiopsis alba, Mycobacterium hassiacum, Helicobacter suis, Candida albicans, Candida parapsilosis, Candida orthopsilosis, Candida metapsilosis, Grosmannia clavigera* and *Scheffersomyces stipitis*.

In a further embodiment, the alcohol dehydrogenase comprises an amino acid sequence selected from the group consisting of SEQ ID NOs: 106 and 108. In yet another embodiment, the alcohol dehydrogenase is encoded by a nucleic acid sequence selected from the group consisting of SEQ ID NOs: 104, 105 and 107.

Dehydratase (EC 4.2.1.-)

The present disclosure describes enzymes that can catalyze the following reactions:

isopropanol ⇆ propene+H20

D-xylulose 1-kinase (EC 2.7.1.-)

The present disclosure describes enzymes that can catalyze the conversion of D-xylulose to D-xylulose-1-phosphate. In some embodiments, the conversion can be catalyzed by a human ketohexokinase C (khk-C), also known as fructokinase.

Ketohexokinase, or fructokinase, phosphorylates fructose to fructose-1-phosphate. The enzyme is involved in fructose metabolism, which is part of carbohydrate metabolism. It is found in the liver, intestine and kidney cortex.

In human liver, purified fructokinase, when coupled with aldolase, has been discovered to contribute to an alternative mechanism to produce oxalate from xylitol. In coupled sequence, fructokinase and aldolase produce glycolaldehyde, a precursor to oxalate, from D-xylulose via D-xylulose 1-phosphate.

In particular embodiments, the enzyme converts D-xylulose to D-xylulose-1-phosphate. In some embodiments, the D-xylulose 1-kinase is a ketohexokinase C. In some embodiments, the ketohexokinase C is from *Homo sapiens*. In some embodiments, the human ketohexokinase C is encoded by the khk-C gene.

In one embodiment, the D-xylulose 1-kinase is encoded by one or more nucleic acid molecules obtained from *Homo sapiens*. In some embodiments, the one or more nucleic acid molecules encoding the D-xylulose 1-kinase is ketohexokinase C (khk-C), or homolog thereof. In another embodiment, the one or more nucleic acid molecules encoding the D-xylulose 1-kinase comprises an amino acid sequence set forth in SEQ ID NO: 55. In a further embodiment, the one or more nucleic acid molecules encoding the D-xylulose 1-kinase is encoded by a nucleic acid sequence selected from the group consisting of SEQ ID NOs: 53 and 54.

D-xylulose-1-phosphate aldolase (EC 4.1.2.-)

The present disclosure describes enzymes that can catalyze the conversion of D-xylulose-1-phosphate to glycolaldehyde and DHAP. In some embodiments, the conversion can be catalyzed by a human aldolase B, which is also known as fructose-bisphosphate aldolase B or liver-type aldolase.

Aldolase B is one of three isoenzymes (A, B, and C) of the class I fructose 1,6-bisphosphate aldolase enzyme (EC 4.1.2.13), and plays a key role in both glycolysis and gluconeogenesis. The generic fructose 1,6-bisphosphate aldolase enzyme catalyzes the reversible cleavage of fructose 1,6-bisphosphate (FBP) into glyceraldehyde 3-phosphate and dihydroxyacetone phosphate (DHAP) as well as the reversible cleavage of fructose 1-phosphate (FIP) into glyceraldehyde and dihydroxyacetone phosphate. In mammals, aldolase B is preferentially expressed in the liver, while aldolase A is expressed in muscle and erythrocytes and aldolase C is expressed in the brain. Slight differences in isozyme structure result in different activities for the two substrate molecules: FBP and fructose 1-phosphate. Aldolase B exhibits no preference and thus catalyzes both reactions, while aldolases A and C prefer FBP.

Aldolase B is a homotetrameric enzyme, composed of four subunits. Each subunit has a molecular weight of 36 kDa and contains an eight-stranded α/β barrel, which encloses lysine 229 (the Schiff-base forming amino acid that is key for catalysis).

In particular embodiments, the enzyme converts D-xylulose-1-phosphate to glycolaldehyde and DHAP. In some embodiments, the D-xylulose-1-phosphate aldolase is an aldolase B. In some embodiments, the aldolase B is from *Homo sapiens*. In some embodiments, the human aldolase B is encoded by the ALDOB gene.

In one embodiment, the D-xylulose-1-phosphate aldolase is encoded by one or more nucleic acid molecules obtained from *Homo sapiens*. In another embodiment, the one or more nucleic acid molecules encoding the D-xylulose-1-phosphate aldolase is aldolase B (ALDOB), or homolog thereof. In some embodiments, the one or more nucleic acid molecules encoding the D-xylulose-1-phosphate aldolase comprises an amino acid sequence set forth in SEQ ID NO: 58. In some embodiments, the one or more nucleic acid molecules encoding the D-xylulose-1-phosphate aldolase is encoded by a nucleic acid sequence selected from the group consisting of SEQ ID NOs: 56 and 57.

D-xylose Isomerase (EC 5.3.1.5)

The present disclosure describes enzymes that can catalyze the following reversible reaction:

$$\text{D-xylopyranose} \leftrightharpoons \text{D-xylulose}$$

D-xylose isomerase may also be known as xylose isomerase or D-xylose ketol-isomerase.

Thus, in some embodiments, the disclosure provides for an enzyme that plays a role in xylose degradation.

Xylose isomerase catalyzes the first reaction in the catabolism of D-xylose.

Two conserved histidine residues, H101 and H271, were shown to be essential for catalytic activity. The fluorescence of two conserved tryptophan residues, W49 and W188, is quenched during binding of xylose, and W49 was shown to be essential for catalytic activity. The presence of $Mg^{2+}$, $Mn^{2+}$ or $Co^{2+}$ protects the enzyme from thermal denaturation.

The subunit composition has not been established experimentally.

In particular embodiments, the enzyme converts D-xylose to D-xylulose. In some embodiments, the D-xylose isomerase is from *Escherichia coli*. In some embodiments, the D-xylose isomerase is encoded by the xylA gene.

In some embodiments, a recombinant microorganism producing MEG and a three-carbon compound comprises a deletion, insertion, or loss of function mutation in a gene encoding a D-xylose isomerase to prevent conversion of D-xylose to D-xylulose and instead shunt the reaction toward the conversion of D-xylose to D-xylonate.

In one embodiment, the recombinant microorganism comprises an endogenous or exogenous xylose isomerase that catalyzes the conversion of D-xylose to D-xylulose. In one embodiment, the xylose isomerase is exogenous. In another embodiment, the xylose isomerase is encoded by one or more nucleic acid molecules obtained from *Pyromyces* sp. In another embodiment, the one or more nucleic acid molecules encoding the xylose isomerase is xylA, or homolog thereof. In yet another embodiment, the one or more nucleic acid molecules encoding the xylose isomerase comprises an amino acid sequence set forth in SEQ ID NO: 95. In a further embodiment, the one or more nucleic acid molecules encoding the xylose isomerase is encoded by a nucleic acid sequence selected from the group consisting of SEQ ID NOs: 93 and 94.

D-xylulose-5-kinase/xylulokinase

The present disclosure describes enzymes that can catalyze the following reactions:

$$\text{D-xylulose+ATP} \rightarrow \text{D-xylulose 5-phosphate+ADP+H}^+ \text{ (EC 2.7.1.17)}$$

$$\text{ATP+1-deoxy-D-xylulose} \rightarrow \text{1-deoxy-D-xylulose 5-phosphate+ADP+H}^+ \text{ (EC 2.7.1.-)}$$

D-xylulose-5-kinase may also be known as xylulose kinase or xylulokinase.

Xylulokinase catalyzes the phosphorylation of D-xylulose, the second step in the xylose degradation pathway, producing D-xylulose-5-phosphate, an intermediate of the pentose phosphate pathway.

In the absence of substrate, xylulokinase has weak ATPase activity. Xylulokinase can also catalyze the phosphorylation of 1-deoxy-D-xylulose. This would allow a potential salvage pathway for generating 1-deoxy-D-xylulose 5-phosphate for use in the biosynthesis of terpenoids, thiamine and pyridoxal. The rate of phosphorylation of 1-deoxy-D-xylulose is 32-fold lower than the rate of phosphorylation of D-xylulose.

The kinetic mechanism of the bacterial enzyme has been studied, suggesting a predominantly ordered reaction mechanism. The enzyme undergoes significant conformational changes upon binding of the substrate and of ATP. Two conserved aspartate residues, D6 and D233, were found to be essential for catalytic activity, and a catalytic mechanism has been proposed.

Crystal structures of bacterial xylulokinase in the apo form and bound to D-xylulose have been determined at 2.7 and 2.1 Å resolution, respectively.

In particular embodiments, the enzyme converts D-xylulose to D-xylulose-5-phosphate. In some embodiments, the D-xylulose-5-kinase is from *Escherichia coli*. In some embodiments, the D-xylulose-5-kinase is encoded by the xylB gene. In some embodiments, the D-xylulose-5-kinase is from *Saccharomyces cerevisiae*. In some embodiments the D-xylulose-5-kinase is encoded by the XKS1 gene. In some embodiments, the D-xylulose-5-kinase is from *Pichia stipitis*. In some embodiments the D-xylulose-5-kinase is encoded by the XYL3 gene.

In some embodiments, a recombinant microorganism producing MEG and a three-carbon compound comprises a deletion, insertion, or loss of function mutation in a gene encoding a D-xylulose-5-kinase to prevent the conversion of D-xylulose to D-xylulose-5-phosphate and instead shunt the reaction toward conversion of D-xylulose to D-xylulose-1-phosphate.

Xylose dehydrogenase (EC 1.1.1.175 or EC 1.1.1.179)

The present disclosure describes enzymes that can catalyze the following reactions:

aldehydo-D-xylose+$NAD^+$+$H_2O$→D-xylonate+NADH+$2H^+$

α-D-xylopyranose+$NAD^+$⇆D-xylonolactone+NADH+$H^+$ (reversibility unspecified, EC 1.1.1.175)

Xylose dehydrogenase may also be known as D-xylose dehydrogenase, D-xylose 1-dehydrogenase, ($NAD^+$)-linked D-xylose dehydrogenase, $NAD^+$-D-xylose dehydrogenase, D-xylose:$NAD^+$1-oxidoreductase D-Xylose dehydrogenase catalyzes the $NAD^+$-dependent oxidation of D-xylose to D-xylonolactone. This is the first reaction in the oxidative, non-phosphorylative pathway for the degradation of D-xylose in *Caulobacter crescentus*. This pathway is similar to the pathway for L-arabinose degradation in *Azospirillum brasilense*. The amino acid sequence of the *C. crescentus* enzyme is unrelated to that of xylose dehydrogenase from the archaeon *Haloarcula marismortui*, or the L-arabinose 1-dehydrogenase of *Azospirillum brasilense*.

D-xylose is the preferred substrate for recombinant D-xylose dehydrogenase from *Caulobacter crescentus*. The enzyme can use L-arabinose, but it is a poorer substrate. The Km for L-arabinose is 166 mM. Other substrates such as D-arabinose, L-xylose, D-ribose, D-galactose, D-glucose and D-glucose-6-phosphate showed little or no activity in the assay, as measured by NADH production. *C. crescentus* D-xylose dehydrogenase can convert D-xylose to D-xylonate directly.

Partially purified, native D-xylose dehydrogenase from *C. crescentus* had a Km of 70 μM for D-xylose. This value was lower than the Km of 760 μM for the recombinant, His-tagged enzyme.

In some embodiments, the D-Xylose dehydrogenase is from the halophilic archaeon *Haloferax volcanii*. The *Haloferax volcanii* D-Xylose dehydrogenase catalyzes the first reaction in the oxidative xylose degradation pathway of the halophilic archaeon *Haloferax volcanii*. The *H. volcanii* D-Xylose dehydrogenase shows 59% amino acid sequence identity to a functionally characterized xylose dehydrogenase from *Haloarcula marismortui* and 56% identity to an ortholog in *Halorubrum lacusprofundi*, but is only 11% identical to the bacterial NAD+-dependent xylose dehydrogenase from *Caulobacter crescentus* CB15.

In particular embodiments, the enzyme converts D-xylose to D-xylonolactone. In some embodiments, the D-Xylose dehydrogenase is from *Caulobacter crescentus*. In some embodiments, the D-Xylose dehydrogenase is encoded by the xylB gene. In some embodiments, the D-Xylose dehydrogenase is from *Haloferax volcanii*. In some embodiments, the D-Xylose dehydrogenase is from *Haloarcula marismortui*. In some embodiments, the D-Xylose dehydrogenase is from *Halorubrum lacusprofundi*. In some embodiments, the D-Xylose dehydrogenase is encoded by the xdh gene.

In one embodiment, the xylose dehydrogenase is encoded by one or more nucleic acid molecules obtained from a microorganism selected from the group consisting of *Caulobacter* sp., *Haloarcula* sp., *Haloferax* sp., *Halorubrum* sp. and *Trichoderma* sp. In another embodiment, the xylose dehydrogenase is encoded by one or more nucleic acid molecules obtained from a microorganism selected from the group consisting of *Caulobacter crescentus, Haloarcula marismortui, Haloferax volcanii, Halorubrum lacusprofundi* and *Trichoderma reesei*. In some embodiments, the one or more nucleic acid molecules encoding the xylose dehydrogenase is selected from xylB, xdh1 (HVO_B0028) and/or xyd1, or homolog thereof. In a further embodiment, the one or more nucleic acid molecules encoding the xylose dehydrogenase comprises an amino acid sequence selected from the group consisting of SEQ ID NOs: 61, 63 and 65. In yet another embodiment, the one or more nucleic acid molecules encoding the xylose dehydrogenase is encoded by a nucleic acid sequence selected from the group consisting of SEQ ID NOs: 59, 60, 62 and 64.

Xylonolactonase (3.1.1.68)

The present disclosure describes enzymes that can catalyze the following reaction:

D-xylono-1,4-lactone+$H_2O$↔D-xylonate

This enzyme belongs to the family of hydrolases, specifically those acting on carboxylic ester bonds. This enzyme participates in pentose and glucuronate interconversions.

Xylonolactonase may also be known as D-xylonolactonase, xylono-1,4-lactonase, xylono-gamma-lactonase or D-xylono-1,4-lactonelactonohydrolase.

In particular embodiments, the enzyme converts D-xylonolactone to D-xylonate. In some embodiments, the D-xylonolactonase is from *Haloferax* sp. In some embodiments, the D-xylonolactonase is from *Haloferax volcanii*. In some embodiments, the D-xylonolactonase is from *Haloferax gibbonsii*. In some embodiments, the D-xylonolactonase is from *Caulobacter crescentus*. In some embodiments, the D-xylonolactonase is encoded by the xylC gene.

In one embodiment, the xylonolactonase is encoded by one or more nucleic acid molecules obtained from a microorganism selected from *Caulobacter* sp. and *Haloferax* sp. In another embodiment, the xylonolactonase is encoded by one or more nucleic acid molecules obtained from a microorganism selected from the group consisting of *Caulobacter crescentus, Haloferax volcanii* and *Haloferax gibbonsii*. In some embodiments, the one or more nucleic acid molecules encoding the xylonolactonase is xylC, or homolog thereof. In a further embodiment, the one or more nucleic acid molecules encoding the xylonolactonase comprises an amino acid sequence set forth in SEQ ID NO: 67. In yet another embodiment, the one or more nucleic acid molecules encoding the xylonolactonase is encoded by a nucleic acid sequence set forth in SEQ ID NO: 66.

Xylonate dehydratase (EC 4.2.1.82)

The present disclosure describes enzymes that can catalyze the following reaction:

D-xylonate↔2-keto-3-deoxy-D-xylonate+$H_2O$

This enzyme belongs to the family of lyases, specifically the hydro-lyases, which cleave carbon-oxygen bonds. This enzyme participates in pentose and glucuronate interconversions.

Xylonate dehydratase may also be known as D-xylonate hydro-lyase, D-xylo-aldonate dehydratase or D-xylonate dehydratase.

In particular embodiments, the enzyme converts D-xylonate to 2-keto-3-deoxy-D-xylonate. In some embodiments, the xylonate dehydratase is from *Caulobacter crescentus*. In some embodiments, the xylonate dehydratase is encoded by the xylD gene. In some embodiments, the xylonate dehydratase is from *Escherichia coli*. In some embodiments, the xylonate dehydratase is encoded by the yjhG gene. In some embodiments, the xylonate dehydratase is encoded by the yagF gene. In some embodiments, the xylonate dehydratase is from *Haloferax volcanii*. In some embodiments, the xylonate dehydratase is encoded by the xad gene. In some embodiments, the xylonate dehydratase is from *Sulfolobus solfataricus*.

In one embodiment, the xylonate dehydratase is encoded by one or more nucleic acid molecules obtained from a microorganism selected from the group consisting of *Caulobacter* sp., *Sulfolobus* sp. and *E. coli*. In another embodiment, the xylonate dehydratase is encoded by one or more nucleic acid molecules obtained from a microorganism selected from the group consisting of *Caulobacter crescentus, Sulfolobus solfataricus* and *E. coli*. In some embodiments, the one or more nucleic acid molecules encoding the xylonate dehydratase is selected from xylD, yjhG and/or yagF, or homolog thereof. In a further embodiment, the one or more nucleic acid molecules encoding the xylonate dehydratase comprises an amino acid sequence selected from the group consisting of SEQ ID NOs: 69, 72 and 75. In yet another embodiment, the one or more nucleic acid molecules encoding the xylonate dehydratase is encoded by a nucleic acid sequence selected from the group consisting of SEQ ID NOs: 68, 70, 71, 73 and 74.

2-keto-3-deoxy-D-pentonate aldolase (4.1.2.28)

The present disclosure describes enzymes that can catalyze the following reaction:

2-dehydro-3-deoxy-D-pentonate⇆glycolaldehyde+pyruvate (reversibility unspecified)

This enzyme belongs to the family of lyases, specifically the aldehyde-lyases, which cleave carbon-carbon bonds. This enzyme participates in pentose and glucuronate interconversions.

2-keto-3-deoxy-D-pentonate aldolase may also be known as 2-dehydro-3-deoxy-D-pentonate glycolaldehyde-lyase (pyruvate-forming), 2-dehydro-3-deoxy-D-pentonate aldolase, 3-deoxy-D-pentulosonic acid aldolase, and 2-dehydro-3-deoxy-D-pentonate glycolaldehyde-lyase.

YjhH appears to be a 2-dehydro-3-deoxy-D-pentonate aldolase. Genetic evidence suggests that YagE may also function as a 2-dehydro-3-deoxy-D-pentonate aldolase. yagE is part of the prophage CP4-6.

A yjhH yagE double mutant cannot use D-xylonate as the sole source of carbon, and crude cell extracts do not contain 2-dehydro-3-deoxy-D-pentonate aldolase activity. Both phenotypes are complemented by providing yjhH on a plasmid.

ArcA appears to activate yjhH gene expression under anaerobiosis. Two putative ArcA binding sites were identified 211 and 597 bp upstream of this gene, but no promoter upstream of it has been identified.

The crystal structure of YagE suggests that the protein is a homotetramer. Co-crystal structures of YagE in the presence of pyruvate and 2-keto-3-deoxygalactonate have been solved.

In particular embodiments, the enzyme converts 2-keto-3-deoxy-xylonate to glycolaldehyde and pyruvate. In some embodiments, the 2-keto-3-deoxy-D-pentonate aldolase is from *Pseudomonas* sp. In some embodiments, the 2-keto-3-deoxy-D-pentonate aldolase is from *Escherichia coli*. In some embodiments, the 2-keto-3-deoxy-D-pentonate aldolase is encoded by the yjhH gene. In some embodiments, the 2-keto-3-deoxy-D-pentonate aldolase is encoded by the yagE gene.

In one embodiment, the 2-keto-3-deoxy-D-pentonate aldolase is encoded by one or more nucleic acid molecules obtained from a microorganism selected from *Pseudomonas* sp. and *E. coli*. In another embodiment, the 2-keto-3-deoxy-D-pentonate aldolase is encoded by one or more nucleic acid molecules obtained from *E. coli*. In some embodiments, the one or more nucleic acid molecules encoding the 2-keto-3-deoxy-D-pentonate aldolase is selected from yjhH and/or yagE, or homolog thereof. In a further embodiment, the one or more nucleic acid molecules encoding the 2-keto-3-deoxy-D-pentonate aldolase comprises an amino acid sequence selected from the group consisting of SEQ ID NOs: 78 and 81. In yet another embodiment, the one or more nucleic acid molecules encoding the 2-keto-3-deoxy-D-pentonate aldolase is encoded by a nucleic acid sequence selected from the group consisting of SEQ ID NOs: 76, 77, 79 and 80.

Glycolaldehyde Dehydrogenase (1.2.1.21)

The present disclosure describes enzymes that can catalyze the following reaction:

glycolaldehyde+$NAD^+$+$H_2O$↔glycolate+$NADH^+$ $2H^+$

This enzyme belongs to the family of oxidoreductases, specifically those acting on the aldehyde or oxo group of donor with $NAD^+$ or $NADP^+$ as acceptor. This enzyme participates in glyoxylate and dicarboxylate metabolism.

Glycolaldehyde dehydrogenase may also be known as glycolaldehyde:$NAD^+$ oxidoreductase or glycol aldehyde dehydrogenase.

In *E. coli* aldehyde dehydrogenase A (AldA) is an enzyme of relatively broad substrate specificity for small α-hydroxyaldehyde substrates. It is thus utilized in several metabolic pathways.

L-fucose and L-rhamnose are metabolized through parallel pathways which converge after their corresponding aldolase reactions yielding the same products: dihydoxyacetone phosphate and L-lactaldehyde. Aerobically, aldehyde dehydrogenase A oxidizes L-lactaldehyde to L-lactate.

In parallel pathways utilizing the same enzymes, D-arabinose and L-xylose can be metabolized to dihydoxy-acetone phosphate and glycolaldehyde, which is oxidized to glycolate by aldehyde dehydrogenase A.

Crystal structures of the enzyme alone and in ternary and binary complexes have been solved.

Aldehyde dehydrogenase A is only present under aerobic conditions and is most highly induced by the presence of fucose, rhamnose or glutamate. The enzyme is inhibited by NADH, which may act as a switch to shift from oxidation of lactaldehyde to its reduction by propanediol oxidoreductase. AldA is upregulated during short-term adaptation to glucose limitation.

Based on sequence similarity, AldA was predicted to be a succinate-semialdehyde dehydrogenase.

Regulation of aldA expression has been investigated. The gene is regulated by catabolite repression, repression under anaerobic conditions via ArcA, and induction by the carbon source.

In particular embodiments, the enzyme converts glycolaldehyde to glycolate. In some embodiments, the glycolaldehyde dehydrogenase is from *Escherichia coli*. In some embodiments, the glycolaldehyde dehydrogenase is encoded by the aldA gene.

In some embodiments, a recombinant microorganism producing MEG and a three-carbon compound comprises a deletion, insertion, or loss of function mutation in a gene encoding a glycolaldehyde dehydrogenase to prevent the production of glycolic acid from glycolaldehyde and instead shunt the reaction toward conversion of glycolaldehyde to MEG.

Lactate Dehydrogenase (1.1.1.28)

The present disclosure describes enzymes that can catalyze the following reaction:

$$(R)\text{-lactate}+NAD^+ \leftarrow \text{pyruvate}+NADH+H^+$$

Lactate dehydrogenase (LDH) is an enzyme found in nearly all living cells such as in animals, plants and prokaryotes. LDH catalyzes the conversion of lactate to pyruvic acid and back, as it converts NADH to $NAD^+$ and back. A dehydrogenase is an enzyme that transfers a hydride from one molecule to another.

LDH exist in four distinct enzyme classes. The most common one is NAD(P)-dependent L-lactate dehydrogenase. Other LDHs act on D-lactate and/or are dependent on cytochrome c: D-lactate dehydrogenase (cytochrome) and L-lactate dehydrogenase (cytochrome).

LDH has been of medical significance because it is found extensively in body tissues, such as blood cells and heart muscle. Because it is released during tissue damage, it is a marker of common injuries and disease such as heart failure.

Lactate dehydrogenase may also be known as lactic acid dehydrogenase, (R)-lactate:$NAD^+$ oxidoreductase or D-lactate dehydrogenase-fermentative.

In *E. coli*, lactate dehydrogenase (LdhA) is a soluble NAD-linked lactate dehydrogenase (LDH) that is specific for the production of D-lactate. LdhA is a homotetramer and shows positive homotropic cooperativity under higher pH conditions.

*E. coli* contains two other lactate dehydrogenases: D-lactate dehydrogenase and L-lactate dehydrogenase. Both are membrane-associated flavoproteins required for aerobic growth on lactate.

LdhA is present under aerobic conditions but is induced when *E. coli* is grown on a variety of sugars under anaerobic conditions at acidic pH. Unlike most of the genes involved in anaerobic respiration, ldhA is not activated by Fnr; rather the ArcAB system and several genes involved in the control of carbohydrate metabolism (csrAB and mlc) appear to regulate expression. The expression of ldhA is negatively affected by the transcriptional regulator ArcA. ldhA belongs to the σ32 regulon.

The ldhA gene is a frequent target for mutations in metabolic engineering, most often to eliminate production of undesirable fermentation side products, but also to specifically produce D-lactate.

In particular embodiments, the enzyme converts pyruvate to lactate. In some embodiments, the lactate dehydrogenase is from *Escherichia coli*. In some embodiments, the lactate dehydrogenase is encoded by the ldhA gene.

In some embodiments, a recombinant microorganism producing MEG and a three-carbon compound comprises a deletion, insertion, or loss of function mutation in a gene encoding a lactate dehydrogenase to prevent the production of lactate from pyruvate and instead shunt the reaction toward production of a three-carbon compound.

Xylose Reductase or Aldose Reductase (EC 1.1.1.21)

The present disclosure describes enzymes that can catalyze the following reactions:

$$\alpha\text{-D-xylose}+NADPH+H^+ \leftrightarrow \text{xylitol}+NADP$$

$$\text{an alditol}+NAD(P)^+ \leftrightarrow NAD(P)H+\text{aldose}$$

Aldose reductase may also be known as alditol:$NAD(P)^+$ 1-oxidoreductase, polyol dehydrogenase or aldehyde reductase.

Aldose reductase is a cytosolic oxidoreductase that catalyzes the reduction of a variety of aldehydes and carbonyls, including monosaccharides.

Aldose reductase may be considered a prototypical enzyme of the aldo-keto reductase enzyme superfamily. The enzyme comprises 315 amino acid residues and folds into a β/α-barrel structural motif composed of eight parallel β strands. Adjacent strands are connected by eight peripheral α-helical segments running anti-parallel to the β sheet. The catalytic active site is situated in the barrel core. The NADPH cofactor is situated at the top of the β/α barrel, with the nicotinamide ring projecting down in the center of the barrel and pyrophosphate straddling the barrel lip.

The reaction mechanism of aldose reductase in the direction of aldehyde reduction follows a sequential ordered path where NADPH binds, followed by the substrate. Binding of NADPH induces a conformational change (Enzyme•NADPH→Enzyme*•NADPH) that involves hinge-like movement of a surface loop (residues 213-217) so as to cover a portion of the NADPH in a manner similar to that of a safety belt. The alcohol product is formed via a transfer of the pro-R hydride of NADPH to the face of the substrate's carbonyl carbon. Following release of the alcohol product, another conformational change occurs (E*•NAD(P)+→E•NAD(P)+) in order to release $NADP^+$. Kinetic studies have shown that reorientation of this loop to permit release of $NADP^+$ appears to represent the rate-limiting step in the direction of aldehyde reduction. As the rate of coenzyme release limits the catalytic rate, it can be seen that perturbation of interactions that stabilize coenzyme binding can have dramatic effects on the maximum velocity (Vmax).

D-xylose-fermenting *Pichia stipitis* and *Candida shehatae* were shown to produce one single aldose reductase (ALR) that is active both with NADPH and NADH. Other yeasts such as *Pachysolen tannophilus* and *C. tropicalis* synthesize multiple forms of ALR with different coenzyme specificities. The significant dual coenzyme specificity distinguishes the *P. stipitis* and the *C. shehatae* enzymes from most other ALRs so far isolated from mammalian or microbial sources. The yeast *Candida tenuis* CBS 4435 produces comparable NADH- and NADPH-linked aldehyde-reducing activities during growth on D-xylose.

In particular embodiments, the enzyme converts D-xylose to xylitol. In some embodiments, the xylose reductase or aldose reductase is from *Hypocrea jecorina*. In some embodiments, the xylose reductase or aldose reductase is encoded by the xyl1 gene. In some embodiments, the xylose reductase or aldose reductase is from *Saccharomyces cerevisiae*. In some embodiments, the xylose reductase or aldose reductase is encoded by the GRE3 gene. In some embodiments, the xylose reductase or aldose reductase is from *Pachysolen tannophilus*. In some embodiments, the xylose reductase or aldose reductase is from *Pichia* sp. In some embodiments, the xylose reductase or aldose reductase is from *Pichia stipitis*. In some embodiments, the xylose reductase or aldose reductase is from *Pichia quercuum*. In some embodiments, the xylose reductase or aldose reductase is from *Candida* sp. In some embodiments, the xylose reductase or aldose reductase is from *Candida shehatae*. In some embodiments, the xylose reductase or aldose reductase is from *Candida tenuis*. In some embodiments, the xylose reductase or aldose reductase is from *Candida tropicalis*. In some embodiments, the xylose reductase or aldose reductase is from *Aspergillus niger*. In some embodiments, the xylose reductase or aldose reductase is from *Neurospora crassa*. In some embodiments, the xylose reductase or aldose reductase is from *Cryptococcus lactativorus*.

In some embodiments, the xylose reductase or aldose reductase is encoded by one or more nucleic acid molecules obtained from a microorganism selected from the group consisting of *Hypocrea* sp., *Scheffersomyces* sp., *Saccharomyces* sp., *Pachysolen* sp., *Pichia* sp., *Candida* sp., *Aspergillus* sp., *Neurospora* sp., and *Cryptococcus* sp. In some embodiments, the xylose reductase or aldose reductase is encoded by one or more nucleic acid molecules obtained from a microorganism selected from the group consisting of *Hypocrea jecorina, Scheffersomyces Saccharomyces cerevisiae, Pachysolen tannophilus, Pichia stipitis, Pichia quercuum, Candida shehatae, Candida tenuis, Candida tropicalis, Aspergillus niger, Neurospora crassa* and *Cryptococcus lactativorus*. In another embodiment, the one or more nucleic acid molecules encoding the xylose reductase or aldose reductase is xyl1 and/or GRE3 or homolog thereof. In some embodiments, the one or more nucleic acid molecules encoding the xylose reductase or aldose reductase comprises an amino acid sequence selected from the group consisting of SEQ ID NOs: 84 and 87. In some embodiments, the one or more nucleic acid molecules encoding the xylose reductase or aldose reductase is encoded by a nucleic acid sequence selected from the group consisting of SEQ ID NOs: 82, 83, 85 and 86.

Xylitol Dehydrogenase (1.1.1.9)

The present disclosure describes enzymes that can catalyze the following reaction:

$$xylitol+NAD^{+}\leftrightarrow D\text{-}xylulose+NADH+H^{+}$$

Xylitol dehydrogenase may also be known as D-xylulose reductase, $NAD^+$-dependent xylitol dehydrogenase, erythritol dehydrogenase, 2,3-cis-polyol(DPN) dehydrogenase (C3-5), pentitol-DPN dehydrogenase, xylitol-2-dehydrogenase or xylitol:$NAD^+$ 2-oxidoreductase (D-xylulose-forming).

Xylitol dehydrogenase (XDH) is one of several enzymes responsible for assimilating xylose into eukaryotic metabolism and is useful for fermentation of xylose contained in agricultural byproducts to produce ethanol. For efficient xylose utilization at high flux rates, cosubstrates should be recycled between the $NAD^+$-specific XDH and the NADPH-preferring xylose reductase, another enzyme in the pathway.

In particular embodiments, the enzyme converts xylitol to D-xylulose. In some embodiments, the xylitol dehydrogenase is from yeast. In some embodiments, the xylitol dehydrogenase is from *Pichia* sp., *Saccharomyces* sp., *Gluconobacter* sp., *Galactocandida* sp., *Neurospora* sp. or *Serratia* sp. In some embodiments, the xylitol dehydrogenase is from *Pichia stipitis, S. cerevisiae, Gluconobacter oxydans, Galactocandida mastotermitis, Neurospora crassa* or *Serratia marcescens*. In some embodiments, the xylitol dehydrogenase is encoded by xyl2 or xdh1.

In one embodiment, the xylitol dehydrogenase is encoded by one or more nucleic acid molecules obtained from a microorganism selected from the group consisting of *Scheffersomyces* sp., *Trichoderma* sp., *Pichia* sp., *Saccharomyces* sp., *Gluconobacter* sp., *Galactocandida* sp., *Neurospora* sp., and *Serratia* sp. In another embodiment, the xylitol dehydrogenase is encoded by one or more nucleic acid molecules obtained from a microorganism selected from the group consisting of *Scheffersomyces stipitis, Trichoderma reesei, Pichia stipitis, Saccharomyces cerevisiae, Gluconobacter oxydans, Galactocandida mastotermitis, Neurospora crassa* and *Serratia marcescens*. In another embodiment, the one or more nucleic acid molecules encoding the xylitol dehydrogenase is xyl2 and/or xdh1, or homolog thereof. In some embodiments, the one or more nucleic acid molecules encoding the xylitol dehydrogenase comprises an amino acid sequence selected from the group consisting of SEQ ID NOs: 90 and 92. In some embodiments, the one or more nucleic acid molecules encoding the xylitol dehydrogenase is encoded by a nucleic acid sequence selected from the group consisting of SEQ ID NOs: 88, 89 and 91.

Alkaline Phosphatase (EC 3.1.3.1)

Alkaline phosphatase is a hydrolase enzyme responsible for removing phosphate groups from many types of molecules, including nucleotides, proteins, and alkaloids. As the name suggests, alkaline phosphatases are most effective in an alkaline environment. It is sometimes used synonymously as basic phosphatase.

The *S. cerevisiae* Pho13 alkaline phosphatase enzyme is a monomeric protein with molecular mass of 60 kDa and hydrolyzes p-nitrophenyl phosphate with maximal activity at pH 8.2 with strong dependence on $Mg^{2+}$ ions and an apparent Km of $3.6\times10^{-5}$ M. No other substrates tested except phosphorylated histone II-A and casein were hydrolyzed at any significant rate. These data suggest that the physiological role of the p-nitrophenyl phosphate-specific phosphatase may involve participation in reversible protein phosphorylation.

In particular embodiments, the enzyme converts D-xylulose-5-phosphate to D-xylulose. In some embodiments, the alkaline phosphatase is from yeast. In some embodiments, the alkaline phosphatase is from *Saccharomyces* sp. In some embodiments, the alkaline phosphatase is from *S. cerevisiae*. In some embodiments, the alkaline phosphatase is encoded by the PHO13 gene.

In some embodiments, a recombinant microorganism producing MEG and a three-carbon compound comprises a deletion, insertion, or loss of function mutation in a gene encoding an alkaline phosphatase to prevent the conversion of D-xylulose-5-phosphate to D-xylulose.

Soluble Pyridine Nucleotide Transhydrogenase (EC 1.6.1.1.)

The present disclosure describes enzymes that can catalyze the following reaction:

$$NADH+NADP^{+}\rightleftharpoons NAD^{+}+NADPH$$

Soluble pyridine nucleotide transhydrogenase may also be known as $NAD(P)^+$ transhydrogenase (B-specific), STH, pyridine nucleotide transhydrogenase, or transhydrogenase.

*E. coli* contains both a soluble and a membrane-bound pyridine nucleotide transhydrogenase. The soluble pyridine nucleotide transhydrogenase is the sthA or udhA gene product; its primary physiological role appears to be the reoxidation of NADPH (Canonaco F. et al. (2001) Metabolic flux response to phosphoglucose isomerase knock-out in

*Escherichia coli* and impact of overexpression of the soluble transhydrogenase UdhA. FEMS Microbiol Lett 204(2): 247-252; Sauer U. et al. (2004) The soluble and membrane-bound transhydrogenases UdhA and PntAB have divergent functions in NADPH metabolism of *Escherichia coli*. J Biol Chem 279(8): 6613-6619). The membrane-bound proton-translocating transhydrogenase is the pntAB gene product; PntAB is a major source of NADPH (Sauer et al. 2004).

UdhA contains noncovalently bound FAD and is present in a form consisting of seven or eight monomers (Boonstra B. et al. (1999) The udhA gene of *Escherichia coli* encodes a soluble pyridine nucleotide transhydrogenase. J Bacteriol 181(3): 1030-1034).

Moderate overexpression of UdhA (SthA) allows an increased maximal growth rate of a phosphoglucose isomerase mutant (Canonaco et al. 2001), and a pgi sthA double mutant is not viable (Sauer et al. 2004). These phenotypes may be due to the ability of UdhA to restore the cellular redox balance under conditions of excess NADPH formation (Canonaco et al. 2001; Sauer et al. 2004). Mutations in sthA appear during adaptation of apgi mutant strain to growth on glucose minimal medium (Charusanti P. et al. (2010) Genetic basis of growth adaptation of *Escherichia coli* after deletion of pgi, a major metabolic gene." PLoS Genet 6(11): e1001186).

Transcription of sthA is downregulated by growth on glycerol (Sauer et al. 2004).

In some embodiments, expression of a transhydrogenase can increase activity of a NADPH-dependent alcohol dehydrogenase, leading to improved acetone to 2-propanol conversion. In one embodiment, the soluble pyridine nucleotide transhydrogenase is encoded by one or more nucleic acid molecules obtained from *E. coli*. In another embodiment, the one or more nucleic acid molecules encoding the soluble pyridine nucleotide transhydrogenase is udhA, or homolog thereof. In some embodiments, the one or more nucleic acid molecules encoding the soluble pyridine nucleotide transhydrogenase comprises an amino acid sequence set forth in SEQ ID NO: 110. In some embodiments, the one or more nucleic acid molecules encoding the soluble pyridine nucleotide transhydrogenase is encoded by a nucleic acid sequence set forth in SEQ ID NO: 109.

Enzyme Overexpression or Enzyme Downregulation/Deletion for Increased Pathway Flux In various embodiments described herein, the exogenous and endogenous enzymes in the recombinant microorganism participating in the biosynthesis pathways described herein may be overexpressed.

The terms "overexpressed" or "overexpression" refers to an elevated level (e.g., aberrant level) of mRNAs encoding for a protein(s), and/or to elevated levels of protein(s) in cells as compared to similar corresponding unmodified cells expressing basal levels of mRNAs or having basal levels of proteins. In particular embodiments, mRNA(s) or protein(s) may be overexpressed by at least 2-fold, 3-fold, 4-fold, 5-fold, 6-fold, 8-fold, 10-fold, 12-fold, 15-fold or more in microorganisms engineered to exhibit increased gene mRNA, protein, and/or activity.

In some embodiments, a recombinant microorganism of the disclosure is generated from a host that contains the enzymatic capability to synthesize substrates such as D-xylulose, D-ribulose, D-ribulose-1-phosphate, D-xylulose-1-phosphate, D-xylonolactone, D-xylonate, 2-keto-3-deoxy-xylonate, glycolaldehyde, DHAP, pyruvate, acetoacetyl-CoA or acetoacetate. In some embodiments, it can be useful to increase the synthesis or accumulation of, for example, D-xylulose, D-ribulose, D-ribulose-1-phosphate, D-xylulose-1-phosphate, D-xylonolactone, D-xylonate, 2-keto-3-deoxy-xylonate, glycolaldehyde, DHAP, pyruvate, acetoacetyl-CoA or acetoacetate, to increase the production of MEG and one or more three-carbon compounds.

In some embodiments, it may be useful to increase the expression of endogenous or exogenous enzymes involved in the MEG and three-carbon compound biosynthesis pathways to increase flux from, for example, D-xylulose, D-ribulose, D-ribulose-1-phosphate, D-xylulose-1-phosphate, D-xylonolactone, D-xylonate, 2-keto-3-deoxy-xylonate, glycolaldehyde, DHAP, pyruvate, acetoacetyl-CoA or acetoacetate, thereby resulting in increased synthesis or accumulation of MEG and one or more three-carbon compounds.

Increased synthesis or accumulation can be accomplished by, for example, overexpression of nucleic acids encoding one or more of the above-described MEG and three-carbon compound biosynthesis pathway enzymes. Overexpression of a MEG and three-carbon compound biosynthesis pathway enzyme or enzymes can occur, for example, through increased expression of an endogenous gene or genes, or through the expression, or increased expression, of an exogenous gene or genes. Therefore, naturally occurring organisms can be readily modified to generate non-natural, MEG and three-carbon compound producing microorganisms through overexpression of one or more nucleic acid molecules encoding a MEG and three-carbon compound biosynthesis pathway enzyme. In addition, a non-naturally occurring organism can be generated by mutagenesis of an endogenous gene that results in an increase in activity of an enzyme in the MEG and three-carbon compound biosynthesis pathways.

Equipped with the present disclosure, the skilled artisan will be able to readily construct the recombinant microorganisms described herein, as the recombinant microorganisms of the disclosure can be constructed using methods well known in the art as exemplified above to exogenously express at least one nucleic acid encoding a MEG and three-carbon compound biosynthesis pathway enzyme in sufficient amounts to produce MEG and one or more three-carbon compounds.

Methods for constructing and testing the expression levels of a non-naturally occurring MEG and three-carbon compound-producing host can be performed, for example, by recombinant and detection methods well known in the art. Such methods can be found described in, for example, Sambrook et al., Molecular Cloning: A Laboratory Manual, Third Ed., Cold Spring Harbor Laboratory, New York (2001); Ausubo et al., Current Protocols in Molecular Biology, John Wiley and Sons, Baltimore, Md. (1999).

A variety of mechanisms known in the art can be used to express, or overexpress, exogenous or endogenous genes. For example, an expression vector or vectors can be constructed to harbor one or more MEG and three-carbon compound biosynthesis pathway enzymes encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218).

Those of skill in the art will recognize that, due to the degenerate nature of the genetic code, a variety of nucleic acid sequences can be used to encode a given enzyme of the disclosure. The nucleic acid sequences encoding the biosynthetic enzymes are referenced herein merely to illustrate an embodiment of the disclosure, and the disclosure includes any nucleic acid sequences that encode the amino acid sequences of the polypeptides and proteins of the enzymes of the present disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the nucleic acid sequences shown herein merely illustrate embodiments of the disclosure.

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., Science, 236: 1237-1245 (1987)). Exemplary expression control sequences are described in, for example, Goeddel, Gene Expression Technology: Methods in Enzymology, Vol. 185, Academic Press, San Diego, Calif. (1990).

In various embodiments, an expression control sequence may be operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

In some embodiments, the recombinant microorganism is manipulated to delete, disrupt, mutate, and/or reduce the activity of one or more endogenous enzymes that catalyzes a reaction in a pathway that competes with the biosynthesis pathway for the production of MEG and one or more three-carbon compounds.

In some embodiments, the recombinant microorganism is manipulated to delete, disrupt, mutate, and/or reduce the activity of one or more endogenous enzymes that catalyzes the conversion of D-xylulose to D-xylulose-5-phosphate. In some such embodiments, the enzyme that catalyzes the conversion of D-xylulose to D-xylulose-5-phosphate is a D-xylulose-5-kinase. In some embodiments, the D-xylulose-5-kinase is from *Escherichia coli*. In some embodiments, the D-xylulose-5-kinase is encoded by the xylB gene or homologs thereof. In some embodiments, the manipulation prevents the conversion of D-xylulose to D-xylulose-5-phosphate and instead shunts the reaction toward conversion of D-xylulose to D-xylulose-1-phosphate.

In some embodiments, the recombinant microorganism is manipulated to delete, disrupt, mutate, and/or reduce the activity of one or more endogenous enzymes that catalyzes the conversion of glycolaldehyde to glycolic acid. In some such embodiments, the enzyme that catalyzes the conversion of glycolaldehyde to glycolic acid is a glycolaldehyde dehydrogenase. In some embodiments, the glycolaldehyde dehydrogenase is from *Escherichia coli*. In some embodiments, the glycolaldehyde dehydrogenase is encoded by the aldA gene or homologs thereof. In some embodiments, the manipulation prevents the production of glycolic acid from glycolaldehyde and instead shunts the reaction toward conversion of glycolaldehyde to MEG.

In some embodiments, the recombinant microorganism is manipulated to delete, disrupt, mutate, and/or reduce the activity of one or more endogenous enzymes that catalyzes the conversion of pyruvate to lactate. In some such embodiments, the enzyme that catalyzes the conversion of pyruvate to lactate is a lactate dehydrogenase. In some embodiments, the lactate dehydrogenase is from *Escherichia coli*. In some embodiments, the lactate dehydrogenase is encoded by the ldhA gene or homologs thereof. In some embodiments, the manipulation prevents the production of lactate from pyruvate and instead shunts the reaction toward production of a three-carbon compound.

In some embodiments, the recombinant microorganism is manipulated to delete, disrupt, mutate, and/or reduce the activity of one or more endogenous enzymes that catalyzes the conversion of D-xylulose to D-xylulose-5-phosphate. In some such embodiments, the enzyme that catalyzes the conversion of D-xylulose to D-xylulose-5-phosphate is a D-xylulose-5-kinase. In some embodiments, the D-xylulose-5-kinase is from *Saccharomyces cerevisiae*. In some embodiments the D-xylulose-5-kinase is encoded by the XKS1 gene or homologs thereof. In some embodiments, the D-xylulose-5-kinase is from *Pichia stipitis*. In some embodiments the D-xylulose-5-kinase is encoded by the XYL3 gene or homologs thereof. In some embodiments, the manipulation prevents the conversion of D-xylulose to D-xylulose-5-phosphate and instead shunts the reaction toward conversion of D-xylulose to D-xylulose-1-phosphate.

In some embodiments, the recombinant microorganism is manipulated to delete, disrupt, mutate, and/or reduce the activity of one or more endogenous enzymes that catalyzes the conversion of D-xylose to D-xylulose. In some such embodiments, the enzyme that catalyzes the conversion of D-xylose to D-xylulose is a D-xylose isomerase. In some embodiments, the D-xylose isomerase is from *E. coli*. In some embodiments, the D-xylose isomerase is encoded by the xylA gene or homologs thereof. In some embodiments, the manipulation prevents conversion of D-xylose to D-xylulose and instead shunts the reaction toward the conversion of D-xylose to D-xylonate.

In some embodiments, the recombinant microorganism is manipulated to delete, disrupt, mutate, and/or reduce the activity of one or more endogenous enzymes that catalyzes the conversion of D-xylulose-5-phosphate to D-xylulose. In some such embodiments, the enzyme that catalyzes the conversion of D-xylulose-5-phosphate to D-xylulose is an alkaline phosphatase. In some embodiments, the alkaline phosphatase is from *S. cerevisiae*. In some embodiments, the alkaline phosphatase is encoded by the PHO13 gene or homologs thereof. In some embodiments, the manipulation prevents the conversion of D-xylulose-5-phosphate to D-xylulose.

In some embodiments, the recombinant microorganism is manipulated to delete, disrupt, mutate, and/or reduce the activity of one or more endogenous enzymes that catalyzes the conversion of D-xylose to D-xylulose. In some such embodiments, the enzyme that catalyzes the conversion of D-xylose to D-xylulose is a D-xylose isomerase. In some embodiments, the D-xylose isomerase is from *E. coli*. In some embodiments, the D-xylose isomerase is encoded by the xylA gene or homologs thereof. In some embodiments, the manipulation prevents conversion of D-xylose to D-xylulose and instead shunts the reaction toward the conversion of D-xylose to D-xylonate.

Modified Microbes and Compositions Thereof

Microbial Compositions

In some aspects, the microbes of the disclosure are combined into microbial compositions.

In some aspects, the microbial compositions of the present disclosure are solid. Where solid compositions are used, it may be desired to include one or more carrier materials including, but not limited to: mineral earths such as silicas, talc, kaolin, limestone, chalk, clay, dolomite, diatomaceous earth; calcium sulfate; magnesium sulfate; magnesium oxide; zeolites, calcium carbonate; magnesium carbonate; trehalose; chitosan; shellac; albumins; starch; skim milk powder; sweet whey powder; maltodextrin; lactose; inulin; dextrose; and products of vegetable origin such as cereal meals, tree bark meal, wood meal, and nutshell meal.

In some aspects, the microbial compositions of the present disclosure are liquid. In further embodiments, the liquid comprises a solvent that may include water or an alcohol or a saline or carbohydrate solution. In some embodiments, the microbial compositions of the present disclosure include binders such as polymers, carboxymethylcellulose, starch, polyvinyl alcohol, and the like.

In some aspects, microbial compositions of the present disclosure comprise saccharides (e.g., monosaccharides, disaccharides, trisaccharides, polysaccharides, oligosaccharides, and the like), polymeric saccharides, lipids, polymeric lipids, lipopolysaccharides, proteins, polymeric proteins, lipoproteins, nucleic acids, nucleic acid polymers, silica, inorganic salts and combinations thereof. In a further embodiment, microbial compositions comprise polymers of agar, agarose, gelrite, gellan gum, and the like. In some aspects, microbial compositions comprise plastic capsules, emulsions (e.g., water and oil), membranes, and artificial membranes. In some embodiments, emulsions or linked polymer solutions may comprise microbial compositions of the present disclosure. See Harel and Bennett (U.S. Pat. No. 8,460,726 B2).

In some aspects, microbial compositions of the present disclosure occur in a solid form (e.g., dispersed lyophilized spores) or a liquid form (microbes interspersed in a storage medium). In some embodiments, microbial compositions of the present disclosure are added in dry form to a liquid to form a suspension immediately prior to use.

In some aspects, the microbial composition of the present disclosure possesses a water activity (aw) of less than 0.750, 0.700, 0.650, 0.600, 0.550, 0.500, 0.475, 0.450, 0.425, 0.400, 0.375, 0.350, 0.325, 0.300, 0.275, 0.250, 0.225, 0.200, 0.190, 0.180, 0.170, 0.160, 0.150, 0.140, 0.130, 0.120, 0.110, 0.100, 0.095, 0.090, 0.085, 0.080, 0.075, 0.070, 0.065, 0.060, 0.055, 0.050, 0.045, 0.040, 0.035, 0.030, 0.025, 0.020, 0.015, 0.010, or 0.005.

In some aspects, the microbial composition of the present disclosure possesses a water activity (aw) of less than about 0.750, about 0.700, about 0.650, about 0.600, about 0.550, about 0.500, about 0.475, about 0.450, about 0.425, about 0.400, about 0.375, about 0.350, about 0.325, about 0.300, about 0.275, about 0.250, about 0.225, about 0.200, about 0.190, about 0.180, about 0.170, about 0.160, about 0.150, about 0.140, about 0.130, about 0.120, about 0.110, about 0.100, about 0.095, about 0.090, about 0.085, about 0.080, about 0.075, about 0.070, about 0.065, about 0.060, about 0.055, about 0.050, about 0.045, about 0.040, about 0.035, about 0.030, about 0.025, about 0.020, about 0.015, about 0.010, or about 0.005.

The water activity values are determined by the method of Saturated Aqueous Solutions (Multon, "Techniques d'Analyse E De Controle Dans Les Industries Agroalimentaires" APRIA (1981)) or by direct measurement using a viable Robotronic BT hygrometer or other hygrometer or hygroscope.

Feedstock

In some aspects, the disclosure is drawn to a method of producing MEG and/or one or more C3 products in a culture medium containing a feedstock providing a carbon source such that the MEG and/or one or more C3 products are produced and recovered/collected/isolated. The recovery/collection/isolation can be by methods known in the art, such as distillation, membrane-based separation gas stripping, solvent extraction, and expanded bed adsorption.

In some aspects, the feedstock comprises a carbon source. In some aspects, the carbon source may be selected from sugars, glycerol, alcohols, organic acids, alkanes, fatty acids, lignocellulose, proteins, carbon dioxide, and carbon monoxide. In one aspect, the carbon source is a sugar. In one aspect, the sugar is glucose or oligomers of glucose thereof. In one aspect, the oligomers of glucose are selected from fructose, sucrose, starch, cellobiose, maltose, lactose and cellulose. In one aspect, the sugar is a five carbon sugar. In one aspect, the sugar is a six carbon sugar. In some aspects, the feedstock comprises one or more five carbon sugars and/or one or more six carbon sugars. In some aspects, the feedstock comprises one or more of xylose, glucose, arabinose, galactose, maltose, fructose, mannose, sucrose, and/or combinations thereof. In some aspects, the feedstock comprises one or more of xylose and/or glucose. In some aspects, the feedstock comprises one or more of arabinose, galactose, maltose, fructose, mannose, sucrose, and/or combinations thereof.

In some aspects, the microbes utilize one or more five carbon sugars (pentoses) and/or one or more six carbon sugars (hexoses). In some aspects, the microbes utilize one or more of xylose and/or glucose. In some aspects, the microbes utilize one or more of arabinose, galactose, maltose, fructose, mannose, sucrose, and/or combinations thereof. In some aspects, the microbes utilize one or more of xylose, glucose, arabinose, galactose, maltose, fructose, mannose, sucrose, and/or combinations thereof.

In some aspects, hexoses may be selected from D-allose, D-altrose, D-glucose, D-mannose, D-gulose, D-idose, D-galactose, D-talose, D-tagtose, D-sorbose, D-fructose, D-psicose, and other hexoses known in the art. In some aspects, pentoses may be selected from D-xylose, D-ribose, D-arabinose, D-lyxose, D-xylulose, D-ribulose, and other pentoses known in the art. In some embodiments, the hexoses and pentoses may be selected from the levorotary or dextrorotary enantiomer of any of the hexoses and pentoses disclosed herein.

In some aspects, total amount of C5 and/or C6 carbohydrates fed to a bioreactor/growth medium during the growth phase is at least 5 kg carbohydrate/m3, at least 10 kg carbohydrate/m3, at least 20 kg carbohydrate/m3, at least 30 kg carbohydrate/m3, at least 40 kg carbohydrate/m3, at least 50 kg carbohydrate/m3, at least 60 kg carbohydrate/m3, at least 70 kg carbohydrate/m3, at least 80 kg carbohydrate/m3, at least 90 kg carbohydrate/m3, at least 100 kg carbohydrate/m3, at least 150 kg carbohydrate/m3, at least 200 kg carbohydrate/m3, at least 250 kg carbohydrate/m3, at least 300 kg carbohydrate/m3, at least 400 kg carbohydrate/m3 at least 500 kg carbohydrate/m3, at least 600 kg carbohydrate/m3, at least 700 kg carbohydrate/m3, up to 800 kg carbohydrate/m3. In some embodiments, total amount of C5 and/or C6 carbohydrates fed to the bioreactor/growth medium during the growth phase ranges from about 10 kg carbohydrate/m3 up to 500 kg carbohydrate/m3.

In some aspects, time required for the growth phase varies between 1 to 200 hours. In further embodiments, the time of the growth phase is between 5 to 50 hours. The time is dependent on carbohydrate feeds and/or feedstocks.

In some aspects, the total amount of C5 and/or C6 carbohydrates fed to the bioreactor/growth medium during the production phase is at least 50 kg carbohydrate/m3, at least 60 kg carbohydrate/m3, at least 70 kg carbohydrate/m3, at least 80 kg carbohydrate/m3, at least 90 kg carbohydrate/m3, at least 100 kg carbohydrate/m3, at least 150 kg carbohydrate/m3, at least 200 kg carbohydrate/m3, at least 250 kg carbohydrate/m3, at least 300 kg carbohydrate/m3, at least 400 kg carbohydrate/m3, at least 500 kg carbohydrate/m3, at least 600 kg carbohydrate/m3, at least 700 kg carbohydrate/m3, at least 800 kg carbohydrate/m3, at least 900 kg carbohydrate/m3 up to 1000 kg carbohydrate/m3. In some embodiments, total amount of C5 and/or C6 carbohydrates fed to the bioreactor/growth medium during the production phase ranges from about 100 kg carbohydrate/m3 up to 800 kg carbohydrate/m3.

In some aspects, time required for the production phase varies between 5 to 500 hours. In further embodiments, the time for the production phase varies from 10 to 300 hours for batch and fed-batch operations. In other embodiments, the time of the production phase is up to 300 hours with continuous fermentation.

In some aspects, the total amount of C5 and/or C6 carbohydrates fed to the bioreactor/growth medium for one-phase process is at least 50 kg carbohydrate/m3, at least 60 kg carbohydrate/m3, at least 70 kg carbohydrate/m3, at least 80 kg carbohydrate/m3, at least 90 kg carbohydrate/m3, at least 100 kg carbohydrate/m3, at least 150 kg carbohydrate/m3, at least 200 kg carbohydrate/m3, at least 250 kg carbohydrate/m3, at least 300 kg carbohydrate/m3, at least 400 kg carbohydrate/m3, at least 500 kg carbohydrate/m3, at least 600 kg carbohydrate/m3, at least 700 kg carbohydrate/m3, at least 800 kg carbohydrate/m3, at least 900 kg carbohydrate/m3 up to 1000 kg carbohydrate/m3. In some aspects, total amount of C5 and/or C6 carbohydrates fed to the bioreactor/growth medium during the production phase ranges from about 100 kg carbohydrate/m3 up to 800 kg carbohydrate/m3.

In some aspects, time required for the production phase in the one-phase process varies between 5 to 500 hours. In further aspects, the time required for production phase in the one-phase process varies between 5 to 300 hours.

In some aspects, the one-phase or multi-phase production processes take about 5, about 10, about 25, about 50, about 75, about 100, about 125, about 150, about 175, about 200, about 225, about 250, about 275, about 300 about 325, about 350, about 375, about 400, about 425, about 450, about 475, or about 500 hours.

In some aspects, the one-phase or multi-phase production processes take 5, 10, 25, 50, 75, 100, 125, 150, 175, 200, 225, 250, 275, 300 325, 350, 375, 400, 425, 450, 475, or 500 hours.

Improvement of Traits

Methods of the present disclosure may be employed to introduce or improve one or more of a variety of desirable traits. Examples of traits that may be introduced or improved include: increased rate of production of MEG and/or one or more C3 compounds, increased rate of production of MEG, increased rate of production of one or more C3 compounds, increased rate of production of MEG and one or more C3 compounds, increased yield of MEG and/or one or more C3 compounds, increased yield of MEG, increased yield of one or more C3 compounds, increased yield of MEG and one or more C3 compounds, and other traits described herein.

In some aspects, a microbe resulting from the methods described herein exhibits a difference in the trait that is at least about 1% greater, for example at least about 1%, at least about 2%, at least about 3%, at least about 4%, at least about 5%, at least about 6%, at least about 7%, at least about 9%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 75%, at least about 80%, at least about 90%, or at least 100%, at least about 200%, at least about 300%, at least about 400% or greater than a reference under control conditions. In additional examples, a microbe resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference unmodified microbe or base strain.

In some aspects, the increase or decrease of any one or more of the traits of the present disclosure is an increase of about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% relative to an unmodified microbe or a base strain.

In some aspects, the increase or decrease of any one or more of the traits of the present disclosure is an increase of at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 100% relative an unmodified microbe or a base strain.

In some aspects, a microbe resulting from the methods described herein exhibits an increase in MEG yield by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe or a base strain.

In some aspects, a microbe resulting from the methods described herein exhibits an increase in the yield of one or more C3 compounds by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe or a base strain.

In some aspects, a microbe resulting from the methods described herein exhibits an increase in MEG yield by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe or a base strain; and an increase in one or more C3 compounds yield by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe or a base strain.

In some aspects, a microbe resulting from the methods described herein exhibits an increase in the rate of MEG production by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe or a base strain.

In some aspects, a microbe resulting from the methods described herein exhibits an increase in the rate of production of one or more C3 compounds by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe or a base strain.

In some aspects, a microbe resulting from the methods described herein exhibits an increase in the rate of MEG production by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe or a base strain; and an increase in the rate of production of one or more C3 compounds by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe or a base strain.

In some aspects, a microbe resulting from the methods described herein exhibits (1) an increase in the rate of MEG production by at least 2%, (2) an increase in the rate of production of one or more C3 compounds by at least 2%, (3) an increase in MEG yield by at least 2%, and (4) an increase in the yield of one or more C3 compounds by at least 2%.

In some aspects, a microbe resulting from the methods described herein exhibits (1) an increase in the rate of MEG production by at least 5%, 10%, or 15%, (2) an increase in the rate of production of one or more C3 compounds by at least 5%, 10%, or 15%, (3) an increase in MEG yield by at least 5%, 10%, or 15%, and (4) an increase in the yield of one or more C3 compounds by at least 5%, 10%, or 15%.

In some aspects, a microbe resulting from the methods described herein exhibits (1) an increase in the rate of MEG production by at least 10%, 15%, 20%, 25%, or 30%, (2) an increase in the rate of production of one or more C3 compounds by at least 10%, 15%, 20%, 25%, or 30%, (3) an increase in MEG yield by at least 10%, 15%, 20%, 25%, or 30%, and (4) an increase in the yield of one or more C3 compounds by at least 10%, 15%, 20%, 25%, or 30%.

In some aspects, MEG is produced at least 0.5 kg/m3 h, 1 kg/m3 h, at least 2 kg/m3 h, at least 3 kg/m3 h, at least 4 kg/m3 h, at least 5 kg/m3 h, 6 kg/m3 h, at least 7 kg/m3 h, at least 8 kg/m3 h, at least 9 kg/m3 h, at least 10 kg/m3 h, at least 15 kg/m3 h, or at least 20 kg/m3 h.

In some aspects, acetone is produced at least 0.2 kg/m3 h, 0.5 kg/m3 h, at least 1 kg/m3 h, at least 2 kg/m3 h, at least 3 kg/m3 h, at least 4 kg/m3 h, at least 5 kg/m3 h, 6 kg/m3 h, at least 7 kg/m3 h, at least 8 kg/m3 h, at least 9 kg/m3 h, at least 10 kg/m3 h, at least 15 kg/m3 h, or at least 20 kg/m3 h.

In some aspects, isopropanol is produced at least at least 0.2 kg/m3 h, 0.5 kg/m3 h, 1 kg/m3 h, at least 2 kg/m3 h, at least 3 kg/m3 h, at least 4 kg/m3 h, at least 5 kg/m3 h, 6 kg/m3 h, at least 7 kg/m3 h, at least 8 kg/m3 h, at least 9 kg/m3 h, at least 10 kg/m3 h, at least 15 kg/m3 h, or at least 20 kg/m3 h.

In some aspects, isopropanol is produced at least at least 0.5 kg/m3 h, 1 kg/m3 h, at least 2 kg/m3 h, at least 3 kg/m3 h, at least 4 kg/m3 h, at least 5 kg/m3 h, 6 kg/m3 h, at least 7 kg/m3 h, at least 8 kg/m3 h, at least 9 kg/m3 h, at least 10 kg/m3 h, at least 15 kg/m3 h, or at least 20 kg/m3 h.

In some aspects, propene is produced at least at least 0.5 kg/m3 h, 1 kg/m3 h, at least 2 kg/m3 h, at least 3 kg/m3 h, at least 4 kg/m3 h, at least 5 kg/m3 h, 6 kg/m3 h, at least 7 kg/m3 h, at least 8 kg/m3 h, at least 9 kg/m3 h, at least 10 kg/m3 h, at least 15 kg/m3 h, or at least 20 kg/m3 h.

In some aspects, the combined products of the biological processes of the present disclosure result in a production of at least 0.5 kg/m3 h, 1 kg/m3 h, at least 2 kg/m3 h, at least 3 kg/m3 h, at least 4 kg/m3 h, at least 5 kg/m3 h, 6 kg/m3 h, at least 7 kg/m3 h, at least 8 kg/m3 h, at least 9 kg/m3 h, at least 10 kg/m3 h, at least 15 kg/m3 h, or at least 20 kg/m3 h of MEG, acetone, isopropanol, propene, precursors thereof, and/or mixtures thereof.

Metabolic Engineering to Improve Flux Through the C3 Pathway

C3 compounds are produced from Acetyl-CoA, which is a key metabolite in synthetic and oxidative pathways. The production of C3 has to compete for Acetyl-CoA with natural reactions of the cell. Irreversible and strongly pushed reactions towards the C3 production are essential for improving C3 compounds yield, titer and/or productivity. Acetoacetyl CoA synthase and/or hydroxymethylglutaryl-CoA synthase and hydroxymethylglutaryl-CoA lyase are enzymes capable of pulling the flux through the C3 pathway.

The utilization of both strategies for expression of these enzymes to improve yield, titer and/or productivity of MEG pathway is new. MEG improvement is due to the higher flux of carbon through the pathway, pulled by the higher production of C3 from acetic acid. More acetic acid is produced to be converted to C3, accelerating the overall carbon through MEG pathway and decreasing leakages.

Acetoacetyl CoA synthase (npht7)—Malonyl-CoA bypass with or without acetoacetyl-CoA thiolase (thlA) deletion. Acetoacetyl CoA synthase (NphT7—EC:2.3.1.19) catalyzes the condensation of acetyl-CoA and malonyl-CoA to form acetoacetyl-CoA and CoA. The synthesis of acetoacetyl-CoA in *E. coli* is a reversible reaction catalyzed by acetoacetyl-CoA thiolase (EC 2.3.1.9) from two molecules of acetyl-CoA. Although acetoacetyl-CoA thiolase produces acetoacetyl-CoA, this enzyme prefers acetoacetyl-CoA thiolysis to acetoacetyl-CoA synthesis. The expression of nphT7 gene can be used to significantly increase the concentration of acetoacetyl-CoA in cells since the reaction is not reversible and has a strong pull due to the use of one ATP. It is expected that the expression of nphT7 improve yield, titer and/or productivity for C3 pathways due to a higher concentration of acetoacetyl-CoA that is converted to acetone, isopropanol or propene. However, the improvement of flux through the C3 pathway has a synergetic effect on xylose assimilation and conversion to MEG, improving yield, titer and/or productivity in the C2 pathway.

HMG-COA bypass—hydroxymethylglutaryl-CoA synthase (ERG13) and hydroxymethylglutaryl-CoA lyase (YngG) with or without acetoacetyl-CoA transferase (AtoDA) deletion. HMG-CoA bypass is composed by two steps: condensation of Acetyl-CoA and acetoacetyl-CoA to form (S)-3-hydroxy-3-methylglutaryl-CoA and CoA by the Hydroxymethylglutaryl-CoA synthase (ERG13EC:2.3.3.10) and conversion of (S)-3-hydroxy-3-methylglutaryl-CoA to acetyl-CoA and acetoacetate by the Hydroxymethylglutaryl-CoA lyase (YngG—EC:4.1.3.4). Acetoacetate is the direct precursor of the C3 pathways for acetone, propanol and propene and can be produced by the Acetate CoA-transferase (AtoDA) native from *E. coli*. The expression of ERG13 and YngG can be used to significantly increase the concentration of acetoacetate compared to the reaction performed by the Acetate CoA-transferase (AtoDA), since the transferase is reversible and dependent on the acetate concentration. HMG-CoA bypass poses an alternative that is essentially an energy-favored reaction and not dependent on acetate concentration and regulation. It is expected that the expression of HGM-CoA bypass improve yield, titer and/or productivity for C3 pathways due to a higher concentration of acetoacetate that is converted to C3 products. However, as already mentioned, the improvement of flux through the C3 pathway has a synergetic effect on xylose assimilation and conversion to MEG, improving yield, titer and/or productivity in the C2 pathway.

Metabolic Engineering of the Xylonate Pathway

The optimization of gene expression of the entire xylonate pathway will avoid carbon loss to side reactions, avoid intermediate accumulation and generate strains with better performance regarding yields, titer and productivity to both ethylene glycol and C3 compounds. In some aspects, the described optimizations are focused on the first and last step. In some aspects, different enzyme sources are considered for steps 1 to 4.

In some aspects, optimization is conducted not only aiming ethylene glycol production but also with attention to benefits/prejudice on C3 co-production.

The production of ethylene glycol through the xylonate pathway consists of 5 enzymatic steps. The optimized pathway for the co-production of ethylene glycol and acetone is described below:

D-xylonolactone is produced by the oxidation of D-xylose (EC 1.1.1.175 or 1.1.1.179).

Sources: *Caulobacter crescentus, Burkholderia xenovorans, Haloferax volcanii, Halomonas elongata, Pseudomonas fluorescens, Trichoderma reesei, Sus scrofa, Pseudomonas putida, Sphingomonas elodea* xylonolactone is hydrolyzed to yield D-xylonate (EC 3.1.1.68)

Sources: *Caulobacter crescentus, Burkholderia xenovorans, Haloferax volcanii, Halomonas elongata, Sphingomonas elodea*

D-xylonate is dehydrated to 2-keto-3-deoxy pentanoic acid (EC 4.2.1.82)

Sources: *Escherichia coli, Caulobacter crescentus, Burkholderia xenovorans, Haloferax volcanii, Halomonas elongata, Sphingomonas elodea, Pseudomonas* sp., *Achromobacter xylosoxidans, Mesorhizobium* sp., *Zymomonas mobilis, Agrobacterium tumefaciens, Herbaspirillum seropedicae, Actinoplanes missouriensis, Aspergillus oryzae*

2-keto-3-deoxy-pentanoic acid is converted to glycolaldehyde and pyruvate (EC 4.1.2.20).

Sources: *Escherichia coli, Sulfolobus* sp., *Paraburkholderia phytofirmans, Sphingomonas wittichii, Pseudomonas* sp., *Azotobacter vinelandii, Scheffersomyces stipites, Picrophilus torridus. Trichoderma reesei.*

Glycoaldehyde is reduced to ethylene glycol (EC 1.1.1.77)

Sources: *Escherichia coli*

The variations on the xylonate pathway, particularly in steps 1-3 that are responsible for initiating the flux of xylose through the pathway, can have a large impact on ethylene glycol productivity even though the overall yield might not be improved. C3 pathway is also positively affected, on both yield, titer and productivity. This aspect is probably related to the decrease of xylonic acid accumulation that in certain levels can be toxic to the host cell and decreases the carbon flux to pyruvate, decreasing the pool of acetyl-CoA for C3 production.

In some aspects, a modified microbe of the present disclosure comprises an overexpressed heterologous xylose dehydrogenase.

In some aspects, a modified microbe of the present disclosure comprises an overexpressed heterologous xylonolactonase.

In some aspects, a modified microbe of the present disclosure comprises a overexpressed homologous xylonate dehydratase or overexpression or expression of a heterologous xylonate dehydratase.

In some aspects, a modified microbe of the present disclosure comprises a overexpressed homologous 3-deoxy-D-glycerol pentanone sugar acid aldolase or overexpression or expression of a heterologous 3-deoxy-D-glycerol pentanone sugar acid aldolase.

In some aspects, a modified microbe of the present disclosure comprises a overexpressed homologous glycoaldehyde reductase.

In some aspects, a modified microbe of the present disclosure comprises a overexpressed homologous glycoaldehyde reductase.

In some aspects, a modified microbe of the present disclosure comprises (1) an overexpressed heterologous xylose dehydrogenase, (2) an overexpressed heterologous xylonolactonase, (3) a overexpressed homologous xylonate dehydratase or overexpression or expression of a heterologous xylonate dehydratase, (4) a overexpressed homologous glycoaldehyde reductase, and/or (5) overexpression of a homologous glycoaldehyde reductase.

In some aspects, the overexpressed, or expressed sequences are such due to being placed under the control of a non-native control sequences. In some aspects, the expression of heterologous xylose dehydrogenase in a modified microbe of the present disclosure is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 100%, 125%, 150%, 200%, 250%, 300%, 400%, or 500% relative to an unmodified microbe.

In some aspects, the expression of a heterologous xylonolactonase in a modified microbe of the present disclosure is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 100%, 125%, 150%, 200%, 250%, 300%, 400%, or 500% relative to an unmodified microbe.

In some aspects, the expression of a heterologous or homologous xylonate dehydratase in a modified microbe of the present disclosure is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 100%, 125%, 150%, 200%, 250%, 300%, 400%, or 500% relative to an unmodified microbe.

In some aspects, the expression of a homologous or heterologous 3-deoxy-D-glycerol pentanone sugar acid aldolase in a modified microbe of the present disclosure is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 100%, 125%, 150%, 200%, 250%, 300%, 400%, or 500% relative to an unmodified microbe.

In some aspects, the expression of a homologous glycoaldehyde reductase in a modified microbe of the present disclosure is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 100%, 125%, 150%, 200%, 250%, 300%, 400%, or 500% relative to an unmodified microbe.

Metabolic Engineering of the Acetate Pathway

In some aspects, the alteration of key enzymes of acetate metabolism can change the activity of the central pathways of *E. coli*. Deletions of genes pta, ackA, or poxB, or overexpression of acs can alter the co-regulation of the acetate metabolism, glyoxylate shunt, and the anaplerotic/gluconeogenic pathways, affecting the efficient assimilation of the carbon sources. The deletion of genes pta, ackA, poxB, or overexpression of acetyl-CoA synthetase improves xylulose assimilation and thus increase flux through the entire pathway, resulting in higher yields and productivity of ethylene glycol and consequently, C3 compounds. In addition, a higher expression of acetyl-CoA synthetase can enhance the ability of strains to use the acetate already present in the substrate as a carbon source.

The acetate pathway is composed by four enzymes: a phosphate acetyltransferase, an acetate kinase, a pyruvate oxidase and an acetyl-CoA synthetase. The phosphate acetyltransferase is codified by pta gene and catalyzes the reversible reaction: acetyl-CoA+phosphate↔acetyl phosphate+coenzyme A (EC Number: 2.3.1.8). The acetate kinase is codified by ackA gene and catalyzes the reversible reaction: acetate+ATP↔acetyl phosphate+ADP (EC Number: 2.7.2.1), being involved in the generation of most of the ATP formed catabolically during anaerobic growth (reaction 22, 23 and 24 FIG. 1). The pyruvate oxidase is codified by poxB gene and catalyzes the reaction: pyruvate+a ubiquinone [inner membrane]+H2O→CO2+acetate+an ubiquinol [inner membrane] (EC Number: 1.2.5.1), being the main pathway for acetate production in stationary phase. The acetyl-CoA synthetase is codified by acs gene and catalyzes the irreversible reaction: acetate+ATP+coenzyme A→acetyl-CoA+AMP+diphosphate (EC Number: 6.2.1.1), having a mainly anabolic role, scavenging acetate present in the extracellular medium.

The deletion of pta, ackA or poxB genes can alter the flux of carbon through the pathway, increasing not only the pool of acetyl-CoA available for C3 production but also the uptake and assimilation of xylose through MEG pathway. The disruption of the acetate futile cycle discharges more acetyl-CoA that is rapidly converted to C3 compounds through C3 synthetic pathway. In order to avoid a shortage of acetyl-CoA, more pyruvate has to be produced through the conversion of xylose to MEG and DHAP or pyruvate, increasing the carbon flux through the pathway and leading to higher yields and productivity.

The pool of acetyl-CoA can also be increased by overexpressing acs gene (acetyl-CoA synthetase) or by increasing the amount of active Acs. The enzyme Acs is regulated by the Pat/CobB system, where the protein lysine acetyltransferase (Pka) inactivates Acs by acetylation, while the $NAD^+$-dependent regulator protein deacetylase CobB releases Acs from repression by deacetylating it. Therefore, deletion of patZ gene, also known as pka, or overexpression of cobB gene can guarantee higher amounts of active Acs. Another way to increase Acs amount is by arcA gene deletion, a regulator of TCA genes expression, whose deletion takes to higher expression of acs gene.

In some aspects, a modified microbe of the present disclosure comprises a disrupted or deleted phosphate acetyltransferase (pta) nucleic acid sequence.

In some aspects, a modified microbe of the present disclosure comprises a disrupted or deleted acetate kinase (ackA) nucleic acid sequence.

In some aspects, a modified microbe of the present disclosure comprises a disrupted or deleted pyruvate oxidase (poxB) nucleic acid sequence.

In some aspects, a modified microbe of the present disclosure comprises a disrupted or deleted arcA regulator nucleic acid sequence.

In some aspects, a modified microbe of the present disclosure comprises a disrupted or deleted lysine acetyltransferase (pka) nucleic acid sequence.

In some aspects, a modified microbe of the present disclosure comprises a disrupted or deleted phosphate acetyltransferase (pta) nucleic acid sequence, acetate kinase (ackA) nucleic acid sequence, pyruvate oxidase (poxB) nucleic acid sequence, arcA regulator nucleic acid sequence, and/or lysine acetyltransferase (pka) nucleic acid sequence.

In some aspects, a modified microbe of the present disclosure comprises an overexpressed CobB regulator.

In some aspects, a modified microbe of the present disclosure comprises an overexpressed acs (acetyl-CoA synthetase).

In some aspects, a modified microbe of the present disclosure comprises an overexpressed CobB regulator and/or an overexpressed acs (acetyl-CoA synthetase).

In some aspects, a modified microbe of the present disclosure comprises an overexpressed CobB regulator, overexpressed acs (acetyl-CoA synthetase), a disrupted or deleted phosphate acetyltransferase (pta) nucleic acid sequence, acetate kinase (ackA) nucleic acid sequence, pyruvate oxidase (poxB) nucleic acid sequence, arcA regulator nucleic acid sequence, and/or lysine acetyltransferase (pka) nucleic acid sequence.

In some aspects, the overexpressed acs and/or CobB regulator are overexpressed due to being placed under the control of a non-native control sequences. In some aspects, the control sequence is an operator. In some aspects, the control sequence is a promoter. In some aspects, the control sequence is a constitutive promoter. In some aspects, the native control sequences are modified to cause the overexpression.

In some aspects, a modified microbe of the present disclosure comprises one or more mutations in one or more phosphate acetyltransferase nucleic acid sequences, in one or more acetate kinase nucleic acid sequences, in one or more pyruvate oxidase nucleic acid sequences, in one or more arcA regulator nucleic acid sequences, in one or more lysine acetyltransferase nucleic acid sequences.

In some aspects, the translation of one or more nucleic acid sequences encoding a phosphate acetyltransferase (pta) in a modified microbe of the present disclosure is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe.

In some aspects, the translation of one or more nucleic acid sequences encoding a acetate kinase (ackA) in a modified microbe of the present disclosure is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe.

In some aspects, the translation of one or more nucleic acid sequences encoding a pyruvate oxidase (poxB) in a modified microbe of the present disclosure is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe.

In some aspects, the translation of one or more nucleic acid sequences encoding an arcA regulator in a modified microbe of the present disclosure is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe.

In some aspects, the translation of one or more nucleic acid sequences encoding a lysine acetyltransferase (pka) in a modified microbe of the present disclosure is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe.

In some aspects, the expression of CobB regulator in a modified microbe of the present disclosure is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 100%, 125%, 150%, 200%, 250%, 300%, 400%, or 500% relative to an unmodified microbe.

In some aspects, the expression of acs (acetyl-CoA synthetase) in a modified microbe of the present disclosure is increased by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, 100%, 125%, 150%, 200%, 250%, 300%, 400%, or 500% relative to an unmodified microbe.

Deletion of Competing Pathways to Improve Carbon Flux Through MEG and C3 Pathways In some aspects, the deletion of key enzymes of competing pathways such as methylglyoxal synthase and glyoxylate carboligase will avoid carbon loss to side reactions redirecting the flux of carbon through the MEG and C3 pathways.

In some aspects, the modifications described herein are performed in microbes that have already been modified to coproduce MEG and one or more C3 compound such that the carbon flux is modulated in the MEG and/or C3 pathways in such a way as to allow for more efficient production of MEG and/or C3 compounds.

Methylglyoxal synthase (mgsA—EC:4.2.3.3) converts DHAP to methylglyoxal+Pi in *E. Coli*. Methylglyoxal synthase can be further converted to pyruvate through D-lactate. This sequence provides a by-pass of the normal glycolytic reactions for the conversion of DHAP to pyruvate. Although methylglyoxal synthase is present in *E. coli* at a reasonable activity, it is possible that the normal intracellular concentrations of Pi and DHAP may prevent it being fully active. However, any factor which raised the DHAP concentration or decreased the Pi concentration would tend to de-inhibit the enzyme. DHAP can accumulate depending on the flux of carbon through glycolysis. The synthetic pathway for production of MEG from xylose has DHAP as an intermediate (Xylulose and Ribulose-1P pathways, for xylonate pathway methylglyoxal can be formed from pyruvate) and since the flux to the Pentose Phosphate Pathway is blocked, all the xylose has to pass through MEG synthetic pathway. This can generate an overflow of carbon through the synthetic pathway leading to accumulation of DHAP, which does not happen on WT uptake of xylose. Accumulation of DHAP de-inhibits mgsA that converts the DHPA to methylglyoxal. Deletion of mgsA can force the flux through MEG and C3 pathways improving MEG and C3 production and decreasing accumulation of intermediates.

Glyoxylate carboligase (gcl—EC:4.1.1.47) condenses two molecules of glyoxylate to form tartronate semialdehyde and carbon dioxide in *E. coli*. Glyoxylate carboligase can be formed from TCA or glycolate. Glycolate can be produced from glycolaldehyde decreasing the yield of MEG. The deletion of gel can improve the overall yield of MEG and C3 by preventing the loss of glycolaldehyde (C2 branch) and glyoxylate through side reactions. The deletion of gel can also maintain the carbon within the TCA cycle or converted it to pyruvate. The conversion of carbon from the TCA to pyruvate can increase the concentration of acetyl-CoA increasing the yield of C3 pathway.

Surprisingly, the deletion or disruption of mgsA and gel has not only an effect on MEG production, but also increases the overall yield and/or productivity (rate of production) and or titer of compounds of the C3 pathway. This improvement is due to an optimization of the flux through the pathway, modifying the acetic acid production profile and increasing or accelerating acetone production.

In some aspects, a modified microbe of the present disclosure comprises a disrupted methylglyoxal synthase (mgsA) nucleic acid sequence. In some aspects, a modified microbe of the present disclosure comprises a disrupted glyoxylate carboligase (gel) nucleic acid sequence. In some aspects, a modified microbe of the present disclosure comprises (1) a disrupted methylglyoxal synthase (mgsA) nucleic acid sequence and (2) a disrupted glyoxylate carboligase (gel) nucleic acid sequence.

In some aspects, a modified microbe of the present disclosure comprises one or more mutations in one or more methylglyoxal synthase nucleic acid sequences and/or one or more mutations in one or more glyoxylate carboligase nucleic acid sequences.

In some aspects, the translation of one or more nucleic acid sequences encoding a methylglyoxal synthase in a modified microbe of the present disclosure is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe.

In some aspects, the translation of one or more nucleic acid sequences encoding a glyoxylate carboligase in a modified microbe of the present disclosure is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe.

In some aspects, the translation of one or more nucleic acid sequences encoding (1) a glyoxylate carboligase and (2) a methylglyoxal synthase in a modified microbe of the present disclosure is reduced by at least about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, about 95%, or about 100% relative to an unmodified microbe.

In some aspects, the translation of one or more nucleic acid sequences encoding (1) a glyoxylate carboligase and (2) a methylglyoxal synthase in a modified microbe of the present disclosure is reduced by at least 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, 85%, 90%, 95%, or 100% relative to an unmodified microbe.

TABLE 3

| Description of Sequences | |
|---|---|
| SEQ ID NO: 1 | *Pseudomonas cichorii* D-tagatose 3-epimerase DTE NT sequence |
| SEQ ID NO: 2 | *Pseudomonas cichorii* D-tagatose 3-epimerase DTE codon optimized NT sequence |
| SEQ ID NO: 3 | *Pseudomonas cichorii* D-tagatose 3-epimerase DTE AA sequence |
| SEQ ID NO: 4 | *Rhodobacter sphaeroides* D-tagatose 3-epimerase FJ851309.1 NT sequence |
| SEQ ID NO: 5 | *Rhodobacter sphaeroides* D-tagatose 3-epimerase FJ851309.1 AA sequence |
| SEQ ID NO: 6 | *Escherichia coli* L-fuculokinase FucK NT sequence |
| SEQ ID NO: 7 | *Escherichia coli* L-fuculokinase FucK codon optimized NT sequence |
| SEQ ID NO: 8 | *Escherichia coli* L-fuculokinase fucK AA sequence |
| SEQ ID NO: 9 | *Escherichia coli* L-fuculose phosphate aldolase fucA NT sequence |
| SEQ ID NO: 10 | *Escherichia coli* L-fuculose phosphate aldolase fucA codon optimized NT sequence |
| SEQ ID NO: 11 | *Escherichia coli* L-fuculose phosphate aldolase fucA AA sequence |
| SEQ ID NO: 12 | *Escherichia coli* glycerol dehydrogenase gldA NT sequence |
| SEQ ID NO: 13 | *Escherichia coli* glycerol dehydrogenase gldA AA sequence |

TABLE 3-continued

| Description of Sequences | |
|---|---|
| SEQ ID NO: 14 | *Saccharomyces cerevisiae* methylglyoxal reductase GRE2 NT sequence |
| SEQ ID NO: 15 | *Saccharomyces cerevisiae* methylglyoxal reductase GRE2 AA sequence |
| SEQ ID NO: 16 | *Saccharomyces cerevisiae* aldose reductase GRE3 NT sequence |
| SEQ ID NO: 17 | *Saccharomyces cerevisiae* aldose reductase GRE3 AA sequence |
| SEQ ID NO: 18 | *Escherichia coli* alcohol dehydrogenase yqhD* NT sequence |
| SEQ ID NO: 19 | *Escherichia coli* alcohol dehydrogenase yqhD* codon optimized NT sequence |
| SEQ ID NO: 20 | *Escherichia coli* alcohol dehydrogenase yqhD* AA sequence |
| SEQ ID NO: 21 | *Escherichia coli* alcohol dehydrogenase yqhD NT sequence |
| SEQ ID NO: 22 | *Escherichia coli* alcohol dehydrogenase yqhD codon optimized NT sequence |
| SEQ ID NO: 23 | *Escherichia coli* alcohol dehydrogenase yqhD AA sequence |
| SEQ ID NO: 24 | *Escherichia coli* methylglyoxal reductase ydjG NT sequence |
| SEQ ID NO: 25 | *Escherichia coli* methylglyoxal reductase ydjG AA sequence |
| SEQ ID NO: 26 | *Escherichia coli* lactaldehyde reductase fucO NT sequence |
| SEQ ID NO: 27 | *Escherichia coli* lactaldehyde reductase fucO codon optimized NT sequence |
| SEQ ID NO: 28 | *Escherichia coli* lactaldehyde reductase fucO AA sequence |
| SEQ ID NO: 29 | *Escherichia coli* methylglyoxal reductase yafB (dkgB) [multifunctional] NT sequence |
| SEQ ID NO: 30 | *Escherichia coli* methylglyoxal reductase yafB (dkgB) [multifunctional] AA sequence |
| SEQ ID NO: 31 | *Escherichia coli* 2,5-diketo-D-gluconic acid reductase A yqhE (dkgA) NT sequence |
| SEQ ID NO: 32 | *Escherichia coli* 2,5-diketo-D-gluconic acid reductase A yqhE (dkgA) AA sequence |
| SEQ ID NO: 33 | *Clostridium acetobutylicum* acetyl coenzyme A acetyltransferase thlA NT sequence |
| SEQ ID NO: 34 | *Clostridium acetobutylicum* acetyl coenzyme A acetyltransferase thlA codon optimized NT sequence |
| SEQ ID NO: 35 | *Clostridium acetobutylicum* acetyl coenzyme A acetyltransferase thlA AA sequence |
| SEQ ID NO: 36 | *Escherichia coli* acetyl coenzyme A acetyltransferase atoB NT sequence |
| SEQ ID NO: 37 | *Escherichia coli* acetyl coenzyme A acetyltransferase atoB AA sequence |
| SEQ ID NO: 38 | *Saccharomyces cerevisiae* acetyl coenzyme A acetyltransferase ERG10 NT sequence |
| SEQ ID NO: 39 | *Saccharomyces cerevisiae* acetyl coenzyme A acetyltransferase ERG10 codon optimized NT sequence |
| SEQ ID NO: 40 | *Saccharomyces cerevisiae* acetyl coenzyme A acetyltransferase ERG10 AA sequence |
| SEQ ID NO: 41 | *Escherichia coli* Acetyl-CoA:acetoacetate-CoA transferase subunit atoA NT sequence |
| SEQ ID NO: 42 | *Escherichia coli* Acetyl-CoA:acetoacetate-CoA transferase subunit atoA codon optimized NT sequence |
| SEQ ID NO: 43 | *Escherichia coli* Acetyl-CoA:acetoacetate-CoA transferase subunit atoA AA sequence |
| SEQ ID NO: 44 | *Escherichia coli* Acetyl-CoA:acetoacetate-CoA transferase subunit atoD NT sequence |
| SEQ ID NO: 45 | *Escherichia coli* Acetyl-CoA:acetoacetate-CoA transferase subunit atoD codon optimized NT sequence |
| SEQ ID NO: 46 | *Escherichia coli* Acetyl-CoA:acetoacetate-CoA transferase subunit atoD AA sequence |
| SEQ ID NO: 47 | *Clostridium acetobutylieum* acetoacetate decarboxylase adc NT sequence |
| SEQ ID NO: 48 | *Clostridium acetobutylieum* acetoacetate decarboxylase adc codon optimized NT sequence |
| SEQ ID NO: 49 | *Clostridium acetobutylieum* acetoacetate decarboxylase adc AA sequence |
| SEQ ID NO: 50 | *Clostridium beijerinckii* acetoacetate decarboxylase adc NT sequence |
| SEQ ID NO: 51 | *Clostridium beijerinckii* acetoacetate decarboxylase adc codon optimized NT sequence |
| SEQ ID NO: 52 | *Clostridium beijerinckii* acetoacetate decarboxylase adc AA sequence |
| SEQ ID NO: 53 | *Homo sapiens* ketohexokinase C khk-C cDNA sequence |
| SEQ ID NO: 54 | *Homo sapiens* ketohexokinase C khk-C codon optimized cDNA sequence |
| SEQ ID NO: 55 | *Homo sapiens* ketohexokinase C khk-C AA sequence |
| SEQ ID NO: 56 | *Homo sapiens* Fructose-bisphosphate aldolase B aldoB cDNA sequence |
| SEQ ID NO: 57 | *Homo sapiens* Fructose-bisphosphate aldolase B aldoB codon optimized cDNA sequence |
| SEQ ID NO: 58 | *Homo sapiens* Fructose-bisphosphate aldolase B aldoB AA sequence |
| SEQ ID NO: 59 | *Caulobacter crescentus* D-xylose 1-dehydrogenase xylB NT sequence |
| SEQ ID NO: 60 | *Caulobacter crescentus* D-xylose 1-dehydrogenase xylB codon optimized NT sequence |
| SEQ ID NO: 61 | *Caulobacter crescentus* D-xylose 1-dehydrogenase xylB AA sequence |
| SEQ ID NO: 62 | *Haloferax volcanii* D-xylose 1-dehydrogenase xdh1, HVO__B0028 NT sequence |
| SEQ ID NO: 63 | *Haloferax volcanii* D-xylose 1-dehydrogenase xdh1, HVO__B0028 AA sequence |
| SEQ ID NO: 64 | *Trichoderma reesei* D-xylose 1-dehydrogenase xyd1 NT sequence |
| SEQ ID NO: 65 | *Trichoderma reesei* D-xylose 1-dehydrogenase xyd1 AA sequence |
| SEQ ID NO: 66 | *Caulobacter crescentus* Xylonolactonase xylC NT sequence |
| SEQ ID NO: 67 | *Caulobacter crescentus* Xylonolactonase xylC AA sequence |
| SEQ ID NO: 68 | *Caulobacter crescentus* xylonate dehydratase xylD NT sequence |

TABLE 3-continued

| Description of Sequences | |
|---|---|
| SEQ ID NO: 69 | *Caulobacter crescentus* xylonate dehydratase xylD AA sequence |
| SEQ ID NO: 70 | *Escherichia coli* xylonate dehydratase yjhG NT sequence |
| SEQ ID NO: 71 | *Escherichia coli* xylonate dehydratase yjhG codon optimized NT sequence |
| SEQ ID NO: 72 | *Escherichia coli* xylonate dehydratase yjhG AA sequence |
| SEQ ID NO: 73 | *Escherichia coli* xylonate dehydratase yagF NT sequence |
| SEQ ID NO: 74 | *Escherichia coli* xylonate dehydratase yagF codon optimized NT sequence |
| SEQ ID NO: 75 | *Escherichia coli* xylonate dehydratase yagF AA sequence |
| SEQ ID NO: 76 | *Escherichia coli* Uncharacterized lyase yjhH NT sequence |
| SEQ ID NO: 77 | *Escherichia coli* Uncharacterized lyase yjhH codon optimized NT sequence |
| SEQ ID NO: 78 | *Escherichia coli* Uncharacterized lyase yjhH AA sequence |
| SEQ ID NO: 79 | *Escherichia coli* Probable 2-keto-3-deoxy-galactonate aldolase yagE NT sequence |
| SEQ ID NO: 80 | *Escherichia coli* Probable 2-keto-3-deoxy-galactonate aldolase yagE codon optimized NT sequence |
| SEQ ID NO: 81 | *Escherichia coli* Probable 2-keto-3-deoxy-galactonate aldolase yagE AA sequence |
| SEQ ID NO: 82 | *Scheffersomyces stipitis* D-xylose reductase xyl1 NT sequence |
| SEQ ID NO: 83 | *Scheffersomyces stipitis* D-xylose reductase xyl1 codon optimized NT sequence |
| SEQ ID NO: 84 | *Scheffersomyces stipitis* D-xylose reductase xyl1 AA sequence |
| SEQ ID NO: 85 | *Saccharomyces cerevisiae* aldose reductase GRE3 NT sequence |
| SEQ ID NO: 86 | *Saccharomyces cerevisiae* aldose reductase GRE3 codon optimized NT sequence |
| SEQ ID NO: 87 | *Saccharomyces cerevisiae* aldose reductase GRE3 AA sequence |
| SEQ ID NO: 88 | *Scheffersomyces stipitis* D-xylulose reductase xyl2 NT sequence |
| SEQ ID NO: 89 | *Scheffersomyces stipitis* D-xylulose reductase xyl2 codon optimized NT sequence |
| SEQ ID NO: 90 | *Scheffersomyces stipitis* D-xylulose reductase xyl2 AA sequence |
| SEQ ID NO: 91 | *Trichoderma reesei* Xylitol dehydrogenase xdh1 NT sequence |
| SEQ ID NO: 92 | *Trichoderma reesei* Xylitol dehydrogenase xdh1 AA sequence |
| SEQ ID NO: 93 | *Pyromyces* sp. xylose isomerase xylA NT sequence |
| SEQ ID NO: 94 | *Pyromyces* sp. xylose isomerase xylA codon optimized NT sequence |
| SEQ ID NO: 95 | *Pyromyces* sp. xylose isomerase xylA AA sequence |
| SEQ ID NO: 96 | *Clostridium acetobutylicum* butyrate-acetoacetate CoA-transferase, complex A ctfA NT sequence |
| SEQ ID NO: 97 | *Clostridium acetobutylicum* butyrate-acetoacetate CoA-transferase, complex A ctfA AA sequence |
| SEQ ID NO: 98 | *Clostridium acetobutylicum* butyrate-acetoacetate CoA-transferase, subunit B ctfB NT sequence |
| SEQ ID NO: 99 | *Clostridium acetobutylicum* butyrate-acetoacetate CoA-transferase, subunit B ctfB AA sequence |
| SEQ ID NO: 100 | *Escherichia coli* (strain K12) Acetyl-CoA:acetoacetate-CoA transferase subunit atoA NT sequence |
| SEQ ID NO: 101 | *Escherichia coli* (strain K12) Acetyl-CoA:acetoacetate-CoA transferase subunit atoA AA sequence |
| SEQ ID NO: 102 | *Escherichia coli* (strain K12) Acetyl-CoA:acetoacetate-CoA transferase subunit atoD NT sequence |
| SEQ ID NO: 103 | *Escherichia coli* (strain K12) Acetyl-CoA:acetoacetate-CoA transferase subunit atoD AA sequence |
| SEQ ID NO: 104 | *Clostridium beijerinckii* secondary alcohol dehydrogenase adh NT sequence |
| SEQ ID NO: 105 | *Clostridium beijerinckii* secondary alcohol dehydrogenase adh codon optimized NT sequence |
| SEQ ID NO: 106 | *Clostridium beijerinckii* secondary alcohol dehydrogenase adh AA sequence |
| SEQ ID NO: 107 | *Clostridium carboxidivorans* alcohol dehydrogenase adh NT sequence |
| SEQ ID NO: 108 | *Clostridium carboxidivorans* alcohol dehydrogenase adh AA sequence |
| SEQ ID NO: 109 | *Escherichia coli* soluble pyridine nucleotide transhydrogenase NT sequence |
| SEQ ID NO: 110 | *Escherichia coli* soluble pyridine nucleotide transhydrogenase AA sequence |
| SEQ ID NO: 111 | Forward primer to amplify fucA and fucO |
| SEQ ID NO: 112 | Reverse primer to amplify fucA and fucO |
| SEQ ID NO: 113 | Forward primer to amplify fucK |
| SEQ ID NO: 114 | Reverse primer to amplify fucK |
| SEQ ID NO: 115 | Forward primer to amplify thl |
| SEQ ID NO: 116 | Reverse primer to amplify thl |
| SEQ ID NO: 117 | Forward primer to amplify fucO |
| SEQ ID NO: 118 | Reverse primer to amplify fucO |
| SEQ ID NO: 119 | Forward primer to amplify atoA/D |
| SEQ ID NO: 120 | Reverse primer to amplify atoA/D |

EXAMPLES

Example 1. Co-Production of Ethylene Glycol (MEG), Acetone and Isopropanol (IPA) in *E. coli* Using Xylulose-1-Phosphate Pathway

*E. coli* K12 strain MG1655 was used as host for the expression of MEG+IPA pathways. Two genes that could divert the carbon flux from MEG+IPA pathway were identified as target for deletion: aldA and xylB genes. A MEG pathway was integrated at xylB locus, enabling a stable integration concomitantly with xylB deletion. Production of MEG through xylulose-1-phosphate pathway requires the expression of three genes: khkC (D-xylulose-1-kinase enzyme), aldoB (D-xylulose-1-phosphate aldolase enzyme) and fucO (aldehyde reductase enzyme). khkC (KhkC amino acid sequence set forth in SEQ ID NO: 55) and aldoB (AldoB amino acid sequence set forth in SEQ ID NO: 58) genes were codon optimized for *E. coli* and synthesized. FucO gene is native from *E. coli* and was PCR amplified (Forward Primer: ATGGCTAACAGAATGATTCTG (SEQ ID NO: 117) and Reverse Primer: TTACCAGGCGGTATGGTAAAGCT (SEQ ID NO: 118)).

A MEG integration cassette was composed of an operon containing khkC (D-xylulose-1-kinase enzyme), aldoB (D-xylulose-1-phosphate aldolase enzyme), fucO (aldehyde reductase enzyme) genes and rplM terminator under the control of proD promoter (constitutive promoter) flanked by regions homologous to upstream and downstream of xylB gene. For each gene a specific RBS sequence was utilized. An antibiotic marker was also added to the cassette for the selection of transformants. The cassette was constructed using In-fusion commercial kit, confirmed by sequencing and transformed in *E. coli* K12 MG1655 strain. The proper integration of a MEG pathway at xylB locus, yielding a deleted xylB strain with a MEG pathway integrated, was confirmed by sequencing.

The strain harboring a MEG pathway at xylB locus was used as host for integration of an IPA pathway at aldA locus, enabling a stable integration concomitantly with aldA deletion. Production of isopropanol requires the expression of five genes: thl (thiolase), atoA/D (acetate:acetoacetyl-CoA transferase), adc (acetoacetate decarboxylase) and adh (secondary alcohol dehydrogenase). atoA/D gene is native from *E. coli* and was PCR amplified (Forward Primer: CTGTTGTTATATTGTAATGATGTATGCAAGAGGGATAAA (SEQ ID NO: 119) and Reverse Primer: TATATCTCCTTCTTAAAGTTCATAAATCACCCCGTTGC (SEQ ID NO: 120)). thl (Thl amino acid sequence set forth in SEQ ID NO: 35), adc (Adc amino acid sequence set forth in SEQ ID NO: 49) and adh (Adh amino acid sequence set forth in SEQ ID NO: 106) were codon optimized for *E. coli* and synthesized.

An IPA integration cassette was composed of an operon containing thl (thiolase), adh (secondary alcohol dehydrogenase), adc (acetoacetate decarboxylase), atoA/D (acetate: acetoacetyl-CoA transferase) genes and T1 terminator under the control of a medium strength constitutive promoter (modified from RecA) flanked by regions homologous to upstream and downstream of aldA gene. For each gene a specific RBS sequence was utilized. An antibiotic marker was included into the cassette for the selection of transformants. The cassette was constructed using In-fusion commercial kit, confirmed by sequencing and transformed in *E. coli* K12 MG1655 strain. The proper integration of an IPA pathway at aldA locus, yielding a deleted aldA strain with an IPA pathway integrated, was confirmed by sequencing.

The xylB aldA deleted strain with MEG and IPA pathways integrated in the genome was inoculated in 3 mL of TB media for pre-culture. After 16 hours of cultivation, 100% of the pre-culture was transferred to 100 mL of TB media containing 15 g/L of xylose. The flasks were incubated at 37° C., 250 rpm until complete consumption of xylose. The initial OD of the cultivation was 0.3.

Figure 4:
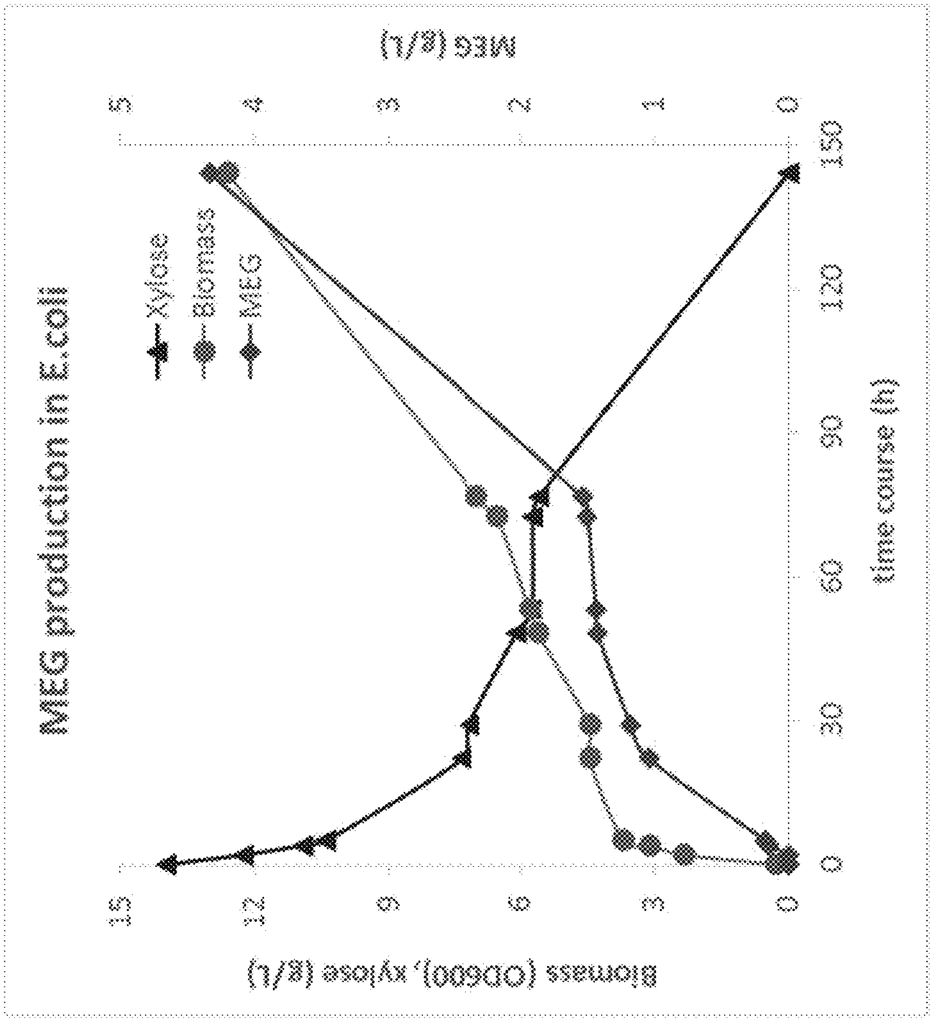
FIG. 4 illustrates improved MEG production from xylose in *E. coli.*

Xylose was fully consumed after 30 hours of cultivation (FIG. 4). Ethylene glycol, acetone and isopropanol reached a maximum titer of 3.5 g/L, 70 mg/L and 400 mg/L respectively.

Figure 7:
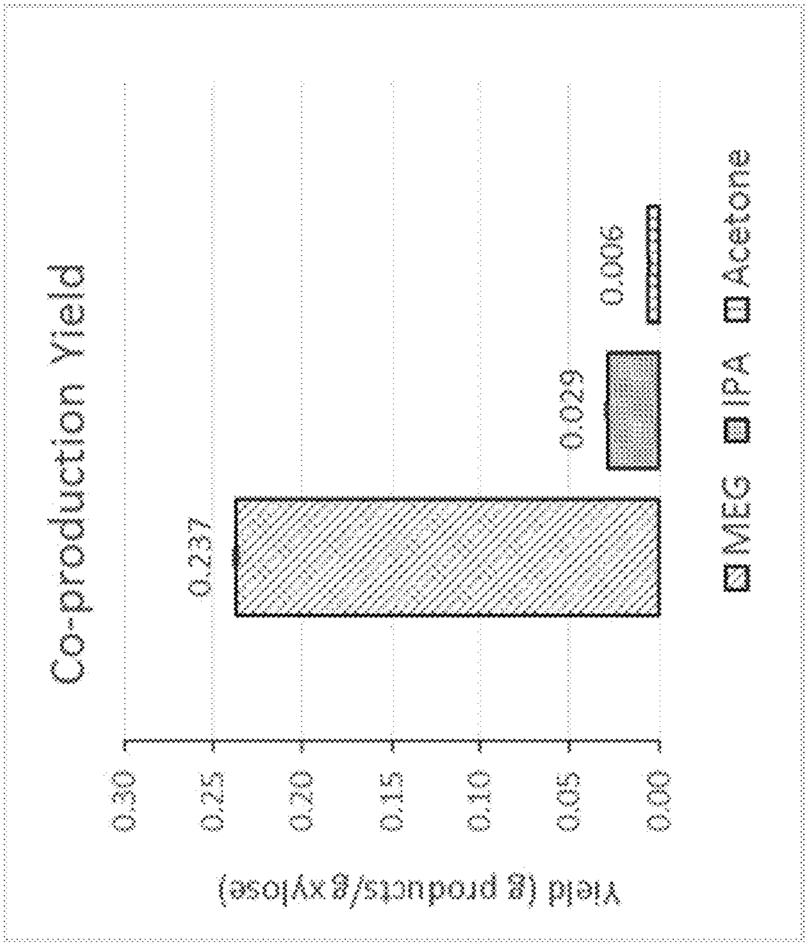
FIG. 7 illustrates overall yield (g products/g xylose) of ethylene glycol, isopropanol and acetone produced using a xylulose-1-phosphate pathway.

The overall yield of co-production was calculated considering the amount of ethylene glycol, isopropanol and acetone produced per gram of xylose consumed. MEG is the product with the highest yield, 0.237 g/g, followed by isopropanol, 0.029 g/g and acetone, 0.006 g/g (FIG. 7). The best co-production yield, obtained after 48 hours of fermentation, was 0.27 g products/g xylose (44% of maximum theoretical yield).

Example 2. Co-Production of Ethylene Glycol (MEG), Acetone and Isopropanol (IPA) in *E. coli* Using Xylonate Pathway

*E. coli* K12 strain MG1655 was used as host for the expression of MEG+IPA pathways. Two genes that could divert the carbon flux from MEG+IPA pathway were identified as target for deletion: aldA and xylA genes. A MEG pathway was integrated at xylA locus, enabling a stable integration concomitantly with xylA deletion. Production of MEG through a xylonate pathway requires the expression of two genes: xdh (Xdh amino acid sequence set forth in SEQ ID NO: 61) from *Caulobacter crescentus* was codon optimized for *E. coli* and synthesized. FucO gene is native from *E. coli* and was PCR amplified (Forward Primer: ATGGCTAACAGAATGATTCTG (SEQ ID NO: 117) and Reverse Primer: TTACCAGGCGGTATGGTAAAGCT (SEQ ID NO: 118)). Two other native enzymes could be overexpressed to improve MEG production through a xylonate pathway: D-xylonate dehydratase (yjhG, yagF, or homologs thereof) and aldolase (yjhH, yagE, or homologs thereof).

A MEG integration cassette was composed of an operon containing xdh (D-xylose dehydrogenase), fucO (aldehyde reductase enzyme) genes and rnpB terminator under the control of proD promoter (constitutive promoter) flanked by regions homologous to upstream and downstream of xylA gene. For each gene a specific RBS sequence was utilized. An antibiotic marker was also added to the cassette for the selection of transformants. The cassette was constructed using In-fusion commercial kit, confirmed by sequencing and transformed in *E. coli* K12 MG1655 strain. The proper integration of a MEG pathway at xylA locus, yielding a deleted xylA strain with a MEG pathway integrated, was confirmed by sequencing.

The strain harboring a MEG pathway at xylA locus was used as host for integration of an IPA pathway at aldA locus, enabling a stable integration concomitantly with aldA deletion. Production of isopropanol requires the expression of five genes: thl (thiolase), atoA/D (acetate:acetoacetyl-CoA transferase), adc (acetoacetate decarboxylase) and adh (secondary alcohol dehydrogenase). AtoA/D gene is native from *E. coli* and was PCR amplified (Forward Primer: CTGTTGTTATATTGTAATGATGTATGCAAGAGGGATAAA (SEQ ID NO: 119) and Reverse Primer: TATATCTCCTTCTTAAAGTTCATAAATCACCCCGTTGC (SEQ ID NO: 120)). thl (Thl amino acid sequence set forth in SEQ ID NO: 35), adc (Adc amino acid sequence set forth in SEQ ID NO: 49) and adh (Adh amino acid sequence set forth in SEQ ID NO: 106) were codon optimized for *E. coli* and synthesized.

An IPA integration cassette was composed of an operon containing thl (thiolase), adh (secondary alcohol dehydrogenase), adc (acetoacetate decarboxylase), atoA/D (acetate: acetoacetyl-CoA transferase) genes and T1 terminator under the control of a medium strength constitutive promoter (modified from RecA) flanked by regions homologous to upstream and downstream of aldA gene. For each gene a specific RBS sequence was utilized. An antibiotic marker was included into the cassette for the selection of transformants. The cassette was constructed using In-fusion commercial kit, confirmed by sequencing and transformed in *E. coli* K12 MG1655 strain. The proper integration of an IPA pathway at aldA locus, yielding a deleted aldA strain with an IPA pathway integrated, was confirmed by sequencing.

The xylA aldA deleted strain with MEG and IPA pathways integrated in the genome was inoculated in 3 mL of TB media for pre-culture. After 16 hours of cultivation, 100% of the pre-culture was transferred to 100 mL of TB media containing 15 g/L of xylose. The flasks were incubated at 37° C., 250 rpm until complete consumption of xylose. The initial OD of the cultivation was 0.3.

Figure 8:
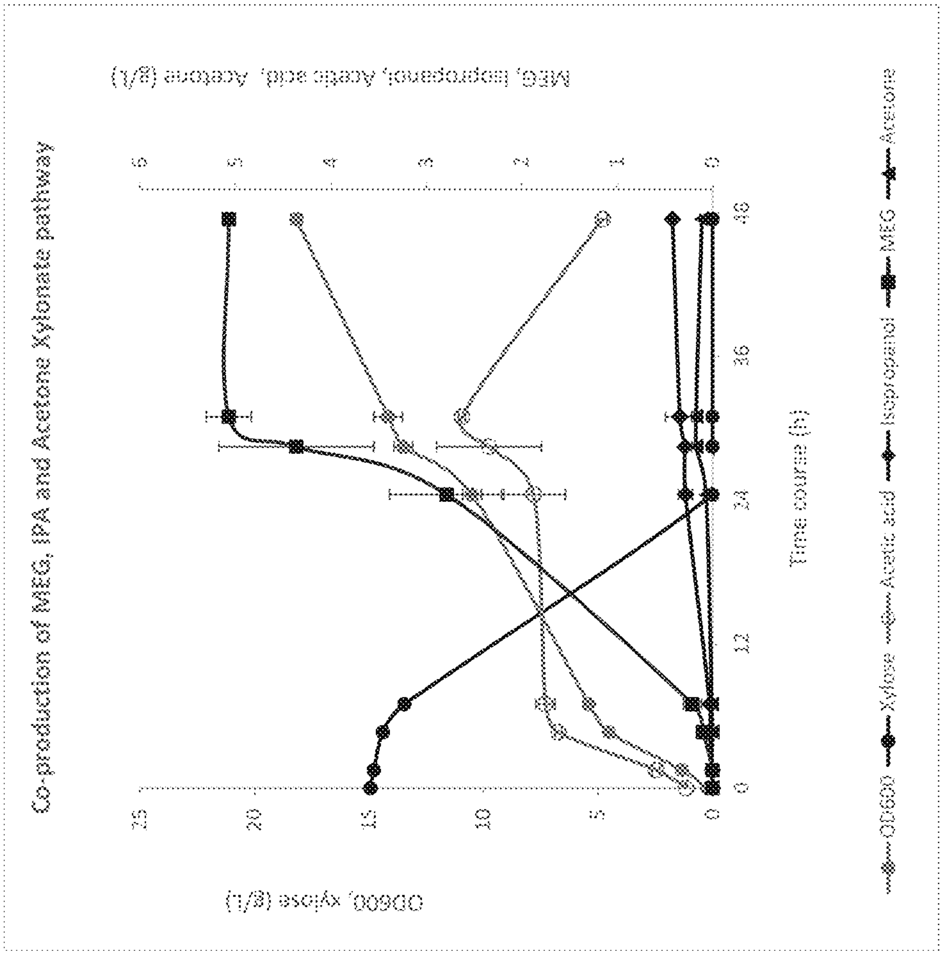
FIG. 8 illustrates co-production of MEG, isopropanol, and acetone using a xylonate pathway in *E. coli.*

Xylose was fully consumed before 24 hours of cultivation (FIG. 8). Ethylene glycol, acetone and isopropanol reached a maximum titer of 5 g/L, 170 mg/L and 420 mg/L respectively.

Figure 9:
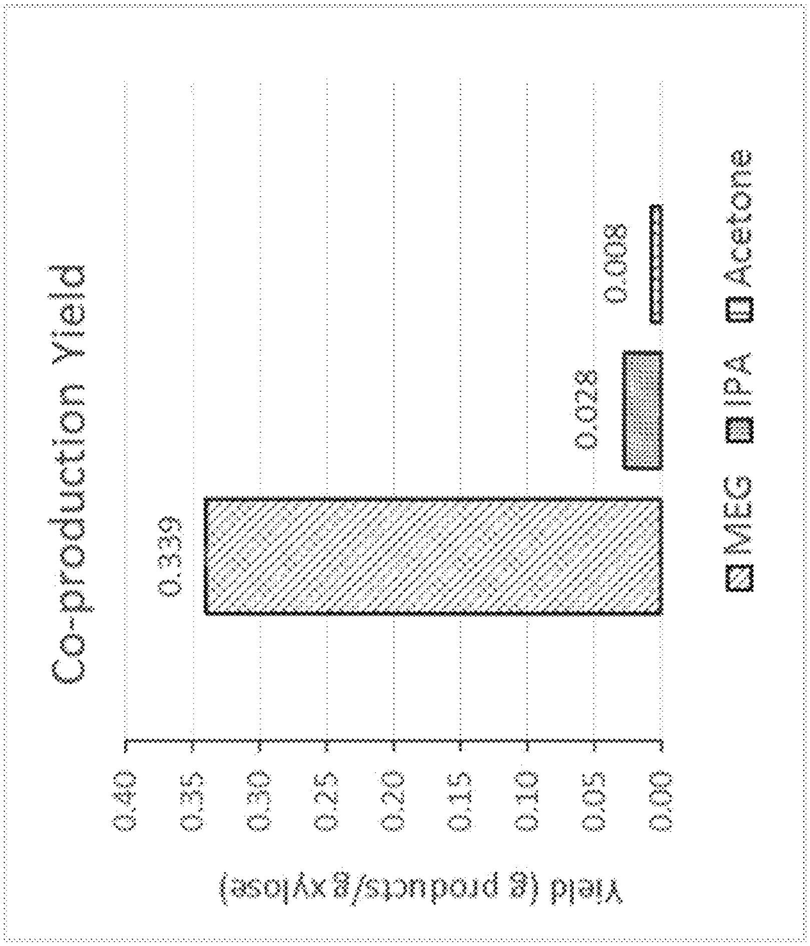
FIG. 9 illustrates overall yield (g products/g xylose) of ethylene glycol, isopropanol and acetone produced using a xylulose-1-phosphate pathway.

The overall yield of co-production was calculated considering the amount of ethylene glycol, isopropanol and acetone produced per gram of xylose consumed. MEG is the product with the highest yield, 0.339 g/g, followed by isopropanol, 0.028 g/g and acetone, 0.008 g/g (FIG. 9). The best co-production yield, obtained after 48 hours of fermentation, was 0.375 g products/g xylose (61% of maximum theoretical yield).

Example 3. Direct Production of Propylene from Glucose

Vectors pZs*13 containing an IPA pathway in an operon under plLacO promoter and pET28a containing LinD gene were co-transformed into BL21Star (DE3) using electroporation. Production of isopropanol requires the expression of five genes: thl (thiolase), atoA/D (acetate:acetoacetyl-CoA transferase), adc (acetoacetate decarboxylase) and adh (secondary alcohol dehydrogenase). atoA/D gene is native from *E. coli* and was PCR amplified (Forward Primer: CTGTTGTTATATTGTAATGATGTATGCAAGAGGGA-TAAA (SEQ ID NO: 119) and Reverse Primer: TATATCTCCTTCTTAAAGTTCATAAAT-CACCCCGTTGC (SEQ ID NO: 120)). thl (Thl amino acid sequence set forth in SEQ ID NO: 35), adc (Adc amino acid sequence set forth in SEQ ID NO: 49) and adh (Adh amino acid sequence set forth in SEQ ID NO: 106) were codon optimized for *E. coli* and synthesized. An operon containing thl (thiolase), adh (secondary alcohol dehydrogenase), adc (acetoacetate decarboxylase), atoA/D (acetate:acetoacetyl-CoA transferase) genes and T1 terminator under the control of the inducible promoter pLLacO was constructed in a pZS*13 backbone. The candidate selection was done using kanamycin and ampicillin in LB medium. The strain herein was referred to as IPA+LinD. This combination of plasmids provides a strain capable of producing isopropanol from glucose and also expressing linalool isomerase dehydratase enzyme.

One single colony of IPA+LinD, pZs*13_IPA and pET28a_LinD was inoculated in TB medium containing 10 g/L glycerol supplemented with kanamycin (50 μg/mL) and ampicillin (100 μg/mL) at 37° C., 220 rpm. After 20 hours, a new inoculation was done using optical density of 0.2 in TB medium containing 1.5 g/L glycerol supplemented with appropriate antibiotics at 37° C., 220 rpm. After 3 hours, the OD achieved 1.0 at 600 nm and IPTG was added to a final concentration of 1 mM. The flasks were incubated at 18° C., 220 rpm.

After 16 hours, the OD was measured and the cultures were concentrated to reach OD 20 using the following media as described for each assay:

(a) pZs*13_IPA in TB 20 g/L glucose (control for isopropanol production),
(b) IPA+LinD in TB 10 g/L glycerol and 3 g/L isopropanol (control for propylene production),
(c) IPA+LinD in TB 20 g/L glucose and 3 g/L isopropanol (control for propylene production),
(d) IPA+LinD in TB 20 g/L glucose (candidate 1 for propylene production),
(e) IPA+LinD in TB 20 g/L glucose (candidate 2 for propylene production)

Figure 10:
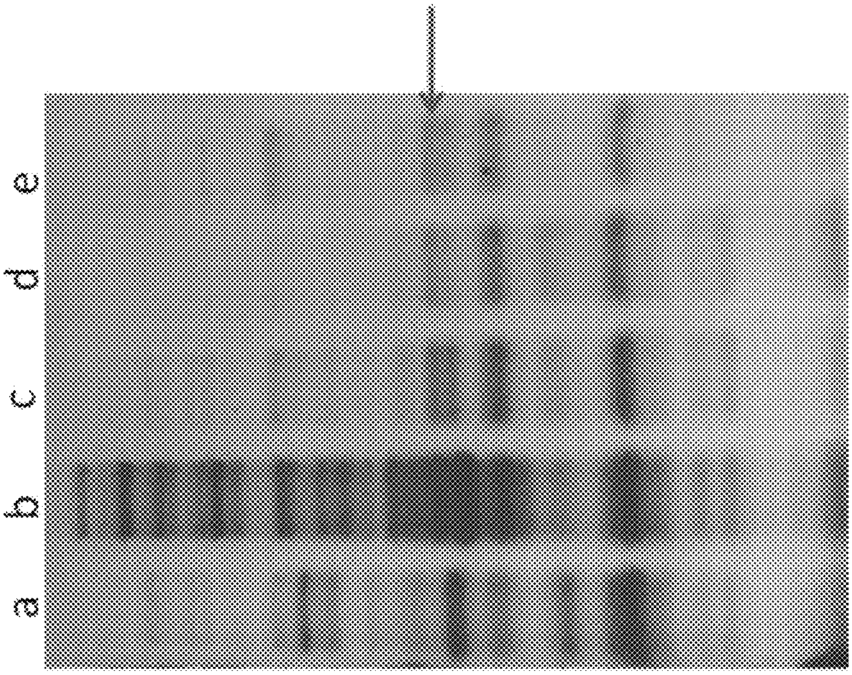
FIG. 10 shows an SDS-PAGE of soluble fraction of assays (a) to (e) as described in Example 3. The arrow indicates LinD expression in (b), (c), (d) and (e).

One aliquot of all cultures were lysate for expression analysis and the cells were collected by centrifugation at 5000 rpm for 20 min and 4° C. The pellet was kept in −80° C. for 1 hour then it was thawed on ice and resuspended in 10% of original volume in Tris-HCl 50 mM pH 7.5. The lysis was done by sonication (3-5 cycles, 10/10 minutes, 25% amplitude) on ice after that to separate the soluble fraction it was centrifuged at 5000 rpm for 30 min at 4° C. The samples were heated at 95° C. for 10 minutes and analyzed in SDS-PAGE (FIG. 10).

1.0 mL aliquots of each culture were placed in 2 mL headspace vials in triplicate and incubated at 37° C., 225 rpm. At the end of 116 hours of incubation the vials were removed from the shaking incubator and the propylene and isopropanol concentration was analyzed in GC-MS. A control containing only TB medium 20 g/L glucose was done in order to verify contamination in the end of incubation period. 1.0 mL of the headspace phase was injected in gas chromatograph (Focus GC—Thermo) equipped with electron impact mass spectrometer detector (ISQ—Thermo). Helium was used as a carrier gas with a flow rate of 1.5 mL/min, the split rate used was 10 with a split flow of 15 mL/min. The volatile compounds were separated in a HP-Plot/Q column (Agilent) with initial temperature held at 90° C. for 1.0 min followed by a first ramp at 13.3° C./min to 130° C. and a second one at 45° C./min to 200° C. held for 1 min. The retention time of propylene under these conditions was 1.51 min and of isopropanol was 4.3 min. The product reaction was identified both by comparison with propylene and isopropanol standards and by comparison with a data base of mass fragmentation.

Figure 11:
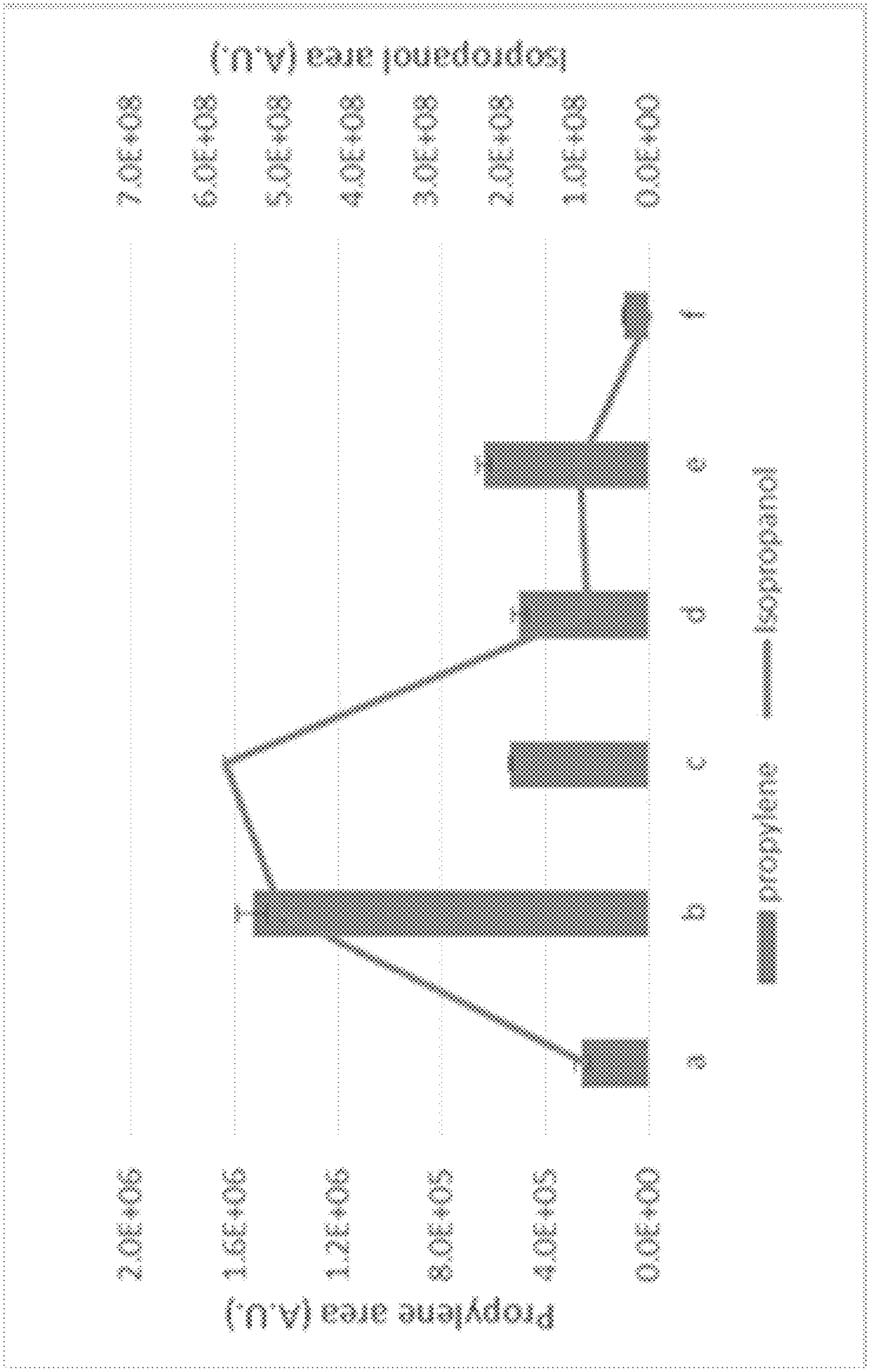
FIG. 11 illustrates that assays (d) and (e) showed the production of propylene and isopropanol in IPA+LinD candidates. Assay (a) showed isopropanol production of pZs*13_IPA and a small amount of propylene. Assays (b) and (c) showed propylene production in medium supplemented with 3.0 g/L isopropanol using glycerol and glucose as carbon source, respectively.

The production of isopropanol in assays (a), (d) and (e) were 0.5 g/L and in (b) and (c) 3.0 g/L as expected. The production of 4 10-5 mM of propylene was observed in the assay (b) positive control for propylene and a significant production was observed in the assays (d) and (e), candidates with IPA+LinD co-transformed (FIG. 11). No amount of propylene was observed in the control reaction that contained only TB medium.

Example 4: Expression of Malonyl-CoA Bypass in MEG+Acetone Co-Producing Strain—Via Xylonate Pathway The *E. coli* K12 strain MG1655 was used as the host for the deletion of two genes that could divert the carbon flux from MEG+Acetone pathway: aldA and xylA. The genes were successfully deleted and the deletions were confirmed by PCR and sequencing.

The next step was the integration of the MEG pathway. An operon expressed under control of the proD promoter containing xdh gene (xylose dehydrogenase) and fucO gene (glycoaldehyde reductase), encoding respectively for the first and last enzymes of the xylonate pathway, was integrated in the *E. coli* genome and an additional copy of xdh gene also under control of proD promoter was integrated in a different loci.

The last step was the integration of the acetone pathway. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated in the *E. coli* genome, generating the base strain. All the integrations were confirmed by PCR and sequencing. nphT7 gene (acetoacetyl CoA synthase) was expressed under the control of the GAPDH promoter in a pZS* vector backbone. The plasmid was constructed using an In-fusion commercial kit and confirmed by sequencing. The confirmed plasmid was transformed in the base strain. Colonies from transformations were inoculated in 5 mL of mineral media containing 12.85 g/L of xylose and 2.15 g/L of glucose for pre-culture. After 16 hours of cultivation 5% of the pre-culture was transferred to 100 mL of fresh media. The flasks were incubated at 37° C., 250 rpm until complete consumption of glucose and xylose. The initial OD of the cultivation was 0.1. For all strains, xylose was fully consumed after 48 hours of cultivation.

Figure 12A:
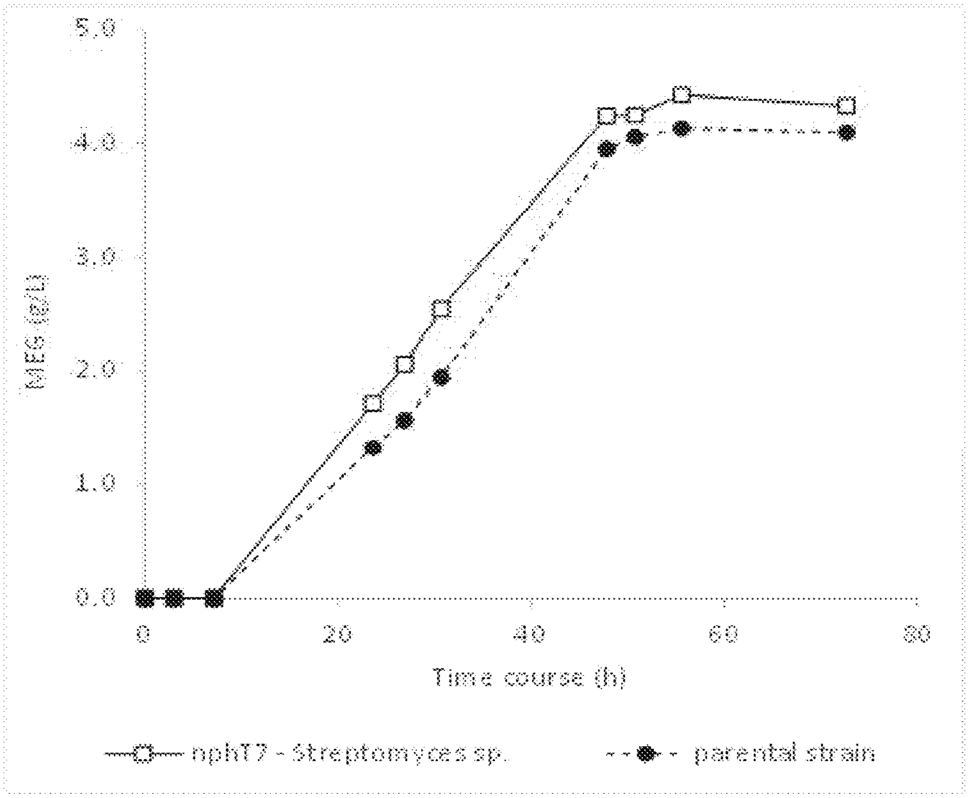
FIG. 12A-FIG. 12D illustrates the increased MEG production in the strain with nphT7 expressed vs the parental strain (FIG. 12A), with increased acetone production in the strain (FIG. 12B), with increased acetic acid production (FIG. 12C), and with a decreased peak production of xylonic acid compared with the parent (FIG. 12D).
Figure 12B:
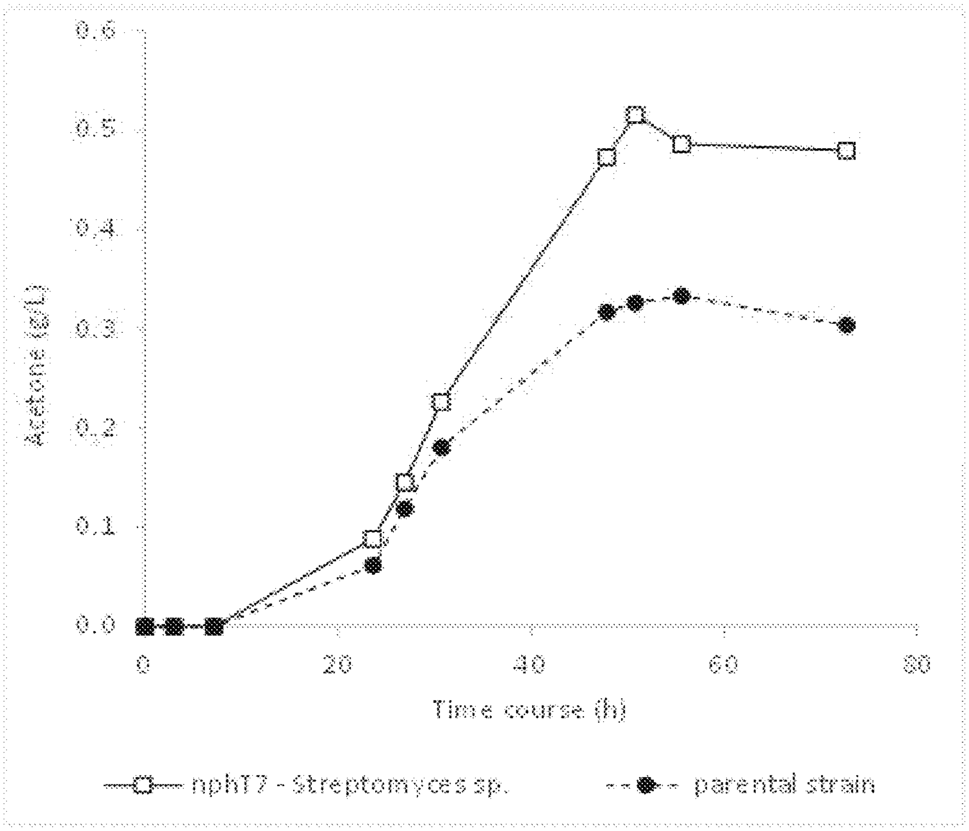
Figure 12C:
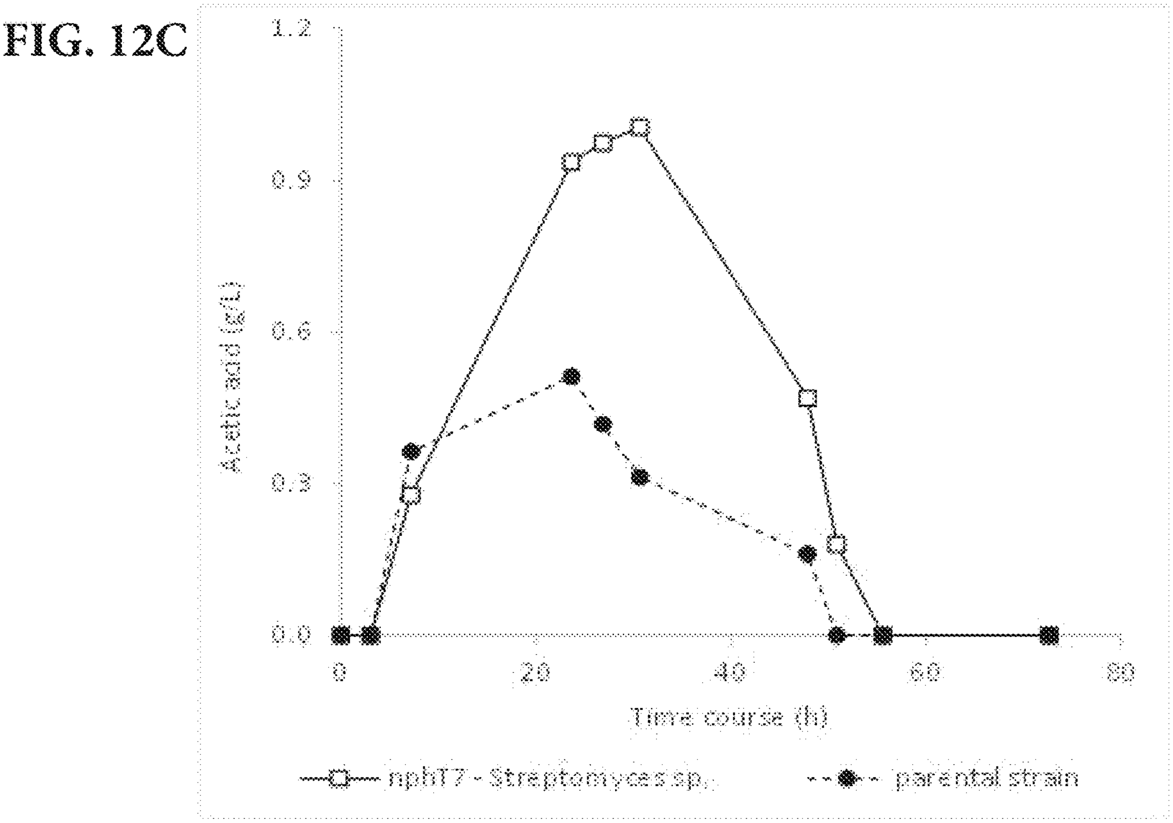
Figure 12D:
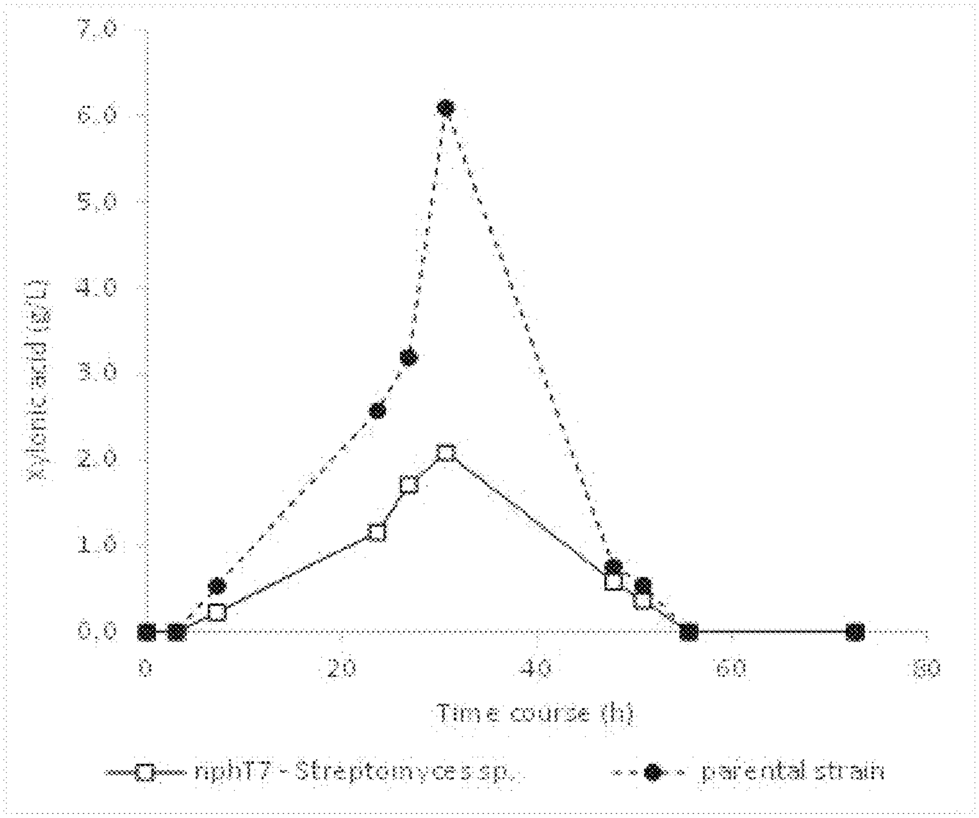

After 24 hours of cultivation approximately 1.3 g/L of MEG could be detected in the parental strain while 1.7 g/L could be detected at the same time in the strain with nphT7 expressed (FIG. 12A). The strains produced approximately 4 g/L of MEG in 48 h of cultivation while the total amount of acetone was increased 60% (FIG. 12B), probably related to the higher production of acetic acid (FIG. 12C). The peak production of xylonic acid was decreased 2.9 times (FIG. 12D). The expression of nhpT7 gene provided an improvement at velocity of co-production in relation with its parental strain.

Example 5: Expression HMG-CoA in MEG+Acetone Co-Producing Strain—Via Xylulose Pathway The *E. coli* K12 strain MG1655 was used as the host for the deletion of two genes that could divert the carbon flux from MEG+Acetone pathway: aldA and xylB. The genes were successfully deleted and the deletions were confirmed by PCR and sequencing.

The next step was the integration of the MEG pathway. An operon expressed under control of the proD promoter containing khk-C gene (ketohexokinase), aldoB gene (fructose-1,6-bisphosphate aldolase) and fucO gene (glycoaldehyde reductase) was integrated in the *E. coli* genome and an additional copy of khk-C and aldoB genes also under control of proD promoter was integrated in a different loci.

The last step was the integration of acetone pathway. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated in the *E. coli* genome, generating the base strain. All the integrations were confirmed by PCR and sequencing. ERG13 gene (hydroxymethylglutaryl-CoA synthase) and yngG gene (hydroxymethylglutaryl-CoA lyase) were expressed in operon and under the control of the Tac promoter in a pZA vector backbone. The plasmid was constructed using an In-fusion commercial kit and confirmed by sequencing. The confirmed plasmid was transformed in the base strain. Colonies from transformations were inoculated in 5 mL of mineral media containing 12.85 g/L of xylose and 2.15 g/L of glucose for pre-culture. After 16 hours of cultivation 5% of the pre-culture was transferred to 100 mL of fresh media. The flasks were incubated at 37° C., 250 rpm until complete consumption of glucose and xylose. The initial OD of the cultivation was 0.1. For all strains, xylose was fully consumed after 55 hours of cultivation.

Figure 13A:
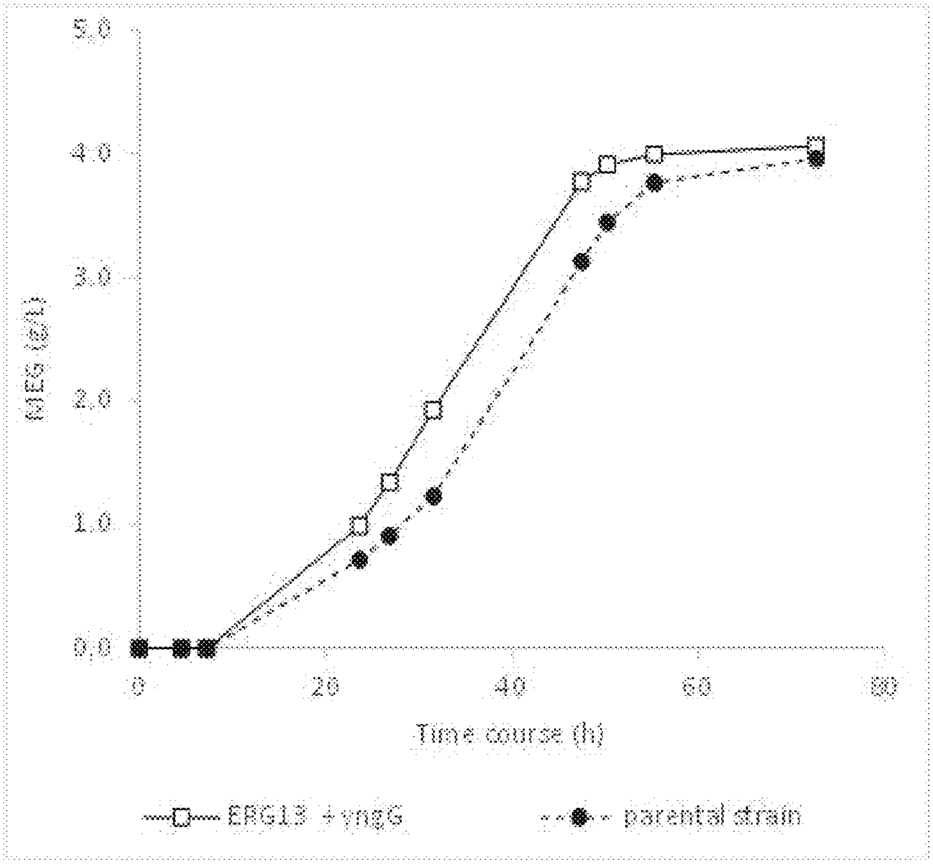
FIG. 13A-FIG. 13D illustrates the increased MEG production in the strain with HMG-CoA expressed vs the parental strain (FIG. 13A), with increased acetone production in the strain (FIG. 13B), with little effect on acetic acid production (FIG. 13C), and with little effect on xylulose accumulation compared with the parent (FIG. 13D).
Figure 13B:
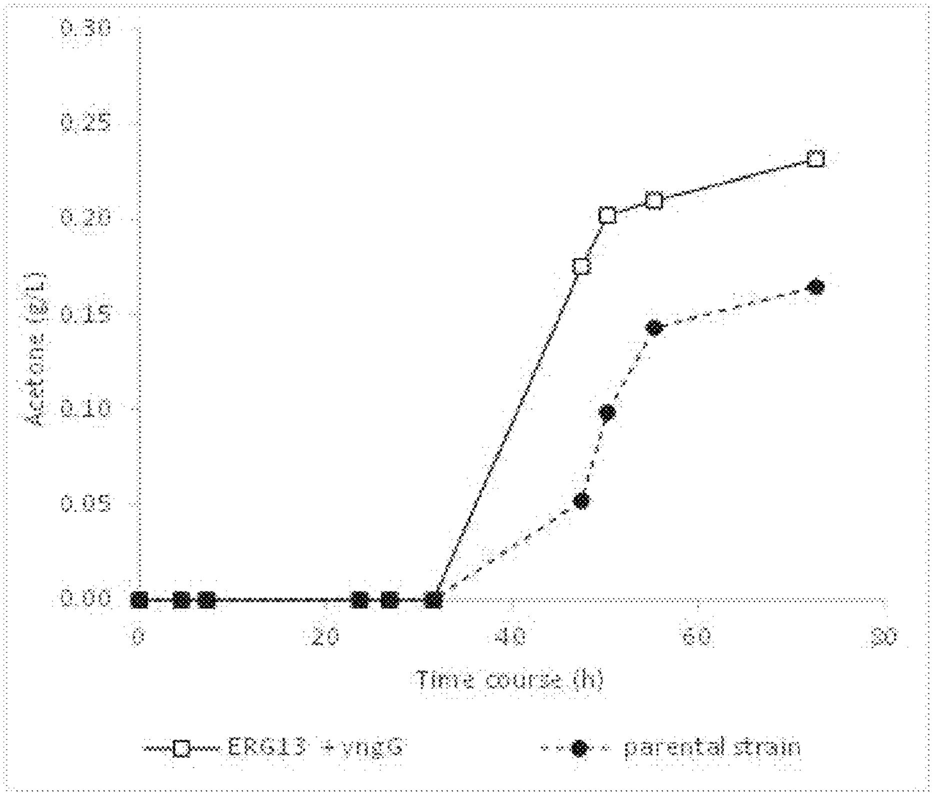
Figure 13C:
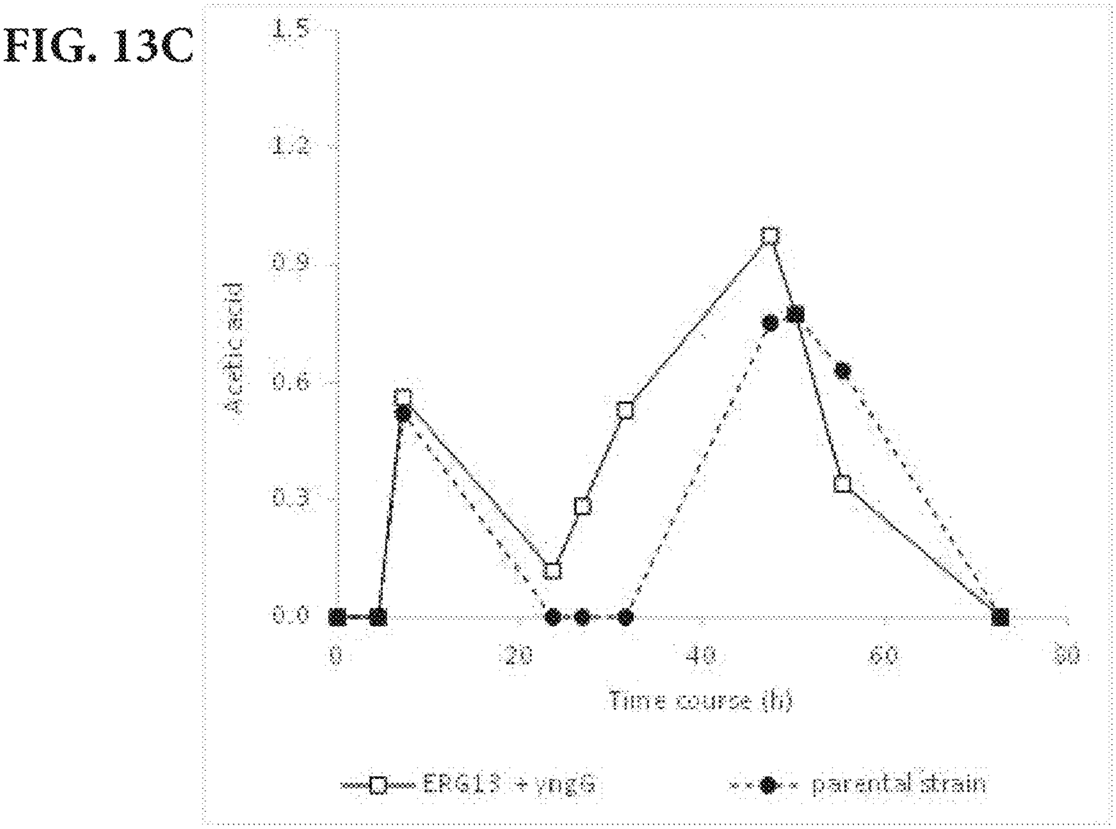
Figure 13D:
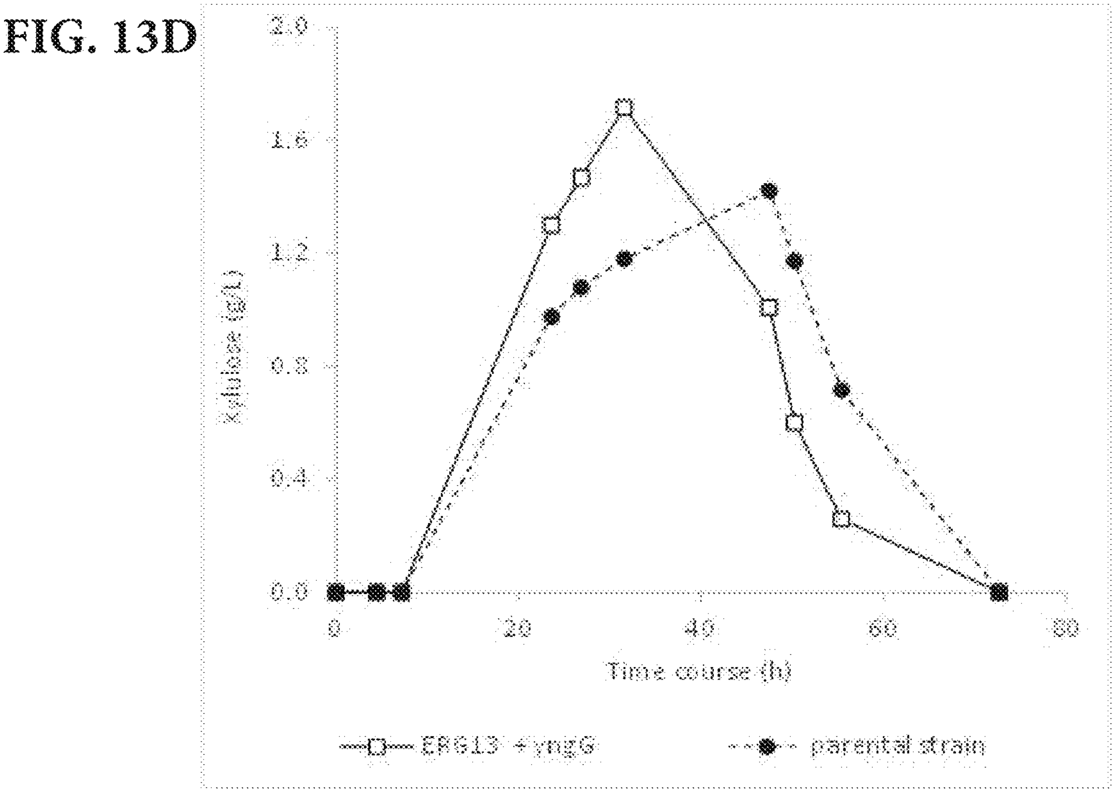

After 32 hours of cultivation approximately 1.2 g/L of MEG could be detected in the parental strain while 1.9 g/L could be detected at the same time in the strain with HMG-CoA expressed (FIG. 13A). The strains produced approximately 4 g/L of MEG in 55 h of cultivation while the total amount of acetone was increased 41% (FIG. 13B), with little effect on acetic acid production (FIG. 13C) and xylulose accumulation (FIG. 13D). The expression of HMG-CoA by-pass guaranteed an improvement at velocity of co-production in relation with its parental strain.

Example 6: Replacement of Exogenous atoDA by ERG13 and yngG in Acetone Operon and Deletion of Endogenous atoDA in a MEG+Acetone Co-Producing Strain Via Xylulose Pathway with Deletion of Pta Gene The *E. coli* K12 strain MG1655 was used as host for the deletion of two genes that could divert the carbon flux from the MEG+Acetone pathway: aldA and xylB. The genes were successfully deleted and the deletions were confirmed by PCR and sequencing.

The next step was the integration of the MEG pathway. An operon expressed under the control of the proD promoter containing khk-C gene (ketohexokinase), aldoB gene (fructose-1,6-bisphosphate aldolase), and fucO gene (glycoaldehyde reductase) was integrated in the *E. coli* genome and an additional copy of khk-C and aldoB genes also under the control of the OXB20 promoter were integrated in a different locus.

The next step was the integration of the acetone pathway via an operon in the *E. coli* genome. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated into the *E. coli* genome, generating the base strain. All the integrations were confirmed by PCR and sequencing.

The next step was the deletion of pta gene. This gene was successfully deleted and the deletion was confirmed by PCR and sequencing. The base strain was used as the host strain for the deletion of exogenous atoDA present at acetone operon with integration of ERG13 and yngG genes and deletion of endogenous atoDA. The ERG13 and yngG genes were successfully integrated, atoDA gene was successfully deleted, and both modifications were confirmed by PCR and sequencing.

Colonies of the modified strains were inoculated in 5 mL of mineral media for pre-culture. After 16 hours of cultivation, the pre-culture was transferred to 100 ml of mineral media containing 12.85 g/L of xylose and 2.15 g/L of glucose. The flasks were incubated at 37° C., 250 rpm until complete consumption of xylose. The initial OD of the cultivation was 0.2.

Figure 14A:
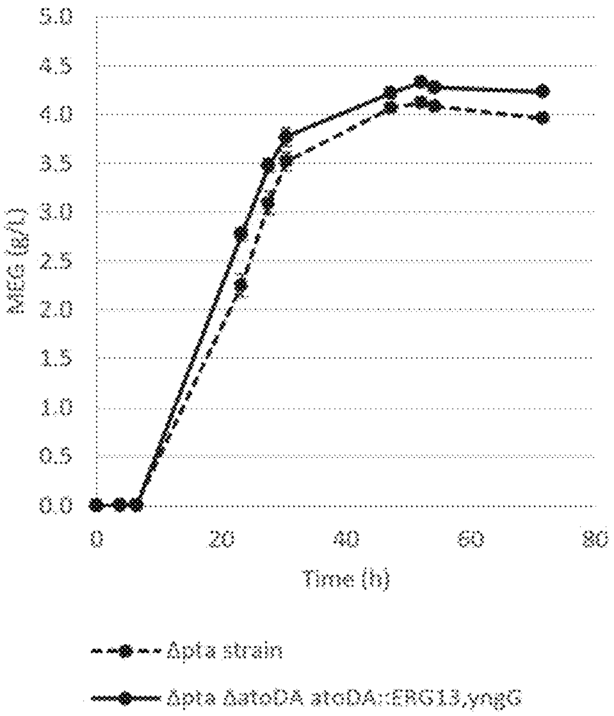
FIG. 14A-FIG. 14B illustrates the amounts of MEG detected for Δpta ΔatoDA atoDA::ERG13,ynG strain (FIG. 14A) and Δpta atoDA::ERG13,ynG ΔatoDA strain (FIG. 14B) relative to the Δpta strain.
Figure 14B:
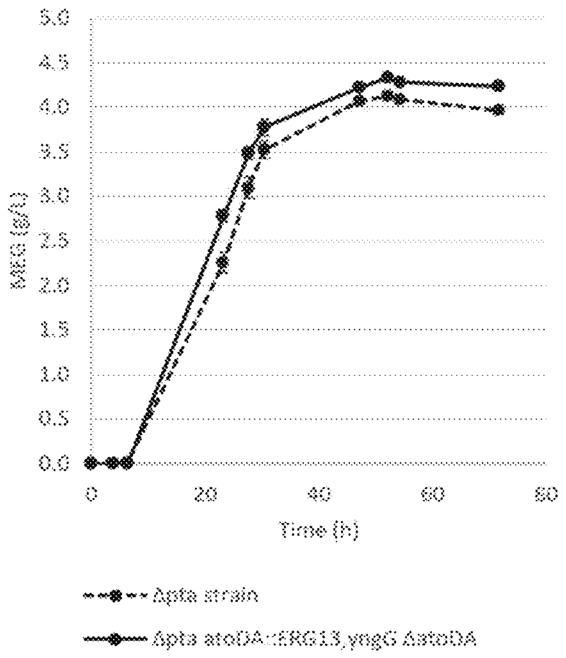

Higher amounts of MEG were detected for atoDA::ERG13,yngG ΔatoDA (FIG. 14B) strain in relation with the parental strain. Compare with FIG. 14A. The replacement of exogenous atoDA gene by ERG13 and yngG gene coupled with the deletion of endogenous atoDA resulted in an improved rate and amount of MEG production compared to the parental strain.

Example 7: Expression of Xylonate Dehydratase yagF and Pta Deletion in a MEG+Acetone Co-Producing Strain Via Xylonate Pathway The *E. coli* K12 strain MG1655 was used as host for the deletion of two genes that could divert the carbon flux from the MEG+Acetone pathway: aldA and xylA. The genes were successfully deleted and the deletions were confirmed by PCR and sequencing.

The next step was the integration of the MEG pathway. An operon expressed under control of the proD promoter containing xdh gene (xylose dehydrogenase) and fucO gene (glycoaldehyde reductase), encoding respectively for the first and last enzymes of the xylonate pathway, was integrated in the *E. coli* genome and an additional copy of xdh gene also under control of proD promoter was integrated in a different loci.

The next step was the integration of the acetone pathway via an operon in the *E. coli* genome. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated into the *E. coli* genome, generating the base strain. All the integrations were confirmed by PCR and sequencing.

The last step was the deletion of pta gene. This gene was successfully deleted and the deletion was confirmed by PCR and sequencing. Plasmid containing xylonate dehydratase yagF sequence was expressed under the control of the OXB11 promoter in a pZS* vector backbone. The plasmid was constructed using an In-fusion commercial kit and confirmed by sequencing. The confirmed plasmid was transformed in the base strain.

Colonies from transformations were inoculated in 5 mL of mineral media for pre-culture. After 16 hours of cultivation, the pre-culture was transferred to 100 ml of mineral media containing 12.85 g/L of xylose and 2.15 g/L of glucose. The flasks were incubated at 37° C., 250 rpm until complete consumption of xylose. The initial OD of the cultivation was 0.2.

Figure 15:
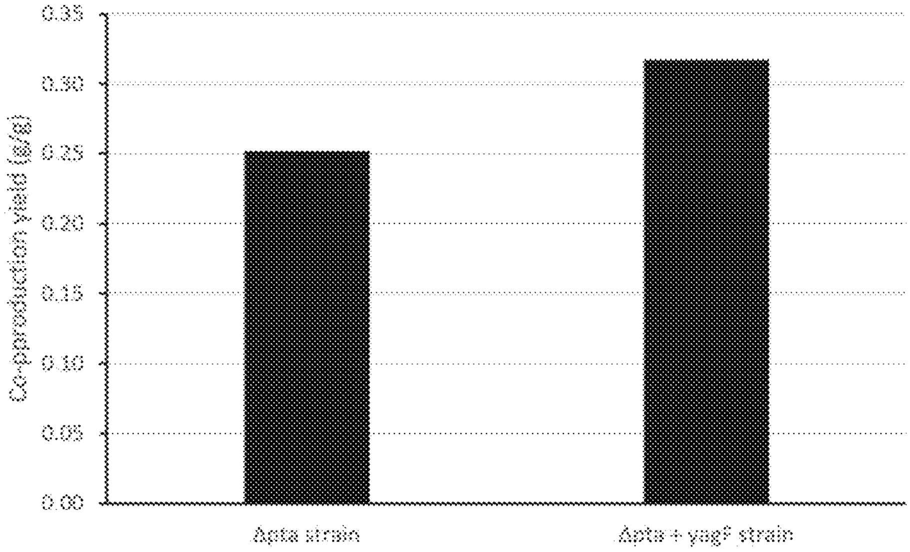
FIG. 15 illustrates the co-production of MEG and acetone for Δpta+yagF overexpression strain vs. the Δpta strain.

Higher amounts of MEG and acetone were detected for Δpta+yagF overexpression (FIG. 15) strain in relation with the Δpta strain. Expression of yagF resulted in an improvement at amount of MEG and acetone production compared to the parental strain.

Example 8: Deletion of mgsA in a MEG+Acetone Co-Producing Strain Via Xylonate Pathway The *E. coli* K12 strain MG1655 was used as host for the deletion of two genes that could divert the carbon flux from the MEG+C3 compound pathway: aldA and xylA. The deletions were confirmed by PCR and sequencing.

The next step was the integration of the MEG pathway. An operon expressed under the control of the proD promoter containing xdh gene (xylose dehydrogenase) and fucO gene (glycoaldehyde reductase), encoding respectively the first and last enzymes of the xylonate pathway, were integrated in a different loci.

The last step was the integration of the acetone pathway via an operon in the *E. coli* genome. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated into the *E. coli* genome, generating the base strain. All the integrations were confirmed by PCR and sequencing. The mgsA gene was deleted in the base strain and the deletion was confirmed by PCR and sequencing.

Colonies were inoculated in 5 mL of mineral media containing 12.85 g/L of xylose and 2.15 g/L of glucose for pre-culture. After 16 hours of cultivation, 5% of the pre-culture was transferred to 100 mL of fresh media. The flasks were incubated at 37° C., 250 rpm until complete consumption of glucose and xylose. The initial OD of the cultivation was 0.1. For all strains, xylose was fully consumed after 48 hours of cultivation.

Figure 16A:
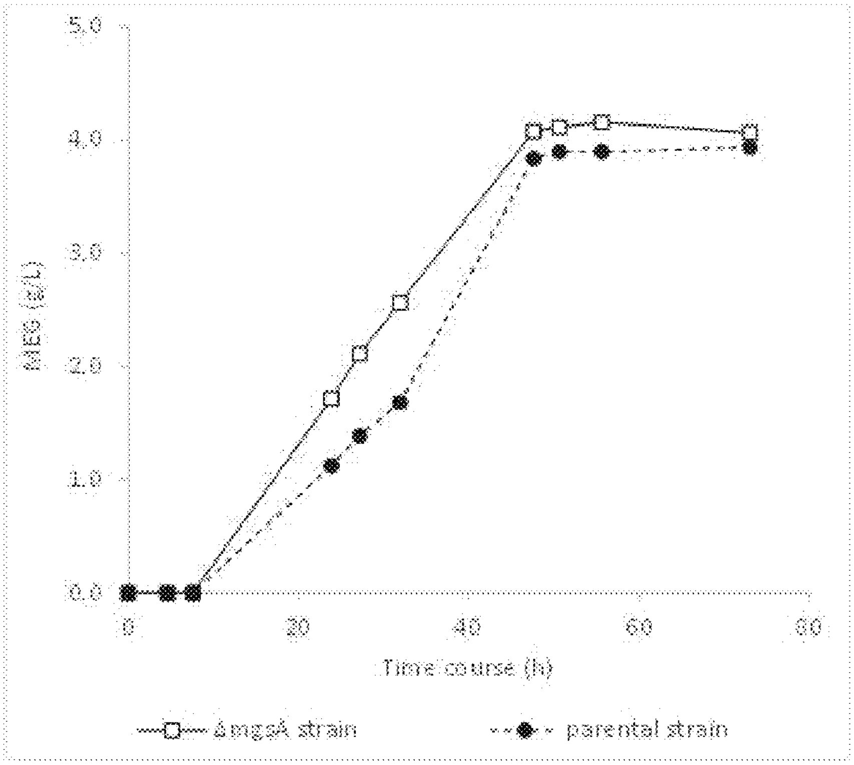
FIG. 16A-FIG. 16D illustrates the increased MEG production in the mgsA deleted strain vs the parental strain (FIG. 16A), the increased acetone production in the in the mgsA deleted strain vs the parental strain (FIG. 16B), the increased acetic acid production in the mgsA deleted strain vs the parental strain (FIG. 16C), and the decreased xylonic acid peak in the mgsA deleted strain vs the parental strain (FIG. 16D) as it pertains to Example 4 (xylonate pathway).
Figure 16B:
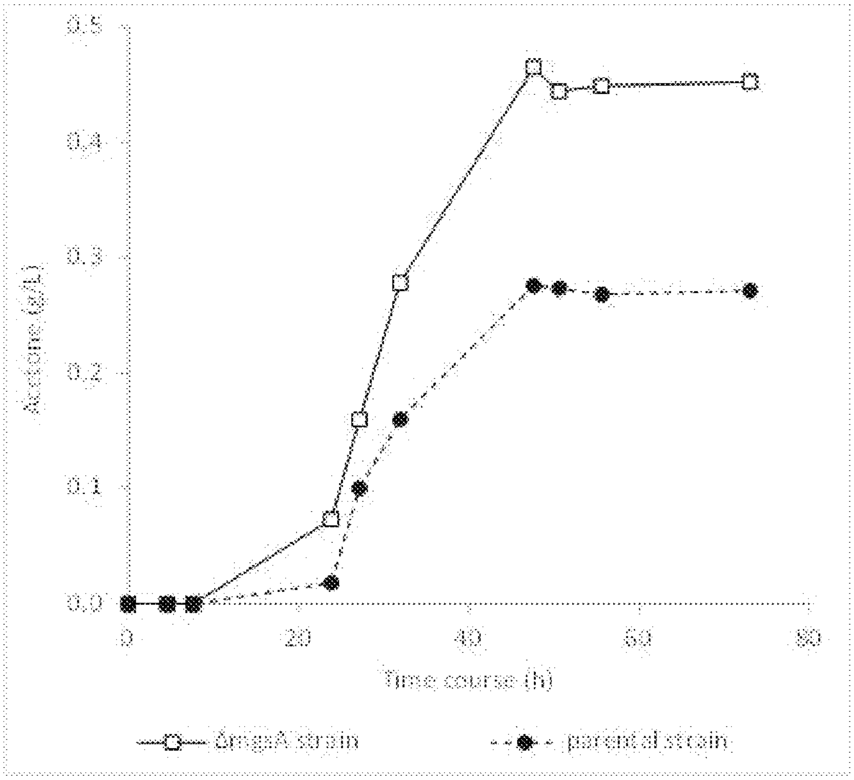
Figure 16C:
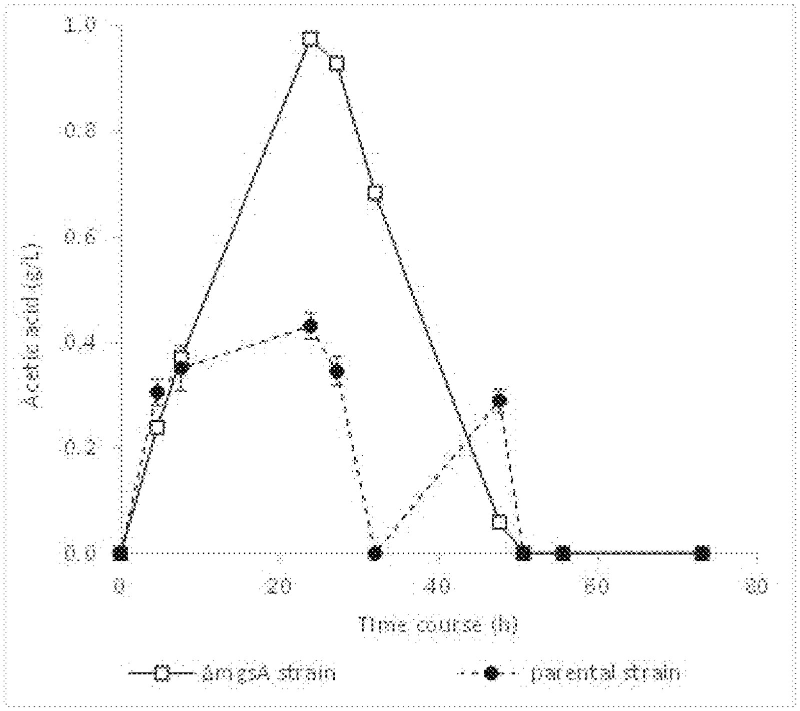
Figure 16D:
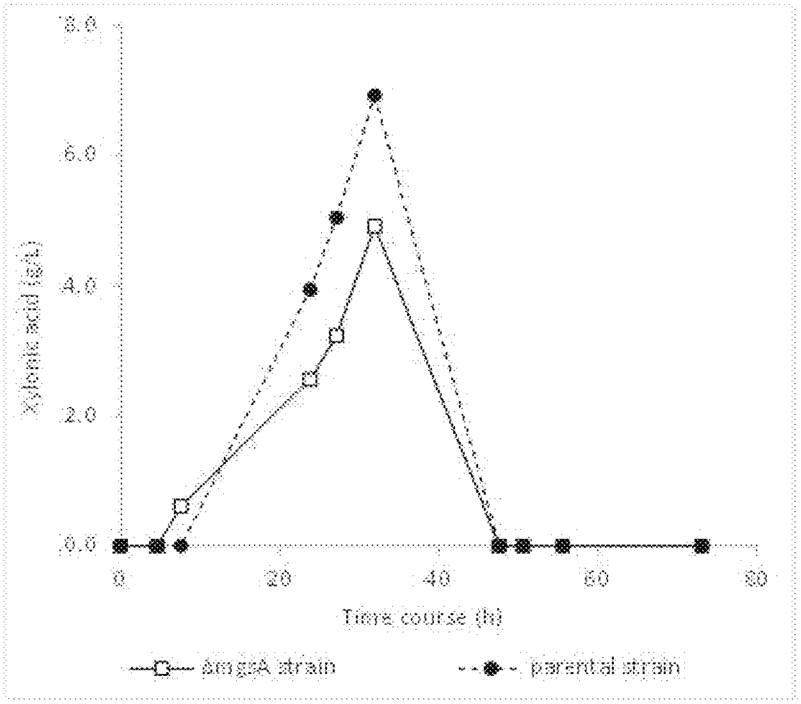

After 24 hours of cultivation approximately 1.1 g/L of MEG was detected in the parental strain while 1.7 g/L was detected at the same time point in the strain with mgsA deleted (FIG. 16A). The strains produced approximately 4 g/L of MEG in 48 h of cultivation while the total amount of acetone was increased 1.7 times (FIG. 16B), that was related to the higher production of acetic acid (FIG. 16C). The peak production of xylonic acid was decreased by 41% (FIG. 16D). The deletion of mgsA provided an improvement at velocity of co-production in relation with the parental strain.

Example 9: Deletion of mgsA in a MEG+Acetone Co-Producing Strain Via Xylulose Pathway The *E. coli* K12 strain MG1655 was used as host for the deletion of two genes that could divert the carbon flux from MEG+IPA pathway: aldA and xylB. The genes were successfully deleted and deletion confirmed by PCR and sequencing.

The next step was the integration of the MEG pathway. An operon expressed under control of the proD promoter containing khk-C gene (ketohexokinase), aldoB gene (fructose-1,6-bisphosphate aldolase) and fucO gene (glycoaldehyde reductase) was integrated in *E. coli* genome and an additional copy of khk-C and aldoB genes also under control of proD promoter was integrated in a different loci.

The last step was the integration of acetone pathway. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated in *E. coli* genome, generating the base strain. All the integrations were confirmed by PCR and sequencing. The mgsA gene were deleted in the base strain and the deletion was confirmed by PCR and sequencing.

Colonies were inoculated in 5 mL of mineral media containing 12.85 g/L of xylose and 2.15 g/L of glucose for pre-culture. After 16 hours of cultivation 5% of the pre-culture was transferred to 100 mL of fresh media. The flasks were incubated at 37° C., 250 rpm until complete consumption of glucose and xylose. The initial OD of the cultivation was 0.1. For all strains, xylose was fully consumed after 55 hours of cultivation.

Figure 17A:
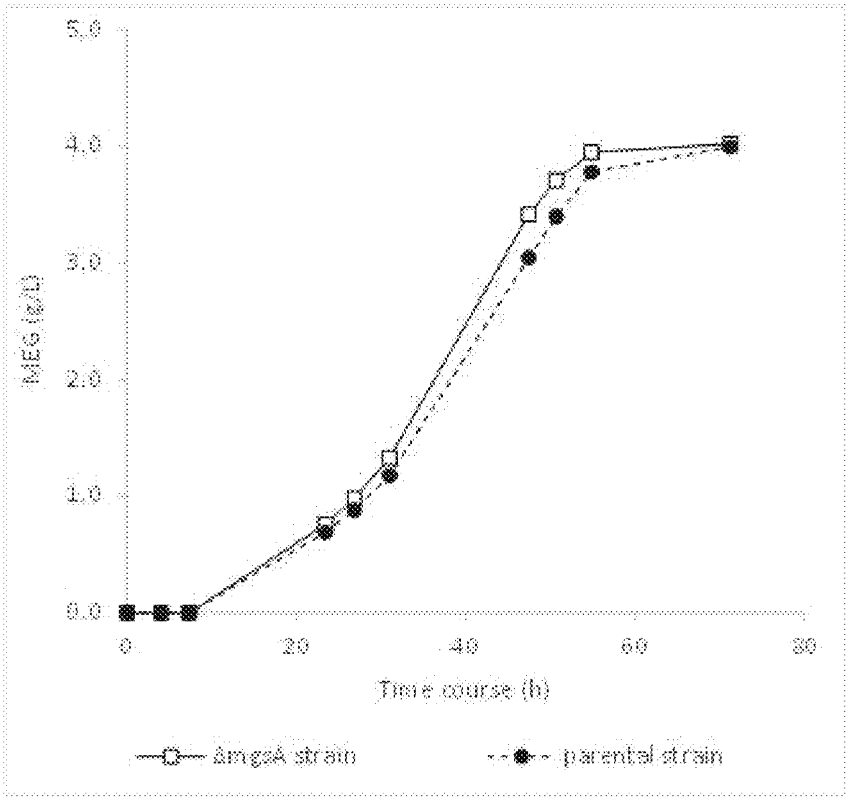
FIG. 17A-FIG. 17D illustrates the increased MEG production in the mgsA deleted strain vs the parental strain (FIG. 17A), the increased acetone production in the mgsA deleted strain vs the parental strain (FIG. 17B), the change in acetic acid production in the mgsA deleted strain vs the parental strain (FIG. 17C), and the xylulose accumulation in the mgsA deleted strain vs the parental strain (FIG. 17D) as it pertains to Example 5 (xylulose pathway).
Figure 17B:
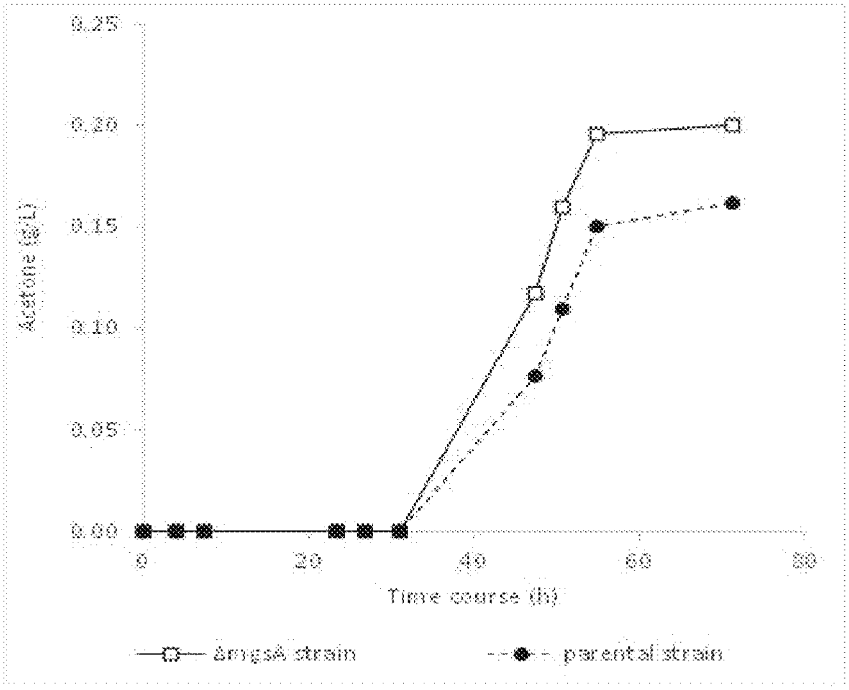
Figure 17C:
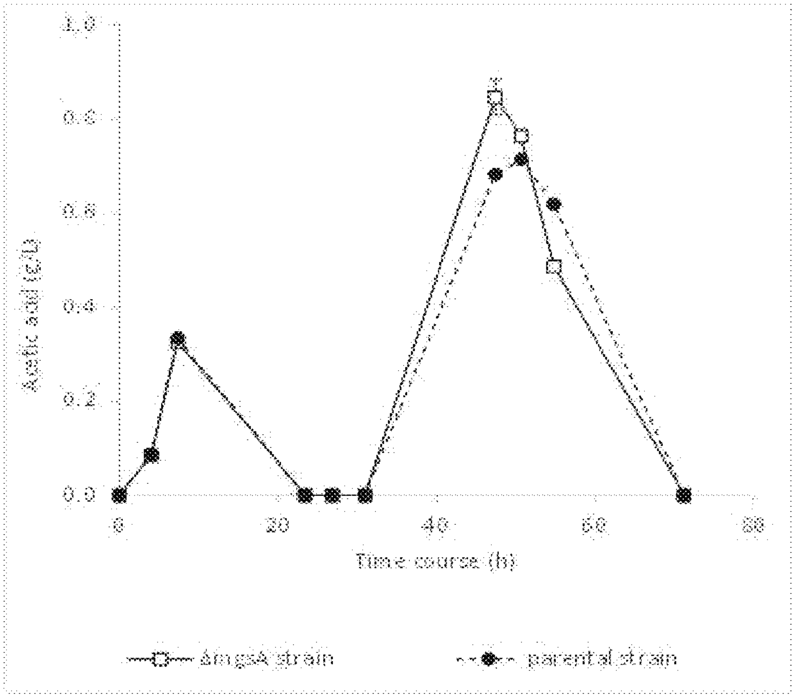
Figure 17D:
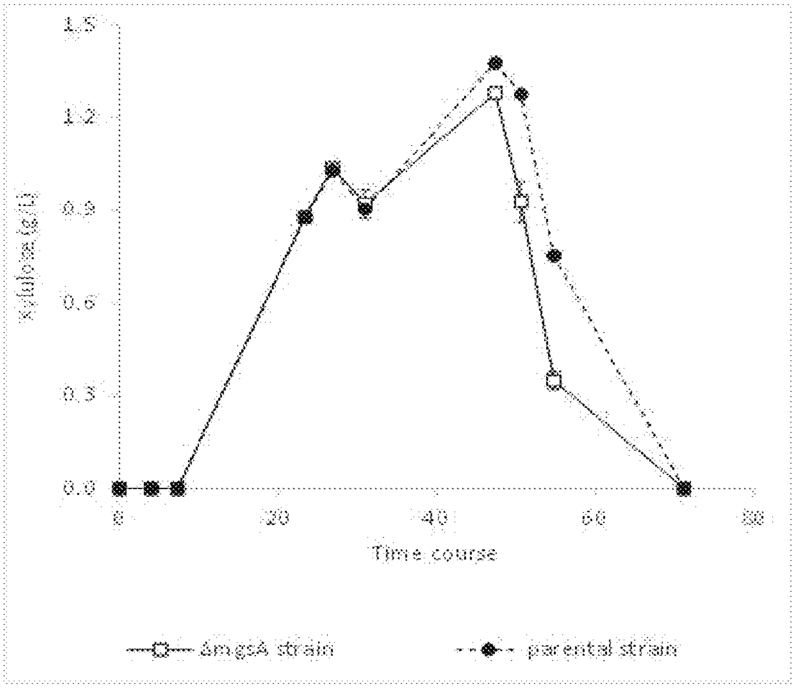

The strains produced approximately 4 g/L of MEG in 55 h of cultivation (FIG. 17A) while the total amount of acetone was increased 31% (FIG. 17B) with little effect on acetic acid production (FIG. 17C) and xylulose accumulation (FIG. 17D). The deletion of mgsA provided an improvement at velocity of co-production in relation with its parental strain.

Example 10: Deletion of Gcl in a MEG+Acetone Co-Producing Strain—Via Xylonate Pathway The *E. coli* K12 strain MG1655 was used as host for the deletion of two genes that could divert the carbon flux from MEG+IPA pathway: aldA and xylA. The genes were successfully deleted and the deletions were confirmed by PCR and sequencing.

The next step was the integration of the MEG pathway. An operon expressed under control of the proD promoter containing xdh gene (xylose dehydrogenase) and fucO gene (glycoaldehyde reductase), encoding respectively for the first and last enzymes of the xylonate pathway, was integrated in *E. coli* genome and an additional copy of xdh gene also under control of proD promoter was integrated in a different loci.

The last step was the integration of acetone pathway. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated in *E. coli* genome, generating the base strain. All the integrations were confirmed by PCR and sequencing. The gcl gene were deleted in the base strain and the deletion was confirmed by PCR and sequencing.

Colonies were inoculated in 5 mL of mineral media containing 12.85 g/L of xylose and 2.15 g/L of glucose for pre-culture. After 16 hours of cultivation 5% of the pre-culture was transferred to 100 mL of fresh media. The flasks were incubated at 37° C., 250 rpm until complete consumption of glucose and xylose. The initial OD of the cultivation was 0.1. For all strains, xylose was fully consumed after 48 hours of cultivation.

Figure 18A:
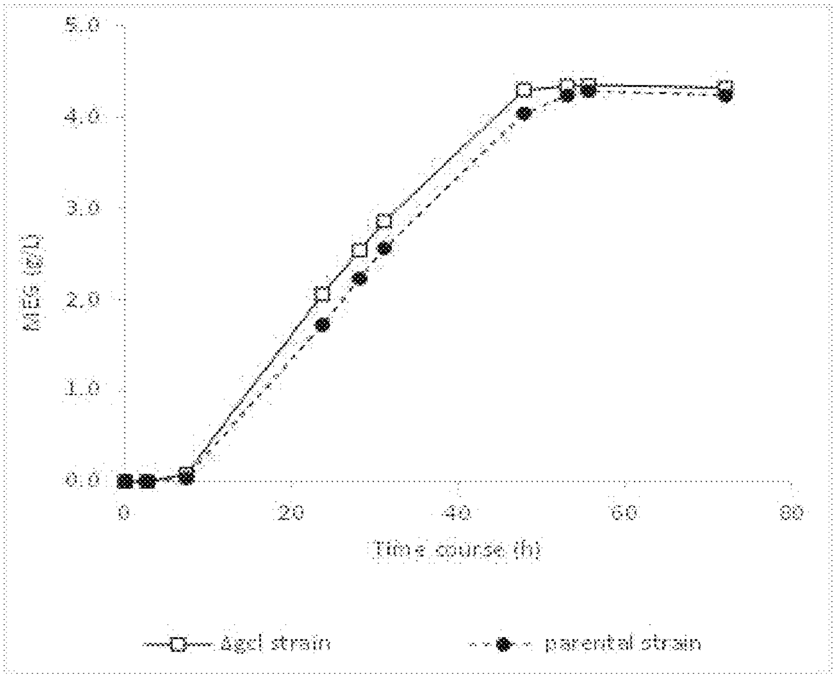
FIG. 18A-FIG. 18D illustrates the increased MEG production in the gcl deleted strain vs the parental strain (FIG. 18A), the increased acetone production in the gcl deleted strain vs the parental strain (FIG. 18B), the increase in acetic acid production in the gcl deleted strain vs the parental strain (FIG. 18C), and the decreased xylonic acid peak in the gcl deleted strain vs the parental strain (FIG. 18D) as it pertains to Example 6 (xylonate pathway).
Figure 18B:
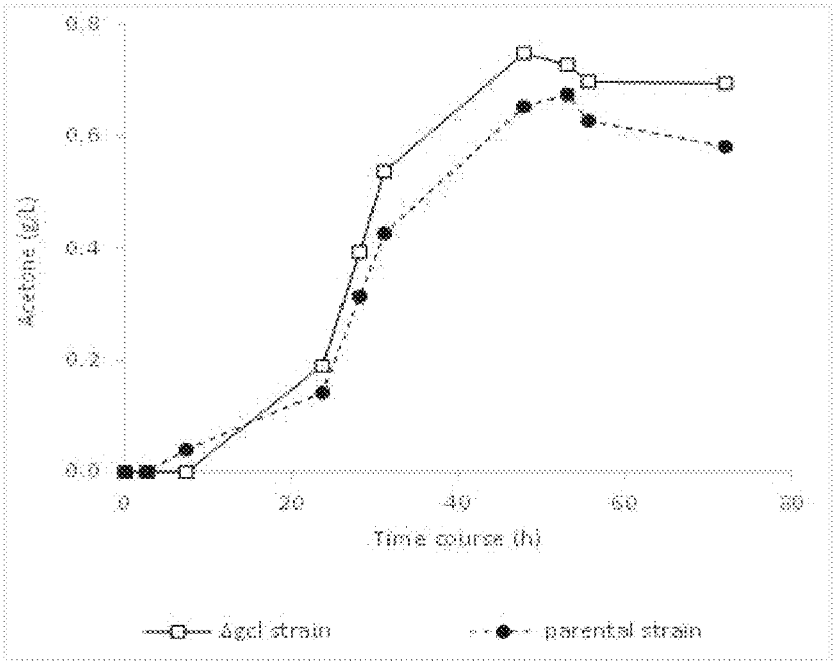
Figure 18C:
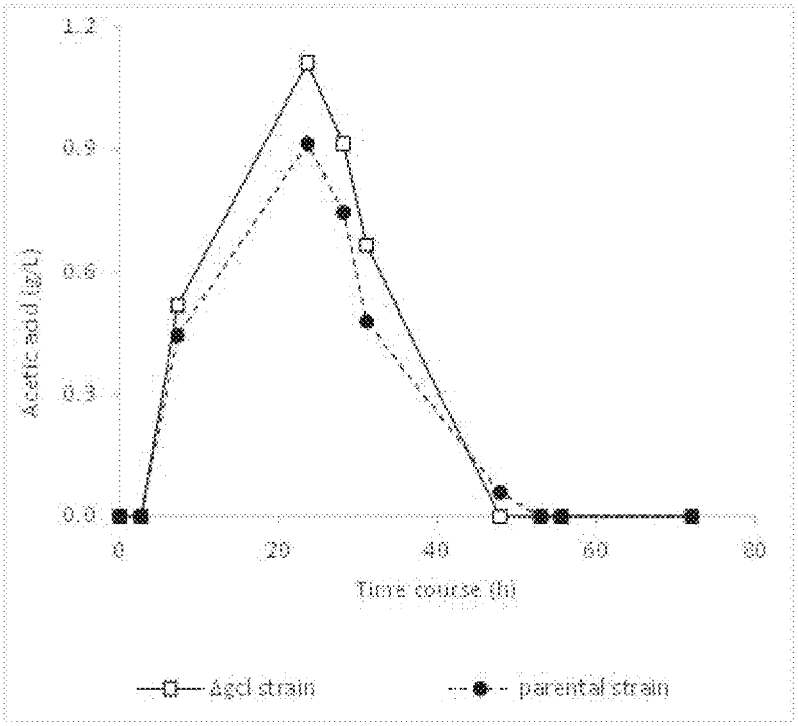
Figure 18D:
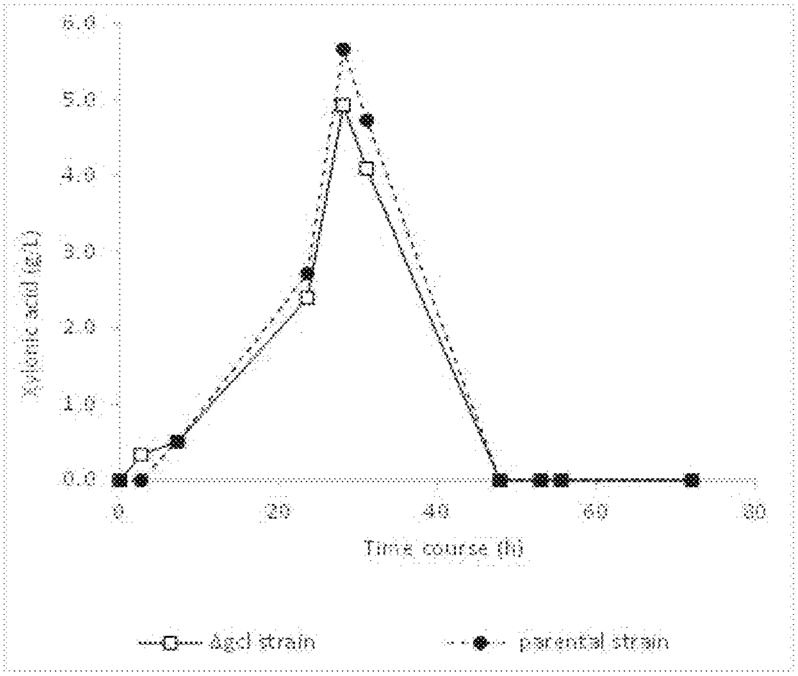

After 24 hours of cultivation approximately 1.7 g/L of MEG could be detected in the parental strain while 2.1 g/L could be detected at the same time point in the strain with gcl deleted (FIG. 18A). The strains produced approximately 4 g/L of MEG in 48 h of cultivation while the total amount of acetone was increased by 15% (FIG. 18B), probably related to the higher production of acetic acid (FIG. 18C). The peak production of xylonic acid was decreased in 15% (FIG. 18D). The deletion of gcl provided an improvement at velocity of co-production in relation with its parental strain.

Example 11: Deletion of ackA in a MEG+Acetone Co-Producing Strain Via Xylulose Pathway The *E. coli* K12 strain MG1655 was used as host for the deletion of two genes that could divert the carbon flux from the MEG+Acetone pathway: aldA and xylB. The genes were successfully deleted and the deletions were confirmed by PCR and sequencing.

The next step was the integration of the MEG pathway. An operon expressed under the control of the proD promoter containing khk-C gene (ketohexokinase), aldoB gene (fructose-1,6-bisphosphate aldolase), and fucO gene (glycoaldehyde reductase) was integrated in the *E. coli* genome and an additional copy of khk-C and aldoB genes also under the control of the proD promoter were integrated in a different locus.

The last step was the integration of the acetone pathway via an operon in the *E. coli* genome. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated into the *E. coli* genome, generating the base strain. All the integrations were confirmed by PCR and sequencing. The base strain was used as the host strain for the deletion of two genes related to the acetate pathway: pta and ackA. The genes were successfully deleted and the deletion was confirmed by sequencing.

Colonies of the deleted strains were inoculated in 5 mL of mineral media for pre-culture. After 16 hours of cultivation, the pre-culture was transferred to 100 ml of mineral media containing 12.85 g/L of xylose and 2.15 g/L of glucose. The flasks were incubated at 37° C., 250 rpm until complete consumption of xylose. The initial OD of the cultivation was 0.2.

Figure 19A:
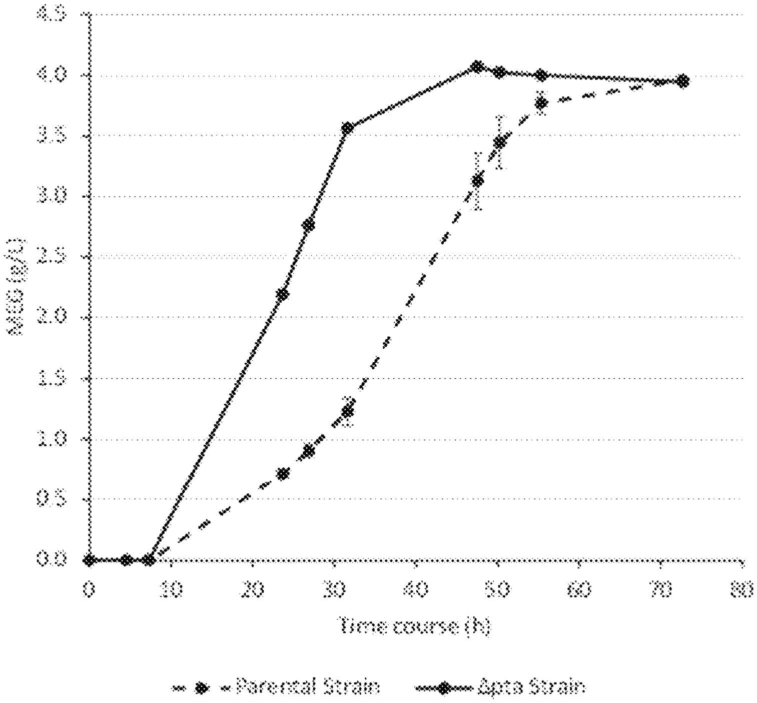
FIG. 19A-FIG. 19B illustrates the increased MEG production in the Δpta strain vs the parental strain (FIG. 19A), and the increased MEG production in the ΔackA strain vs the parental strain (FIG. 19B).
Figure 19B:
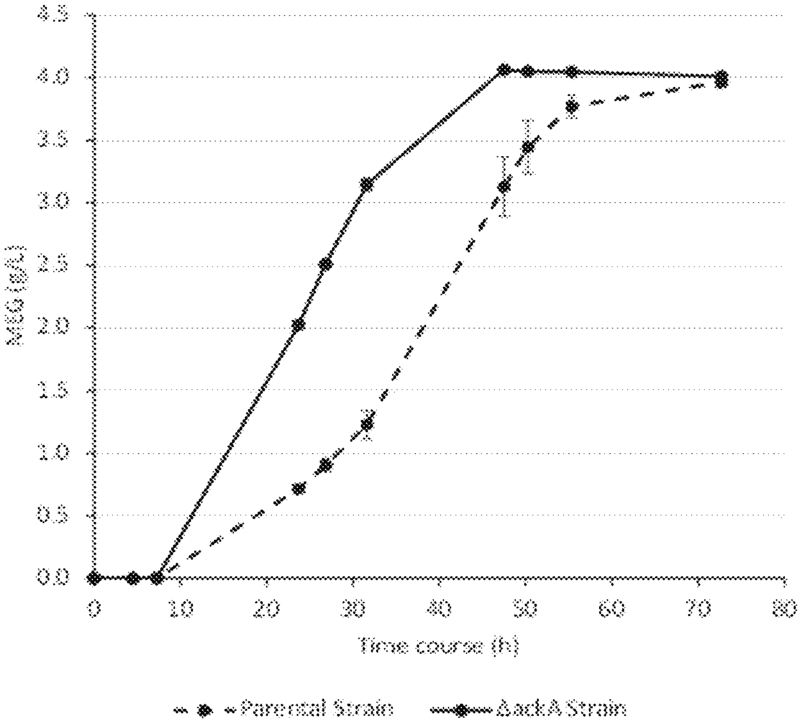

Higher amounts of MEG were detected for Δpta (FIG. 19A) and ΔackA (FIG. 19B) strains in relation with the parental strain. The deletion of pta or ackA resulted in an improvement at velocity of MEG production in relation with the parental strain.

Example 12: Deletion of arcA in a MEG+Acetone Co-Producing Strain Via Xylulose Pathway The *E. coli* K12 strain MG1655 was used as host for the deletion of two genes that could divert the carbon flux from the MEG+Acetone pathway: aldA and xylB. The genes were successfully deleted and the deletions were confirmed by PCR and sequencing.

The next step was the integration of the MEG pathway. An operon expressed under the control of the proD promoter containing khk-C gene (ketohexokinase), aldoB gene (fructose-1,6-bisphosphate aldolase), and fucO gene (glycoaldehyde reductase) was integrated in the *E. coli* genome and an additional copy of khk-C and aldoB genes also under the control of the proD promoter were integrated in a different locus.

The last step was the integration of the acetone pathway via an operon in the *E. coli* genome. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated into the *E. coli* genome, generating the base strain. All the integrations were confirmed by PCR and sequencing. The base strain was used as the host strain for the deletion of arcA gene, which deletion is related to induction of TCA cycle genes and higher expression of acs gene when compared to WT. This gene was successfully deleted and the deletion was confirmed by PCR and sequencing.

Colonies of the deleted strains were inoculated in 5 mL of mineral media for pre-culture. After 16 hours of cultivation, the pre-culture was transferred to 100 ml of mineral media containing 12.85 g/L of xylose and 2.15 g/L of glucose. The flasks were incubated at 37° C., 250 rpm until complete consumption of xylose. The initial OD of the cultivation was 0.2.

Figure 20A:
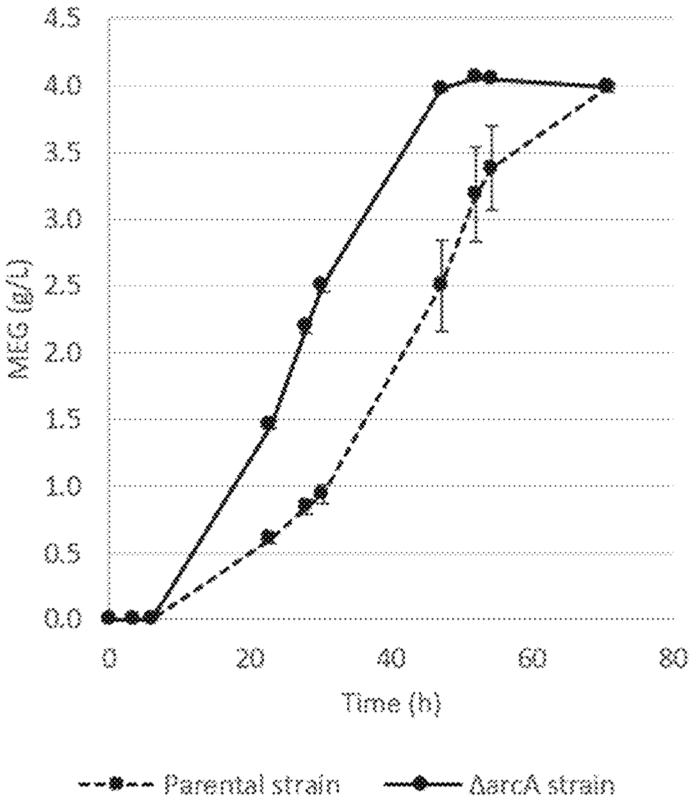
FIG. 20A-FIG. 20B illustrate the higher productivity of MEG (FIG. 20A) and acetone (FIG. 20B) for ΔarcA compared to the parental strain.
Figure 20B:
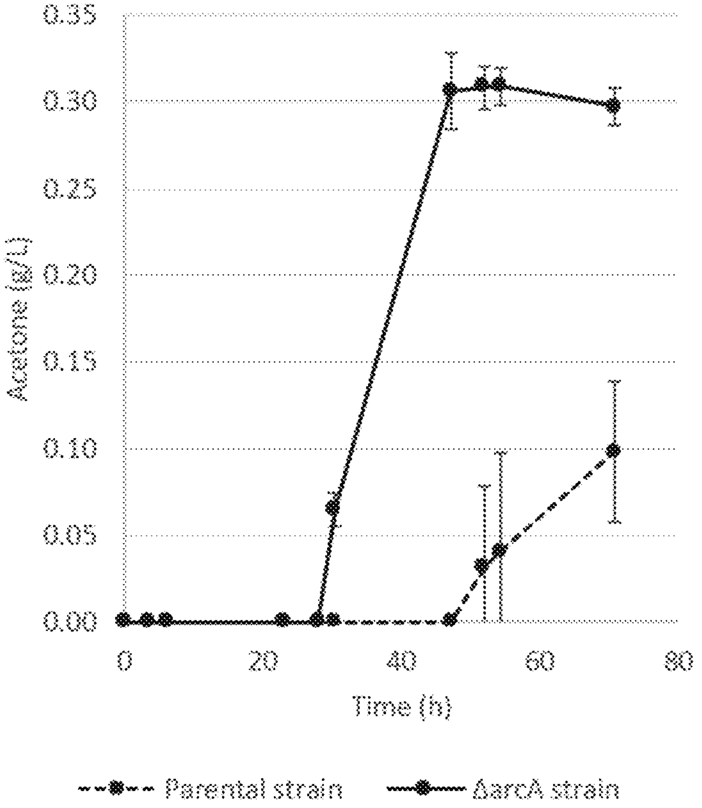

Higher productivity of MEG (FIG. 20A) and higher productivity and titer of acetone (FIG. 20B) were detected for ΔarcA strain in relation with the parental strain. The deletion of arcA resulted in an improvement at velocity of MEG production and improvement at velocity and amount of acetone production in relation with the parental strain.

Example 13: Deletion of arcA and Pka in a MEG+Acetone Co-Producing Strain Via Xylonate Pathway and with Deletion of Pta The *E. coli* K12 strain MG1655 was used as host for the deletion of two genes that could divert the carbon flux from the MEG+Acetone pathway: aldA and xylA. The genes were successfully deleted and the deletions were confirmed by PCR and sequencing.

The next step was the integration of the MEG pathway. An operon expressed under control of the proD promoter containing xdh gene (xylose dehydrogenase) and fucO gene (glycoaldehyde reductase), encoding respectively for the first and last enzymes of the xylonate pathway, was integrated in the *E. coli* genome and an additional copy of xdh gene also under control of proD promoter was integrated in a different loci.

The next step was the integration of the acetone pathway via an operon in the *E. coli* genome. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated into the *E. coli* genome, generating the base strain. All the integrations were confirmed by PCR and sequencing.

The last step was the deletion of pta gene. This gene was successfully deleted and the deletion was confirmed by PCR and sequencing. The base strain was used as the host strain for the deletion of two genes related to the acetate pathway: pka and arcA. The genes were successfully deleted and the deletion was confirmed by sequencing.

Colonies of the deleted strains were inoculated in 5 mL of mineral media for pre-culture. After 16 hours of cultivation, the pre-culture was transferred to 100 ml of mineral media containing 12.85 g/L of xylose and 2.15 g/L of glucose. The flasks were incubated at 37° C., 250 rpm until complete consumption of xylose. The initial OD of the cultivation was 0.2.

Figure 21A:
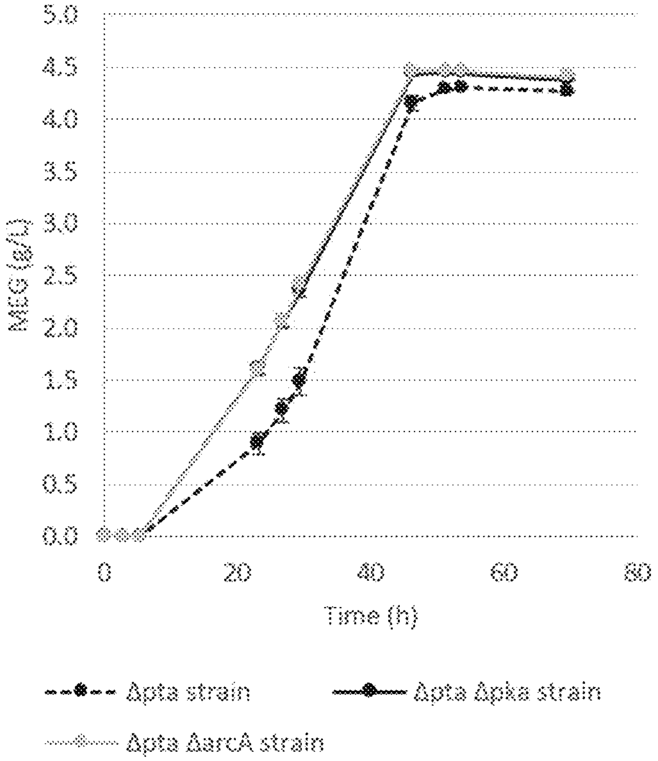
FIG. 21A-FIG. 21B illustrate the higher amounts of MEG (FIG. 21A) and acetone (FIG. 21B) for ΔptaΔarcA and ΔptaΔpka compared to the Δpta strain.
Figure 21B:
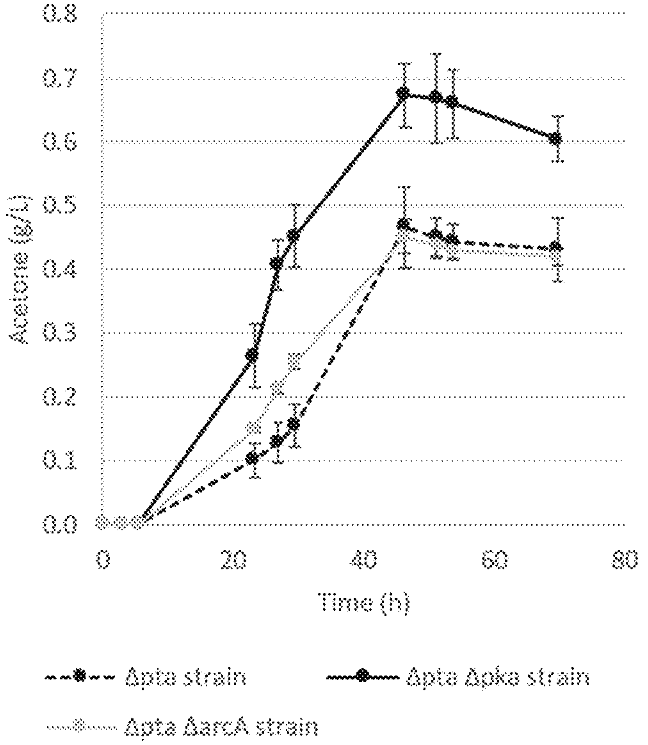

Higher amounts of MEG (FIG. 21A) and acetone (FIG. 21B) were detected for ΔptaΔarcA and ΔptaΔpka strain in relation with the Δpta strain. The deletion of arcA and pka resulted in an improvement at velocity and amount of MEG and acetone production in relation with the parental strain.

Example 14: Expression of Heterologous Xylolactonase in MEG+Acetone Co-Producing Strain—Via Xylonate Pathway The *E. coli* K12 strain MG1655 was used as the host for the deletion of two genes that could divert the carbon flux from MEG+Acetone pathway: aldA and xylA. The genes were successfully deleted and the deletions were confirmed by PCR and sequencing.

The next step was the integration of the MEG pathway. An operon expressed under control of the proD promoter containing xdh gene (xylose dehydrogenase) and fucO gene (glycoaldehyde reductase), encoding respectively for the first and last enzymes of the xylonate pathway, was integrated in the *E. coli* genome and an additional copy of xdh gene also under control of proD promoter was integrated in a different loci.

The last step was the integration of the acetone pathway. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated in *E. coli* genome, generating the base strain. All the integrations were confirmed by PCR and sequencing. Plasmids containing different sequences encoding the second enzyme of the xylonate pathway (xylolactonase), were expressed under the control of the OXB11 promoter in a pZS* vector backbone. The plasmids were constructed using an In-fusion commercial kit and confirmed by sequencing. The confirmed plasmids were transformed in the base strain. Colonies from transformations were inoculated in 5 mL of mineral media containing 12.85 g/L of xylose and 2.15 g/L of glucose for pre-culture. After 16 hours of cultivation 5% of the pre-culture was transferred to 100 mL of fresh media. The flasks were incubated at 37° C., 250 rpm until complete consumption of glucose and xylose. The initial OD of the cultivation was 0.1. For all strains, xylose was fully consumed after 48 hours of cultivation.

Figure 22A:
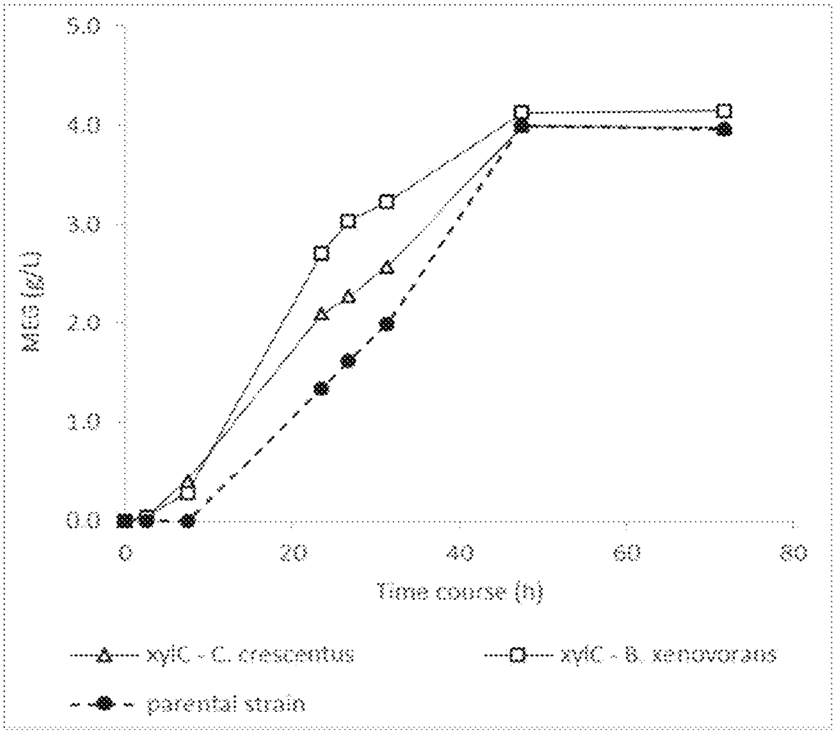
FIG. 22A-FIG. 22D illustrates the increased MEG production in the strains harboring xylonolactonase expressed in plasmids vs the parental strain (FIG. 22A), the increased acetone production in the strains harboring xylonolactonase expressed in plasmids vs the parental strain (FIG. 22B), the increased production of acetic acid in the strains harboring xylonolactonase expressed in plasmids vs the parental strain (FIG. 22C), and the decrease in the peak production of xylonic acid in the strains harboring xylonolactonase expressed in plasmids vs the parental strain (FIG. 22D).
Figure 22B:
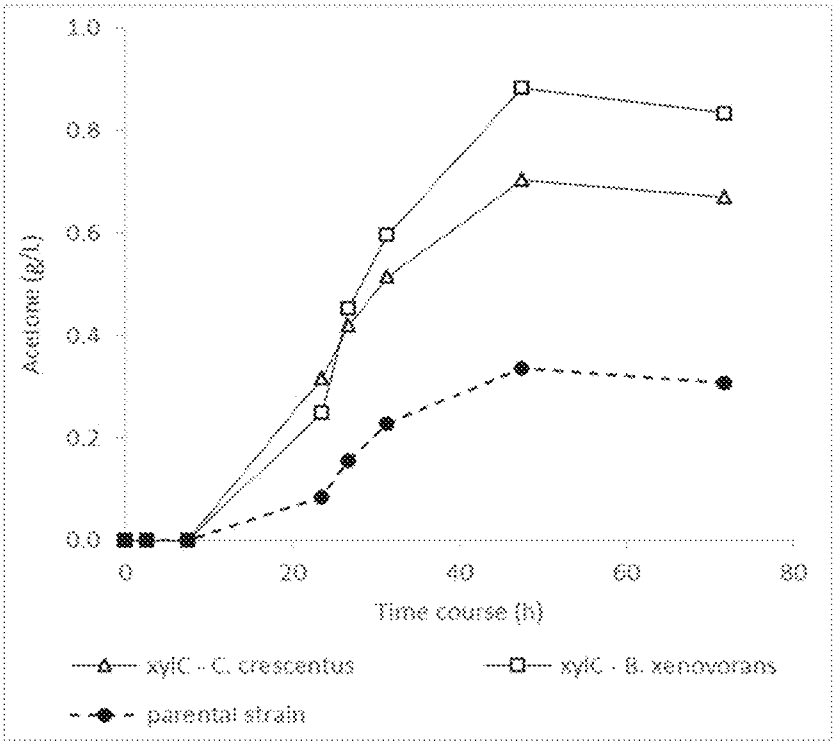
Figure 22C:
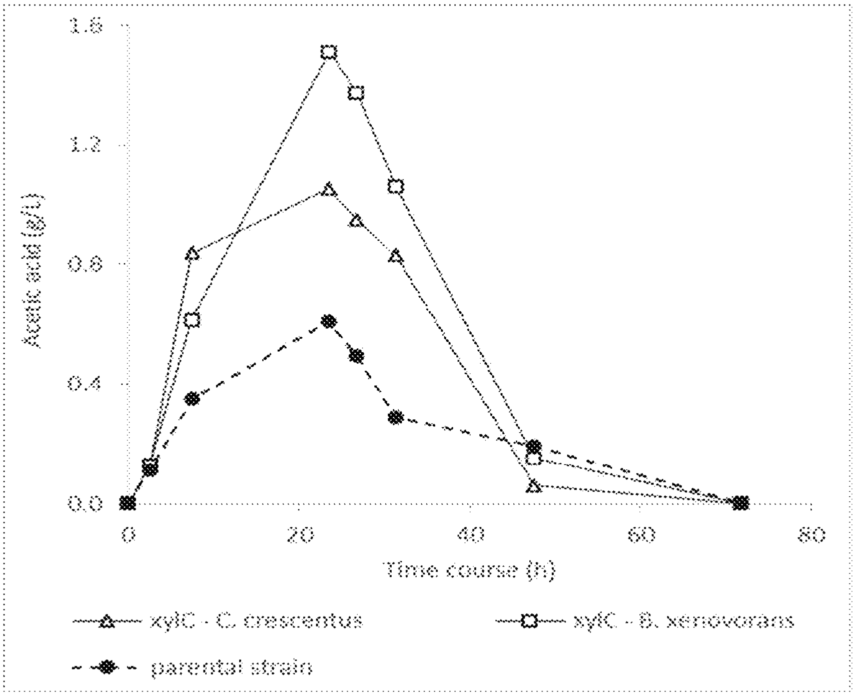
Figure 22D:
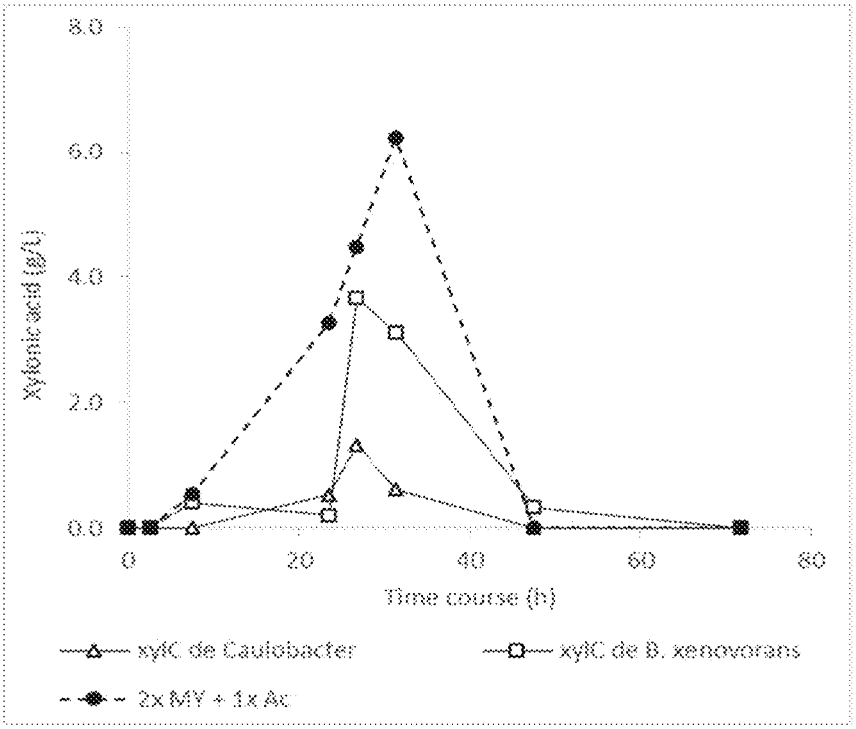

After 24 hours of cultivation, approximately 1.3 g/L of MEG could be detected in the parental strain while 2.1 up to 2.7 g/L could be detected at the same time in strains harboring xylolactonase expressed in plasmids (FIG. 22A). All the strains produced approximately 4 g/L of MEG in 48 h of cultivation while the total amount of acetone was increased 2.1 to 2.6 times (FIG. 22B), probably related to the higher production of acetic acid (FIG. 22C). The peak production of xylonic acid was decreased up to 4.7 times (FIG. 22D). The expression of xylolactonase provided an improvement at velocity of co-production in relation with its parental strain.

Example 15: Expression of Heterologous Xylonate Dehydratase in MEG+Acetone Co-Producing Strain—Via Xylonate Pathway The *E. coli* K12 strain MG1655 was used as the host for the deletion of two genes that could divert the carbon flux from MEG+Acetone pathway: aldA and xylA. The genes were successfully deleted and the deletions were confirmed by PCR and sequencing.

The next step was the integration of the MEG pathway. An operon expressed under control of the proD promoter containing xdh gene (xylose dehydrogenase) and fucO gene (glycoaldehyde reductase), encoding respectively for the first and last enzymes of the xylonate pathway, was integrated in the *E. coli* genome and an additional copy of xdh gene also under control of proD promoter was integrated in a different loci.

The last step was the integration of acetone pathway. An operon expressed under control of OXB11 promoter containing thlA gene (acetoacetyl-CoA thiolase); atoAD genes (acetate:acetoacetyl-CoA transferase) and adc gene (acetoacetate decarboxylase) was integrated in the *E. coli* genome, generating the base strain. All the integrations were confirmed by PCR and sequencing. Plasmids containing different sequences encoding the third enzyme of the xylonate pathway (xylonate dehydratase), were expressed under the control of the OXB11 promoter in a pZS* vector backbone. The plasmids were constructed using an In-fusion commercial kit and confirmed by sequencing. The confirmed plasmids were transformed in the base strain. Colonies from transformations were inoculated in 5 mL of mineral media containing 12.85 g/L of xylose and 2.15 g/L of glucose for pre-culture. After 16 hours of cultivation 5% of the pre-culture was transferred to 100 mL of fresh media. The flasks were incubated at 37° C., 250 rpm until complete consumption of glucose and xylose. The initial OD of the cultivation was 0.1. For all strains, xylose was fully consumed after 48 hours of cultivation.

Figure 23A:
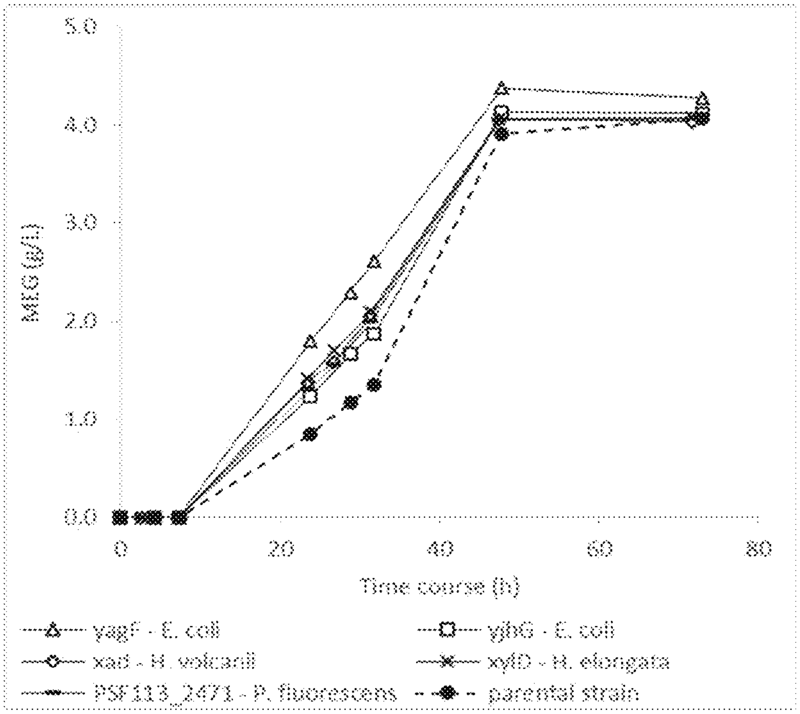
FIG. 23A-FIG. 23D illustrates the increased MEG production in the strains harboring xylonolactonase expressed in plasmids vs the parental strain (FIG. 23A), the increased acetone production in the strains harboring xylonolactonase expressed in plasmids vs the parental strain (FIG. 23B), the increased production of acetic acid in the strains harboring xylonolactonase expressed in plasmids vs the parental strain (FIG. 23C), and the decrease in the peak production of xylonic acid in the strains harboring xylonolactonase expressed in plasmids vs the parental strain (FIG. 23D).
Figure 23B:
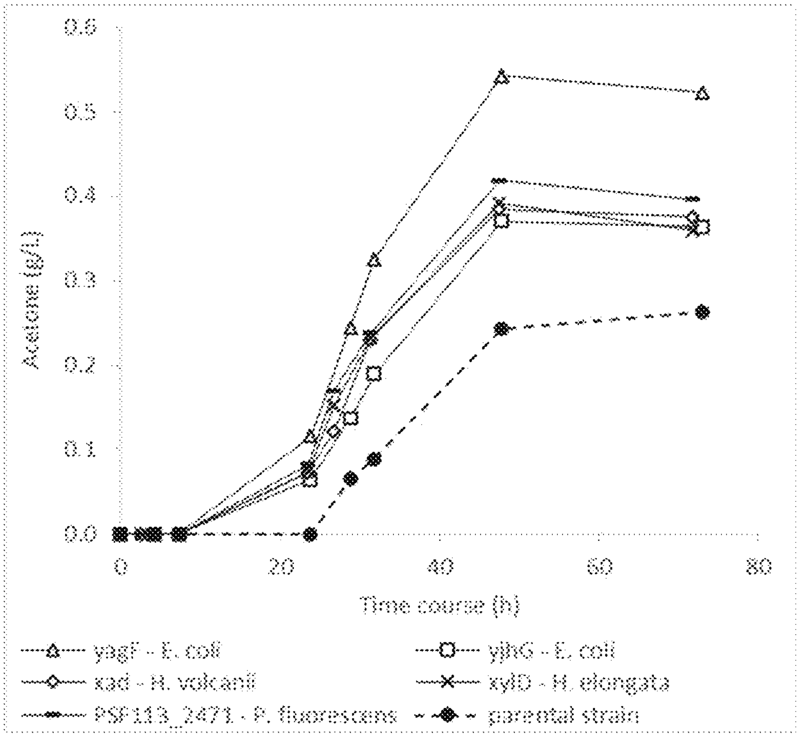
Figure 23C:
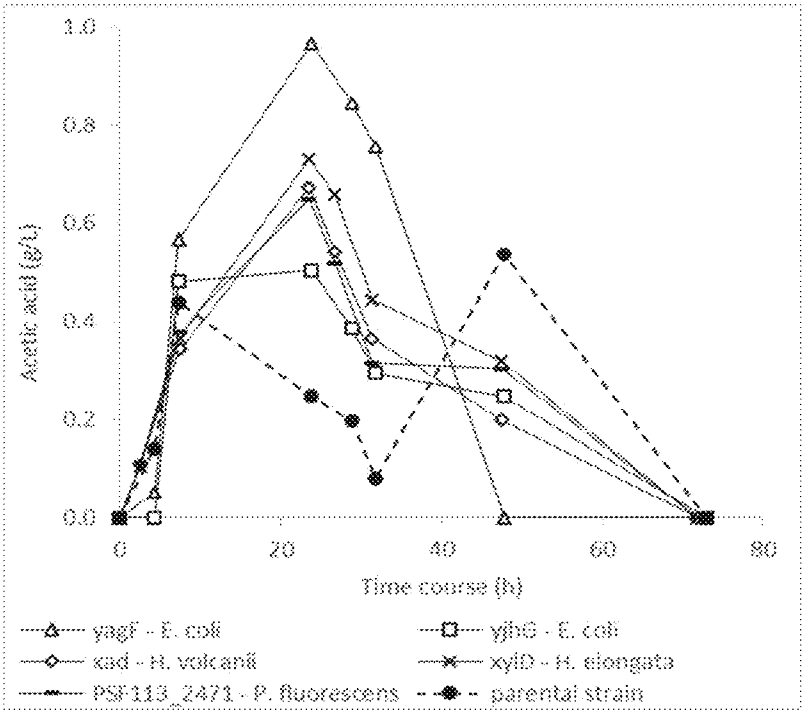
Figure 23D:
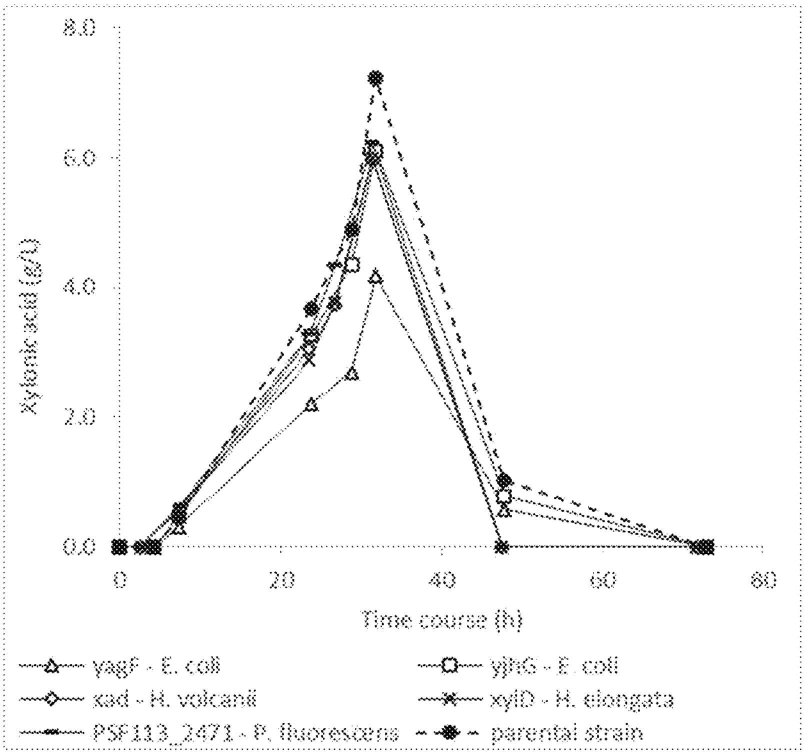

After 24 hours of cultivation approximately 0.8 g/L of MEG could be detected in the parental strain while 1.3 up to 1.8 g/L could be detected at the same time in strains harboring xylonate dehydrataseexpressed in plasmids (FIG. 23A). All the strains produced approximately 4 g/L of MEG in 48 h of cultivation while the total amount of acetone was increased 1.5 to 2.2 times (FIG. 23B), probably related to the higher production of acetic acid (FIG. 23C). The peak production of xylonic acid was decreased up to 70% (FIG. 23D). The expression of xylonate dehydratase provided an improvement at velocity of co-production in relation with its parental strain.

ENUMERATED EMBODIMENTS

Embodiment 1. A method of modulating the flux of carbon through the monoethylene glycol (MEG) biosynthesis pathway and one or more C3 compound biosynthesis pathways, the method comprising:

modifying a microbe coproducing MEG and one or more C3 compounds by:

i. disrupting one or more nucleic acid sequences encoding methylglyoxal synthase (mgsA), and/or ii disrupting one or more nucleic acid sequences encoding glyoxylate carboligase (gcl);

wherein the MEG and/or the one or more C3 compounds is produced at a faster rate or exhibits an increased yield and/or titer; as compared to a microbe lacking a disruption of one or more nucleic acid sequences encoding methylglyoxal synthases and/or glyoxylate carboligases.

Embodiment 2. The method of Embodiment 1, wherein the C3 compounds are selected from acetone, isopropanol, and propene.

Embodiment 3. The method of Embodiment 1, wherein the disrupting is selected from a deletion, a point mutation, a substitution, an insertion, or a frameshift.

Embodiment 4. The method of Embodiment 3, wherein the deletion comprises the deletion of the one or more nucleic acid sequences.

Embodiment 5. The method of Embodiment 1, wherein translation of the one or more nucleic acid sequences encoding methylglyoxal synthase and/or the one or more nucleic acid sequences encoding glyoxylate carboligase is reduced by at least 50%.

Embodiment 6. The method of Embodiment 1, wherein the MEG and/or the one or more C3 compounds is produced at a faster rate and an increased yield or titer.

Embodiment 7. The method of Embodiment 1, wherein the one or more nucleic acid sequences encoding methylglyoxal synthase and the one or more nucleic acid sequences encoding glyoxylate carboligase are disrupted.

Embodiment 8. The method of Embodiment 1, wherein the microbe is a bacterium or a fungus.

Embodiment 9. The method of Embodiment 8, wherein the microbe is selected from one of the following genera: *Escherichia, Corynebacterium, Saccharomyces, Lactobacillus, Bacillus, Clostridium, Pichia*, and *Aspergillus*.

Embodiment 10. The method of Embodiment 8, wherein the bacterium is an *Escherichia coli*.

Embodiment 11. The method of Embodiment 1, wherein the MEG exhibits an increased yield or titer.

Embodiment 12. The method of Embodiment 11, wherein the increased yield or titer is an increase of at least 2%.

Embodiment 13. The method of Embodiment 11, wherein the increased yield or titer is an increase of at least 15%.

Embodiment 14. The method of Embodiment 1, wherein the MEG is produced at a faster rate.

Embodiment 15. The method of Embodiment 14, wherein the faster rate is an increase of at least 2%.

Embodiment 16. The method of Embodiment 14, wherein the faster rate is an increase of at least 15%.

Embodiment 17. The method of Embodiment 1, wherein the one or more C3 compounds is acetone.

Embodiment 18. The method of Embodiment 17, wherein the acetone exhibits an increased yield or titer.

Embodiment 19. The method of Embodiment 18, wherein the increased yield or titer is an increase of at least 2%.

Embodiment 20. The method of Embodiment 18, wherein the increased yield or titer is an increase of at least 15%.

Embodiment 21. The method of Embodiment 17, wherein the acetone is produced at a faster rate.

Embodiment 22. The method of Embodiment 21, wherein the faster rate is an increase of at least 2%.

Embodiment 23. The method of Embodiment 21, wherein the faster rate is an increase of at least 15%.

Embodiment 24. The method of Embodiment 1, wherein (i) the MEG exhibits an increased yield or titer of at least 2%, and (ii) the one or more C3 compounds exhibits an increased yield or titer of at least 2%.

Embodiment 25. The method of Embodiment 1, wherein (i) the MEG exhibits an increased yield or titer of at least 15%, and (ii) the one or more C3 compounds exhibits an increased yield or titer of at least 15%.

Embodiment 26. The method of Embodiment 1, wherein (i) the rate of MEG production exhibits an increase of at least 2%, and (ii) the rate of the one or more C3 compound production exhibits an increase of at least 2%.

Embodiment 27. The method of Embodiment 1, wherein (i) the rate of MEG production exhibits an increase of at least 15%, and (ii) the rate of the one or more C3 compound production exhibits an increase of at least 15%.

Embodiment 28. The method of Embodiment 1, wherein the microbe utilizes xylose, glucose and/or a mixture of xylose and glucose in the coproduction of the MEG and the one or more C3 compounds.

Embodiment 29. The method of Embodiment 1, wherein the microbe utilizes arabinose, galactose, maltose, fructose, mannose, sucrose, and/or combinations thereof in the coproduction of the MEG and the one or more C3 compounds.

Embodiment 30. A recombinant microbe capable of coproducing MEG and one or more C3 compounds by:

(i) disrupting one or more nucleic acid sequences encoding methylglyoxal synthase (mgsA), and/or (ii) disrupting one or more nucleic acid sequences encoding glyoxylate carboligase (gcl);

wherein the MEG and/or the one or more C3 compounds is produced at a faster rate or exhibits an increased yield or titer; as compared to a microbe lacking a disruption of one or more nucleic acid sequences encoding methylglyoxal synthases and/or glyoxylate carboligases.

Embodiment 31. The recombinant microbe of Embodiment 30, wherein the C3 compounds are selected from acetone, isopropanol, and propene.

Embodiment 32. The recombinant microbe of Embodiment 31, wherein the disrupting is selected from a deletion, a point mutation, a substitution, an insertion, or a frameshift.

Embodiment 33. The recombinant microbe of Embodiment 32, wherein the deletion comprises the deletion of the one or more nucleic acid sequences.

Embodiment 34. The recombinant microbe of Embodiment 30, wherein the translation of the one or more nucleic acid sequences encoding methylglyoxal synthase and/or the one or more nucleic acid sequences encoding glyoxylate carboligase is reduced by at least 50%.

Embodiment 35. The recombinant microbe of Embodiment 30, wherein the MEG and/or the one or more C3 compounds is produced at a faster rate and an increased yield or titer.

Embodiment 36. The recombinant microbe of Embodiment 30, wherein the one or more nucleic acid sequences encoding methylglyoxal synthase and the one or more nucleic acid sequences encoding glyoxylate carboligase are disrupted.

Embodiment 37. The recombinant microbe of Embodiment 30, wherein the microbe is a bacterium or a fungus.

Embodiment 38. The recombinant microbe of Embodiment 37, wherein the microbe is selected from one of the following genera: *Escherichia, Corynebacterium, Saccharomyces, Lactobacillus, Bacillus, Clostridium, Pichia*, and *Aspergillus.*

Embodiment 39. The recombinant microbe of Embodiment 38, wherein the bacterium is an *Escherichia coli.*

Embodiment 40. The recombinant microbe of Embodiment 30, wherein the MEG exhibits an increased yield or titer.

Embodiment 41. The recombinant microbe of Embodiment 40, wherein the increased yield or titer is an increase of at least 2%.

Embodiment 42. The recombinant microbe of Embodiment 40, wherein the increased yield or titer is an increase of at least 15%.

Embodiment 43. The method of Embodiment 30, wherein the MEG is produced at a faster rate.

Embodiment 44. The method of Embodiment 43, wherein the faster rate is an increase of at least 2%.

Embodiment 45. The method of Embodiment 43, wherein the faster rate is an increase of at least 15%.

Embodiment 46. The recombinant microbe of Embodiment 30, wherein the one or more C3 compounds is acetone.

Embodiment 47. The recombinant microbe of Embodiment 46, wherein the acetone exhibits an increased yield or titer.

Embodiment 48. The recombinant microbe of Embodiment 47, wherein the increased yield or titer is an increase of at least 2%.

Embodiment 49. The recombinant microbe of Embodiment 47, wherein the increased yield or titer is an increase of at least 15%.

Embodiment 50. The method of Embodiment 46, wherein the acetone is produced at a faster rate.

Embodiment 51. The method of Embodiment 50, wherein the faster rate is an increase of at least 2%.

Embodiment 52. The method of Embodiment 50, wherein the faster rate is an increase of at least 15%.

Embodiment 53. The method of Embodiment 30, wherein (i) the MEG exhibits an increased yield or titer of at least 2%, and (ii) the one or more C3 compounds exhibits an increased yield or titer of at least 2%.

Embodiment 54. The method of Embodiment 30, wherein (i) the MEG exhibits an increased yield or titer of at least 15%, and (ii) the one or more C3 compounds exhibits an increased yield or titer of at least 15%.

Embodiment 55. The method of Embodiment 30, wherein (i) the rate of MEG production exhibits an increase of at least 2%, and (ii) the rate of the one or more C3 compound production exhibits an increase of at least 2%.

Embodiment 56. The method of Embodiment 30, wherein (i) the rate of MEG production exhibits an increase of at least 15%, and (ii) the rate of the one or more C3 compound production exhibits an increase of at least 15%.

Embodiment 57. The recombinant microbe of Embodiment 30, wherein the microbe utilizes xylose, glucose and/or a mixture of xylose and glucose in the coproduction of the MEG and the one or more C3 compounds.

Embodiment 58. The recombinant microbe of Embodiment 30, wherein the microbe utilizes arabinose, galactose, maltose, fructose, mannose, sucrose, and/or combinations thereof in the coproduction of the MEG and the one or more C3 compounds.

Embodiment 59. A method of modulating the flux of carbon through the monoethylene glycol (MEG) biosynthesis pathway and one or more C3 compound biosynthesis pathways, the method comprising:

modifying a microbe coproducing MEG and one or more C3 compounds by performing one or more of the following:

i. disrupting one or more polynucleotide sequences encoding a phosphate acetyltransferase, ii. disrupting one or more polynucleotide sequences encoding an acetate kinase, iii. disrupting one or more polynucleotide sequences encoding a pyruvate oxidase, iv. disrupting one or more polynucleotide sequences encoding an ArcA regulator, v. disrupting one or more polynucleotide sequences encoding a lysine acetyltransferase, vi. overexpressing one or more endogenous or exogenous polynucleotide sequences encoding a CobB regulator, and vii. overexpressing one or more endogenous or exogenous polynucleotide sequences encoding an acetyl-CoA synthetase;

wherein the MEG and/or the one or more C3 compounds are produced at a faster rate or exhibit an increased yield or titer; as compared to a microbe lacking the disruption and/or the overexpression of the endogenous or exogenous polynucleotides of any one or more of i-vii.

Embodiment 60. The method of Embodiment 59, wherein the disrupting is selected from a deletion, a point mutation, a substitution, an insertion, or a frameshift.

Embodiment 61. The method of Embodiment 60, wherein the deletion comprises the deletion of the one or more nucleic acid sequences.

Embodiment 62. The method of Embodiment 59, wherein the translation of the one or more polypeptides in i-v is reduced by at least 50%

Embodiment 63. The method of Embodiment 59, wherein the one or more polynucleotide sequences encoding at least two of the following polypeptides are disrupted: phosphate acetyltransferase, acetate kinase, pyruvate oxidase, ArcA regulator, and lysine acetyltransferase.

Embodiment 64. The method of Embodiment 59, wherein the overexpression of the one or more endogenous or exogenous polynucleotide sequences in vi and/or vii yields an increase of at least 5% of the polypeptide encoded by the one or more endogenous or exogenous polynucleotide sequences.

Embodiment 65. The method of Embodiment 59, wherein the overexpression of the one or more endogenous or exogenous polynucleotide sequences in vi and/or vii yields an increase of at least 30% of the polypeptide encoded by the one or more endogenous or exogenous polynucleotide sequences.

Embodiment 66. The method of Embodiment 59, wherein the overexpression of the one or more endogenous or exogenous polynucleotide sequences in vi and/or vii yields an increase of at least 70% of the polypeptide encoded by the one or more endogenous or exogenous polynucleotide sequences.

Embodiment 67. The method of Embodiment 59, wherein the overexpression of the one or more endogenous or exogenous polynucleotide sequences yields an increase of at least 300% of the polypeptide encoded by the one or more endogenous or exogenous polynucleotide sequences.

Embodiment 68. The method of Embodiment 59, wherein the MEG and/or the one or more C3 compounds is produced at a faster rate and/or an increased yield or titer.

Embodiment 69. The method of Embodiment 59, wherein the microbe is a bacterium or a fungus.

Embodiment 70. The method of Embodiment 69, wherein the microbe is selected from one of the following genera: *Escherichia, Corynebacterium, Saccharomyces, Lactobacillus, Bacillus, Clostridium, Pichia*, and *Aspergillus*.

Embodiment 71. The method of Embodiment 59, wherein the MEG exhibits an increased yield or titer.

Embodiment 72. The method of Embodiment 71, wherein the increased yield or titer is an increase of at least 2%.

Embodiment 73. The method of Embodiment 71, wherein the increased yield or titer is an increase of at least 15%.

Embodiment 74. The method of Embodiment 59, wherein the MEG is produced at a faster rate.

Embodiment 75. The method of Embodiment 74, wherein the faster rate is an increase of at least 2%.

Embodiment 76. The method of Embodiment 74, wherein the faster rate is an increase of at least 15%.

Embodiment 77. The method of Embodiment 59, wherein the one or more C3 compounds is acetone.

Embodiment 78. The method of Embodiment 77, wherein the acetone exhibits an increased yield or titer.

Embodiment 79. The method of Embodiment 78, wherein the increased yield or titer is an increase of at least 2%.

Embodiment 80. The method of Embodiment 78, wherein the increased yield or titer is an increase of at least 15%.

Embodiment 81. The method of Embodiment 77, wherein the acetone is produced at a faster rate.

Embodiment 82. The method of Embodiment 81, wherein the faster rate is an increase of at least 2%.

Embodiment 83. The method of Embodiment 81, wherein the faster rate is an increase of at least 15%.

Embodiment 84. The method of Embodiment 59, wherein (i) the MEG exhibits an increased yield or titer of at least 2%, and (ii) the one or more C3 compounds exhibits an increased yield or titer of at least 2%.

Embodiment 85. The method of Embodiment 59, wherein (i) the MEG exhibits an increased yield or titer of at least 15%, and (ii) the one or more C3 compounds exhibits an increased yield or titer of at least 15%.

Embodiment 86. The method of Embodiment 59, wherein (i) the rate of MEG production exhibits an increase of at least 2%, and (ii) the rate of the one or more C3 compound production exhibits an increase of at least 2%.

Embodiment 87. The method of Embodiment 59, wherein (i) the rate of MEG production exhibits an increase of at least 15%, and (ii) the rate of the one or more C3 compound production exhibits an increase of at least 15%.

Embodiment 88. The method of Embodiment 59, wherein the microbe utilizes xylose, cellobiose, arabinose, mannose, and/or glucose in the coproduction of the MEG and the one or more C3 compounds.

Embodiment 89. The method of Embodiment 59, wherein the C3 compounds are selected from acetone, isopropanol, and propene.

Embodiment 90. A recombinant microbe capable of coproducing MEG and one or more C3 compounds, wherein the microbe coproducing MEG and one or more C3 compounds by performing one or more of the following:

i. disrupting one or more polynucleotide sequences encoding a phosphate acetyltransferase, ii. disrupting one or more polynucleotide sequences encoding an acetate kinase, iii. disrupting one or more polynucleotide sequences encoding a pyruvate oxidase, iv. disrupting one or more polynucleotide sequences encoding an ArcA regulator, v. disrupting one or more polynucleotide sequences encoding a lysine acetyltransferase, vi. overexpressing one or more endogenous or exogenous polynucleotide sequences encoding a CobB regulator, and vii. overexpressing one or more endogenous or exogenous polynucleotide sequences encoding an acetyl-CoA synthetase;

wherein the MEG and/or the one or more C3 compounds are produced at a faster rate or exhibit an increased yield or titer; as compared to a microbe lacking the disruption and/or the overexpression of the endogenous or exogenous polynucleotides of any one or more of i-vii.

Embodiment 91. The recombinant microbe of Embodiment 90, wherein the disrupting is selected from a deletion, a point mutation, a substitution, an insertion, or a frameshift.

Embodiment 92. The recombinant microbe of Embodiment 91, wherein the deletion comprises the deletion of the one or more nucleic acid sequences.

Embodiment 93. The recombinant microbe of Embodiment 90, wherein the translation of the one or more polypeptides in i-v is reduced by at least 50%

Embodiment 94. The recombinant microbe of Embodiment 92, wherein the one or more polynucleotide sequences encoding at least two of the following polypeptides are disrupted: phosphate acetyltransferase, acetate kinase, pyruvate oxidase, ArcA regulator, and lysine acetyltransferase.

Embodiment 95. The recombinant microbe of Embodiment 90, wherein the overexpression of the one or more endogenous or exogenous polynucleotide sequences in vi and/or vii yields an increase of at least 5% of the polypeptide encoded by the one or more endogenous or exogenous polynucleotide sequences.

Embodiment 96. The recombinant microbe of Embodiment 90, wherein the overexpression of the one or more endogenous or exogenous polynucleotide sequences in vi and/or vii yields an increase of at least 30% of the polypeptide encoded by the one or more endogenous or exogenous polynucleotide sequences.

Embodiment 97. The recombinant microbe of Embodiment 90, wherein the overexpression of the one or more endogenous or exogenous polynucleotide sequences in vi and/or vii yields an increase of at least 70% of the polypeptide encoded by the one or more endogenous or exogenous polynucleotide sequences.

Embodiment 98. The recombinant microbe of Embodiment 90, wherein the overexpression of the one or more endogenous or exogenous polynucleotide sequences yields an increase of at least 30% of the enzyme encoded by the one or more endogenous or exogenous polynucleotide sequences.

Embodiment 99. The recombinant microbe of Embodiment 90, wherein the overexpression of the one or more endogenous or exogenous polynucleotide sequences yields an increase of at least 70% of the enzyme encoded by the one or more endogenous or exogenous polynucleotide sequences.

Embodiment 100. The recombinant microbe of Embodiment 90, wherein the overexpression of the one or more endogenous or exogenous polynucleotide sequences yields an increase of at least 300% of the polypeptide encoded by the one or more endogenous or exogenous polynucleotide sequences.

Embodiment 101. The recombinant microbe of Embodiment 90, wherein the MEG and/or the one or more C3 compounds is produced at a faster rate and/or an increased yield or titer.

Embodiment 102. The recombinant microbe of Embodiment 90, wherein the microbe is a bacterium or a fungus.

Embodiment 103. The recombinant microbe of Embodiment 102, wherein the microbe is selected from one of the following genera: *Escherichia, Corynebacterium, Saccharomyces, Lactobacillus, Bacillus, Clostridium, Pichia*, and *Aspergillus.*

Embodiment 104. The recombinant microbe of Embodiment 90, wherein the MEG exhibits an increased yield or titer.

Embodiment 105. The recombinant microbe of Embodiment 104, wherein the increased yield or titer is an increase of at least 2%.

Embodiment 106. The recombinant microbe of Embodiment 104, wherein the increased yield or titer is an increase of at least 15%.

Embodiment 107. The method of Embodiment 90, wherein the MEG is produced at a faster rate.

Embodiment 108. The method of Embodiment 107, wherein the faster rate is an increase of at least 2%.

Embodiment 109. The method of Embodiment 107, wherein the faster rate is an increase of at least 15%.

Embodiment 110. The recombinant microbe of Embodiment 90, wherein the one or more C3 compounds is acetone.

Embodiment 111. The recombinant microbe of Embodiment 110, wherein the acetone exhibits an increased yield or titer.

Embodiment 112. The recombinant microbe of Embodiment 111, wherein the increased yield or titer is an increase of at least 2%.

Embodiment 113. The recombinant microbe of Embodiment 111, wherein the increased yield or titer is an increase of at least 15%.

Embodiment 114. The method of Embodiment 110, wherein the acetone is produced at a faster rate.

Embodiment 115. The method of Embodiment 114, wherein the faster rate is an increase of at least 2%.

Embodiment 116. The method of Embodiment 114, wherein the faster rate is an increase of at least 15%.

Embodiment 117. The method of Embodiment 90, wherein
- (i) the MEG exhibits an increased yield or titer of at least 2%, and
- (ii) the one or more C3 compounds exhibits an increased yield or titer of at least 2%.

Embodiment 118. The method of Embodiment 90, wherein
- (i) the MEG exhibits an increased yield or titer of at least 15%, and
- (ii) the one or more C3 compounds exhibits an increased yield or titer of at least 15%.

Embodiment 119. The method of Embodiment 90, wherein
- (i) the rate of MEG production exhibits an increase of at least 2%, and
- (ii) the rate of the one or more C3 compound production exhibits an increase of at least 2%.

Embodiment 120. The method of Embodiment 90, wherein
- (i) the rate of MEG production exhibits an increase of at least 15%, and
- (ii) the rate of the one or more C3 compound production exhibits an increase of at least 15%.

Embodiment 121. The method of Embodiment 90, wherein the microbe utilizes xylose, cellobiose, arabinose, mannose, and/or glucose in the coproduction of the MEG and the one or more C3 compounds.

Embodiment 122. The method of Embodiment 90, wherein the C3 compounds are selected from acetone, isopropanol, and propene.

Embodiment 123. A method of modulating the flux of carbon through the monoethylene glycol (MEG) biosynthesis pathway and one or more C3 compound biosynthesis pathways, the method comprising:

modifying a microbe coproducing MEG and one or more C3 compounds by performing one or more of the following:
- i. introducing one or more exogenous polynucleotide sequences encoding a xylose dehydrogenase,
- ii. introducing one or more endogenous or exogenous polynucleotide sequences encoding a xylonolactonase,
- iii. introducing one or more endogenous or exogenous polynucleotide sequences encoding a xylonate dehydratase,
- iv. introducing one or more endogenous or exogenous polynucleotide sequences encoding a 3-deoxy-D-glycerol pentanone sugar acid aldolase,
- v. overexpressing one or more endogenous or exogenous polynucleotide sequences encoding a xylonate dehydratase,
- vi. overexpressing one or more endogenous or exogenous polynucleotide sequences encoding a 3-deoxy-D-glycerol pentanone sugar acid aldolase, and
- vii. overexpressing one or more endogenous or exogenous polynucleotide sequences encoding a glycoaldehyde reductase;

wherein the MEG and/or the one or more C3 compounds are produced at a faster rate or exhibit an increased yield or titer; as compared to a microbe lacking the endogenous or exogenous introduced enzymes and/or the overexpression of the endogenous or exogenous enzymes of any one or more of i-vii.

Embodiment 124. The method of Embodiment 123, wherein the microbe comprises one or more exogenous polynucleotide sequences encoding a xylose dehydrogenase.

Embodiment 125. The method of Embodiment 123, wherein the microbe comprises one or more endogenous or exogenous polynucleotide sequences encoding a xylonolactonase.

Embodiment 126. The method of Embodiment 123, wherein the microbe comprises one or more endogenous or exogenous polynucleotide sequences encoding a xylonate dehydratase.

Embodiment 127. The method of Embodiment 123, wherein the microbe comprises one or more endogenous or exogenous polynucleotide sequences encoding a 3-deoxy-D-glycerol pentanone sugar acid aldolase.

Embodiment 128. The method of Embodiment 123, wherein the microbe overexpresses one or more endogenous or exogenous polynucleotide sequences encoding a xylonate dehydratase.

Embodiment 129. The method of Embodiment 123, wherein the microbe overexpresses one or more endogenous or exogenous polynucleotide sequences encoding a 3-deoxy-D-glycerol pentanone sugar acid aldolase.

Embodiment 130. The method of Embodiment 123, wherein the microbe overexpresses one or more endogenous or exogenous polynucleotide sequences encoding a glycoaldehyde reductase.

Embodiment 131. The method of Embodiment 123, wherein the overexpression of the one or more endogenous or exogenous polynucleotide sequences yields an increase of at least 5% of the enzyme encoded by the one or more endogenous or exogenous polynucleotide sequences.

Embodiment 132. The method of Embodiment 123, wherein the overexpression of the one or more endogenous or exogenous polynucleotide sequences yields an increase of at least 30% of the enzyme encoded by the one or more endogenous or exogenous polynucleotide sequences.

Embodiment 133. The method of Embodiment 123, wherein the overexpression of the one or more endogenous or exogenous polynucleotide sequences yields an increase of at least 70% of the enzyme encoded by the one or more endogenous or exogenous polynucleotide sequences.

Embodiment 134. The method of Embodiment 123, wherein the overexpression of the one or more endogenous or exogenous polynucleotide sequences yields an increase of at least 300% of the enzyme encoded by the one or more endogenous or exogenous polynucleotide sequences.

Embodiment 135. The method of Embodiment 123, wherein the MEG and/or the one or more C3 compounds is produced at a faster rate and/or an increased yield or titer.

Embodiment 136. The method of Embodiment 123, wherein the microbe is a bacterium or a fungus.

Embodiment 137. The method of Embodiment 136, wherein the microbe is selected from one of the following genera: *Escherichia, Corynebacterium, Saccharomyces, Lactobacillus, Bacillus, Clostridium, Pichia*, and *Aspergillus*.

Embodiment 138. The method of Embodiment 123, wherein the MEG exhibits an increased yield or titer.

Embodiment 139. The method of Embodiment 138, wherein the increased yield or titer is an increase of at least 2%.

Embodiment 140. The method of Embodiment 138, wherein the increased yield or titer is an increase of at least 15%.

Embodiment 141. The method of Embodiment 123, wherein the MEG is produced at a faster rate.

Embodiment 142. The method of Embodiment 138, wherein the faster rate is an increase of at least 2%.

Embodiment 143. The method of Embodiment 138, wherein the faster rate is an increase of at least 15%.

Embodiment 144. The method of Embodiment 123, wherein the one or more C3 compounds is acetone.

Embodiment 145. The method of Embodiment 144, wherein the acetone exhibits an increased yield or titer.

Embodiment 146. The method of Embodiment 145, wherein the increased yield or titer is an increase of at least 2%.

Embodiment 147. The method of Embodiment 145, wherein the increased yield or titer is an increase of at least 15%.

Embodiment 148. The method of Embodiment 144, wherein the acetone is produced at a faster rate.

Embodiment 149. The method of Embodiment 148, wherein the faster rate is an increase of at least 2%.

Embodiment 150. The method of Embodiment 148, wherein the faster rate is an increase of at least 15%.

Embodiment 151. The method of Embodiment 123, wherein (i) the MEG exhibits an increased yield or titer of at least 2%, and/or (ii) the one or more C3 compounds exhibits an increased yield or titer of at least 2%.

Embodiment 152. The method of Embodiment 123, wherein (i) the MEG exhibits an increased yield or titer of at least 15%, and (ii) the one or more C3 compounds exhibits an increased yield or titer of at least 15%.

Embodiment 153. The method of Embodiment 123, wherein (i) the rate of MEG production exhibits an increase of at least 2%, and (ii) the rate of the one or more C3 compound production exhibits an increase of at least 2%.

Embodiment 154. The method of Embodiment 123, wherein (i) the rate of MEG production exhibits an increase of at least 15%, and (ii) the rate of the one or more C3 compound production exhibits an increase of at least 15%.

Embodiment 155. The method of Embodiment 123, wherein the microbe utilizes xylose, cellobiose, arabinose, mannose, and/or glucose in the coproduction of the MEG and the one or more C3 compounds.

Embodiment 156. The method of Embodiment 123, wherein the C3 compounds are selected from acetone, isopropanol, and propene.

Embodiment 157. A recombinant microbe capable of coproducing MEG and one or more C3 compounds, wherein the microbe coproducing MEG and one or more C3 compounds comprises one or more of the following:

i. one or more exogenous polynucleotide sequences encoding a xylose dehydrogenase, ii. one or more endogenous or exogenous polynucleotide sequences encoding a xylonolactonase, iii. one or more endogenous or exogenous polynucleotide sequences encoding a xylonate dehydratase, iv. one or more endogenous or exogenous polynucleotide sequences encoding a 3-deoxy-D-glycerol pentanone sugar acid aldolase, v. one or more endogenous or exogenous polynucleotide sequences encoding a xylonate dehydratase, vi. one or more endogenous or exogenous polynucleotide sequences encoding a 3-deoxy-D-glycerol pentanone sugar acid aldolase, and vii. one or more endogenous or exogenous polynucleotide sequences encoding a glycoaldehyde reductase;

wherein the enzymes of v-vii are overexpressed as compared to their native expression; and wherein the MEG and/or the one or more C3 compounds are produced at a faster rate or exhibit an increased yield or titer; as compared to a microbe lacking the endogenous or exogenous introduced enzymes and/or lacking the overexpression of the endogenous or exogenous enzymes of any one or more of i-vii.

Embodiment 158. The recombinant microbe of Embodiment 157, wherein the microbe comprises one or more exogenous polynucleotide sequences encoding a xylose dehydrogenase.

Embodiment 159. The recombinant microbe of Embodiment 157, wherein the microbe comprises one or more endogenous or exogenous polynucleotide sequences encoding a xylonolactonase.

Embodiment 160. The recombinant microbe of Embodiment 157, wherein the microbe comprises one or more endogenous or exogenous polynucleotide sequences encoding a xylonate dehydratase.

Embodiment 161. The recombinant microbe of Embodiment 157, wherein the microbe comprises one or more endogenous or exogenous polynucleotide sequences encoding a 3-deoxy-D-glycerol pentanone sugar acid aldolase.

Embodiment 162. The recombinant microbe of Embodiment 157, wherein the microbe overexpresses one or more endogenous or exogenous polynucleotide sequences encoding a xylonate dehydratase.

Embodiment 163. The recombinant microbe of Embodiment 157, wherein the microbe overexpresses one or more endogenous or exogenous polynucleotide sequences encoding a 3-deoxy-D-glycerol pentanone sugar acid aldolase.

Embodiment 164. The recombinant microbe of Embodiment 157, wherein the microbe overexpresses one or more endogenous or exogenous polynucleotide sequences encoding a glycoaldehyde reductase.

Embodiment 165. The recombinant microbe of Embodiment 157, wherein the overexpression of the one or more endogenous or exogenous polynucleotide sequences yields an increase of at least 5% of the enzyme encoded by the one or more endogenous or exogenous polynucleotide sequences.

Embodiment 166. The recombinant microbe of Embodiment 157, wherein the overexpression of the one or more endogenous or exogenous polynucleotide sequences yields an increase of at least 30% of the enzyme encoded by the one or more endogenous or exogenous polynucleotide sequences.

Embodiment 167. The recombinant microbe of Embodiment 157, wherein the overexpression of the one or more endogenous or exogenous polynucleotide sequences yields an increase of at least 70% of the enzyme encoded by the one or more endogenous or exogenous polynucleotide sequences.

Embodiment 168. The recombinant microbe of Embodiment 157, wherein the overexpression of the one or more endogenous or exogenous polynucleotide sequences yields an increase of at least 300% of the enzyme encoded by the one or more endogenous or exogenous polynucleotide sequences.

Embodiment 169. The recombinant microbe of Embodiment 157, wherein the MEG and/or the one or more C3 compounds is produced at a faster rate and/or an increased yield or titer.

Embodiment 170. The recombinant microbe of Embodiment 157, wherein the microbe is a bacterium or a fungus.

Embodiment 171. The recombinant microbe of Embodiment 170, wherein the microbe is selected from one of the following genera: *Escherichia, Corynebacterium, Saccharomyces, Lactobacillus, Bacillus, Clostridium, Pichia*, and *Aspergillus*.

Embodiment 172. The recombinant microbe of Embodiment 157, wherein the MEG exhibits an increased yield or titer.

Embodiment 173. The recombinant microbe of Embodiment 172, wherein the increased yield or titer is an increase of at least 2%.

Embodiment 174. The recombinant microbe of Embodiment 172, wherein the increased yield or titer is an increase of at least 15%.

Embodiment 175. The method of Embodiment 157, wherein the MEG is produced at a faster rate.

Embodiment 176. The method of Embodiment 175, wherein the faster rate is an increase of at least 2%.

Embodiment 177. The method of Embodiment 175, wherein the faster rate is an increase of at least 15%.

Embodiment 178. The recombinant microbe of Embodiment 157, wherein the one or more C3 compounds is acetone.

Embodiment 179. The recombinant microbe of Embodiment 178, wherein the acetone exhibits an increased yield or titer.

Embodiment 180. The recombinant microbe of Embodiment 179, wherein the increased yield or titer is an increase of at least 5%.

Embodiment 181. The recombinant microbe of Embodiment 179, wherein the increased yield or titer is an increase of at least 30%.

Embodiment 182. The method of Embodiment 178, wherein the acetone is produced at a faster rate.

Embodiment 183. The method of Embodiment 182, wherein the faster rate is an increase of at least 2%.

Embodiment 184. The method of Embodiment 182, wherein the faster rate is an increase of at least 15%.

Embodiment 185. The method of Embodiment 157, wherein (i) the MEG exhibits an increased yield or titer of at least 2%, and (ii) the one or more C3 compounds exhibits an increased yield or titer of at least 2%.

Embodiment 186. The method of Embodiment 157, wherein (i) the MEG exhibits an increased yield or titer of at least 15%, and (ii) the one or more C3 compounds exhibits an increased yield or titer of at least 15%.

Embodiment 187. The method of Embodiment 157, wherein (i) the rate of MEG production exhibits an increase of at least 2%, and (ii) the rate of the one or more C3 compound production exhibits an increase of at least 2%.

Embodiment 188. The method of Embodiment 157, wherein (i) the rate of MEG production exhibits an increase of at least 15%, and (ii) the rate of the one or more C3 compound production exhibits an increase of at least 15%.

Embodiment 189. The recombinant microbe of Embodiment 157, wherein the microbe utilizes xylose, cellobiose, arabinose, mannose, and/or glucose in the coproduction of the MEG and the one or more C3 compounds.

Embodiment 190. The recombinant microbe of Embodiment 157, wherein the C3 compounds are selected from acetone, isopropanol, and propene.

Embodiment 191. A method of modulating the flux of carbon through the monoethylene glycol (MEG) biosynthesis pathway and one or more C3 compound biosynthesis pathways, the method comprising:

modifying a microbe coproducing MEG and one or more C3 compounds by:

i. introducing one or more polynucleotide sequences encoding acetoacetyl CoA synthase, and/or ii. introducing one or more polynucleotide sequences encoding hydroxymethylglutaryl-CoA synthase and hydroxymethylglutaryl-CoA lyase;

wherein the MEG and/or the one or more C3 compounds is produced at a faster rate and/or exhibits an increased yield or titer; as compared to a microbe not having been introduced an acetoacetyl CoA, hydroxymethylglutaryl-CoA synthase, and/or hydroxymethylglutaryl-CoA lyase.

Embodiment 192. The method of Embodiment 191, wherein the microbe comprises a deletion of one or more polynucleotide sequences encoding acetoacetyl-CoA thiolase.

Embodiment 193. The method of Embodiment 191, wherein the microbe lacks a functional acetoacetyl-CoA thiolase.

Embodiment 194. The method of Embodiment 191, wherein the microbe comprises a functional acetoacetyl-CoA thiolase.

Embodiment 195. The method of Embodiment 191, wherein the microbe comprises a deletion of one or more polynucleotide sequences encoding acetoacetyl-CoA transferase (AtoDA).

Embodiment 196. The method of Embodiment 191, wherein the microbe comprises a functional acetoacetyl-CoA transferase (AtoDA).

Embodiment 197. The method of Embodiment 192 or Embodiment 195 wherein the deletion comprises the deletion of the one or more polynucleotide sequences.

Embodiment 198. The method of Embodiment 191, wherein the MEG and/or the one or more C3 compounds is produced at a faster rate and/or an increased yield or titer.

Embodiment 199. The method of Embodiment 191, wherein the microbe is a bacterium or a fungus.

Embodiment 200. The method of Embodiment 199, wherein the bacterium is an *Escherichia coli.*

Embodiment 201. The method of Embodiment 191, wherein the MEG exhibits an increased yield or titer.

Embodiment 202. The method of Embodiment 201, wherein the increased yield or titer is an increase of at least 2%.

Embodiment 203. The method of Embodiment 202, wherein the increased yield or titer is an increase of at least 15%.

Embodiment 204. The method of Embodiment 191, wherein the one or more C3 compounds is acetone.

Embodiment 205. The method of Embodiment 204, wherein the acetone exhibits an increased yield or titer.

Embodiment 206. The method of Embodiment 205, wherein the increased yield or titer is an increase of at least 2%.

Embodiment 207. The method of Embodiment 206, wherein the increased yield or titer is an increase of at least 15%.

Embodiment 208. The method of Embodiment 191, wherein the microbe utilizes xylose, cellobiose, arabinose, mannose, and/or glucose in the coproduction of the MEG and the one or more C3 compounds.

Embodiment 209. The method of Embodiment 191, wherein the C3 compounds are selected from acetone, isopropanol, and propene.

Embodiment 210. A recombinant microbe capable of coproducing MEG and one or more C3 compounds by:

modifying a microbe coproducing MEG and one or more C3 compounds by:

i. introducing one or more polynucleotide sequences encoding acetoacetyl CoA synthase, and/or ii. introducing one or more polynucleotide sequences encoding hydroxymethylglutaryl-CoA synthase and hydroxymethylglutaryl-CoA lyase;

wherein the MEG and/or the one or more C3 compounds is produced at a faster rate and/or exhibits an increased yield or titer; as compared to a microbe not having been introduced an acetoacetyl CoA, hydroxymethylglutaryl-CoA synthase, and/or hydroxymethylglutaryl-CoA lyase.

Embodiment 211. The recombinant microbe of Embodiment 210, wherein the microbe comprises a deletion of one or more polynucleotide sequences encoding acetoacetyl-CoA thiolase.

Embodiment 212. The recombinant microbe of Embodiment 211, wherein the microbe lacks a functional acetoacetyl-CoA thiolase.

Embodiment 213. The recombinant microbe of Embodiment 211, wherein the microbe comprises a functional acetoacetyl-CoA thiolase.

Embodiment 214. The recombinant microbe of Embodiment 211, wherein the microbe comprises a deletion of one or more polynucleotide sequences encoding acetoacetyl-CoA transferase (AtoDA).

Embodiment 215. The recombinant microbe of Embodiment 211, wherein the microbe comprises a functional acetoacetyl-CoA transferase (AtoDA).

Embodiment 216. The recombinant microbe of Embodiment 212 or Embodiment 215, wherein the deletion comprises the deletion of the one or more polynucleotide sequences.

Embodiment 217. The recombinant microbe of Embodiment 211, wherein the C3 compounds are selected from acetone, isopropanol, and propene.

Embodiment 218. The recombinant microbe of Embodiment 211, wherein the MEG and/or the one or more C3 compounds is produced at a faster rate and/or an increased yield or titer.

Embodiment 219. The recombinant microbe of Embodiment 211, wherein the microbe is a bacterium or a fungus.

Embodiment 220. The recombinant microbe of Embodiment 219, wherein the bacterium is an *Escherichia coli.*

Embodiment 221. The recombinant microbe of Embodiment 211, wherein the MEG exhibits an increased yield or titer.

Embodiment 222. The recombinant microbe of Embodiment 221, wherein the increased yield or titer is an increase of at least 5%.

Embodiment 223. The recombinant microbe of Embodiment 221, wherein the increased yield or titer is an increase of at least 30%.

Embodiment 224. The recombinant microbe of Embodiment 211, wherein the one or more C3 compounds is acetone.

Embodiment 225. The recombinant microbe of Embodiment 224, wherein the acetone exhibits an increased yield or titer.

Embodiment 226. The recombinant microbe of Embodiment 225, wherein the increased yield or titer is an increase of at least 2%.

Embodiment 227. The recombinant microbe of Embodiment 225, wherein the increased yield or titer is an increase of at least 15%.

Embodiment 228. The recombinant microbe of Embodiment 211, wherein the microbe utilizes xylose, cellobiose, arabinose, mannose, and/or glucose in the coproduction of the MEG and the one or more C3 compounds.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world. Further, the following references are hereby incorporated by reference.

The engineered pathways for the co-production of MEG and C3 compounds in microbes are set forth in WO2017015166, US20180023101A1, and US20180179558A1.

WO2014102180A1, WO2014076232A2, US20150329877A1, US20170260551 U.S. Pat. No. 8,524,472 B2, US 20060073577 A1, US 20160265005 A1, U.S. Pat. No. 7,935,511 B2, WO 2005087940 A1, US 20090253164 A1, U.S. Pat. No. 8,637,286 B2, EP 1546304 B1, US 20070249018 A1, US2016326553 A1, U.S. Pat. No. 7,531,337 B2, US 20060073577 A1, KR101351879B1, and WO2013163230A2; and Berzin et al. 2012. Selective production of acetone during continuous synthesis gas fermentation by engineered biocatalyst *Clostridium* sp. MAceT113—DOI: 10.1111/j.1472-765X.2012.03272.x Causey, T. B., Shanmugam, K. T., Yomano, L. P., & Ingram, L. O. (2004). Engineering *Escherichia coli* for efficient conversion of glucose to pyruvate. PNAS, 101(8), 2235-2240.

Dittrich, C. R., Vadali, R. V., Bennett, G. N., & San, K. Y. (2005). Redistribution of Metabolic Fluxes in the Central Aerobic Metabolic Pathway of *E. coli* Mutant Strains with Deletion of the ackA-pta and poxB Pathways for the Synthesis of Isoamyl Acetate. Biotechnology progress, 21(2), 627-631.

Castaño-Cerezo, S., Pastor, J. M., Renilla, S., Bernal, V., Iborra, J. L., & Cánovas, M. (2009). An insight into the role of phosphotransacetylase (pta) and the acetate/acetyl-CoA node in *Escherichia coli*. Microbial cell factories, 8(1), 54.

Peebo, K., Valgepea, K., Nahku, R., Riis, G., Õun, M., Adamberg, K., & Vilu, R. (2014). Coordinated activation of PTA-ACS and TCA cycles strongly reduces overflow metabolism of acetate in *Escherichia coli*. Applied microbiology and biotechnology, 98(11), 5131-5143.

Lin, H., Castro, N. M., Bennett, G. N., & San, K. Y. (2006). Acetyl-CoA synthetase overexpression in *Escherichia coli* demonstrates more efficient acetate assimilation and lower acetate accumulation: a potential tool in metabolic engineering. Applied microbiology and biotechnology, 71(6), 870-874.

Liu H1, Ramos K R, Valdehuesa K N, Nisola G M, Lee W K, Chung W J. —Myongji University. Biosynthesis of ethylene glycol in *Escherichia coli*. Appl Microbiol Biotechnol. 2013 April; 97(8):3409-17. doi: 10.1007/s00253-012-4618-7.

Rhudith B. Cabulonga, Kris Niño G. Valdehuesaa, Kristine Rose M. Ramos, Grace M. Nisola, Won-Keun Lee, Chang Ro Lee, Wook-Jin Chung—Myongji University. Enhanced yield of ethylene glycol production from d-xylose by pathway optimization in *Escherichia coli* Enzyme and Microbial Technology 97 (2017) 11-20 ttp://dx-.doi.org/10.1016/j.enzmictec.2016.10.020.

What is claimed is:

1. A recombinant *Escherichia coli* capable of coproducing MEG and one or more C3 compounds, wherein the recombinant *E. coli* comprises:

a disruption of endogenous *E. coli* pta and one or more of the following (i) to (iii):

(i) a disruption of endogenous *E. coli* ackA, (ii) a disruption of endogenous *E. coli* arcA, and (iii) a disruption of endogenous *E. coli* pka;

wherein the recombinant *E. coli* comprises a pathway for MEG production; and wherein one of the one or more C3 compounds is acetone and the recombinant *E. coli* comprises a pathway for acetone production.

2. The recombinant *E. coli* of claim 1, wherein the recombinant *E. coli* further comprises one or more of the following:

(i) one or more polynucleotide sequences encoding acetoacetyl COA synthase for converting acetyl-CoA and malonyl-CoA to acetoacetyl-CoA, wherein the acetoacetyl CoA synthase is *Streptomyces* sp. NphT7, and/or (ii) one or more polynucleotide sequences encoding (a) hydroxymethylglutaryl-CoA synthase for converting acetyl-CoA and acetoacetyl-CoA to(S)-3-hydroxy-3-methylglutaryl-CoA and (b) hydroxymethylglutaryl-CoA lyase for converting the(S)-3-hydroxy-3-methylglutaryl-CoA acetyl-CoA and acetoacetate, wherein the hydroxymethylglutaryl-CoA synthase is ERG13 and the hydroxymethylglutaryl-CoA lyase is YngG.

3. The recombinant *E. coli* of claim 1, wherein the MEG exhibits an increased yield or titer.

4. The recombinant *E. coli* of claim 3, wherein the increased yield or titer is an increase of at least 2%.

5. The recombinant *E. coli* of claim 3, wherein the increased yield or titer is an increase of at least 15%.

6. The recombinant *E. coli* of claim 1, wherein the acetone exhibits an increased yield or titer.

7. The recombinant *E. coli* of claim 6, wherein the increased yield or titer is an increase of at least 2%.

8. The recombinant *E. coli* of claim 6, wherein the increased yield or titer is an increase of at least 15%.

9. The recombinant *E. coli* of claim 1, wherein the *E. coli* utilizes xylose, cellobiose, arabinose, mannose, and/or glucose in the coproduction of the MEG and the one or more C3 compounds.

10. The recombinant *E. coli* of claim 1, wherein the C3 compounds further comprise isopropanol and/or propene.

11. The recombinant *E. coli* of claim 1, wherein the recombinant *E. coli* further comprises a disruption of endogenous *E. coli* poxB.

12. The recombinant *E. coli* of claim 1, wherein the recombinant *E. coli* further comprises one or more of the following:

(i) one or more overexpressed endogenous polynucleotide sequences encoding a CobB regulator, and/or (ii) one or more overexpressed endogenous polynucleotide sequences encoding an acetyl-CoA synthetase, wherein the acetyl-CoA synthetase is *E. coli* acs.

13. The recombinant *E. coli* of claim 1, wherein the recombinant *E. coli* further comprises one or more of the following:

(i) one or more polynucleotide sequences encoding one or more polypeptides comprising means for converting acetyl-CoA and malonyl-CoA to acetoacetyl-CoA, and/or (ii) one or more polynucleotide sequences encoding one or more polypeptides comprising means for converting acetyl-CoA and acetoacetyl-CoA to (S)-3-hydroxy-3-methylglutaryl-CoA and means for converting the (S)-3-hydroxy-3-methylglutaryl-CoA to acetyl-CoA and acetoacetate.

14. The recombinant *E. coli* of claim 13, wherein the means for converting acetyl-CoA and malonyl-CoA to acetoacetyl-CoA is NphT7.

15. The recombinant *E. coli* of claim 13, wherein the means for converting acetyl-CoA and acetoacetyl-CoA to (S)-3-hydroxy-3-methylglutaryl-CoA is ERG13 and the means for converting the(S)-3-hydroxy-3-methylglutaryl-CoA to acetyl-CoA and acetoacetate is YngG.

* * * * *